United States Patent
Gauthier et al.

(10) Patent No.: US 10,113,003 B2
(45) Date of Patent: Oct. 30, 2018

(54) MULTISPECIFIC NK ENGAGER PROTEINS

(71) Applicant: INNATE PHARMA, Marseilles (FR)

(72) Inventors: Laurent Gauthier, Marseilles (FR); Nadia Anceriz, Aubagne (FR); Ariane Morel, Marseilles (FR); Benjamin Rossi, Marseilles (FR)

(73) Assignee: INNATE PHARMA, Marseilles (FR)

( * ) Notice: Subject to any disclaimer, the term of this patent is extended or adjusted under 35 U.S.C. 154(b) by 0 days.

(21) Appl. No.: 15/190,337

(22) Filed: Jun. 23, 2016

(65) Prior Publication Data

US 2016/0369002 A1   Dec. 22, 2016

Related U.S. Application Data

(63) Continuation-in-part of application No. PCT/EP2015/064063, filed on Jun. 23, 2015.

(60) Provisional application No. 62/271,459, filed on Dec. 28, 2015.

(51) Int. Cl.
  *A61K 39/00* (2006.01)
  *C07K 16/28* (2006.01)

(52) U.S. Cl.
  CPC ...... *C07K 16/2896* (2013.01); *C07K 16/2803* (2013.01); *C07K 16/283* (2013.01); *C07K 16/2809* (2013.01); *C07K 16/2866* (2013.01); *C07K 16/2887* (2013.01); *C07K 2317/31* (2013.01); *C07K 2317/522* (2013.01); *C07K 2317/524* (2013.01); *C07K 2317/526* (2013.01); *C07K 2317/565* (2013.01); *C07K 2317/622* (2013.01); *C07K 2317/71* (2013.01); *C07K 2317/732* (2013.01); *C07K 2317/75* (2013.01); *C07K 2317/92* (2013.01); *C07K 2319/30* (2013.01)

(58) Field of Classification Search
  None
  See application file for complete search history.

(56) References Cited

FOREIGN PATENT DOCUMENTS

| WO | 2005/000086 | 1/2005 |
|---|---|---|
| WO | 2005/061547 | 7/2005 |
| WO | 2005/105858 | 11/2005 |
| WO | 2015/197593 | 12/2015 |
| WO | 2015/197598 | 12/2015 |
| WO | WO 2015/197593 A1 * | 12/2015 |
| WO | 2016/207273 | 12/2016 |
| WO | 2016/207278 | 12/2016 |

OTHER PUBLICATIONS

Kim et al (Canc. Immunol. Immunother., 2009, 58: 1691-1700).*
Holmes et al (J. Immunol., 2011, 186: 1538-1545).*
Torres and Casadevall (Trends in Immunol. 2007, 29(2): 91-97).*
Weiner (Sem. Hematol. 2010, 47(2): 115-123).*
Germain et al (Prot. Eng. Design Select., 2008, 21 (11): 665-672).*
Vyas et al (Trends Molec. Med., Feb. 2014, 20(2): 72-82).*
Weidle et al (Canc. Genom. Prot., 2013, 10: 1-18).*
Baeuerle PA, et al. "Bispecific T-cell engaging antibodies for cancer therapy," Cancer Res. Jun. 15, 2009;69(12):4941-4.
Bolzhauser, Markus: "Immuntherapie der kindlichen ALL: Einfluss eines bispezifischen CD19*NKp46-Antikörpers auf die zytotoxische Aktivität von NK-Zellen gegenüber CD19 + ALL-Blasten padiatrischer Patienten", Inaugural-Dissertation Zur Erlangung Des Doktorgrades Der Medizin Der Medizinischen Fakultät Der Eberhard-Karls-Universität Zu Tübingen, Jan. 1, 2010 (Jan. 1, 2010), pp. 116 pp., <URL:http://d-nb.info/1003819621/34>; Translation Provided.
Chames P, et al. "Bispecific antibodies for cancer therapy: the light at the end of the tunnel?" MAbs. Nov.-Dec. 2009;1(6):539-47.
Germain C, et al. "Redirecting NK cells mediated tumor cell lysis by a new recombinant bifunctional protein," Protein Eng Des Sel. Nov. 2008;21(11):665-72.
Hollander, Nurit. "Bispecific antibodies for cancer therapy," Immunotherapy. Mar. 2009;1(2):211-22.
Jackman J, et al. "Development of a two-part strategy to identify a therapeutic human bispecific antibody that inhibits IgE receptor signaling," J Biol Chem. Jul. 2, 2010;285(27):20850-9.
Kellner C, et al. "Heterodimeric bispecific antibody-derivatives against CD19 and CD16 induce effective antibody-dependent cellular cytotoxicity against B-lymphoid tumor cells," Cancer Lett. Apr. 28, 2011;303(2):128-39.
Kufer P, et al. "A revival of bispecific antibodies," Trends Biotechnol. May 2004;22(5):238-44.
Low SC, et al. "Inhibitors of the FcRn:IgG protein-protein interaction," AAPS J. Sep. 2009;11(3):432-4.
Willer KM, et al. "The first constant domain (C(H)1 and C(L)) of an antibody used as heterodimerization domain for bispecific miniantibodies," FEBS Lett. Jan. 30, 1998;422(2):259-64.
Rozan C, et al. "Single-domain antibody-based and linker-free bispecific antibodies targeting FcγRIII induce potent antitumor activity without recruiting regulatory T cells," Mol Cancer Ther. Aug. 2013;12(8):1481-91.
Communication from the International Searching Authority received in PCT/EP2016/064537 dated Sep. 7, 2016.

* cited by examiner

*Primary Examiner* — Michael Szperka
*Assistant Examiner* — Marianne DiBrino
(74) *Attorney, Agent, or Firm* — Robin L. Teskin; LeClairRyan PLLC

(57) ABSTRACT

Multispecific proteins that bind and specifically redirect NK cells to lyse a target cell of interest are provided without non-specific activation of NK cells in absence of target cells. The proteins have utility in the treatment of disease, notably cancer or infectious disease.

28 Claims, 18 Drawing Sheets
Specification includes a Sequence Listing.

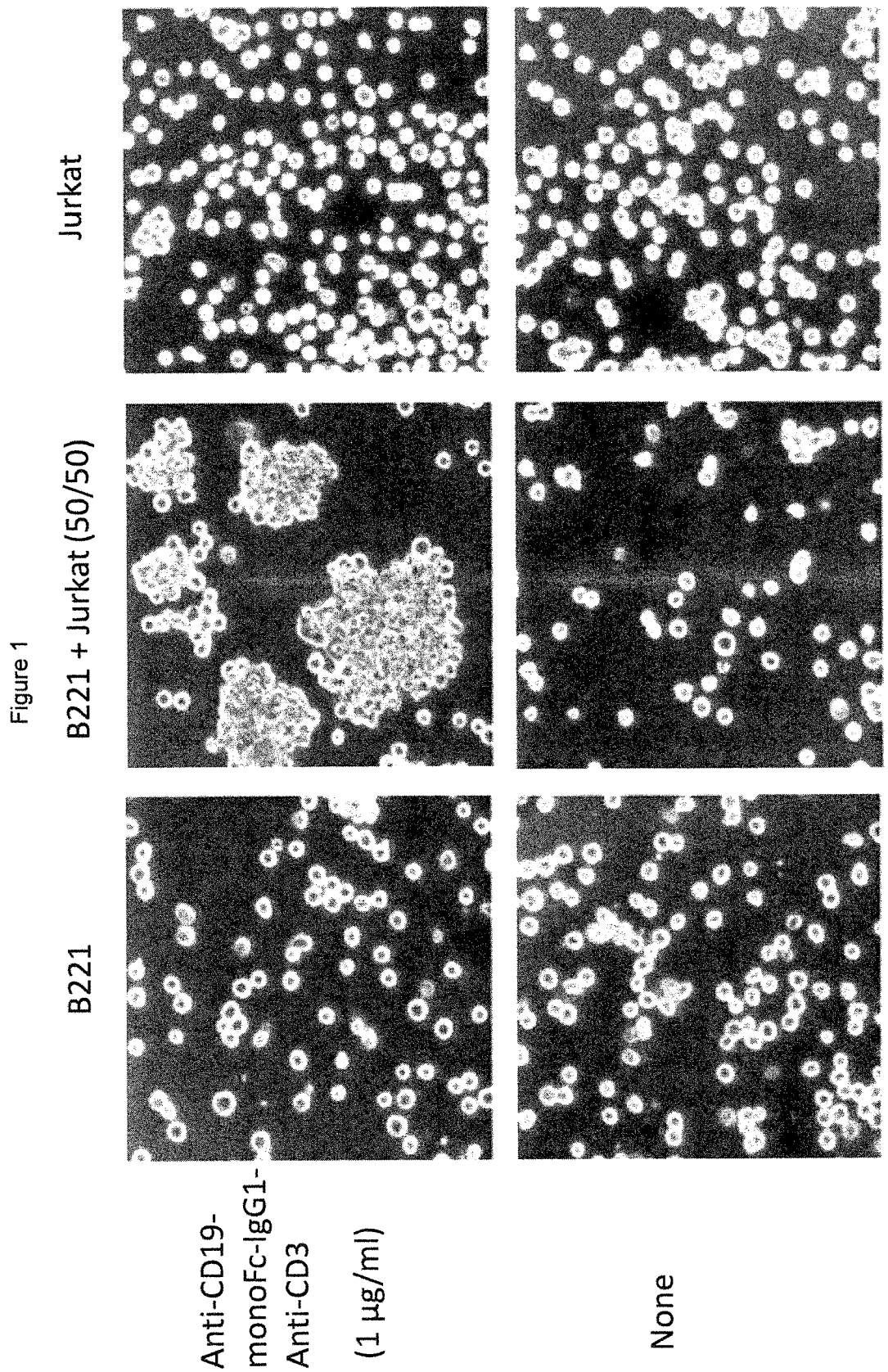

Figure 2B
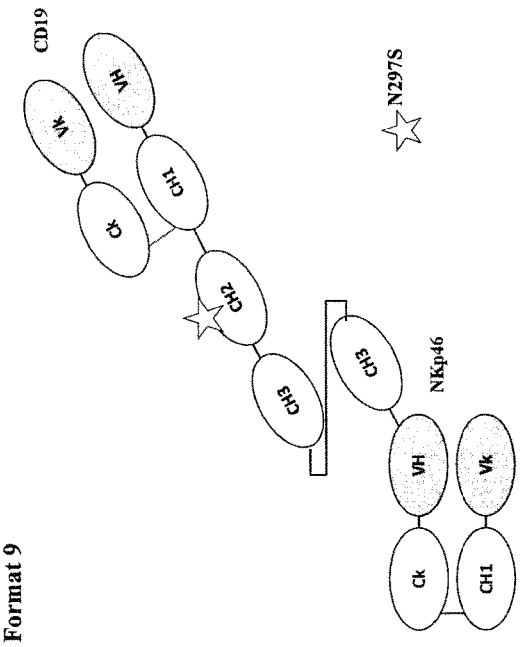
Format 9
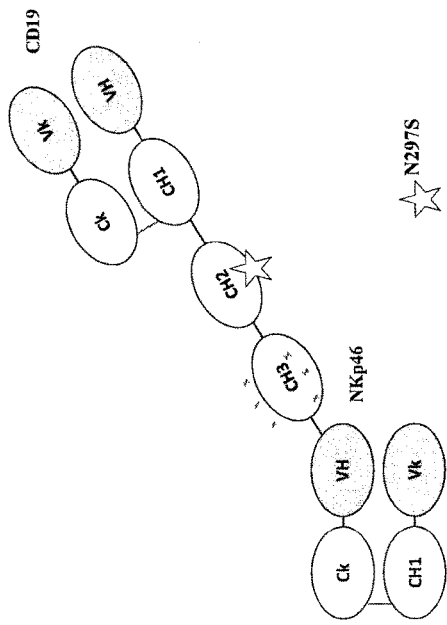
Format 8
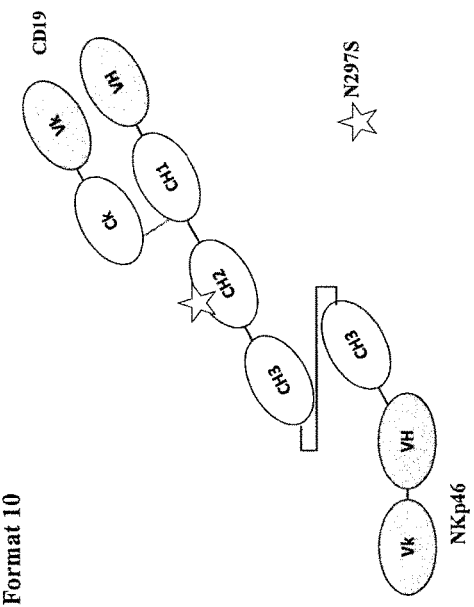
Format 10

Figure 2C
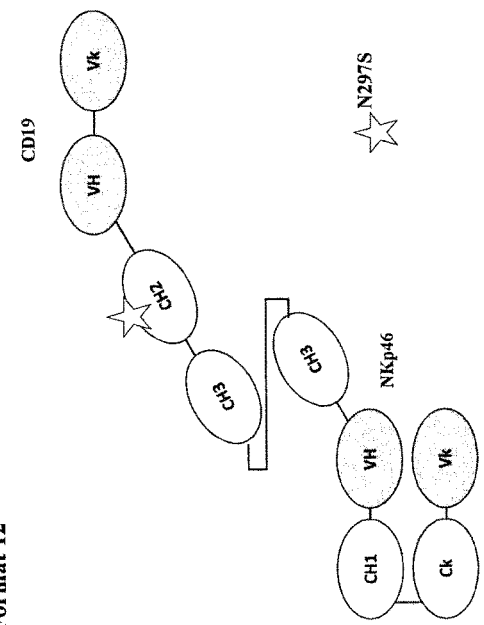
Format 12
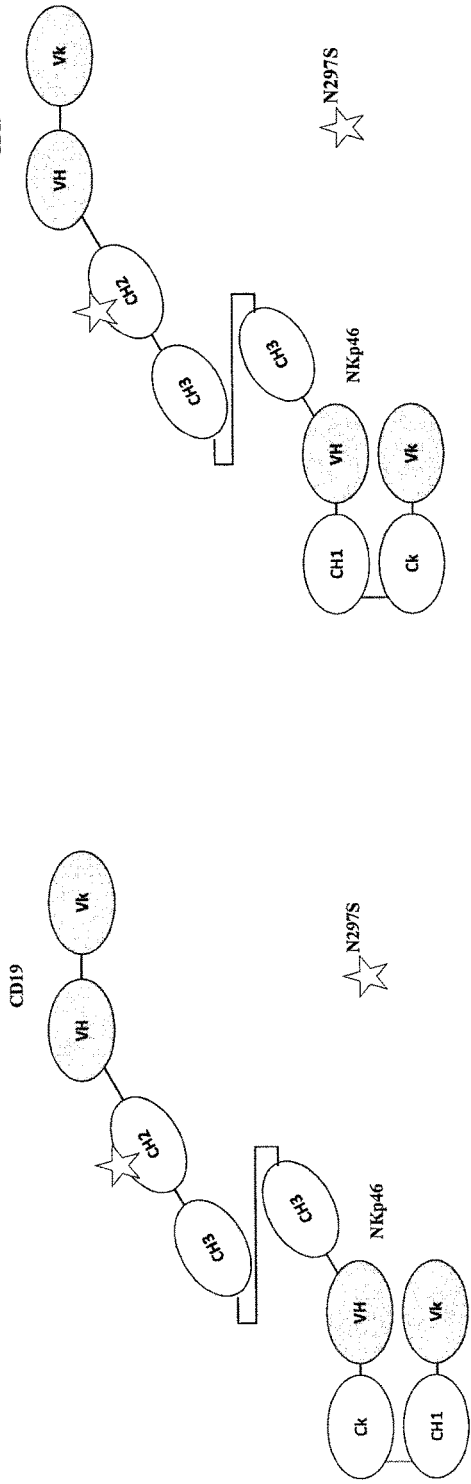
Format 11
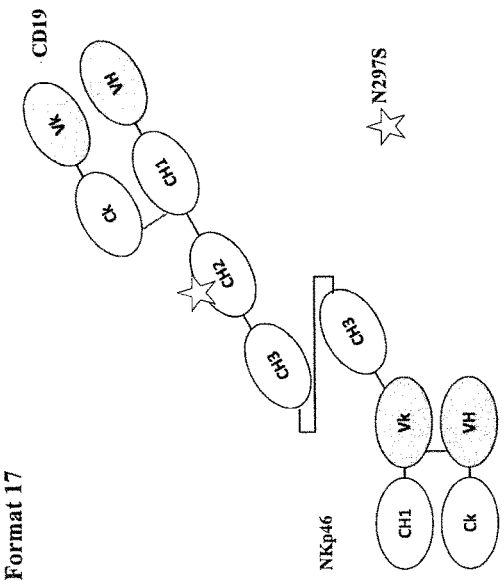
Format 17

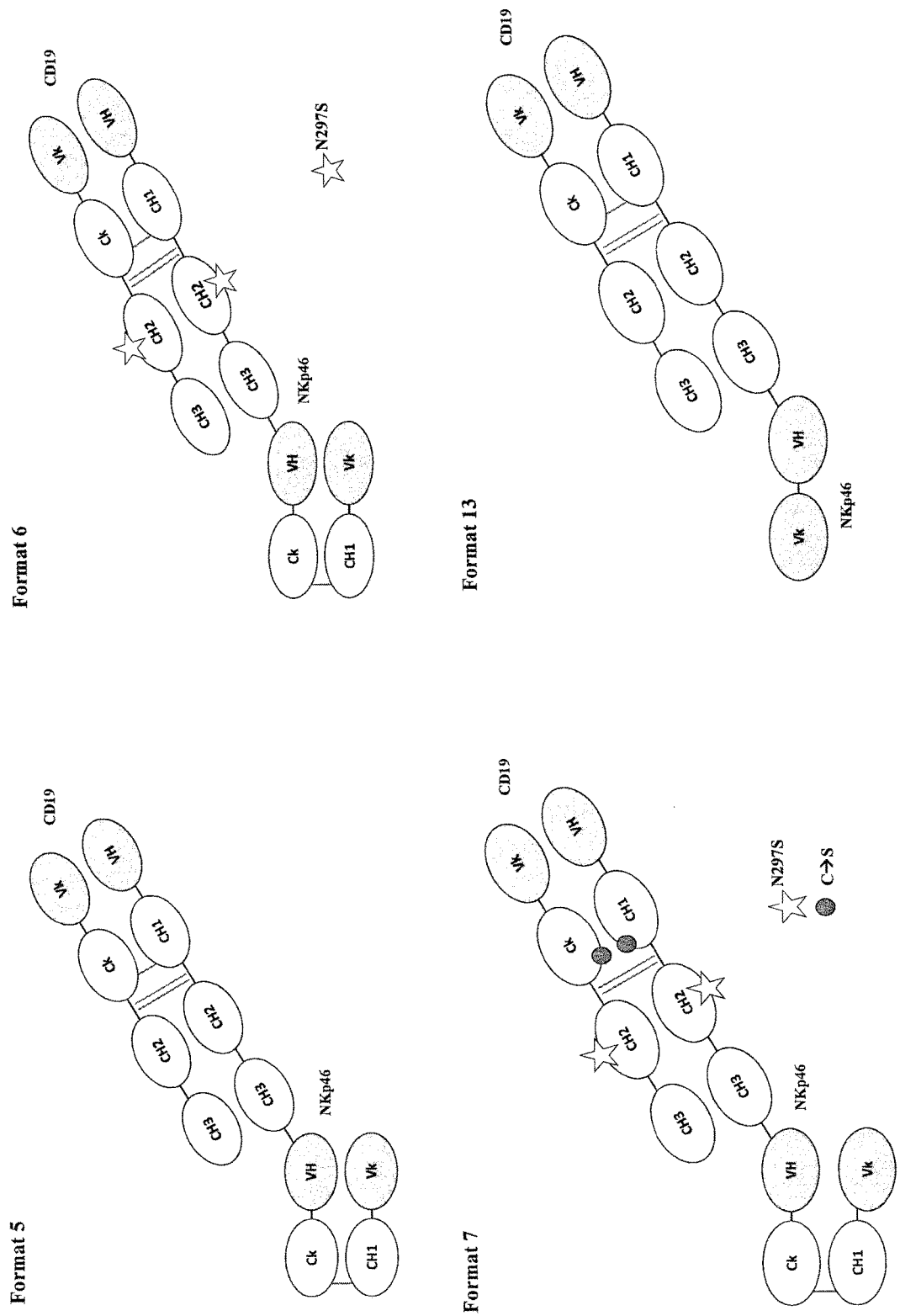

Figure 4A
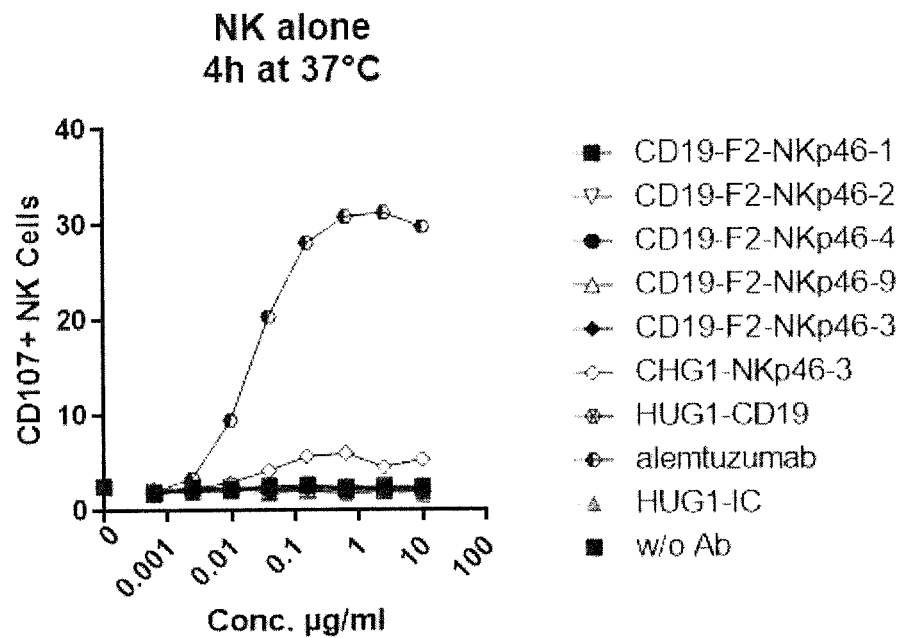
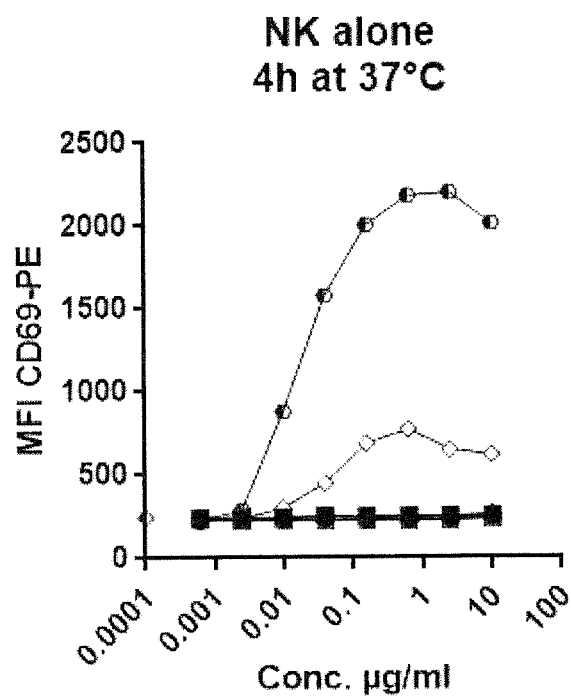

Figure 4B
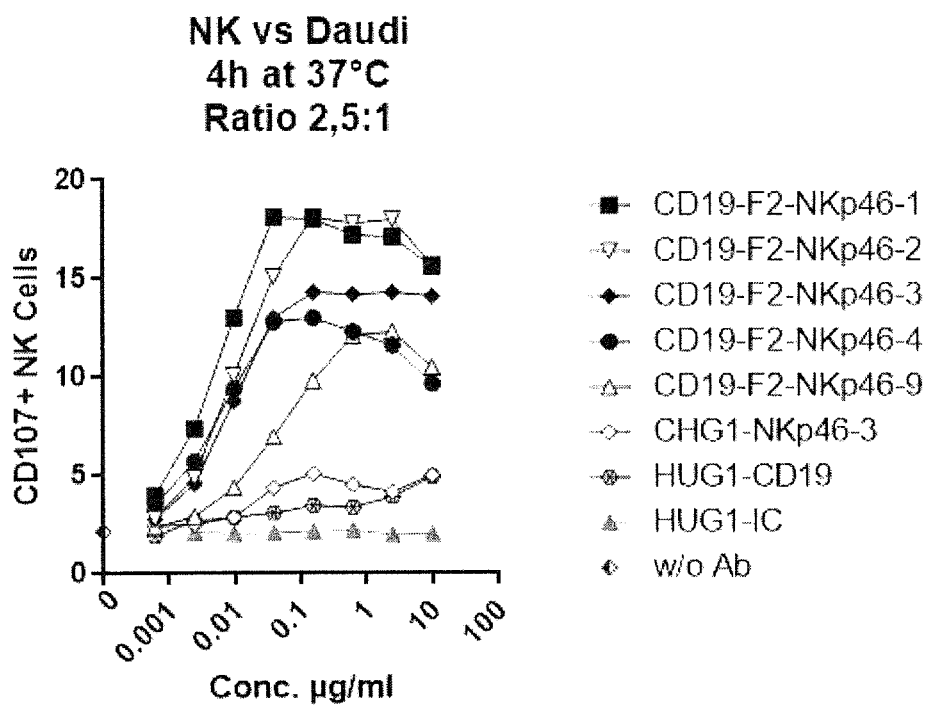
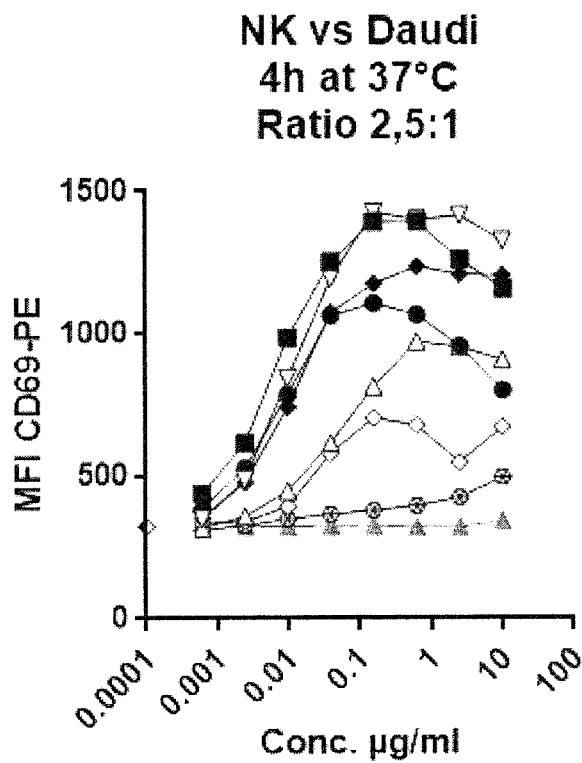

SEQUENCE LISTING

```
<160> NUMBER OF SEQ ID NOS: 206

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95
```

```
Ser Cys Ile Tyr Arg Val Gly Glu Leu Trp Ser Pro Ser Asn Leu
            100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
        130                 135                 140

Arg Leu Asp Thr Ala Thr Ser Met Phe Leu Leu Leu Lys Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
            195                 200                 205

Leu Val Thr Gly Asp Ile Glu Asn Thr Ser Leu Ala Pro Glu Asp Pro
            210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
                260                 265                 270

Leu Val Glu Asp Trp Leu Ser Arg Lys Arg Thr Arg Glu Arg Ala Ser
            275                 280                 285

Arg Ala Ser Thr Trp Glu Gly Arg Arg Arg Leu Asn Thr Gln Thr Leu
        290                 295                 300

<210> SEQ ID NO 2
<211> LENGTH: 216
<212> TYPE: PRT
<213> ORGANISM: homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

```
            165                 170                 175
Thr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly
            210                 215

<210> SEQ ID NO 3
<211> LENGTH: 120
<212> TYPE: PRT
<213> ORGANISM: Mus musculus

<400> SEQUENCE: 3

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110

Gly Thr Ser Val Thr Val Ser Ser
        115                 120

<210> SEQ ID NO 4
<211> LENGTH: 107
<212> TYPE: PRT
<213> ORGANISM: Mus musculus

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Leu Glu Ile Lys
            100                 105

<210> SEQ ID NO 5
<211> LENGTH: 122
<212> TYPE: PRT
<213> ORGANISM: Mus musculus

<400> SEQUENCE: 5
```

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Ser Ile Thr Arg Asp Thr Ser Thr Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ala
            115                 120

<210> SEQ ID NO 6
<211> LENGTH: 107
<212> TYPE: PRT
<213> ORGANISM: Mus musculus

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Val Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 7
<211> LENGTH: 116
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

-continued

Ala Arg Arg Gly Gly Ser Phe Asp Tyr Trp Gly Gln Gly Thr Thr Leu
              100                 105                 110

Thr Val Ser Ser
        115

<210> SEQ ID NO 8
<211> LENGTH: 107
<212> TYPE: PRT
<213> ORGANISM: Mus musculus

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105

<210> SEQ ID NO 9
<211> LENGTH: 117
<212> TYPE: PRT
<213> ORGANISM: Mus musculus

<400> SEQUENCE: 9

Gln Val Gln Leu Gln Gln Ser Ala Val Glu Leu Ala Arg Pro Gly Ala
1               5                   10                  15

Ser Val Lys Met Ser Cys Lys Ala Ser Gly Tyr Thr Phe Thr Ser Phe
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
50                  55                  60

Lys Asp Lys Thr Thr Leu Thr Ala Asp Lys Ser Ser Ser Thr Ala Tyr
65                  70                  75                  80

Met Gln Leu Asp Ser Leu Thr Ser Asp Ser Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ala
        115

<210> SEQ ID NO 10
<211> LENGTH: 107
<212> TYPE: PRT
<213> ORGANISM: Mus musculus

<400> SEQUENCE: 10

Asp Ile Gln Met Ile Gln Ser Pro Ala Ser Leu Ser Val Ser Val Gly
1               5                   10                  15

```
Glu Thr Val Thr Ile Thr Cys Arg Ala Ser Glu Asn Ile Tyr Ser Asn
             20                  25                  30

Leu Ala Trp Phe Gln Gln Lys Gln Gly Lys Ser Pro Gln Leu Leu Val
         35                  40                  45

Tyr Ala Ala Thr Asn Leu Ala Asp Gly Val Pro Ser Arg Phe Ser Gly
     50                  55                  60

Ser Gly Ser Gly Thr Gln Tyr Ser Leu Lys Ile Asn Ser Leu Gln Ser
65              70                  75                  80

Glu Asp Phe Gly Ile Tyr Tyr Cys Gln His Phe Trp Gly Thr Pro Arg
                 85                  90                  95

Thr Phe Gly Gly Gly Thr Lys Leu Glu Ile Lys
                100                 105
```

```
<210> SEQ ID NO 11
<211> LENGTH: 115
<212> TYPE: PRT
<213> ORGANISM: Mus musculus

<400> SEQUENCE: 11

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
             20                  25                  30

Trp Met His Trp Ala Lys Gln Arg Pro Gly Gln Gly Leu Glu Trp Ile
         35                  40                  45

Gly His Ile His Pro Asn Ser Gly Ile Ser Asn Tyr Asn Glu Lys Phe
     50                  55                  60

Lys Gly Lys Ala Thr Leu Thr Val Asp Thr Ser Ser Thr Ala Tyr
65              70                  75                  80

Val Asp Leu Ser Ser Leu Thr Ser Glu Asp Ser Ala Val Tyr Tyr Cys
                 85                  90                  95

Ala Arg Gly Gly Arg Phe Asp Asp Trp Gly Ala Gly Thr Thr Val Thr
            100                 105                 110

Val Ser Ser
        115
```

```
<210> SEQ ID NO 12
<211> LENGTH: 108
<212> TYPE: PRT
<213> ORGANISM: Mus musculus

<400> SEQUENCE: 12

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
     50                  55                  60

Ser Gly Ser Gly Ser Asp Phe Thr Leu Ser Ile Asn Ser Val Glu Pro
65              70                  75                  80

Glu Asp Val Gly Val Tyr Tyr Cys Gln Asn Gly His Ser Phe Leu Met
                 85                  90                  95

Tyr Thr Phe Gly Gly Gly Thr Lys Leu Glu Ile Lys
                100                 105
```

<210> SEQ ID NO 13
<211> LENGTH: 120
<212> TYPE: PRT
<213> ORGANISM: Mus musculus

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Cys Trp Asp Tyr Ala Leu Tyr Ala Met Asp Cys Trp Gly Gln
            100                 105                 110

Gly Thr Ser Val Thr Val Ser Ser
            115                 120

<210> SEQ ID NO 14
<211> LENGTH: 107
<212> TYPE: PRT
<213> ORGANISM: Mus musculus

<400> SEQUENCE: 14

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Cys Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr His Phe Ser Leu Lys Ile Asn Ser Leu Gln Pro
65                  70                  75                  80

Glu Asp Phe Gly Ile Tyr Tyr Cys Gln His His Tyr Asp Thr Pro Leu
                85                  90                  95

Thr Phe Gly Ala Gly Thr Lys Leu Glu Leu Lys
            100                 105

<210> SEQ ID NO 15
<211> LENGTH: 5
<212> TYPE: PRT
<213> ORGANISM: mus musculus

<400> SEQUENCE: 15

Asp Tyr Val Ile Asn
1               5

<210> SEQ ID NO 16
<211> LENGTH: 7
<212> TYPE: PRT
<213> ORGANISM: mus musculus

<400> SEQUENCE: 16

```
Gly Tyr Thr Phe Thr Asp Tyr
1               5
```

<210> SEQ ID NO 17
<211> LENGTH: 8
<212> TYPE: PRT
<213> ORGANISM: mus musculus

<400> SEQUENCE: 17

```
Gly Tyr Thr Phe Thr Asp Tyr Val
1               5
```

<210> SEQ ID NO 18
<211> LENGTH: 17
<212> TYPE: PRT
<213> ORGANISM: mus musculus

<400> SEQUENCE: 18

```
Glu Ile Tyr Pro Gly Ser Gly Thr Asn Tyr Tyr Asn Glu Lys Phe Lys
1               5                   10                  15

Ala
```

<210> SEQ ID NO 19
<211> LENGTH: 4
<212> TYPE: PRT
<213> ORGANISM: mus musculus

<400> SEQUENCE: 19

```
Pro Gly Ser Gly
1
```

<210> SEQ ID NO 20
<211> LENGTH: 16
<212> TYPE: PRT
<213> ORGANISM: mus musculus

<400> SEQUENCE: 20

```
Gly Tyr Thr Phe Thr Asp Tyr Val Ile Tyr Pro Gly Ser Gly Thr Asn
1               5                   10                  15
```

<210> SEQ ID NO 21
<211> LENGTH: 11
<212> TYPE: PRT
<213> ORGANISM: mus musculus

<400> SEQUENCE: 21

```
Arg Gly Arg Tyr Gly Leu Tyr Ala Met Asp Tyr
1               5                   10
```

<210> SEQ ID NO 22
<211> LENGTH: 9
<212> TYPE: PRT
<213> ORGANISM: mus musculus

<400> SEQUENCE: 22

```
Gly Arg Tyr Gly Leu Tyr Ala Met Asp
1               5
```

<210> SEQ ID NO 23
<211> LENGTH: 13
<212> TYPE: PRT
<213> ORGANISM: mus musculus

<400> SEQUENCE: 23

```
Ala Arg Arg Gly Arg Tyr Gly Leu Tyr Ala Met Asp Tyr
1               5                   10

<210> SEQ ID NO 24
<211> LENGTH: 11
<212> TYPE: PRT
<213> ORGANISM: mus musculus

<400> SEQUENCE: 24

Arg Ala Ser Gln Asp Ile Ser Asn Tyr Leu Asn
1               5                   10

<210> SEQ ID NO 25
<211> LENGTH: 7
<212> TYPE: PRT
<213> ORGANISM: Mus musculus

<400> SEQUENCE: 25

Ser Gln Asp Ile Ser Asn Tyr
1               5

<210> SEQ ID NO 26
<211> LENGTH: 6
<212> TYPE: PRT
<213> ORGANISM: mus musculus

<400> SEQUENCE: 26

Gln Asp Ile Ser Asn Tyr
1               5

<210> SEQ ID NO 27
<211> LENGTH: 7
<212> TYPE: PRT
<213> ORGANISM: Mus musculus

<400> SEQUENCE: 27

Tyr Thr Ser Arg Leu His Ser
1               5

<210> SEQ ID NO 28
<211> LENGTH: 9
<212> TYPE: PRT
<213> ORGANISM: mus musculus

<400> SEQUENCE: 28

Gln Gln Gly Asn Thr Arg Pro Trp Thr
1               5

<210> SEQ ID NO 29
<211> LENGTH: 9
<212> TYPE: PRT
<213> ORGANISM: Mus musculus

<400> SEQUENCE: 29

Tyr Thr Ser Gly Asn Thr Arg Pro Trp
1               5

<210> SEQ ID NO 30
<211> LENGTH: 12
<212> TYPE: PRT
<213> ORGANISM: Mus musculus

<400> SEQUENCE: 30

Tyr Thr Ser Gln Gln Gly Asn Thr Arg Pro Trp Thr
```

-continued

```
<210> SEQ ID NO 31
<211> LENGTH: 6
<212> TYPE: PRT
<213> ORGANISM: Mus musculus

<400> SEQUENCE: 31

Ser Asp Tyr Ala Trp Asn
1               5

<210> SEQ ID NO 32
<211> LENGTH: 8
<212> TYPE: PRT
<213> ORGANISM: Mus musculus

<400> SEQUENCE: 32

Gly Tyr Ser Ile Thr Ser Asp Tyr
1               5

<210> SEQ ID NO 33
<211> LENGTH: 9
<212> TYPE: PRT
<213> ORGANISM: Mus musculus

<400> SEQUENCE: 33

Gly Tyr Ser Ile Thr Ser Asp Tyr Ala
1               5

<210> SEQ ID NO 34
<211> LENGTH: 16
<212> TYPE: PRT
<213> ORGANISM: Mus musculus

<400> SEQUENCE: 34

Tyr Ile Thr Tyr Ser Gly Ser Thr Ser Tyr Asn Pro Ser Leu Glu Ser
1               5                   10                  15

<210> SEQ ID NO 35
<211> LENGTH: 7
<212> TYPE: PRT
<213> ORGANISM: Mus musculus

<400> SEQUENCE: 35

Ile Thr Tyr Ser Gly Ser Thr
1               5

<210> SEQ ID NO 36
<211> LENGTH: 13
<212> TYPE: PRT
<213> ORGANISM: Mus musculus

<400> SEQUENCE: 36

Gly Gly Tyr Tyr Gly Ser Ser Trp Gly Val Phe Ala Tyr
1               5                   10

<210> SEQ ID NO 37
<211> LENGTH: 11
<212> TYPE: PRT
<213> ORGANISM: Mus musculus

<400> SEQUENCE: 37

Gly Tyr Tyr Gly Ser Ser Trp Gly Val Phe Ala
1               5                   10
```

<210> SEQ ID NO 38
<211> LENGTH: 15
<212> TYPE: PRT
<213> ORGANISM: Mus musculus

<400> SEQUENCE: 38

Ala Arg Gly Gly Tyr Tyr Gly Ser Ser Trp Gly Val Phe Ala Tyr
1               5                   10                  15

<210> SEQ ID NO 39
<211> LENGTH: 11
<212> TYPE: PRT
<213> ORGANISM: Mus musculus

<400> SEQUENCE: 39

Arg Val Ser Glu Asn Ile Tyr Ser Tyr Leu Ala
1               5                   10

<210> SEQ ID NO 40
<211> LENGTH: 7
<212> TYPE: PRT
<213> ORGANISM: Mus musculus

<400> SEQUENCE: 40

Ser Glu Asn Ile Tyr Ser Tyr
1               5

<210> SEQ ID NO 41
<211> LENGTH: 6
<212> TYPE: PRT
<213> ORGANISM: Mus musculus

<400> SEQUENCE: 41

Glu Asn Ile Tyr Ser Tyr
1               5

<210> SEQ ID NO 42
<211> LENGTH: 7
<212> TYPE: PRT
<213> ORGANISM: Mus musculus

<400> SEQUENCE: 42

Asn Ala Lys Thr Leu Ala Glu
1               5

<210> SEQ ID NO 43
<211> LENGTH: 9
<212> TYPE: PRT
<213> ORGANISM: Mus musculus

<400> SEQUENCE: 43

Gln His His Tyr Gly Thr Pro Trp Thr
1               5

<210> SEQ ID NO 44
<211> LENGTH: 6
<212> TYPE: PRT
<213> ORGANISM: Mus musculus

<400> SEQUENCE: 44

His Tyr Gly Thr Pro Trp
1               5

<210> SEQ ID NO 45

```
<211> LENGTH: 9
<212> TYPE: PRT
<213> ORGANISM: mus musculus

<400> SEQUENCE: 45

Gln His His Tyr Gly Thr Pro Trp Thr
1               5

<210> SEQ ID NO 46
<211> LENGTH: 5
<212> TYPE: PRT
<213> ORGANISM: Mus musculus

<400> SEQUENCE: 46

Glu Tyr Thr Met His
1               5

<210> SEQ ID NO 47
<211> LENGTH: 7
<212> TYPE: PRT
<213> ORGANISM: Mus musculus

<400> SEQUENCE: 47

Gly Tyr Thr Phe Thr Glu Tyr
1               5

<210> SEQ ID NO 48
<211> LENGTH: 8
<212> TYPE: PRT
<213> ORGANISM: Mus musculus

<400> SEQUENCE: 48

Gly Tyr Thr Phe Thr Glu Tyr Thr
1               5

<210> SEQ ID NO 49
<211> LENGTH: 17
<212> TYPE: PRT
<213> ORGANISM: Mus musculus

<400> SEQUENCE: 49

Gly Ile Ser Pro Asn Ile Gly Gly Thr Ser Tyr Asn Gln Lys Phe Lys
1               5                   10                  15

Gly

<210> SEQ ID NO 50
<211> LENGTH: 8
<212> TYPE: PRT
<213> ORGANISM: Mus musculus

<400> SEQUENCE: 50

Ile Ser Pro Asn Ile Gly Gly Thr
1               5

<210> SEQ ID NO 51
<211> LENGTH: 7
<212> TYPE: PRT
<213> ORGANISM: Mus musculus

<400> SEQUENCE: 51

Arg Gly Gly Ser Phe Asp Tyr
1               5

<210> SEQ ID NO 52
```

```
<211> LENGTH: 5
<212> TYPE: PRT
<213> ORGANISM: Mus musculus

<400> SEQUENCE: 52

Gly Gly Ser Phe Asp
1               5

<210> SEQ ID NO 53
<211> LENGTH: 9
<212> TYPE: PRT
<213> ORGANISM: Mus musculus

<400> SEQUENCE: 53

Ala Arg Arg Gly Gly Ser Phe Asp Tyr
1               5

<210> SEQ ID NO 54
<211> LENGTH: 11
<212> TYPE: PRT
<213> ORGANISM: Mus musculus

<400> SEQUENCE: 54

Arg Ala Ser Gln Ser Ile Ser Asp Tyr Leu His
1               5                   10

<210> SEQ ID NO 55
<211> LENGTH: 7
<212> TYPE: PRT
<213> ORGANISM: Mus musculus

<400> SEQUENCE: 55

Ser Gln Ser Ile Ser Asp Tyr
1               5

<210> SEQ ID NO 56
<211> LENGTH: 6
<212> TYPE: PRT
<213> ORGANISM: Mus musculus

<400> SEQUENCE: 56

Gln Ser Ile Ser Asp Tyr
1               5

<210> SEQ ID NO 57
<211> LENGTH: 7
<212> TYPE: PRT
<213> ORGANISM: Mus musculus

<400> SEQUENCE: 57

Tyr Ala Ser Gln Ser Ile Ser
1               5

<210> SEQ ID NO 58
<211> LENGTH: 9
<212> TYPE: PRT
<213> ORGANISM: Mus musculus

<400> SEQUENCE: 58

Gln Asn Gly His Ser Phe Pro Leu Thr
1               5

<210> SEQ ID NO 59
<211> LENGTH: 6
<212> TYPE: PRT
```

```
<213> ORGANISM: Mus musculus

<400> SEQUENCE: 59

Gly His Ser Phe Pro Leu
1               5

<210> SEQ ID NO 60
<211> LENGTH: 5
<212> TYPE: PRT
<213> ORGANISM: Mus musculus

<400> SEQUENCE: 60

Ser Phe Thr Met His
1               5

<210> SEQ ID NO 61
<211> LENGTH: 7
<212> TYPE: PRT
<213> ORGANISM: Mus musculus

<400> SEQUENCE: 61

Gly Tyr Thr Phe Thr Ser Phe
1               5

<210> SEQ ID NO 62
<211> LENGTH: 8
<212> TYPE: PRT
<213> ORGANISM: Mus musculus

<400> SEQUENCE: 62

Gly Tyr Thr Phe Thr Ser Phe Thr
1               5

<210> SEQ ID NO 63
<211> LENGTH: 17
<212> TYPE: PRT
<213> ORGANISM: Mus musculus

<400> SEQUENCE: 63

Tyr Ile Asn Pro Ser Ser Gly Tyr Thr Glu Tyr Asn Gln Lys Phe Lys
1               5                   10                  15

Asp

<210> SEQ ID NO 64
<211> LENGTH: 8
<212> TYPE: PRT
<213> ORGANISM: Mus musculus

<400> SEQUENCE: 64

Ile Asn Pro Ser Ser Gly Tyr Thr
1               5

<210> SEQ ID NO 65
<211> LENGTH: 8
<212> TYPE: PRT
<213> ORGANISM: Mus musculus

<400> SEQUENCE: 65

Gly Ser Ser Arg Gly Phe Asp Tyr
1               5

<210> SEQ ID NO 66
<211> LENGTH: 6
<212> TYPE: PRT
```

-continued

<213> ORGANISM: Mus musculus

<400> SEQUENCE: 66

Ser Ser Arg Gly Phe Asp
1               5

<210> SEQ ID NO 67
<211> LENGTH: 10
<212> TYPE: PRT
<213> ORGANISM: Mus musculus

<400> SEQUENCE: 67

Val Arg Gly Ser Ser Arg Gly Phe Asp Tyr
1               5                   10

<210> SEQ ID NO 68
<211> LENGTH: 11
<212> TYPE: PRT
<213> ORGANISM: Mus musculus

<400> SEQUENCE: 68

Arg Ala Ser Glu Asn Ile Tyr Ser Asn Leu Ala
1               5                   10

<210> SEQ ID NO 69
<211> LENGTH: 6
<212> TYPE: PRT
<213> ORGANISM: Mus musculur

<400> SEQUENCE: 69

Glu Asn Ile Tyr Ser Asn
1               5

<210> SEQ ID NO 70
<211> LENGTH: 7
<212> TYPE: PRT
<213> ORGANISM: mus musculur

<400> SEQUENCE: 70

Ala Ala Thr Asn Leu Ala Asp
1               5

<210> SEQ ID NO 71
<211> LENGTH: 9
<212> TYPE: PRT
<213> ORGANISM: Mus musculus

<400> SEQUENCE: 71

Gln His Phe Trp Gly Thr Pro Arg Thr
1               5

<210> SEQ ID NO 72
<211> LENGTH: 6
<212> TYPE: PRT
<213> ORGANISM: Mus musculus

<400> SEQUENCE: 72

Phe Trp Gly Thr Pro Arg
1               5

<210> SEQ ID NO 73
<211> LENGTH: 5
<212> TYPE: PRT
<213> ORGANISM: Mus musculus

<400> SEQUENCE: 73

Ser Ser Trp Met His
1               5

<210> SEQ ID NO 74
<211> LENGTH: 7
<212> TYPE: PRT
<213> ORGANISM: Mus musculus

<400> SEQUENCE: 74

Gly Tyr Thr Phe Thr Ser Ser
1               5

<210> SEQ ID NO 75
<211> LENGTH: 8
<212> TYPE: PRT
<213> ORGANISM: Mus musculus

<400> SEQUENCE: 75

Gly Tyr Thr Phe Thr Ser Ser Trp
1               5

<210> SEQ ID NO 76
<211> LENGTH: 17
<212> TYPE: PRT
<213> ORGANISM: Mus musculus

<400> SEQUENCE: 76

His Ile His Pro Asn Ser Gly Ile Ser Asn Tyr Asn Glu Lys Phe Lys
1               5                   10                  15

Gly

<210> SEQ ID NO 77
<211> LENGTH: 8
<212> TYPE: PRT
<213> ORGANISM: Mus musculus

<400> SEQUENCE: 77

Ile His Pro Asn Ser Gly Ile Ser
1               5

<210> SEQ ID NO 78
<211> LENGTH: 6
<212> TYPE: PRT
<213> ORGANISM: Mus musculus

<400> SEQUENCE: 78

Gly Gly Arg Phe Asp Asp
1               5

<210> SEQ ID NO 79
<211> LENGTH: 8
<212> TYPE: PRT
<213> ORGANISM: Mus musculus

<400> SEQUENCE: 79

Ala Arg Gly Gly Arg Phe Asp Asp
1               5

<210> SEQ ID NO 80
<211> LENGTH: 11
<212> TYPE: PRT
<213> ORGANISM: Mus musculus

```
<400> SEQUENCE: 80

Arg Ala Ser Gln Asp Ile Gly Ser Ser Leu Asn
 1               5                  10

<210> SEQ ID NO 81
<211> LENGTH: 7
<212> TYPE: PRT
<213> ORGANISM: Mus musculus

<400> SEQUENCE: 81

Ala Thr Ser Ser Leu Asp Ser
 1               5

<210> SEQ ID NO 82
<211> LENGTH: 9
<212> TYPE: PRT
<213> ORGANISM: Mus musculus

<400> SEQUENCE: 82

Leu Gln Tyr Ala Ser Ser Pro Trp Thr
 1               5

<210> SEQ ID NO 83
<211> LENGTH: 7
<212> TYPE: PRT
<213> ORGANISM: Mus musculus

<400> SEQUENCE: 83

Tyr Ala Ser Ser Pro Trp Thr
 1               5

<210> SEQ ID NO 84
<211> LENGTH: 9
<212> TYPE: PRT
<213> ORGANISM: Mus musculus

<400> SEQUENCE: 84

Leu Gln Tyr Ala Ser Ser Pro Trp Thr
 1               5

<210> SEQ ID NO 85
<211> LENGTH: 6
<212> TYPE: PRT
<213> ORGANISM: mus musculus

<400> SEQUENCE: 85

Ser Asp Tyr Ala Trp Asn
 1               5

<210> SEQ ID NO 86
<211> LENGTH: 8
<212> TYPE: PRT
<213> ORGANISM: Mus musculus

<400> SEQUENCE: 86

Gly Tyr Ser Ile Thr Ser Asp Tyr
 1               5

<210> SEQ ID NO 87
<211> LENGTH: 9
<212> TYPE: PRT
<213> ORGANISM: Mus musculus

<400> SEQUENCE: 87
```

-continued

Gly Tyr Ser Ile Thr Ser Asp Tyr Ala
1               5

<210> SEQ ID NO 88
<211> LENGTH: 16
<212> TYPE: PRT
<213> ORGANISM: Mus musculus

<400> SEQUENCE: 88

Tyr Ile Thr Tyr Ser Gly Ser Thr Asn Tyr Asn Pro Ser Leu Lys Ser
1               5                   10                  15

<210> SEQ ID NO 89
<211> LENGTH: 11
<212> TYPE: PRT
<213> ORGANISM: Mus musculus

<400> SEQUENCE: 89

Cys Trp Asp Tyr Ala Leu Tyr Ala Met Asp Cys
1               5                   10

<210> SEQ ID NO 90
<211> LENGTH: 9
<212> TYPE: PRT
<213> ORGANISM: mus musculus

<400> SEQUENCE: 90

Trp Asp Tyr Ala Leu Tyr Ala Met Asp
1               5

<210> SEQ ID NO 91
<211> LENGTH: 13
<212> TYPE: PRT
<213> ORGANISM: Mus musculus

<400> SEQUENCE: 91

Ala Arg Cys Trp Asp Tyr Ala Leu Tyr Ala Met Asp Cys
1               5                   10

<210> SEQ ID NO 92
<211> LENGTH: 11
<212> TYPE: PRT
<213> ORGANISM: Mus musculus

<400> SEQUENCE: 92

Arg Thr Ser Glu Asn Ile Tyr Ser Tyr Leu Ala
1               5                   10

<210> SEQ ID NO 93
<211> LENGTH: 7
<212> TYPE: PRT
<213> ORGANISM: Mus musculus

<400> SEQUENCE: 93

Asn Ala Lys Thr Leu Ala Glu
1               5

<210> SEQ ID NO 94
<211> LENGTH: 9
<212> TYPE: PRT
<213> ORGANISM: Mus musculus

<400> SEQUENCE: 94

Gln His His Tyr Asp Thr Pro Leu Thr
1               5

```
<210> SEQ ID NO 95
<211> LENGTH: 9
<212> TYPE: PRT
<213> ORGANISM: mus musculus

<400> SEQUENCE: 95

Asn Ala Lys His Tyr Asp Thr Pro Leu
1               5

<210> SEQ ID NO 96
<211> LENGTH: 9
<212> TYPE: PRT
<213> ORGANISM: Mus musculus

<400> SEQUENCE: 96

Gln His His Tyr Asp Thr Pro Leu Thr
1               5

<210> SEQ ID NO 97
<211> LENGTH: 5
<212> TYPE: PRT
<213> ORGANISM: Mus musculus

<400> SEQUENCE: 97

Asn Tyr Gly Met Asn
1               5

<210> SEQ ID NO 98
<211> LENGTH: 7
<212> TYPE: PRT
<213> ORGANISM: mus musculus

<400> SEQUENCE: 98

Gly Tyr Thr Phe Thr Asn Tyr
1               5

<210> SEQ ID NO 99
<211> LENGTH: 8
<212> TYPE: PRT
<213> ORGANISM: mus musculus

<400> SEQUENCE: 99

Gly Tyr Thr Phe Thr Asn Tyr Gly
1               5

<210> SEQ ID NO 100
<211> LENGTH: 17
<212> TYPE: PRT
<213> ORGANISM: mus musculus

<400> SEQUENCE: 100

Trp Ile Asn Thr Asn Thr Gly Glu Pro Thr Tyr Ala Glu Glu Phe Lys
1               5                   10                  15

Gly

<210> SEQ ID NO 101
<211> LENGTH: 8
<212> TYPE: PRT
<213> ORGANISM: Mus musculus

<400> SEQUENCE: 101

Ile Asn Thr Asn Thr Gly Glu Pro
1               5
```

<210> SEQ ID NO 102
<211> LENGTH: 8
<212> TYPE: PRT
<213> ORGANISM: Mus musculus

<400> SEQUENCE: 102

Asp Tyr Leu Tyr Tyr Phe Asp Tyr
1               5

<210> SEQ ID NO 103
<211> LENGTH: 6
<212> TYPE: PRT
<213> ORGANISM: mus musculus

<400> SEQUENCE: 103

Tyr Leu Tyr Tyr Phe Asp
1               5

<210> SEQ ID NO 104
<211> LENGTH: 10
<212> TYPE: PRT
<213> ORGANISM: Mus musculus

<400> SEQUENCE: 104

Ala Arg Asp Tyr Leu Tyr Tyr Phe Asp Tyr
1               5                   10

<210> SEQ ID NO 105
<211> LENGTH: 11
<212> TYPE: PRT
<213> ORGANISM: Mus musculus

<400> SEQUENCE: 105

Lys Ala Ser Glu Asn Val Val Thr Tyr Val Ser
1               5                   10

<210> SEQ ID NO 106
<211> LENGTH: 7
<212> TYPE: PRT
<213> ORGANISM: Mus musculus

<400> SEQUENCE: 106

Ser Glu Asn Val Val Thr Tyr
1               5

<210> SEQ ID NO 107
<211> LENGTH: 6
<212> TYPE: PRT
<213> ORGANISM: Mus musculus

<400> SEQUENCE: 107

Glu Asn Val Val Thr Tyr
1               5

<210> SEQ ID NO 108
<211> LENGTH: 7
<212> TYPE: PRT
<213> ORGANISM: Mus musculus

<400> SEQUENCE: 108

Gly Ala Ser Asn Arg Tyr Thr
1               5

```
<210> SEQ ID NO 109
<211> LENGTH: 9
<212> TYPE: PRT
<213> ORGANISM: mus musculus

<400> SEQUENCE: 109

Gly Gln Gly Tyr Ser Tyr Pro Tyr Thr
1               5

<210> SEQ ID NO 110
<211> LENGTH: 6
<212> TYPE: PRT
<213> ORGANISM: mus musculus

<400> SEQUENCE: 110

Gly Tyr Ser Tyr Pro Tyr
1               5

<210> SEQ ID NO 111
<211> LENGTH: 9
<212> TYPE: PRT
<213> ORGANISM: mus musculus

<400> SEQUENCE: 111

Gly Gln Gly Tyr Ser Tyr Pro Tyr Thr
1               5

<210> SEQ ID NO 112
<211> LENGTH: 227
<212> TYPE: PRT
<213> ORGANISM: homo sapiens

<400> SEQUENCE: 112

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Gly Gly Gly Ser Gly
            100                 105                 110

Gly Gly Gly Ser Gly Gly Gly Ser Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205
```

Met His Glu Ala Leu His Asn His Tyr Thr Gln Lys Ser Leu Ser Leu
210                 215                 220

Ser Pro Gly
225

<210> SEQ ID NO 113
<211> LENGTH: 333
<212> TYPE: DNA
<213> ORGANISM: mus musculus

<400> SEQUENCE: 113
gacattcagc tgacccaatc tccagcttct ttggctgtgt ctctagggca gagggccacc    60
atctcctgca aggccagcca agtgttgat tatgatggtg atagttattt gaactggtac   120
caacagatac caggacagcc acccaaactc ctcatctatg atgcatccaa tctagtatct   180
gggattccac ccaggtttag tggcagtggg tctgggacag acttcaccct caacatccat   240
cctgtggaga aggtggatgc tgcaacctat cactgtcagc aaagtactga ggacccttgg   300
acgttcggtg aggcaccaa gctggaaatc aaa                                333

<210> SEQ ID NO 114
<211> LENGTH: 111
<212> TYPE: PRT
<213> ORGANISM: mus musculus

<400> SEQUENCE: 114

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 115
<211> LENGTH: 372
<212> TYPE: DNA
<213> ORGANISM: mus musculus

<400> SEQUENCE: 115
caggttcagc tgcagcagtc tggggctgag ctggtgcggc ctgggtcctc agtgaagatt    60
tcctgcaaag catctggcta cgcattcagt agctactgga tgaactgggt gaagcagagg   120
cctggacagg gtcttgagtg gattggacag atttggcctg agatggtga tactaactac   180 aacggaaagt tcaagggcaa ggccacactg actgcagacg aatcctccag cacagcctac   240
atgcagctca gcagcctggc ctctgaggac tctgcggtct atttctgtgc aagacgagaa   300
acgaccactg tcgggcgtta ttactatgct atggactact ggggtcaagg aaccacagtc   360
accgtctcct ca                                                      372

<210> SEQ ID NO 116

<211> LENGTH: 124
<212> TYPE: PRT
<213> ORGANISM: Mus musculus

<400> SEQUENCE: 116

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 117
<211> LENGTH: 648
<212> TYPE: DNA
<213> ORGANISM: homo sapiens

<400> SEQUENCE: 117

```
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtacacc   360
aagccccat cccgggagga tgaccaag aaccaggtca gcctgtcctg cctggtcaaa      420
ggcttctatc ccagcgacat cgccgtggag tgggagagca atgggcagcc ggagaacaac   480
tacaagacca cggttcccgt gctggactcc gacggctcct tccgcctcgc tagctacctc   540
accgtggaca gagcaggtg gcagcagggg aacgtcttct catgctccgt gatgcatgag    600
gctctgcaca accactacac gcagaagagc ctctccctgt ccccgggg               648
```

<210> SEQ ID NO 118
<211> LENGTH: 718
<212> TYPE: PRT
<213> ORGANISM: Artificial
<220> FEATURE:
<223> OTHER INFORMATION: Chimeric homo sapiens mus musculus

<400> SEQUENCE: 118

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45
```

```
Lys Leu Leu Ile Tyr Asp Ala Ser Asn Leu Val Ser Gly Ile Pro Pro
     50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
                100                 105                 110

Gly Gly Gly Ser Gly Gly Gly Gly Ser Gly Gly Gly Gly Ser Gln Val
             115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Asp Ile Lys Leu Gln
```

```
               465                 470                 475                 480
          Gln Ser Gly Ala Glu Leu Ala Arg Pro Gly Ala Ser Val Lys Met Ser
                          485                 490                 495
          Cys Lys Thr Ser Gly Tyr Thr Phe Thr Arg Tyr Thr Met His Trp Val
                          500                 505                 510
          Lys Gln Arg Pro Gly Gln Gly Leu Glu Trp Ile Gly Tyr Ile Asn Pro
                          515                 520                 525
          Ser Arg Gly Tyr Thr Asn Tyr Asn Gln Lys Phe Lys Asp Lys Ala Thr
                          530                 535                 540
          Leu Thr Thr Asp Lys Ser Ser Thr Ala Tyr Met Gln Leu Ser Ser
          545                 550                 555                 560
          Leu Thr Ser Glu Asp Ser Ala Val Tyr Tyr Cys Ala Arg Tyr Tyr Asp
                          565                 570                 575
          Asp His Tyr Cys Leu Asp Tyr Trp Gly Gln Gly Thr Thr Leu Thr Val
                          580                 585                 590
          Ser Ser Val Glu Gly Gly Ser Gly Gly Ser Gly Gly Ser
                          595                 600                 605
          Gly Gly Val Asp Asp Ile Gln Leu Thr Gln Ser Pro Ala Ile Met Ser
          610                 615                 620
          Ala Ser Pro Gly Glu Lys Val Thr Met Thr Cys Arg Ala Ser Ser Ser
          625                 630                 635                 640
          Val Ser Tyr Met Asn Trp Tyr Gln Gln Lys Ser Gly Thr Ser Pro Lys
                          645                 650                 655
          Arg Trp Ile Tyr Asp Thr Ser Lys Val Ala Ser Gly Val Pro Tyr Arg
                          660                 665                 670
          Phe Ser Gly Ser Gly Ser Gly Thr Ser Tyr Ser Leu Thr Ile Ser Ser
                          675                 680                 685
          Met Glu Ala Glu Asp Ala Ala Thr Tyr Tyr Cys Gln Gln Trp Ser Ser
                          690                 695                 700
          Asn Pro Leu Thr Phe Gly Ala Gly Thr Lys Leu Glu Leu Lys
          705                 710                 715

<210> SEQ ID NO 119
<211> LENGTH: 249
<212> TYPE: PRT
<213> ORGANISM: mus musculus

<400> SEQUENCE: 119

Ser Thr Gly Ser Gln Val Gln Leu Gln Gln Ser Gly Pro Glu Leu Val
          1               5                   10                  15
          Lys Pro Gly Ala Ser Val Lys Met Ser Cys Lys Ala Ser Gly Tyr Thr
                          20                  25                  30
          Phe Thr Asp Tyr Val Ile Asn Trp Gly Lys Gln Arg Ser Gly Gln Gly
                          35                  40                  45
          Leu Glu Trp Ile Gly Glu Ile Tyr Pro Gly Ser Gly Thr Asn Tyr Tyr
                          50                  55                  60
          Asn Glu Lys Phe Lys Ala Lys Ala Thr Leu Thr Ala Asp Lys Ser Ser
          65                  70                  75                  80
          Asn Ile Ala Tyr Met Gln Leu Ser Ser Leu Thr Ser Glu Asp Ser Ala
                          85                  90                  95
          Val Tyr Phe Cys Ala Arg Arg Gly Arg Tyr Gly Leu Tyr Ala Met Asp
                          100                 105                 110
          Tyr Trp Gly Gln Gly Thr Ser Val Thr Val Ser Ser Val Glu Gly Gly
                          115                 120                 125
```

```
Ser Gly Gly Ser Gly Gly Ser Gly Gly Val Asp Asp Ile
    130             135             140

Gln Met Thr Gln Thr Thr Ser Ser Leu Ser Ala Ser Leu Gly Asp Arg
145                 150                 155                 160

Val Thr Ile Ser Cys Arg Ala Ser Gln Asp Ile Ser Asn Tyr Leu Asn
                165                 170                 175

Trp Tyr Gln Gln Lys Pro Asp Gly Thr Val Lys Leu Leu Ile Tyr Tyr
            180                 185                 190

Thr Ser Arg Leu His Ser Gly Val Pro Ser Arg Phe Ser Gly Ser Gly
        195                 200                 205

Ser Gly Thr Asp Tyr Ser Leu Thr Ile Asn Asn Leu Glu Gln Glu Asp
    210                 215                 220

Ile Ala Thr Tyr Phe Cys Gln Gln Gly Asn Thr Arg Pro Trp Thr Phe
225                 230                 235                 240

Gly Gly Gly Thr Lys Leu Glu Ile Lys
                245

<210> SEQ ID NO 120
<211> LENGTH: 251
<212> TYPE: PRT
<213> ORGANISM: mus musculus

<400> SEQUENCE: 120

Ser Thr Gly Ser Glu Val Gln Leu Gln Glu Ser Gly Pro Gly Leu Val
1               5                   10                  15

Lys Pro Ser Gln Ser Leu Ser Leu Thr Cys Thr Val Thr Gly Tyr Ser
            20                  25                  30

Ile Thr Ser Asp Tyr Ala Trp Asn Trp Ile Arg Gln Phe Pro Gly Asn
        35                  40                  45

Lys Leu Glu Trp Met Gly Tyr Ile Thr Tyr Ser Gly Thr Ser Tyr
    50                  55                  60

Asn Pro Ser Leu Glu Ser Arg Ile Ser Ile Thr Arg Asp Thr Ser Thr
65                  70                  75                  80

Asn Gln Phe Phe Leu Gln Leu Asn Ser Val Thr Thr Glu Asp Thr Ala
                85                  90                  95

Thr Tyr Tyr Cys Ala Arg Gly Gly Tyr Tyr Gly Ser Ser Trp Gly Val
            100                 105                 110

Phe Ala Tyr Trp Gly Gln Gly Thr Leu Val Thr Val Ser Ala Val Glu
        115                 120                 125

Gly Gly Ser Gly Gly Ser Gly Gly Ser Gly Gly Val Asp
    130                 135                 140

Asp Ile Gln Met Thr Gln Ser Pro Ala Ser Leu Ser Ala Ser Val Gly
145                 150                 155                 160

Glu Thr Val Thr Ile Thr Cys Arg Val Ser Glu Asn Ile Tyr Ser Tyr
                165                 170                 175

Leu Ala Trp Tyr Gln Gln Lys Gln Gly Lys Ser Pro Gln Leu Leu Val
            180                 185                 190

Tyr Asn Ala Lys Thr Leu Ala Glu Gly Val Pro Ser Arg Phe Ser Gly
        195                 200                 205

Ser Gly Ser Gly Thr Gln Phe Ser Leu Lys Ile Asn Ser Leu Gln Pro
    210                 215                 220

Glu Asp Phe Gly Ser Tyr Tyr Cys Gln His His Tyr Gly Thr Pro Trp
225                 230                 235                 240

Thr Phe Gly Gly Gly Thr Lys Leu Glu Ile Lys
                245                 250
```

<210> SEQ ID NO 121
<211> LENGTH: 245
<212> TYPE: PRT
<213> ORGANISM: mus musculus

<400> SEQUENCE: 121

Ser Thr Gly Ser Glu Val Gln Leu Gln Gln Ser Gly Pro Glu Leu Val
1               5                   10                  15

Lys Pro Gly Ala Ser Val Lys Ile Ser Cys Lys Thr Ser Gly Tyr Thr
            20                  25                  30

Phe Thr Glu Tyr Thr Met His Trp Val Lys Gln Ser His Gly Lys Ser
        35                  40                  45

Leu Glu Trp Ile Gly Gly Ile Ser Pro Asn Ile Gly Gly Thr Ser Tyr
    50                  55                  60

Asn Gln Lys Phe Lys Gly Lys Ala Thr Leu Thr Val Asp Lys Ser Ser
65                  70                  75                  80

Ser Thr Ala Tyr Met Glu Leu Arg Ser Leu Thr Ser Glu Asp Ser Ala
                85                  90                  95

Val Tyr Tyr Cys Ala Arg Arg Gly Gly Ser Phe Asp Tyr Trp Gly Gln
            100                 105                 110

Gly Thr Thr Leu Thr Val Ser Ser Val Glu Gly Gly Ser Gly Gly Ser
        115                 120                 125

Gly Gly Ser Gly Gly Ser Gly Val Asp Asp Ile Val Met Thr Gln
    130                 135                 140

Ser Pro Ala Thr Leu Ser Val Thr Pro Gly Asp Arg Val Ser Leu Ser
145                 150                 155                 160

Cys Arg Ala Ser Gln Ser Ile Ser Asp Tyr Leu His Trp Tyr Gln Gln
                165                 170                 175

Lys Ser His Glu Ser Pro Arg Leu Leu Ile Lys Tyr Ala Ser Gln Ser
            180                 185                 190

Ile Ser Gly Ile Pro Ser Arg Phe Ser Gly Ser Gly Ser Gly Ser Asp
        195                 200                 205

Phe Thr Leu Ser Ile Asn Ser Val Glu Pro Glu Asp Val Gly Val Tyr
    210                 215                 220

Tyr Cys Gln Asn Gly His Ser Phe Pro Leu Thr Phe Gly Ala Gly Thr
225                 230                 235                 240

Lys Leu Glu Leu Lys
            245

<210> SEQ ID NO 122
<211> LENGTH: 246
<212> TYPE: PRT
<213> ORGANISM: Mus musculus

<400> SEQUENCE: 122

Ser Thr Gly Ser Gln Val Gln Leu Gln Gln Ser Ala Val Glu Leu Ala
1               5                   10                  15

Arg Pro Gly Ala Ser Val Lys Met Ser Cys Lys Ala Ser Gly Tyr Thr
            20                  25                  30

Phe Thr Ser Phe Thr Met His Trp Val Lys Gln Arg Pro Gly Gln Gly
        35                  40                  45

Leu Glu Trp Ile Gly Tyr Ile Asn Pro Ser Ser Gly Tyr Thr Glu Tyr
    50                  55                  60

Asn Gln Lys Phe Lys Asp Lys Thr Thr Leu Thr Ala Asp Lys Ser Ser
65                  70                  75                  80

Ser Thr Ala Tyr Met Gln Leu Asp Ser Leu Thr Ser Asp Ser Ala
                85                  90                  95

Val Tyr Tyr Cys Val Arg Gly Ser Ser Arg Gly Phe Asp Tyr Trp Gly
                100                 105                 110

Gln Gly Thr Leu Val Thr Val Ser Ala Val Glu Gly Gly Ser Gly Gly
            115                 120                 125

Ser Gly Gly Ser Gly Gly Ser Gly Gly Val Asp Asp Ile Gln Met Ile
        130                 135                 140

Gln Ser Pro Ala Ser Leu Ser Val Ser Val Gly Glu Thr Val Thr Ile
145                 150                 155                 160

Thr Cys Arg Ala Ser Glu Asn Ile Tyr Ser Asn Leu Ala Trp Phe Gln
                165                 170                 175

Gln Lys Gln Gly Lys Ser Pro Gln Leu Leu Val Tyr Ala Ala Thr Asn
            180                 185                 190

Leu Ala Asp Gly Val Pro Ser Arg Phe Ser Gly Ser Gly Ser Gly Thr
        195                 200                 205

Gln Tyr Ser Leu Lys Ile Asn Ser Leu Gln Ser Glu Asp Phe Gly Ile
    210                 215                 220

Tyr Tyr Cys Gln His Phe Trp Gly Thr Pro Arg Thr Phe Gly Gly Gly
225                 230                 235                 240

Thr Lys Leu Glu Ile Lys
            245

<210> SEQ ID NO 123
<211> LENGTH: 245
<212> TYPE: PRT
<213> ORGANISM: Mus musculus

<400> SEQUENCE: 123

Ser Thr Gly Ser Gln Val Gln Leu Gln Gln Pro Gly Ser Val Leu Val
1               5                   10                  15

Arg Pro Gly Ala Ser Val Lys Leu Ser Cys Lys Ala Ser Gly Tyr Thr
            20                  25                  30

Phe Thr Ser Ser Trp Met His Trp Ala Lys Gln Arg Pro Gly Gln Gly
        35                  40                  45

Leu Glu Trp Ile Gly His Ile His Pro Asn Ser Gly Ile Ser Asn Tyr
    50                  55                  60

Asn Glu Lys Phe Lys Gly Lys Ala Thr Leu Thr Val Asp Thr Ser Ser
65                  70                  75                  80

Ser Thr Ala Tyr Val Asp Leu Ser Ser Leu Thr Ser Glu Asp Ser Ala
                85                  90                  95

Val Tyr Tyr Cys Ala Arg Gly Gly Arg Phe Asp Asp Trp Gly Ala Gly
                100                 105                 110

Thr Thr Val Thr Val Ser Ser Val Glu Gly Gly Ser Gly Gly Ser Gly
            115                 120                 125

Gly Ser Gly Gly Ser Gly Gly Val Asp Asp Ile Val Met Thr Gln Ser
        130                 135                 140

Pro Ala Thr Leu Ser Val Thr Pro Gly Asp Arg Val Ser Leu Ser Cys
145                 150                 155                 160

Arg Ala Ser Gln Ser Ile Ser Asp Tyr Leu His Trp Tyr Gln Gln Lys
                165                 170                 175

Ser His Glu Ser Pro Arg Leu Leu Ile Lys Tyr Ala Ser Gln Ser Ile
            180                 185                 190

Ser Gly Ile Pro Ser Arg Phe Ser Gly Ser Gly Ser Gly Ser Asp Phe

```
                195                 200                 205
Thr Leu Ser Ile Asn Ser Val Glu Pro Glu Asp Val Gly Val Tyr Tyr
    210                 215                 220

Cys Gln Asn Gly His Ser Phe Leu Met Tyr Thr Phe Gly Gly Gly Thr
225                 230                 235                 240

Lys Leu Glu Ile Lys
            245

<210> SEQ ID NO 124
<211> LENGTH: 249
<212> TYPE: PRT
<213> ORGANISM: Mus musculus

<400> SEQUENCE: 124

Ser Thr Gly Ser Asp Val Gln Leu Gln Glu Ser Gly Pro Gly Leu Val
1               5                   10                  15

Lys Pro Ser Gln Ser Leu Ser Leu Thr Cys Thr Val Thr Gly Tyr Ser
            20                  25                  30

Ile Thr Ser Asp Tyr Ala Trp Asn Trp Ile Arg Gln Phe Pro Gly Asn
        35                  40                  45

Lys Leu Glu Trp Met Gly Tyr Ile Thr Tyr Ser Gly Ser Thr Asn Tyr
    50                  55                  60

Asn Pro Ser Leu Lys Ser Arg Ile Ser Ile Thr Arg Asp Thr Ser Lys
65                  70                  75                  80

Asn Gln Phe Phe Leu Gln Leu Asn Ser Val Thr Thr Glu Asp Thr Ala
                85                  90                  95

Thr Tyr Tyr Cys Ala Arg Cys Trp Asp Tyr Ala Leu Tyr Ala Met Asp
            100                 105                 110

Cys Trp Gly Gln Gly Thr Ser Val Thr Val Ser Ser Val Glu Gly Gly
        115                 120                 125

Ser Gly Gly Ser Gly Gly Ser Gly Gly Ser Gly Gly Val Asp Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Thr Ser Glu Asn Ile Tyr Ser Tyr Leu Ala
                165                 170                 175

Trp Cys Gln Gln Lys Gln Gly Lys Ser Pro Gln Leu Leu Val Tyr Asn
            180                 185                 190

Ala Lys Thr Leu Ala Glu Gly Val Pro Ser Arg Phe Ser Gly Ser Gly
        195                 200                 205

Ser Gly Thr His Phe Ser Leu Lys Ile Asn Ser Leu Gln Pro Glu Asp
    210                 215                 220

Phe Gly Ile Tyr Tyr Cys Gln His His Tyr Asp Thr Pro Leu Thr Phe
225                 230                 235                 240

Gly Ala Gly Thr Lys Leu Glu Leu Lys
                245

<210> SEQ ID NO 125
<211> LENGTH: 246
<212> TYPE: PRT
<213> ORGANISM: Mus musculus

<400> SEQUENCE: 125

Ser Thr Gly Ser Gln Ile Gln Leu Val Gln Ser Gly Pro Glu Leu Gln
1               5                   10                  15

Lys Pro Gly Glu Thr Val Lys Ile Ser Cys Lys Ala Ser Gly Tyr Thr
```

```
                  20                  25                  30
Phe Thr Asn Tyr Gly Met Asn Trp Val Lys Gln Ala Pro Gly Lys Gly
            35                  40                  45

Leu Lys Trp Met Gly Trp Ile Asn Thr Asn Thr Gly Glu Pro Thr Tyr
 50                  55                  60

Ala Glu Glu Phe Lys Gly Arg Phe Ala Phe Ser Leu Glu Thr Ser Ala
 65                  70                  75                  80

Ser Thr Ala Tyr Leu Gln Ile Asn Asn Leu Lys Asn Glu Asp Thr Ala
                85                  90                  95

Thr Tyr Phe Cys Ala Arg Asp Tyr Leu Tyr Tyr Phe Asp Tyr Trp Gly
            100                 105                 110

Gln Gly Thr Thr Leu Thr Val Ser Ser Val Glu Gly Ser Gly Gly
            115                 120                 125

Ser Gly Gly Ser Gly Gly Ser Gly Gly Val Asp Asn Ile Val Met Thr
            130                 135                 140

Gln Ser Pro Lys Ser Met Ser Met Ser Val Gly Glu Arg Val Thr Leu
145                 150                 155                 160

Thr Cys Lys Ala Ser Glu Asn Val Val Thr Tyr Val Ser Trp Tyr Gln
                165                 170                 175

Gln Lys Pro Glu Gln Ser Pro Lys Leu Leu Ile Tyr Gly Ala Ser Asn
            180                 185                 190

Arg Tyr Thr Gly Val Pro Asp Arg Phe Thr Gly Ser Gly Ser Ala Thr
            195                 200                 205

Asp Phe Thr Leu Thr Ile Ser Ser Val Gln Ala Glu Asp Leu Ala Asp
            210                 215                 220

Tyr His Cys Gly Gln Gly Tyr Ser Tyr Pro Tyr Thr Phe Gly Gly Gly
225                 230                 235                 240

Thr Lys Leu Glu Ile Lys
                245

<210> SEQ ID NO 126
<211> LENGTH: 751
<212> TYPE: DNA
<213> ORGANISM: mus musculus

<400> SEQUENCE: 126
gtcgactgga agccaggtac agctgcagca gtctggccct gaactcgtca aaccaggagc        60
ttccgtgaag atgtcctgca aggcttcagg gtacacgttt accgactatg tgatcaattg       120
gggtaagcag cgctctgggc aaggcttgga gtggattggc gagatctatc ctggagtgg        180 gaccaactat tacaacgaga gttcaaggc caaagccact ttgactgcag acaagagctc        240
aaacattgcc tacatgcaac tgagctccct gacatcagag gattctgctg tgtacttctg       300
tgcacgtaga ggtcggtacg gtctgtatgc catggactat ggggccaag gcacttccgt        360 gacagtcagc tctgtggaag gaggaagtgg cggttcagga ggtagcgag ggtccggagg       420 agtggatgac attcagatga cacagaccac ttctagcctc tccgcatccc ttggggatag       480
ggtcaccatc agttgtaggg ctagccagga catttccaat tacctgaact ggtatcagca       540
gaaacccgat ggcacagtta agcttctgat ctactacaca agcagactgc actcaggggt       600
tccatctcgg tttagtggaa gtggctctgg taccgactat tccctgacca tcaacaatct       660
ggaacaggaa gatatcgcca cctacttctg ccaacagggc aatactcgac cctggacatt       720
tggtggcggc acgaaactcg agataaaata a                                      751
```

<210> SEQ ID NO 127
<211> LENGTH: 757
<212> TYPE: DNA
<213> ORGANISM: Mus musculus

<400> SEQUENCE: 127

| | | | | | |
|---|---|---|---|---|---|
| gtcgactgga | tccgaggtac | agttgcagga | gagtgggcct | ggactggtca | aaccctccca | 60 |
| atctctgagc | ttgacatgca | cagtcacagg | ctacagcatc | acctccgact | acgcttggaa | 120 |
| ttggattcga | cagtttcccg | gcaacaagct | ggaatggatg | ggctacatca | cctatagtgg | 180 |
| tagcacttcc | tataatccct | cacttgagag | ccggatttcc | atcactaggg | atacgagcac | 240 |
| caaccagttc | ttcctgcagc | tgaatagcgt | caccaccgaa | gatactgcca | cctattactg | 300 |
| cgcaagaggc | ggttactatg | gcagttcatg | gggtgtattc | gcctattggg | gacaggggac | 360 |
| acttgtgaca | gtgtctgctg | ttgaaggtgg | atccggcgga | tcaggaggga | gtggtggcag | 420 |
| tggaggtgtt | gacgacattc | agatgaccca | atcccctgct | tctctctcag | cctctgtggg | 480 |
| agagactgtg | accataacct | gtcgtgttag | cgagaacatc | tactcctatc | tcgcctggta | 540 |
| tcagcagaaa | caggggaaat | ccccacaact | gctcgtgtac | aatgccaaga | ctctggcaga | 600 |
| aggagtgcca | agccgctttt | ccgggtctgg | gtctgggaca | cagttctcac | tgaagatcaa | 660 |
| ctctttgcaa | cctgaggatt | ttggctctta | ctactgtcag | catcactatg | gcacaccatg | 720 |
| gacgtttggt | ggcggcacta | agctggagat | taagtaa | | | 757 |

<210> SEQ ID NO 128
<211> LENGTH: 739
<212> TYPE: DNA
<213> ORGANISM: Mus musculus

<400> SEQUENCE: 128

| | | | | | |
|---|---|---|---|---|---|
| gtcgactggg | tccgaagtgc | aactgcaaca | gtctggccct | gagctggtca | aacccggtgc | 60 |
| ttcagtgaag | atctcctgca | agacatccgg | ctacaccttc | actgagtaca | ccatgcactg | 120 |
| ggtcaaacag | tctcacggta | agagcctgga | gtggataggc | ggaatttcac | ccaacattgg | 180 |
| agggacctcc | tataaccaga | agttcaaggg | caaagccacc | cttacagttg | acaagagcag | 240 |
| ttcaactgcc | tacatggaac | tgcgctcatt | gacctccgag | gattcagccg | tgtattactg | 300 |
| cgctagaagg | ggaggatcct | tcgattattg | gggccaaggc | actacgctta | ccgtgagcag | 360 |
| cgttgaaggt | ggttctggcg | gctctggtgg | aagtggaggg | agtggcgggg | tagacgacat | 420 |
| cgtgatgact | cagagtccag | caactctgtc | cgttacacct | ggagatcgag | tgtctctgag | 480 |
| ttgtcgtgca | agccagtcta | tctctgacta | tctgcactgg | tatcagcaga | agagccatga | 540 |
| gtcacctagg | ctgttgatca | agtacgcctc | tcagtccatt | agcgggattc | catcccggtt | 600 |
| tagtggctct | ggctccggta | gtgacttcac | actcagcatc | aatagcgtcg | aaccagagga | 660 |
| tgtaggggtg | tactactgtc | agaatgggca | ttcctttccc | ctcacatttg | gagctggtac | 720 |
| caaactcgag | ctgaaataa | | | | | 739 |

<210> SEQ ID NO 129
<211> LENGTH: 742
<212> TYPE: DNA
<213> ORGANISM: Mus musculus

<400> SEQUENCE: 129

| | | | | | |
|---|---|---|---|---|---|
| gtcgactggc | tccaagtac | agcttcagca | gtctgccgtc | gaacttgctc | gaccaggagc | 60 |
| ttcagtgaag | atgagctgca | aagcctctgg | ttacaccttc | acgtcccttta | ccatgcattg | 120 |

| | |
|---|---|
| ggtgaagcag cgtcctggcc aaggcctgga gtggattggc tacatcaatc cctccagcgg | 180 |
| gtataccgag tacaaccaga agttcaagga caaaacaacc ctgactgccg ataagtcaag | 240 |
| tagcacagcc tatatgcagc tggattccct gacatcagac gatagcgctg tgtattactg | 300 |
| cgttaggggc tctagcagag ggttcgacta ttggggtcaa ggcacactgg tcacggttag | 360 |
| tgccgttgaa ggaggctctg gaggcagtgg aggttctgga gggtcaggcg gtgtggatga | 420 |
| cattcagatg attcagagtc ccgctagctt gagtgtaagc gtcggtgaga cagtgaccat | 480 |
| cacttgtcgc gcatccgaaa acatctactc caatctcgca tggttccagc agaaacaggg | 540 |
| caaatcaccc caattgctcg tgtatgccgc aactaatctg gctgatggtg tgccttccag | 600 |
| gtttagcggg tctggatctg ggactcagta ctccctgaag atcaactccc tccagtctga | 660 |
| ggacttcggg atctattact gtcagcactt ttggggaact ccacggacct ttggaggcgg | 720 |
| gaccaaactg gagataaagt aa | 742 |

<210> SEQ ID NO 130
<211> LENGTH: 696
<212> TYPE: DNA
<213> ORGANISM: Mus musculus

<400> SEQUENCE: 130

| | |
|---|---|
| ctggtgaggc caggtgcatc tgtgaagctg tcatgcaaag catccgggta cacgttcacc | 60 |
| tcttcatgga tgcattgggc caaacagcgt ccaggccagg ccttgagtg gattggacac | 120 |
| attcacccca atagcggcat atccaactac aacgagaagt tcaagggcaa agccacactg | 180 |
| acagtggata cttccagctc tacagccttat gtggacctta gtagcttgac cagtgaggat | 240 |
| tctgccgtat actactgtgc tagaggtggg cggtttgacg attggggtgc tgggaccaca | 300 |
| gtcaccgtga gcagtgtcga aggtggatca ggtggatctg gaggctcagg cggttctggc | 360 |
| ggtgttgacg acatcgtgat gactcaaagc cctgctactc tctctgtcac acccggagat | 420 |
| agggtaagcc tcagttgtcg agcaagccag tcaatcagcg actatctgca ctggtatcag | 480 |
| cagaagtccc atgaatcccc acgcttgctc atcaagtacg ccagtcagtc catcagtggc | 540 |
| attccttccc ggttttctgg gtctggatcc gggtcagact tcactctgag cattaactcc | 600 |
| gtcgaacccg aggatgttgg cgtgtattat tgccagaatg gacattcctt cctgatgtac | 660 |
| acctttggcg agggaccaa actggagatc aagtaa | 696 |

<210> SEQ ID NO 131
<211> LENGTH: 751
<212> TYPE: DNA
<213> ORGANISM: Mus musculus

<400> SEQUENCE: 131

| | |
|---|---|
| gtcgactggg tctgatgtgc agttgcagga gtcaggacct gggcttgtca agccaagcca | 60 |
| gagcctcagt ctcacttgca ctgtcacagg ctatagcatc acatccgact atgcttggaa | 120 |
| ttggattagg cagtttcctg gcaataagct ggaatggatg gggtacatca cctattccgg | 180 |
| cagtaccaac tacaatccca gcttgaaatc tcggatttcc ataacacgcg atactagcaa | 240 |
| gaaccagttc ttccttcagc tgaactctgt gacaacagag gataccgcta cgtactattg | 300 |
| cgccagatgc tgggattacg ccctgtatgc catggactgt tggggtcaag gtaccagcgt | 360 |
| tactgtgtct agcgtcgaag gcggaagtgg cggctcagga gggtcaggag gctcaggcgg | 420 |
| agtggatgac attcagatga cccaatctcc cgcatccctg tccgcatcag taggggagac | 480 |
| agtgaccatt acctgtcgta cttccgagaa catctactcc tatcttgcct ggtgtcaaca | 540 |

```
gaaacagggg aaaagtccac agctgctggt gtataacgcc aagaccttgg cagaaggtgt    600
tcccagtcga ttctctggtt ccggatccgg tacacacttc agcctgaaga tcaattctct    660
gcaaccagag gactttggaa tctactactg ccagcatcac tacgacactc ctctgacgtt    720
tggcgctggt accaagctcg aactgaaata a                                    751
```

<210> SEQ ID NO 132
<211> LENGTH: 742
<212> TYPE: DNA
<213> ORGANISM: Mus musculus

<400> SEQUENCE: 132

```
gtcgactggt agccagatac agctggtaca gtcaggacca gagctgcaga aacctggaga     60
gacagtgaag atcagctgca aggctagcgg gtacaccttc acgaattacg ggatgaactg    120
ggtcaagcag gctccaggca aagggctgaa gtggatgggc tggattaaca ccaatactgg    180
ggaaccaacc tatgccgagg aattcaaggg gagatttgcc ttttccctcg aaaccagcgc    240
ctcaaccgcc tatctccaga tcaacaacct gaagaatgag gataccgcta cctacttctg    300
tgcaagggac tacctctact acttcgacta ttggggccaa ggtacgactc ttacagtctc    360
tagtgttgag ggagggagtg gaggttctgg aggctctggt ggctctggag gcgttgacaa    420
catcgtgatg actcagtctc ccaaaagcat gagtatgagt gtgggtgaac gagttacctt    480
gacatgcaaa gcctccgaga atgtcgtgac atacgtgtcc tggtatcagc agaaacccga    540
gcaatcccct aagctgctga tctatggcgc tagcaatcgc tatactgcg tacctgatcg    600 gttcacagga tcaggctcag ccactgactt tactcttacc atttcctccg tgcaggcaga    660
agatttggca gattaccact gtgggcaagg ttactcttat ccctatacat ttggaggcgg    720
cacaaagctg gagattaagt aa                                             742
```

<210> SEQ ID NO 133
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 133

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140
```

```
Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
        180                 185                 190

Lys Ala Thr Leu Thr Ala Asp Glu Ser Ser Ser Thr Ala Tyr Met Gln
    195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Ser Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Val Pro Val Leu Asp Ser Asp Gly Ser Phe Arg Leu Ala
        420                 425                 430

Ser Tyr Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Gln Val Gln Leu Gln
465                 470                 475                 480

Gln Ser Gly Pro Glu Leu Val Lys Pro Gly Ala Ser Val Lys Met Ser
            485                 490                 495

Cys Lys Ala Ser Gly Tyr Thr Phe Thr Asp Tyr Val Ile Asn Trp Gly
        500                 505                 510

Lys Gln Arg Ser Gly Gln Gly Leu Glu Trp Ile Gly Glu Ile Tyr Pro
    515                 520                 525

Gly Ser Gly Thr Asn Tyr Tyr Asn Glu Lys Phe Lys Ala Lys Ala Thr
530                 535                 540

Leu Thr Ala Asp Lys Ser Ser Asn Ile Ala Tyr Met Gln Leu Ser Ser
545                 550                 555                 560
```

```
Leu Thr Ser Glu Asp Ser Ala Val Tyr Phe Cys Ala Arg Arg Gly Arg
                565                 570                 575

Tyr Gly Leu Tyr Ala Met Asp Tyr Trp Gly Gln Gly Thr Ser Val Thr
            580                 585                 590

Val Ser Ser Val Glu Gly Gly Ser Gly Gly Ser Gly Gly Ser Gly Gly
        595                 600                 605

Ser Gly Gly Val Asp Asp Ile Gln Met Thr Gln Thr Thr Ser Ser Leu
    610                 615                 620

Ser Ala Ser Leu Gly Asp Arg Val Thr Ile Ser Cys Arg Ala Ser Gln
625                 630                 635                 640

Asp Ile Ser Asn Tyr Leu Asn Trp Tyr Gln Gln Lys Pro Asp Gly Thr
                645                 650                 655

Val Lys Leu Leu Ile Tyr Tyr Thr Ser Arg Leu His Ser Gly Val Pro
            660                 665                 670

Ser Arg Phe Ser Gly Ser Gly Ser Gly Thr Asp Tyr Ser Leu Thr Ile
        675                 680                 685

Asn Asn Leu Glu Gln Glu Asp Ile Ala Thr Tyr Phe Cys Gln Gln Gly
    690                 695                 700

Asn Thr Arg Pro Trp Thr Phe Gly Gly Gly Thr Lys Leu Glu Ile Lys
705                 710                 715                 720

<210> SEQ ID NO 134
<211> LENGTH: 722
<212> TYPE: PRT
<213> ORGANISM: Artificial
<220> FEATURE:
<223> OTHER INFORMATION: Chimeric homo sapiens mus musculus

<400> SEQUENCE: 134

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205
```

-continued

```
Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Ser Thr Gly Ser Glu Val Gln Leu Gln
465                 470                 475                 480

Glu Ser Gly Pro Gly Leu Val Lys Pro Ser Gln Ser Leu Ser Leu Thr
                485                 490                 495

Cys Thr Val Thr Gly Tyr Ser Ile Thr Ser Asp Tyr Ala Trp Asn Trp
                500                 505                 510

Ile Arg Gln Phe Pro Gly Asn Lys Leu Glu Trp Met Gly Tyr Ile Thr
                515                 520                 525

Tyr Ser Gly Ser Thr Ser Tyr Asn Pro Ser Leu Glu Ser Arg Ile Ser
530                 535                 540

Ile Thr Arg Asp Thr Ser Thr Asn Gln Phe Phe Leu Gln Leu Asn Ser
545                 550                 555                 560

Val Thr Thr Glu Asp Thr Ala Thr Tyr Tyr Cys Ala Arg Gly Gly Tyr
                565                 570                 575

Tyr Gly Ser Ser Trp Gly Val Phe Ala Tyr Trp Gly Gln Gly Thr Leu
                580                 585                 590

Val Thr Val Ser Ala Val Glu Gly Gly Ser Gly Gly Ser Gly Gly Ser
                595                 600                 605

Gly Gly Ser Gly Gly Val Asp Asp Ile Gln Met Thr Gln Ser Pro Ala
610                 615                 620

Ser Leu Ser Ala Ser Val Gly Glu Thr Val Thr Ile Thr Cys Arg Val
```

```
                 625                 630                 635                 640
Ser Glu Asn Ile Tyr Ser Tyr Leu Ala Trp Tyr Gln Gln Lys Gln Gly
                    645                 650                 655

Lys Ser Pro Gln Leu Leu Val Tyr Asn Ala Lys Thr Leu Ala Glu Gly
                660                 665                 670

Val Pro Ser Arg Phe Ser Gly Ser Gly Ser Gly Thr Gln Phe Ser Leu
            675                 680                 685

Lys Ile Asn Ser Leu Gln Pro Glu Asp Phe Ser Tyr Tyr Cys Gln
690                 695                 700

His His Tyr Gly Thr Pro Trp Thr Phe Gly Gly Gly Thr Lys Leu Glu
705                 710                 715                 720

Ile Lys

<210> SEQ ID NO 135
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 135

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Gly Gly Gly Ser Ser Ala
                245                 250                 255

Pro Glu Leu Leu Gly Gly Pro Ser Val Phe Leu Phe Pro Pro Lys Pro
            260                 265                 270
```

-continued

```
Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Glu Val Gln Leu Gln
465                 470                 475                 480

Gln Ser Gly Pro Glu Leu Val Lys Pro Gly Ala Ser Val Lys Ile Ser
                485                 490                 495

Cys Lys Thr Ser Gly Tyr Thr Phe Thr Glu Tyr Thr Met His Trp Val
            500                 505                 510

Lys Gln Ser His Gly Lys Ser Leu Glu Trp Ile Gly Gly Ile Ser Pro
        515                 520                 525

Asn Ile Gly Gly Thr Ser Tyr Asn Gln Lys Phe Lys Gly Lys Ala Thr
    530                 535                 540

Leu Thr Val Asp Lys Ser Ser Ser Thr Ala Tyr Met Glu Leu Arg Ser
545                 550                 555                 560

Leu Thr Ser Glu Asp Ser Ala Val Tyr Tyr Cys Ala Arg Arg Gly Gly
                565                 570                 575

Ser Phe Asp Tyr Trp Gly Gln Gly Thr Thr Leu Thr Val Ser Ser Val
            580                 585                 590

Glu Gly Gly Ser Gly Ser Gly Ser Gly Ser Gly Ser Gly Gly Gly Val
        595                 600                 605

Asp Asp Ile Val Met Thr Gln Ser Pro Ala Thr Leu Ser Val Thr Pro
    610                 615                 620

Gly Asp Arg Val Ser Leu Ser Cys Arg Ala Ser Gln Ser Ile Ser Asp
625                 630                 635                 640

Tyr Leu His Trp Tyr Gln Gln Lys Ser His Glu Ser Pro Arg Leu Leu
                645                 650                 655

Ile Lys Tyr Ala Ser Gln Ser Ile Ser Gly Ile Pro Ser Arg Phe Ser
            660                 665                 670

Gly Ser Gly Ser Gly Ser Asp Phe Thr Leu Ser Ile Asn Ser Val Glu
        675                 680                 685
```

Pro Glu Asp Val Gly Val Tyr Tyr Cys Gln Asn Gly His Ser Phe Pro
    690             695                 700

Leu Thr Phe Gly Ala Gly Thr Lys Leu Glu Leu Lys
705             710                 715

<210> SEQ ID NO 136
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 136

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

```
Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Gln Val Gln Leu Gln
465                 470                 475                 480

Gln Ser Ala Val Glu Leu Ala Arg Pro Gly Ala Ser Val Lys Met Ser
                485                 490                 495

Cys Lys Ala Ser Gly Tyr Thr Phe Thr Ser Phe Thr Met His Trp Val
            500                 505                 510

Lys Gln Arg Pro Gly Gln Gly Leu Glu Trp Ile Gly Tyr Ile Asn Pro
        515                 520                 525

Ser Ser Gly Tyr Thr Glu Tyr Asn Gln Lys Phe Lys Asp Lys Thr Thr
    530                 535                 540

Leu Thr Ala Asp Lys Ser Ser Thr Ala Tyr Met Gln Leu Asp Ser
545                 550                 555                 560

Leu Thr Ser Asp Asp Ser Ala Val Tyr Tyr Cys Val Arg Gly Ser Ser
                565                 570                 575

Arg Gly Phe Asp Tyr Trp Gly Gln Gly Thr Leu Val Thr Val Ser Ala
            580                 585                 590

Val Glu Gly Gly Ser Gly Gly Ser Gly Gly Ser Gly Gly Ser Gly Gly
        595                 600                 605

Val Asp Asp Ile Gln Met Ile Gln Ser Pro Ala Ser Leu Ser Val Ser
    610                 615                 620

Val Gly Glu Thr Val Thr Ile Thr Cys Arg Ala Ser Glu Asn Ile Tyr
625                 630                 635                 640

Ser Asn Leu Ala Trp Phe Gln Gln Lys Gln Gly Lys Ser Pro Gln Leu
                645                 650                 655

Leu Val Tyr Ala Ala Thr Asn Leu Ala Asp Gly Val Pro Ser Arg Phe
            660                 665                 670

Ser Gly Ser Gly Ser Gly Thr Gln Tyr Ser Leu Lys Ile Asn Ser Leu
        675                 680                 685

Gln Ser Glu Asp Phe Gly Ile Tyr Tyr Cys Gln His Phe Trp Gly Thr
    690                 695                 700

Pro Arg Thr Phe Gly Gly Gly Thr Lys Leu Glu Ile Lys
705                 710                 715
```

<210> SEQ ID NO 137
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 137

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
```

```
            405                 410                 415
Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Ser Thr Gly Ser Gln Val Gln Leu Gln
465                 470                 475                 480

Gln Pro Gly Ser Val Leu Val Arg Pro Gly Ala Ser Val Lys Leu Ser
                485                 490                 495

Cys Lys Ala Ser Gly Tyr Thr Phe Thr Ser Ser Trp Met His Trp Ala
            500                 505                 510

Lys Gln Arg Pro Gly Gln Gly Leu Glu Trp Ile Gly His Ile His Pro
        515                 520                 525

Asn Ser Gly Ile Ser Asn Tyr Asn Glu Lys Phe Lys Gly Lys Ala Thr
    530                 535                 540

Leu Thr Val Asp Thr Ser Ser Thr Ala Tyr Val Asp Leu Ser Ser
545                 550                 555                 560

Leu Thr Ser Glu Asp Ser Ala Val Tyr Tyr Cys Ala Arg Gly Gly Arg
                565                 570                 575

Phe Asp Asp Trp Gly Ala Gly Thr Thr Val Thr Val Ser Ser Val Glu
            580                 585                 590

Gly Gly Ser Gly Gly Ser Gly Gly Ser Gly Gly Ser Gly Gly Val Asp
        595                 600                 605

Asp Ile Val Met Thr Gln Ser Pro Ala Thr Leu Ser Val Thr Pro Gly
    610                 615                 620

Asp Arg Val Ser Leu Ser Cys Arg Ala Ser Gln Ser Ile Ser Asp Tyr
625                 630                 635                 640

Leu His Trp Tyr Gln Gln Lys Ser His Glu Ser Pro Arg Leu Leu Ile
                645                 650                 655

Lys Tyr Ala Ser Gln Ser Ile Ser Gly Ile Pro Ser Arg Phe Ser Gly
            660                 665                 670

Ser Gly Ser Gly Ser Asp Phe Thr Leu Ser Ile Asn Ser Val Glu Pro
        675                 680                 685

Glu Asp Val Gly Val Tyr Tyr Cys Gln Asn Gly His Ser Phe Leu Met
    690                 695                 700

Tyr Thr Phe Gly Gly Gly Thr Lys Leu Glu Ile Lys
705                 710                 715

<210> SEQ ID NO 138
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 138

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
```

-continued

```
            50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Gly
            100                 105                 110
Gly Gly Gly Ser Gly Gly Gly Gly Ser Gly Gly Gly Gly Ser Gln Val
            115                 120                 125
Gln Leu Gln Gln Ser Gly Ala Glu Leu Val Arg Pro Gly Ser Ser Val
130                 135                 140
Lys Ile Ser Cys Lys Ala Ser Gly Tyr Ala Phe Ser Ser Tyr Trp Met
145                 150                 155                 160
Asn Trp Val Lys Gln Arg Pro Gly Gln Gly Leu Glu Trp Ile Gly Gln
                165                 170                 175
Ile Trp Pro Gly Asp Gly Asp Thr Asn Tyr Asn Gly Lys Phe Lys Gly
            180                 185                 190
Lys Ala Thr Leu Thr Ala Asp Glu Ser Ser Ser Thr Ala Tyr Met Gln
            195                 200                 205
Leu Ser Ser Leu Ala Ser Glu Asp Ser Ala Val Tyr Phe Cys Ala Arg
210                 215                 220
Arg Glu Thr Thr Thr Val Gly Arg Tyr Tyr Tyr Ala Met Asp Tyr Trp
225                 230                 235                 240
Gly Gln Gly Thr Thr Val Thr Val Ser Ser Gly Gly Gly Ser Ser Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Lys Pro Pro Ser Arg Glu Glu Met Thr
370                 375                 380
Lys Asn Gln Val Ser Leu Ser Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Val Pro Val Leu Asp Ser Asp Gly Ser Phe Arg Leu Ala
            420                 425                 430
Ser Tyr Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
450                 455                 460
Ser Leu Ser Leu Ser Pro Gly Thr Gly Ser Asp Val Gln Leu Gln
465                 470                 475                 480
```

```
Glu Ser Gly Pro Gly Leu Val Lys Pro Ser Gln Ser Leu Ser Leu Thr
            485                 490                 495

Cys Thr Val Thr Gly Tyr Ser Ile Thr Ser Asp Tyr Ala Trp Asn Trp
        500                 505                 510

Ile Arg Gln Phe Pro Gly Asn Lys Leu Glu Trp Met Gly Tyr Ile Thr
    515                 520                 525

Tyr Ser Gly Ser Thr Asn Tyr Asn Pro Ser Leu Lys Ser Arg Ile Ser
530                 535                 540

Ile Thr Arg Asp Thr Ser Lys Asn Gln Phe Phe Leu Gln Leu Asn Ser
545                 550                 555                 560

Val Thr Thr Glu Asp Thr Ala Thr Tyr Tyr Cys Ala Arg Cys Trp Asp
                565                 570                 575

Tyr Ala Leu Tyr Ala Met Asp Cys Trp Gly Gln Gly Thr Ser Val Thr
            580                 585                 590

Val Ser Ser Val Glu Gly Gly Ser Gly Gly Ser Gly Gly Ser Gly Gly
        595                 600                 605

Ser Gly Gly Val Asp Asp Ile Gln Met Thr Gln Ser Pro Ala Ser Leu
    610                 615                 620

Ser Ala Ser Val Gly Glu Thr Val Thr Ile Thr Cys Arg Thr Ser Glu
625                 630                 635                 640

Asn Ile Tyr Ser Tyr Leu Ala Trp Cys Gln Gln Lys Gln Gly Lys Ser
                645                 650                 655

Pro Gln Leu Leu Val Tyr Asn Ala Lys Thr Leu Ala Glu Gly Val Pro
            660                 665                 670

Ser Arg Phe Ser Gly Ser Gly Ser Gly Thr His Phe Ser Leu Lys Ile
        675                 680                 685

Asn Ser Leu Gln Pro Glu Asp Phe Gly Ile Tyr Tyr Cys Gln His His
    690                 695                 700

Tyr Asp Thr Pro Leu Thr Phe Gly Ala Gly Thr Lys Leu Glu Leu Lys
705                 710                 715                 720

<210> SEQ ID NO 139
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 139

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125
```

Gln Leu Gln Gln Ser Gly Ala Glu Leu Val Arg Pro Gly Ser Ser Val
            130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Ser Ala
            245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
            370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Gln Ile Gln Leu Val
465                 470                 475                 480

Gln Ser Gly Pro Glu Leu Gln Lys Pro Gly Glu Thr Val Lys Ile Ser
                485                 490                 495

Cys Lys Ala Ser Gly Tyr Thr Phe Thr Asn Tyr Gly Met Asn Trp Val
            500                 505                 510

Lys Gln Ala Pro Gly Lys Gly Leu Lys Trp Met Gly Trp Ile Asn Thr
                515                 520                 525

Asn Thr Gly Glu Pro Thr Tyr Ala Glu Glu Phe Lys Gly Arg Phe Ala
530                 535                 540

```
Phe Ser Leu Glu Thr Ser Ala Ser Thr Ala Tyr Leu Gln Ile Asn Asn
545                 550                 555                 560

Leu Lys Asn Glu Asp Thr Ala Thr Tyr Phe Cys Ala Arg Asp Tyr Leu
            565                 570                 575

Tyr Tyr Phe Asp Tyr Trp Gly Gln Gly Thr Thr Leu Thr Val Ser Ser
            580                 585                 590

Val Glu Gly Gly Ser Gly Gly Ser Gly Gly Ser Gly Gly Ser Gly Gly
        595                 600                 605

Val Asp Asn Ile Val Met Thr Gln Ser Pro Lys Ser Met Ser Met Ser
610                 615                 620

Val Gly Glu Arg Val Thr Leu Thr Cys Lys Ala Ser Glu Asn Val Val
625                 630                 635                 640

Thr Tyr Val Ser Trp Tyr Gln Gln Lys Pro Glu Gln Ser Pro Lys Leu
            645                 650                 655

Leu Ile Tyr Gly Ala Ser Asn Arg Tyr Thr Gly Val Pro Asp Arg Phe
            660                 665                 670

Thr Gly Ser Gly Ser Ala Thr Asp Phe Thr Leu Thr Ile Ser Ser Val
            675                 680                 685

Gln Ala Glu Asp Leu Ala Asp Tyr His Cys Gly Gln Gly Tyr Ser Tyr
        690                 695                 700

Pro Tyr Thr Phe Gly Gly Gly Thr Lys Leu Glu Ile Lys
705                 710                 715

<210> SEQ ID NO 140
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 140

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
            85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
            180                 185                 190
```

-continued

```
Lys Ala Thr Leu Thr Ala Asp Glu Ser Ser Thr Ala Tyr Met Gln
            195                 200                 205
Leu Ser Ser Leu Ala Ser Glu Asp Ser Ala Val Tyr Phe Cys Ala Arg
            210                 215                 220
Arg Glu Thr Thr Thr Val Gly Arg Tyr Tyr Ala Met Asp Tyr Trp
225                 230                 235                 240
Gly Gln Gly Thr Thr Val Thr Val Ser Ser Gly Gly Ser Ser Ala
                245                 250                 255
Pro Glu Leu Leu Gly Gly Pro Ser Val Phe Leu Phe Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Lys Pro Pro Ser Arg Glu Glu Met Thr
        370                 375                 380
Lys Asn Gln Val Ser Leu Ser Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Val Pro Val Leu Asp Ser Asp Gly Ser Phe Arg Leu Ala
            420                 425                 430
Ser Tyr Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
450                 455                 460
Ser Leu Ser Leu Ser Pro Gly Ser Thr Gly Ser Glu Val Gln Leu Gln
465                 470                 475                 480
Gln Ser Gly Pro Glu Leu Val Lys Pro Gly Ala Ser Val Lys Ile Ser
                485                 490                 495
Cys Lys Thr Ser Gly Tyr Thr Phe Thr Glu Tyr Thr Met His Trp Val
            500                 505                 510
Lys Gln Ser His Gly Lys Ser Leu Glu Trp Ile Gly Gly Ile Ser Pro
            515                 520                 525
Asn Ile Gly Gly Thr Ser Tyr Asn Gln Lys Phe Lys Gly Lys Ala Thr
            530                 535                 540
Leu Thr Val Asp Lys Ser Ser Thr Ala Tyr Met Glu Leu Arg Ser
545                 550                 555                 560
Leu Thr Ser Glu Asp Ser Ala Val Tyr Tyr Cys Ala Arg Arg Gly Gly
                565                 570                 575
Ser Phe Asp Tyr Trp Gly Gln Gly Thr Thr Leu Thr Val Ser Ser Ala
            580                 585                 590
Ser Thr Lys Gly Pro Ser Val Phe Pro Leu Ala Pro Ser Ser Lys Ser
            595                 600                 605
Thr Ser Gly Gly Thr Ala Ala Leu Gly Cys Leu Val Lys Asp Tyr Phe
```

```
                    610                 615                 620
Pro Glu Pro Val Thr Val Ser Trp Asn Ser Gly Ala Leu Thr Ser Gly
625                 630                 635                 640

Val His Thr Phe Pro Ala Val Leu Gln Ser Ser Gly Leu Tyr Ser Leu
                    645                 650                 655

Ser Ser Val Val Thr Val Pro Ser Ser Ser Leu Gly Thr Gln Thr Tyr
                660                 665                 670

Ile Cys Asn Val Asn His Lys Pro Ser Asn Thr Lys Val Asp Lys Arg
            675                 680                 685

Val Glu Pro Lys Ser Cys Asp Lys Thr His
            690                 695
```

<210> SEQ ID NO 141
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 141

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 142

-continued

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
```

```
            420             425             430
Ser Lys Leu Thr Val Asp Lys Ser Arg Trp Gln Gln Gly Asn Val Phe
            435             440             445

Ser Cys Ser Val Met His Glu Ala Leu His Asn His Tyr Thr Gln Lys
            450             455             460

Ser Leu Ser Leu Ser Pro Gly Gly Gly Gly Ser Gly Gly Gly Gly
465             470             475             480

Ser Gly Gly Gly Ser Gly Gln Pro Arg Glu Pro Gln Val Tyr Thr
                485             490             495

Leu Pro Pro Ser Arg Glu Glu Met Thr Lys Asn Gln Val Ser Leu Thr
            500             505             510

Cys Leu Val Lys Gly Phe Tyr Pro Ser Asp Ile Ala Val Glu Trp Glu
            515             520             525

Ser Asn Gly Gln Pro Glu Asn Asn Tyr Lys Thr Thr Pro Pro Val Leu
            530             535             540

Asp Ser Asp Gly Ser Phe Phe Leu Tyr Ser Lys Leu Thr Val Asp Lys
545             550             555             560

Ser Arg Trp Gln Gln Gly Asn Val Phe Ser Cys Ser Val Met His Glu
                565             570             575

Ala Leu His Asn His Tyr Thr Gln Lys Ser Leu Ser Leu Ser Pro Gly
            580             585             590

Ser Thr Gly Ser Glu Val Gln Leu Gln Gln Ser Gly Pro Glu Leu Val
            595             600             605

Lys Pro Gly Ala Ser Val Lys Ile Ser Cys Lys Thr Ser Gly Tyr Thr
            610             615             620

Phe Thr Glu Tyr Thr Met His Trp Val Lys Gln Ser His Gly Lys Ser
625             630             635             640

Leu Glu Trp Ile Gly Gly Ile Ser Pro Asn Ile Gly Thr Ser Tyr
                645             650             655

Asn Gln Lys Phe Lys Gly Lys Ala Thr Leu Thr Val Asp Lys Ser Ser
                660             665             670

Ser Thr Ala Tyr Met Glu Leu Arg Ser Leu Thr Ser Glu Asp Ser Ala
            675             680             685

Val Tyr Tyr Cys Ala Arg Arg Gly Gly Ser Phe Asp Tyr Trp Gly Gln
            690             695             700

Gly Thr Thr Leu Thr Val Ser Ser Val Glu Gly Gly Ser Gly Gly Ser
705             710             715             720

Gly Gly Ser Gly Gly Ser Gly Gly Val Asp Asp Ile Val Met Thr Gln
                725             730             735

Ser Pro Ala Thr Leu Ser Val Thr Pro Gly Asp Arg Val Ser Leu Ser
            740             745             750

Cys Arg Ala Ser Gln Ser Ile Ser Asp Tyr Leu His Trp Tyr Gln Gln
            755             760             765

Lys Ser His Glu Ser Pro Arg Leu Leu Ile Lys Tyr Ala Ser Gln Ser
            770             775             780

Ile Ser Gly Ile Pro Ser Arg Phe Ser Gly Ser Gly Ser Gly Ser Asp
785             790             795             800

Phe Thr Leu Ser Ile Asn Ser Val Glu Pro Glu Asp Val Gly Val Tyr
                805             810             815

Tyr Cys Gln Asn Gly His Ser Phe Pro Leu Thr Phe Gly Ala Gly Thr
                820             825             830

Lys Leu Glu Leu Lys
            835
```

```
<210> SEQ ID NO 143
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 143
```

| | | | | | | | | | | | | | | | |
|---|---|---|---|---|---|---|---|---|---|---|---|---|---|---|---|
| Asp | Ile | Gln | Leu | Thr | Gln | Ser | Pro | Ala | Ser | Leu | Ala | Val | Ser | Leu | Gly |
| 1 | | | | 5 | | | | | 10 | | | | | 15 | |
| Gln | Arg | Ala | Thr | Ile | Ser | Cys | Lys | Ala | Ser | Gln | Ser | Val | Asp | Tyr | Asp |
| | | | 20 | | | | | 25 | | | | | 30 | | |
| Gly | Asp | Ser | Tyr | Leu | Asn | Trp | Tyr | Gln | Gln | Ile | Pro | Gly | Gln | Pro | Pro |
| | | 35 | | | | | 40 | | | | | 45 | | | |
| Lys | Leu | Leu | Ile | Tyr | Asp | Ala | Ser | Asn | Leu | Val | Ser | Gly | Ile | Pro | Pro |
| 50 | | | | | 55 | | | | | 60 | | | | | |
| Arg | Phe | Ser | Gly | Ser | Gly | Ser | Gly | Thr | Asp | Phe | Thr | Leu | Asn | Ile | His |
| 65 | | | | | 70 | | | | | 75 | | | | | 80 |
| Pro | Val | Glu | Lys | Val | Asp | Ala | Ala | Thr | Tyr | His | Cys | Gln | Gln | Ser | Thr |
| | | | | 85 | | | | | 90 | | | | | 95 | |
| Glu | Asp | Pro | Trp | Thr | Phe | Gly | Gly | Gly | Thr | Lys | Leu | Glu | Ile | Lys | Gly |
| | | | 100 | | | | | 105 | | | | | 110 | | |
| Gly | Gly | Gly | Ser | Gly | Gly | Gly | Gly | Ser | Gly | Gly | Gly | Gly | Ser | Gln | Val |
| | | 115 | | | | | 120 | | | | | 125 | | | |
| Gln | Leu | Gln | Gln | Ser | Gly | Ala | Glu | Leu | Val | Arg | Pro | Gly | Ser | Ser | Val |
| | | 130 | | | | | 135 | | | | | 140 | | | |
| Lys | Ile | Ser | Cys | Lys | Ala | Ser | Gly | Tyr | Ala | Phe | Ser | Ser | Tyr | Trp | Met |
| 145 | | | | | 150 | | | | | 155 | | | | | 160 |
| Asn | Trp | Val | Lys | Gln | Arg | Pro | Gly | Gln | Gly | Leu | Glu | Trp | Ile | Gly | Gln |
| | | | | 165 | | | | | 170 | | | | | 175 | |
| Ile | Trp | Pro | Gly | Asp | Gly | Asp | Thr | Asn | Tyr | Asn | Gly | Lys | Phe | Lys | Gly |
| | | | 180 | | | | | 185 | | | | | 190 | | |
| Lys | Ala | Thr | Leu | Thr | Ala | Asp | Glu | Ser | Ser | Ser | Thr | Ala | Tyr | Met | Gln |
| | | | 195 | | | | | 200 | | | | | 205 | | |
| Leu | Ser | Ser | Leu | Ala | Ser | Glu | Asp | Ser | Ala | Val | Tyr | Phe | Cys | Ala | Arg |
| | | 210 | | | | | 215 | | | | | 220 | | | |
| Arg | Glu | Thr | Thr | Thr | Val | Gly | Arg | Tyr | Tyr | Tyr | Ala | Met | Asp | Tyr | Trp |
| 225 | | | | | 230 | | | | | 235 | | | | | 240 |
| Gly | Gln | Gly | Thr | Thr | Val | Thr | Val | Ser | Ser | Gly | Gly | Gly | Ser | Ser | Ala |
| | | | | 245 | | | | | 250 | | | | | 255 | |
| Pro | Glu | Leu | Leu | Gly | Gly | Pro | Ser | Val | Phe | Leu | Phe | Pro | Pro | Lys | Pro |
| | | | 260 | | | | | 265 | | | | | 270 | | |
| Lys | Asp | Thr | Leu | Met | Ile | Ser | Arg | Thr | Pro | Glu | Val | Thr | Cys | Val | Val |
| | | | 275 | | | | | 280 | | | | | 285 | | |
| Val | Asp | Val | Ser | His | Glu | Asp | Pro | Glu | Val | Lys | Phe | Asn | Trp | Tyr | Val |
| | | | 290 | | | | | 295 | | | | | 300 | | |
| Asp | Gly | Val | Glu | Val | His | Asn | Ala | Lys | Thr | Lys | Pro | Arg | Glu | Glu | Gln |
| 305 | | | | | 310 | | | | | 315 | | | | | 320 |
| Tyr | Ser | Ser | Thr | Tyr | Arg | Val | Val | Ser | Val | Leu | Thr | Val | Leu | His | Gln |
| | | | | 325 | | | | | 330 | | | | | 335 | |
| Asp | Trp | Leu | Asn | Gly | Lys | Glu | Tyr | Lys | Cys | Lys | Val | Ser | Asn | Lys | Ala |
| | | | 340 | | | | | 345 | | | | | 350 | | |
| Leu | Pro | Ala | Pro | Ile | Glu | Lys | Thr | Ile | Ser | Lys | Ala | Lys | Gly | Gln | Pro |
| | | | 355 | | | | | 360 | | | | | 365 | | |

```
Arg Glu Pro Gln Val Tyr Thr Leu Pro Pro Ser Arg Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
        450                 455                 460
Ser Leu Ser Leu Ser Pro Gly Gly Gly Gly Ser Gly Gly Gly Gly
465                 470                 475                 480
Ser Gly Gly Gly Ser Gly Gln Pro Arg Glu Pro Gln Val Tyr Thr
                485                 490                 495
Leu Pro Pro Ser Arg Glu Met Thr Lys Asn Gln Val Ser Leu Thr
                500                 505                 510
Cys Leu Val Lys Gly Phe Tyr Pro Ser Asp Ile Ala Val Glu Trp Glu
            515                 520                 525
Ser Asn Gly Gln Pro Glu Asn Asn Tyr Lys Thr Thr Pro Pro Val Leu
530                 535                 540
Asp Ser Asp Gly Ser Phe Phe Leu Tyr Ser Lys Leu Thr Val Asp Lys
545                 550                 555                 560
Ser Arg Trp Gln Gln Gly Asn Val Phe Ser Cys Ser Val Met His Glu
                565                 570                 575
Ala Leu His Asn His Tyr Thr Gln Lys Ser Leu Ser Leu Ser Pro Gly
                580                 585                 590
Ser Thr Gly Ser Glu Val Gln Leu Gln Gln Ser Gly Pro Glu Leu Val
            595                 600                 605
Lys Pro Gly Ala Ser Val Lys Ile Ser Cys Lys Thr Ser Gly Tyr Thr
        610                 615                 620
Phe Thr Glu Tyr Thr Met His Trp Val Lys Gln Ser His Gly Lys Ser
625                 630                 635                 640
Leu Glu Trp Ile Gly Gly Ile Ser Pro Asn Ile Gly Gly Thr Ser Tyr
                645                 650                 655
Asn Gln Lys Phe Lys Gly Lys Ala Thr Leu Thr Val Asp Lys Ser Ser
                660                 665                 670
Ser Thr Ala Tyr Met Glu Leu Arg Ser Leu Thr Ser Glu Asp Ser Ala
            675                 680                 685
Val Tyr Tyr Cys Ala Arg Arg Gly Gly Ser Phe Asp Tyr Trp Gly Gln
        690                 695                 700
Gly Thr Thr Leu Thr Val Ser Ser Val Glu Gly Gly Ser Gly Gly Ser
705                 710                 715                 720
Gly Gly Ser Gly Gly Ser Gly Gly Val Asp Asp Ile Val Met Thr Gln
                725                 730                 735
Ser Pro Ala Thr Leu Ser Val Thr Pro Gly Asp Arg Val Ser Leu Ser
                740                 745                 750
Cys Arg Ala Ser Gln Ser Ile Ser Asp Tyr Leu His Trp Tyr Gln Gln
            755                 760                 765
Lys Ser His Glu Ser Pro Arg Leu Leu Ile Lys Tyr Ala Ser Gln Ser
        770                 775                 780
```

```
Ile Ser Gly Ile Pro Ser Arg Phe Ser Gly Ser Gly Ser Asp
785                 790                 795                 800

Phe Thr Leu Ser Ile Asn Ser Val Glu Pro Glu Asp Val Gly Val Tyr
                805                 810                 815

Tyr Cys Gln Asn Gly His Ser Phe Pro Leu Thr Phe Gly Ala Gly Thr
            820                 825                 830

Lys Leu Glu Leu Lys
        835

<210> SEQ ID NO 144
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 144

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 145
<211> LENGTH: 675
<212> TYPE: PRT
<213> ORGANISM: Artificial
<220> FEATURE:
<223> OTHER INFORMATION: Chimeric homo sapiens mus musculus

<400> SEQUENCE: 145

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Lys Pro Pro Ser Arg Glu Glu Met Thr Lys Asn Gln Val Ser Leu Ser
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Val Leu
385                 390                 395                 400

Asp Ser Asp Gly Ser Phe Arg Leu Ala Ser Tyr Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Ser Thr Gly Ser Glu Val Gln Leu Gln Gln Ser Gly Pro Glu Leu Val
450                 455                 460

Lys Pro Gly Ala Ser Val Lys Ile Ser Cys Lys Thr Ser Gly Tyr Thr
465                 470                 475                 480

Phe Thr Glu Tyr Thr Met His Trp Val Lys Gln Ser His Gly Lys Ser
                485                 490                 495

Leu Glu Trp Ile Gly Gly Ile Ser Pro Asn Ile Gly Gly Thr Ser Tyr
            500                 505                 510

Asn Gln Lys Phe Lys Gly Lys Ala Thr Leu Thr Val Asp Lys Ser Ser
        515                 520                 525

Ser Thr Ala Tyr Met Glu Leu Arg Ser Leu Thr Ser Glu Asp Ser Ala
530                 535                 540

Val Tyr Tyr Cys Ala Arg Arg Gly Gly Ser Phe Asp Tyr Trp Gly Gln
545                 550                 555                 560

Gly Thr Thr Leu Thr Val Ser Ser Arg Thr Val Ala Ala Pro Ser Val
                565                 570                 575

Phe Ile Phe Pro Pro Ser Asp Glu Gln Leu Lys Ser Gly Thr Ala Ser
            580                 585                 590

Val Val Cys Leu Leu Asn Asn Phe Tyr Pro Arg Glu Ala Lys Val Gln
        595                 600                 605

Trp Lys Val Asp Asn Ala Leu Gln Ser Gly Asn Ser Gln Glu Ser Val
610                 615                 620

Thr Glu Gln Asp Ser Lys Asp Ser Thr Tyr Ser Leu Ser Ser Thr Leu
625                 630                 635                 640

Thr Leu Ser Lys Ala Asp Tyr Glu Lys His Lys Val Tyr Ala Cys Glu
                645                 650                 655

Val Thr His Gln Gly Leu Ser Ser Pro Val Thr Lys Ser Phe Asn Arg
            660                 665                 670

Gly Glu Cys
        675

<210> SEQ ID NO 146
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 146

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

```
Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 147
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 147

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 148
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 148
```

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
50                      55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Gly Gly Gly Ser Gly Gly Gly Gly Ser Gly
    450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Arg Thr Val Ala Ala Pro Ser Val Phe Ile
    690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
        755                 760                 765

Ser Lys Ala Asp Tyr Glu Lys His Lys Val Tyr Ala Cys Glu Val Thr
    770                 775                 780

His Gln Gly Leu Ser Ser Pro Val Thr Lys Ser Phe Asn Arg Gly Glu
785                 790                 795                 800

Cys

<210> SEQ ID NO 149
<211> LENGTH: 214
<212> TYPE: PRT
<213> ORGANISM: Artificial

```
<220> FEATURE:
<223> OTHER INFORMATION: Chimeric homo sapiens mus musculus

<400> SEQUENCE: 149

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 150
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 150

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
```

```
            115                 120                 125
Leu Lys Ser Gly Thr Ala Ser Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 151
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 151

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
```

```
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Ser
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Gly Gly Gly Ser Gly Gly Gly Gly Ser Gly
    450                 455                 460
Gly Gly Ser Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
                485                 490                 495
Val Lys Gly Phe Tyr Pro Ser Asp Ile Ala Val Glu Trp Glu Ser Asn
            500                 505                 510
Gly Gln Pro Glu Asn Asn Tyr Lys Thr Thr Pro Pro Val Leu Asp Ser
        515                 520                 525
Asp Gly Ser Phe Phe Leu Tyr Ser Lys Leu Thr Val Asp Lys Ser Arg
    530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Ser Thr
                565                 570                 575
Gly Ser Glu Val Gln Leu Gln Gln Ser Gly Pro Glu Leu Val Lys Pro
            580                 585                 590
Gly Ala Ser Val Lys Ile Ser Cys Lys Thr Ser Gly Tyr Thr Phe Thr
        595                 600                 605
Glu Tyr Thr Met His Trp Val Lys Gln Ser His Gly Lys Ser Leu Glu
    610                 615                 620
Trp Ile Gly Gly Ile Ser Pro Asn Ile Gly Gly Thr Ser Tyr Asn Gln
625                 630                 635                 640
Lys Phe Lys Gly Lys Ala Thr Leu Thr Val Asp Lys Ser Ser Ser Thr
                645                 650                 655
Ala Tyr Met Glu Leu Arg Ser Leu Thr Ser Glu Asp Ser Ala Val Tyr
            660                 665                 670
Tyr Cys Ala Arg Arg Gly Gly Ser Phe Asp Tyr Trp Gly Gln Gly Thr
        675                 680                 685
```

Thr Leu Thr Val Ser Ser Arg Thr Val Ala Ala Pro Ser Val Phe Ile
            690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
                740                 745                 750

Gln Asp Ser Lys Asp Ser Thr Tyr Ser Leu Ser Ser Thr Leu Thr Leu
                755                 760                 765

Ser Lys Ala Asp Tyr Glu Lys His Lys Val Tyr Ala Cys Glu Val Thr
770                 775                 780

His Gln Gly Leu Ser Ser Pro Val Thr Lys Ser Phe Asn Arg Gly Glu
785                 790                 795                 800

Cys

<210> SEQ ID NO 152
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 152

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 153
<211> LENGTH: 218

<212> TYPE: PRT
<213> ORGANISM: Artificial
<220> FEATURE:
<223> OTHER INFORMATION: Chimeric homo sapiens mus musculus

<400> SEQUENCE: 153

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 154
<211> LENGTH: 796
<212> TYPE: PRT
<213> ORGANISM: Artificial
<220> FEATURE:
<223> OTHER INFORMATION: Chimeric homo sapiens mus musculus

<400> SEQUENCE: 154

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

```
Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ser Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Gly Gly Gly Gly Ser Gly Gly Gly Gly Ser Gly Gly Gly Gly Ser Gly
450                 455                 460

Gln Pro Arg Glu Pro Gln Val Tyr Thr Leu Pro Pro Ser Arg Glu Glu
465                 470                 475                 480

Met Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
            515                 520                 525
```

Leu Tyr Ser Lys Leu Thr Val Asp Lys Ser Arg Trp Gln Gln Gly Asn
            530                 535                 540

Val Phe Ser Cys Ser Val Met His Glu Ala Leu His Asn His Tyr Thr
545                 550                 555                 560

Gln Lys Ser Leu Ser Leu Ser Pro Gly Ser Thr Gly Ser Glu Val Gln
            565                 570                 575

Leu Gln Gln Ser Gly Pro Glu Leu Val Lys Pro Gly Ala Ser Val Lys
            580                 585                 590

Ile Ser Cys Lys Thr Ser Gly Tyr Thr Phe Thr Glu Tyr Thr Met His
            595                 600                 605

Trp Val Lys Gln Ser His Gly Lys Ser Leu Glu Trp Ile Gly Gly Ile
610                 615                 620

Ser Pro Asn Ile Gly Gly Thr Ser Tyr Asn Gln Lys Phe Lys Gly Lys
625                 630                 635                 640

Ala Thr Leu Thr Val Asp Lys Ser Ser Ser Thr Ala Tyr Met Glu Leu
            645                 650                 655

Arg Ser Leu Thr Ser Glu Asp Ser Ala Val Tyr Tyr Cys Ala Arg Arg
            660                 665                 670

Gly Gly Ser Phe Asp Tyr Trp Gly Gln Gly Thr Thr Leu Thr Val Ser
            675                 680                 685

Ser Arg Thr Val Ala Ala Pro Ser Val Phe Ile Phe Pro Pro Ser Asp
690                 695                 700

Glu Gln Leu Lys Ser Gly Thr Ala Ser Val Val Cys Leu Leu Asn Asn
705                 710                 715                 720

Phe Tyr Pro Arg Glu Ala Lys Val Gln Trp Lys Val Asp Asn Ala Leu
            725                 730                 735

Gln Ser Gly Asn Ser Gln Glu Ser Val Thr Glu Gln Asp Ser Lys Asp
            740                 745                 750

Ser Thr Tyr Ser Leu Ser Ser Thr Leu Thr Leu Ser Lys Ala Asp Tyr
            755                 760                 765

Glu Lys His Lys Val Tyr Ala Cys Glu Val Thr His Gln Gly Leu Ser
            770                 775                 780

Ser Pro Val Thr Lys Ser Phe Asn Arg Gly Glu Cys
785                 790                 795

<210> SEQ ID NO 155
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 155

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
            85                  90                  95

```
Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
        130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 156
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 156

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 157
<211> LENGTH: 819
```

<212> TYPE: PRT
<213> ORGANISM: Artificial
<220> FEATURE:
<223> OTHER INFORMATION: Chimeric homo sapiens mus musculus

<400> SEQUENCE: 157

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Gly Gly Gly Ser Gly Gly Gly Ser Gly
450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
            485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
            565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
595                 600                 605

Glu Tyr Thr Met His Trp Val Lys Gln Ser His Gly Lys Ser Leu Glu
            610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
            645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
            675                 680                 685

Thr Leu Thr Val Ser Ser Val Glu Gly Gly Ser Gly Gly Ser Gly Gly
            690                 695                 700

Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
            725                 730                 735

Ala Ser Gln Ser Ile Ser Asp Tyr Leu His Trp Tyr Gln Gln Lys Ser
            740                 745                 750

His Glu Ser Pro Arg Leu Leu Ile Lys Tyr Ala Ser Gln Ser Ile Ser
            755                 760                 765

Gly Ile Pro Ser Arg Phe Ser Gly Ser Gly Ser Gly Ser Asp Phe Thr
            770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
```

Glu Leu Lys

<210> SEQ ID NO 158
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 158

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 159
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 159

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr

-continued

```
               65                  70                  75                  80
          Met Gln Leu Ser Ser Leu Ala Ser Glu Asp Ser Ala Val Tyr Phe Cys
                              85                  90                  95
          Ala Arg Arg Glu Thr Thr Thr Val Gly Arg Tyr Tyr Tyr Ala Met Asp
                         100                 105                 110
          Tyr Trp Gly Gln Gly Thr Thr Val Thr Val Ser Ser Ala Ser Thr Lys
                         115                 120                 125
          Gly Pro Ser Val Phe Pro Leu Ala Pro Ser Ser Lys Ser Thr Ser Gly
                    130                 135                 140
          Gly Thr Ala Ala Leu Gly Cys Leu Val Lys Asp Tyr Phe Pro Glu Pro
          145                 150                 155                 160
          Val Thr Val Ser Trp Asn Ser Gly Ala Leu Thr Ser Gly Val His Thr
                              165                 170                 175
          Phe Pro Ala Val Leu Gln Ser Ser Gly Leu Tyr Ser Leu Ser Ser Val
                         180                 185                 190
          Val Thr Val Pro Ser Ser Ser Leu Gly Thr Gln Thr Tyr Ile Cys Asn
                         195                 200                 205
          Val Asn His Lys Pro Ser Asn Thr Lys Val Asp Lys Arg Val Glu Pro
                    210                 215                 220
          Lys Ser Cys Asp Lys Thr His Thr Ser Pro Pro Ser Pro Ala Pro Glu
          225                 230                 235                 240
          Leu Leu Gly Gly Pro Ser Val Phe Leu Phe Pro Pro Lys Pro Lys Asp
                              245                 250                 255
          Thr Leu Met Ile Ser Arg Thr Pro Glu Val Thr Cys Val Val Val Asp
                         260                 265                 270
          Val Ser His Glu Asp Pro Glu Val Lys Phe Asn Trp Tyr Val Asp Gly
                         275                 280                 285
          Val Glu Val His Asn Ala Lys Thr Lys Pro Arg Glu Glu Gln Tyr Ser
                    290                 295                 300
          Ser Thr Tyr Arg Val Val Ser Val Leu Thr Val Leu His Gln Asp Trp
          305                 310                 315                 320
          Leu Asn Gly Lys Glu Tyr Lys Cys Lys Val Ser Asn Lys Ala Leu Pro
                              325                 330                 335
          Ala Pro Ile Glu Lys Thr Ile Ser Lys Ala Lys Gly Gln Pro Arg Glu
                         340                 345                 350
          Pro Gln Val Tyr Thr Leu Pro Pro Ser Arg Glu Glu Met Thr Lys Asn
                         355                 360                 365
          Gln Val Ser Leu Thr Cys Leu Val Lys Gly Phe Tyr Pro Ser Asp Ile
                    370                 375                 380
          Ala Val Glu Trp Glu Ser Asn Gly Gln Pro Glu Asn Asn Tyr Lys Thr
          385                 390                 395                 400
          Thr Pro Pro Val Leu Asp Ser Asp Gly Ser Phe Phe Leu Tyr Ser Lys
                              405                 410                 415
          Leu Thr Val Asp Lys Ser Arg Trp Gln Gln Gly Asn Val Phe Ser Cys
                         420                 425                 430
          Ser Val Met His Glu Ala Leu His Asn His Tyr Thr Gln Lys Ser Leu
                         435                 440                 445
          Ser Leu Ser Pro Gly Gly Gly Gly Ser Gly Gly Gly Gly Ser Gly
                    450                 455                 460
          Gly Gly Gly Ser Gly Gln Pro Arg Glu Pro Gln Val Tyr Thr Leu Pro
          465                 470                 475                 480
          Pro Ser Arg Glu Glu Met Thr Lys Asn Gln Val Ser Leu Thr Cys Leu
                              485                 490                 495
```

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
                515                 520                 525

Asp Gly Ser Phe Phe Leu Tyr Ser Lys Leu Thr Val Asp Lys Ser Arg
            530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
            595                 600                 605

Glu Tyr Thr Met His Trp Val Lys Gln Ser His Gly Lys Ser Leu Glu
        610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
            675                 680                 685

Thr Leu Thr Val Ser Ser Val Glu Gly Gly Ser Gly Gly Ser Gly Gly
            690                 695                 700

Ser Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
                740                 745                 750

His Glu Ser Pro Arg Leu Leu Ile Lys Tyr Ala Ser Gln Ser Ile Ser
            755                 760                 765

Gly Ile Pro Ser Arg Phe Ser Gly Ser Gly Ser Gly Ser Asp Phe Thr
            770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys

<210> SEQ ID NO 160
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 160

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 161
<211> LENGTH: 815
<212> TYPE: PRT
<213> ORGANISM: Artificial
<220> FEATURE:
<223> OTHER INFORMATION: Chimeric homo sapiens mus musculus

<400> SEQUENCE: 161

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

```
Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
            210                 215                 220

Lys Ser Cys Gly Gly Gly Ser Ser Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ser Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Ser Thr Gly Ser Glu Val
                565                 570                 575

Gln Leu Gln Gln Ser Gly Pro Glu Leu Val Lys Pro Gly Ala Ser Val
            580                 585                 590

Lys Ile Ser Cys Lys Thr Ser Gly Tyr Thr Phe Thr Glu Tyr Thr Met
```

```
                595                 600                 605
    His Trp Val Lys Gln Ser His Gly Lys Ser Leu Glu Trp Ile Gly Gly
        610                 615                 620

Ile Ser Pro Asn Ile Gly Gly Thr Ser Tyr Asn Gln Lys Phe Lys Gly
    625                 630                 635                 640

Lys Ala Thr Leu Thr Val Asp Lys Ser Ser Ser Thr Ala Tyr Met Glu
                    645                 650                 655

Leu Arg Ser Leu Thr Ser Glu Asp Ser Ala Val Tyr Tyr Cys Ala Arg
                660                 665                 670

Arg Gly Gly Ser Phe Asp Tyr Trp Gly Gln Gly Thr Thr Leu Thr Val
                675                 680                 685

Ser Ser Val Glu Gly Gly Ser Gly Gly Ser Gly Gly Ser Gly Gly Ser
        690                 695                 700

Gly Gly Val Asp Asp Ile Val Met Thr Gln Ser Pro Ala Thr Leu Ser
    705                 710                 715                 720

Val Thr Pro Gly Asp Arg Val Ser Leu Ser Cys Arg Ala Ser Gln Ser
                    725                 730                 735

Ile Ser Asp Tyr Leu His Trp Tyr Gln Gln Lys Ser His Glu Ser Pro
                740                 745                 750

Arg Leu Leu Ile Lys Tyr Ala Ser Gln Ser Ile Ser Gly Ile Pro Ser
                755                 760                 765

Arg Phe Ser Gly Ser Gly Ser Gly Ser Asp Phe Thr Leu Ser Ile Asn
        770                 775                 780

Ser Val Glu Pro Glu Asp Val Gly Val Tyr Tyr Cys Gln Asn Gly His
    785                 790                 795                 800

Ser Phe Pro Leu Thr Phe Gly Ala Gly Thr Lys Leu Glu Leu Lys
                    805                 810                 815

<210> SEQ ID NO 162
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 162

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
```

-continued

```
         145                 150                 155                 160
Asn Trp Val Lys Gln Arg Pro Gly Gln Gly Leu Glu Trp Ile Gly Gln
                 165                 170                 175
Ile Trp Pro Gly Asp Gly Asp Thr Asn Tyr Asn Gly Lys Phe Lys Gly
                 180                 185                 190
Lys Ala Thr Leu Thr Ala Asp Glu Ser Ser Ser Thr Ala Tyr Met Gln
                 195                 200                 205
Leu Ser Ser Leu Ala Ser Glu Asp Ser Ala Val Tyr Phe Cys Ala Arg
                 210                 215                 220
Arg Glu Thr Thr Thr Val Gly Arg Tyr Tyr Ala Met Asp Tyr Trp
225                  230                 235                 240
Gly Gln Gly Thr Thr Val Thr Val Ser Ser Gly Gly Ser Ser Ala
                 245                 250                 255
Pro Glu Leu Leu Gly Gly Pro Ser Val Phe Leu Phe Pro Pro Lys Pro
                 260                 265                 270
Lys Asp Thr Leu Met Ile Ser Arg Thr Pro Glu Val Thr Cys Val Val
                 275                 280                 285
Val Asp Val Ser His Glu Asp Pro Glu Val Lys Phe Asn Trp Tyr Val
                 290                 295                 300
Asp Gly Val Glu Val His Asn Ala Lys Thr Lys Pro Arg Glu Glu Gln
305                  310                 315                 320
Tyr Ser Thr Tyr Arg Val Val Ser Val Leu Thr Val Leu His Gln
                 325                 330                 335
Asp Trp Leu Asn Gly Lys Glu Tyr Lys Cys Lys Val Ser Asn Lys Ala
                 340                 345                 350
Leu Pro Ala Pro Ile Glu Lys Thr Ile Ser Lys Ala Lys Gly Gln Pro
                 355                 360                 365
Arg Glu Pro Gln Val Tyr Thr Leu Pro Pro Ser Arg Glu Glu Met Thr
                 370                 375                 380
Lys Asn Gln Val Ser Leu Thr Cys Leu Val Lys Gly Phe Tyr Pro Ser
385                  390                 395                 400
Asp Ile Ala Val Glu Trp Glu Ser Asn Gly Gln Pro Glu Asn Asn Tyr
                 405                 410                 415
Lys Thr Thr Pro Pro Val Leu Asp Ser Asp Gly Ser Phe Phe Leu Tyr
                 420                 425                 430
Ser Lys Leu Thr Val Asp Lys Ser Arg Trp Gln Gln Gly Asn Val Phe
                 435                 440                 445
Ser Cys Ser Val Met His Glu Ala Leu His Asn His Tyr Thr Gln Lys
                 450                 455                 460
Ser Leu Ser Leu Ser Pro Gly Gly Gly Gly Ser Gly Gly Gly Gly
465                  470                 475                 480
Ser Gly Gly Gly Gly Ser Gly Gln Pro Arg Glu Pro Gln Val Tyr Thr
                 485                 490                 495
Leu Pro Pro Ser Arg Glu Glu Met Thr Lys Asn Gln Val Ser Leu Thr
                 500                 505                 510
Cys Leu Val Lys Gly Phe Tyr Pro Ser Asp Ile Ala Val Glu Trp Glu
                 515                 520                 525
Ser Asn Gly Gln Pro Glu Asn Asn Tyr Lys Thr Thr Pro Pro Val Leu
                 530                 535                 540
Asp Ser Asp Gly Ser Phe Phe Leu Tyr Ser Lys Leu Thr Val Asp Lys
545                  550                 555                 560
Ser Arg Trp Gln Gln Gly Asn Val Phe Ser Cys Ser Val Met His Glu
                 565                 570                 575
```

Ala Leu His Asn His Tyr Thr Gln Lys Ser Leu Ser Leu Ser Pro Gly
                580                 585                 590

Ser Thr Gly Ser Glu Val Gln Leu Gln Gln Ser Gly Pro Glu Leu Val
            595                 600                 605

Lys Pro Gly Ala Ser Val Lys Ile Ser Cys Lys Thr Ser Gly Tyr Thr
610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Arg Thr Val Ala Ala Pro Ser Val
705                 710                 715                 720

Phe Ile Phe Pro Pro Ser Asp Glu Gln Leu Lys Ser Gly Thr Ala Ser
                725                 730                 735

Val Val Cys Leu Leu Asn Asn Phe Tyr Pro Arg Glu Ala Lys Val Gln
            740                 745                 750

Trp Lys Val Asp Asn Ala Leu Gln Ser Gly Asn Ser Gln Glu Ser Val
        755                 760                 765

Thr Glu Gln Asp Ser Lys Asp Ser Thr Tyr Ser Leu Ser Ser Thr Leu
    770                 775                 780

Thr Leu Ser Lys Ala Asp Tyr Glu Lys His Lys Val Tyr Ala Cys Glu
785                 790                 795                 800

Val Thr His Gln Gly Leu Ser Ser Pro Val Thr Lys Ser Phe Asn Arg
                805                 810                 815

Gly Glu Cys

<210> SEQ ID NO 163
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 163

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

```
Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
            195                 200                 205

Ser Cys Asp Lys Thr His
    210

<210> SEQ ID NO 164
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 164

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255
```

```
Pro Glu Leu Leu Gly Gly Pro Ser Val Phe Leu Phe Pro Lys Pro
              260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
        515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
    610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
```

```
            675                 680                 685
Val Tyr Tyr Cys Ala Arg Arg Gly Gly Ser Phe Asp Tyr Trp Gly Gln
    690                 695                 700

Gly Thr Thr Leu Thr Val Ser Ser Ala Ser Thr Lys Gly Pro Ser Val
705                 710                 715                 720

Phe Pro Leu Ala Pro Ser Ser Lys Ser Thr Ser Gly Gly Thr Ala Ala
                725                 730                 735

Leu Gly Cys Leu Val Lys Asp Tyr Phe Pro Glu Pro Val Thr Val Ser
            740                 745                 750

Trp Asn Ser Gly Ala Leu Thr Ser Gly Val His Thr Phe Pro Ala Val
            755                 760                 765

Leu Gln Ser Ser Gly Leu Tyr Ser Leu Ser Ser Val Val Thr Val Pro
770                 775                 780

Ser Ser Ser Leu Gly Thr Gln Thr Tyr Ile Cys Asn Val Asn His Lys
785                 790                 795                 800

Pro Ser Asn Thr Lys Val Asp Lys Arg Val Glu Pro Lys Ser Cys Asp
                805                 810                 815

Lys Thr His

<210> SEQ ID NO 165
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 165

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 166
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 166

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 167
<211> LENGTH: 792
<212> TYPE: PRT
<213> ORGANISM: Artificial
<220> FEATURE:
<223> OTHER INFORMATION: Chimeric homo sapiens mus musculus

<400> SEQUENCE: 167

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys

```
                    85                  90                  95
Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Gly Gly Gly Ser Gly Gly Gly Gly Ser Gly
    450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510
```

-continued

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
        530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Asp Ile Val Met Thr Gln Ser Pro Ala Thr Leu Ser Val Thr
            580                 585                 590

Pro Gly Asp Arg Val Ser Leu Ser Cys Arg Ala Ser Gln Ser Ile Ser
        595                 600                 605

Asp Tyr Leu His Trp Tyr Gln Gln Lys Ser His Glu Ser Pro Arg Leu
    610                 615                 620

Leu Ile Lys Tyr Ala Ser Gln Ser Ile Ser Gly Ile Pro Ser Arg Phe
625                 630                 635                 640

Ser Gly Ser Gly Ser Gly Ser Asp Phe Thr Leu Ser Ile Asn Ser Val
                645                 650                 655

Glu Pro Glu Asp Val Gly Val Tyr Tyr Cys Gln Asn Gly His Ser Phe
            660                 665                 670

Pro Leu Thr Phe Gly Ala Gly Thr Lys Leu Glu Leu Lys Ala Ser Thr
        675                 680                 685

Lys Gly Pro Ser Val Phe Pro Leu Ala Pro Ser Ser Lys Ser Thr Ser
    690                 695                 700

Gly Gly Thr Ala Ala Leu Gly Cys Leu Val Lys Asp Tyr Phe Pro Glu
705                 710                 715                 720

Pro Val Thr Val Ser Trp Asn Ser Gly Ala Leu Thr Ser Gly Val His
                725                 730                 735

Thr Phe Pro Ala Val Leu Gln Ser Ser Gly Leu Tyr Ser Leu Ser Ser
            740                 745                 750

Val Val Thr Val Pro Ser Ser Ser Leu Gly Thr Gln Thr Tyr Ile Cys
        755                 760                 765

Asn Val Asn His Lys Pro Ser Asn Thr Lys Val Asp Lys Arg Val Glu
    770                 775                 780

Pro Lys Ser Cys Asp Lys Thr His
785                 790

<210> SEQ ID NO 168
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 168

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

```
Met Glu Leu Arg Ser Leu Thr Ser Glu Asp Ser Ala Val Tyr Tyr Cys
             85                  90                  95

Ala Arg Arg Gly Gly Ser Phe Asp Tyr Trp Gly Gln Gly Thr Thr Leu
            100                 105                 110

Thr Val Ser Ser Arg Thr Val Ala Ala Pro Ser Val Phe Ile Phe Pro
            115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
            165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
            195                 200                 205

Gly Leu Ser Ser Pro Val Thr Lys Ser Phe Asn Arg Gly Glu Cys
            210                 215                 220

<210> SEQ ID NO 169
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 169

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
            85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
210                 215                 220
```

```
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 170
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 170

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140
```

```
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560
```

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 171
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 171

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 172
<211> LENGTH: 445

```
<212> TYPE: PRT
<213> ORGANISM: Artificial
<220> FEATURE:
<223> OTHER INFORMATION: Chimeric homo sapiens mus musculus

<400> SEQUENCE: 172
```

| | | | | | | | | | | | | | | | |
|---|---|---|---|---|---|---|---|---|---|---|---|---|---|---|---|
| Asp | Ile | Gln | Leu | Thr | Gln | Ser | Pro | Ala | Ser | Leu | Ala | Val | Ser | Leu | Gly |
| 1 | | | | 5 | | | | | 10 | | | | | 15 | |
| Gln | Arg | Ala | Thr | Ile | Ser | Cys | Lys | Ala | Ser | Gln | Ser | Val | Asp | Tyr | Asp |
| | | | 20 | | | | | 25 | | | | | 30 | | |
| Gly | Asp | Ser | Tyr | Leu | Asn | Trp | Tyr | Gln | Gln | Ile | Pro | Gly | Gln | Pro | Pro |
| | | 35 | | | | | 40 | | | | | 45 | | | |
| Lys | Leu | Leu | Ile | Tyr | Asp | Ala | Ser | Asn | Leu | Val | Ser | Gly | Ile | Pro | Pro |
| 50 | | | | | 55 | | | | | 60 | | | | | |
| Arg | Phe | Ser | Gly | Ser | Gly | Ser | Gly | Thr | Asp | Phe | Thr | Leu | Asn | Ile | His |
| 65 | | | | | 70 | | | | | 75 | | | | | 80 |
| Pro | Val | Glu | Lys | Val | Asp | Ala | Ala | Thr | Tyr | His | Cys | Gln | Gln | Ser | Thr |
| | | | 85 | | | | | 90 | | | | | 95 | | |
| Glu | Asp | Pro | Trp | Thr | Phe | Gly | Gly | Gly | Thr | Lys | Leu | Glu | Ile | Lys | Arg |
| | | | 100 | | | | | 105 | | | | | 110 | | |
| Thr | Val | Ala | Ala | Pro | Ser | Val | Phe | Ile | Phe | Pro | Pro | Ser | Asp | Glu | Gln |
| | | | 115 | | | | | 120 | | | | | 125 | | |
| Leu | Lys | Ser | Gly | Thr | Ala | Ser | Val | Val | Cys | Leu | Leu | Asn | Asn | Phe | Tyr |
| | 130 | | | | | 135 | | | | | 140 | | | | |
| Pro | Arg | Glu | Ala | Lys | Val | Gln | Trp | Lys | Val | Asp | Asn | Ala | Leu | Gln | Ser |
| 145 | | | | | 150 | | | | | 155 | | | | | 160 |
| Gly | Asn | Ser | Gln | Glu | Ser | Val | Thr | Glu | Gln | Asp | Ser | Lys | Asp | Ser | Thr |
| | | | | 165 | | | | | 170 | | | | | 175 | |
| Tyr | Ser | Leu | Ser | Ser | Thr | Leu | Thr | Leu | Ser | Lys | Ala | Asp | Tyr | Glu | Lys |
| | | | 180 | | | | | 185 | | | | | 190 | | |
| His | Lys | Val | Tyr | Ala | Cys | Glu | Val | Thr | His | Gln | Gly | Leu | Ser | Ser | Pro |
| | 195 | | | | | 200 | | | | | 205 | | | | |
| Val | Thr | Lys | Ser | Phe | Asn | Arg | Gly | Glu | Cys | Asp | Lys | Thr | His | Thr | Cys |
| 210 | | | | | 215 | | | | | 220 | | | | | |
| Pro | Pro | Cys | Pro | Ala | Pro | Glu | Leu | Leu | Gly | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | 245 | | | | | 250 | | | | | 255 | | |
| Val | Thr | Cys | Val | Val | Val | Asp | Val | Ser | His | Glu | Asp | Pro | Glu | Val | Lys |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | | 275 | | | | | 280 | | | | | 285 | | |
| Pro | Arg | Glu | Glu | Gln | Tyr | Ser | Ser | Thr | Tyr | Arg | Val | Val | Ser | Val | Leu |
| | 290 | | | | | 295 | | | | | 300 | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Ala | Leu | Pro | Ala | Pro | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Arg | Glu | Glu | Met | Thr | Lys | Asn | Gln | Val | Ser | Leu | Thr | Cys | Leu | Val | Lys |
| | | | 355 | | | | | 360 | | | | | 365 | | |
| Gly | Phe | Tyr | Pro | Ser | Asp | Ile | Ala | Val | Glu | Trp | Glu | Ser | Asn | Gly | Gln |
| | 370 | | | | | 375 | | | | | 380 | | | | |

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 173
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 173

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
290                 295                 300
```

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
            485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
            515                 520                 525

Val Asp Lys Ser Ser Ser Thr Ala Tyr Met Glu Leu Arg Ser Leu Thr
530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
            565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
            595                 600                 605

Glu Ala Lys Val Gln Trp Lys Val Asp Asn Ala Leu Gln Ser Gly Asn
610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
            645                 650                 655

Val Tyr Ala Cys Glu Val Thr His Gln Gly Leu Ser Ser Pro Val Thr
            660                 665                 670

Lys Ser Phe Asn Arg Gly Glu Cys
            675                 680

<210> SEQ ID NO 174
<211> LENGTH: 214
<212> TYPE: PRT
<213> ORGANISM: Artificial
<220> FEATURE:
<223> OTHER INFORMATION: Chimeric homo sapiens mus musculus

```
<400> SEQUENCE: 174

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 175
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 175

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Ser Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Ser Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 176
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 176

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

-continued

```
Gly Gln Ile Trp Pro Gly Asp Gly Asp Thr Asn Tyr Asn Gly Lys Phe
         50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Ser Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
```

```
            465                 470                 475                 480
        Thr Ser Gly Tyr Thr Phe Thr Glu Tyr Thr Met His Trp Val Lys Gln
                        485                 490                 495
        Ser His Gly Lys Ser Leu Glu Trp Ile Gly Gly Ile Ser Pro Asn Ile
                        500                 505                 510
        Gly Gly Thr Ser Tyr Asn Gln Lys Phe Lys Gly Lys Ala Thr Leu Thr
                        515                 520                 525
        Val Asp Lys Ser Ser Ser Thr Ala Tyr Met Glu Leu Arg Ser Leu Thr
                        530                 535                 540
        Ser Glu Asp Ser Ala Val Tyr Tyr Cys Ala Arg Arg Gly Gly Ser Phe
        545                 550                 555                 560
        Asp Tyr Trp Gly Gln Gly Thr Thr Leu Thr Val Ser Ser Arg Thr Val
                        565                 570                 575
        Ala Ala Pro Ser Val Phe Ile Phe Pro Pro Ser Asp Glu Gln Leu Lys
                        580                 585                 590
        Ser Gly Thr Ala Ser Val Val Cys Leu Leu Asn Asn Phe Tyr Pro Arg
                        595                 600                 605
        Glu Ala Lys Val Gln Trp Lys Val Asp Asn Ala Leu Gln Ser Gly Asn
                        610                 615                 620
        Ser Gln Glu Ser Val Thr Glu Gln Asp Ser Lys Asp Ser Thr Tyr Ser
        625                 630                 635                 640
        Leu Ser Ser Thr Leu Thr Leu Ser Lys Ala Asp Tyr Glu Lys His Lys
                        645                 650                 655
        Val Tyr Ala Cys Glu Val Thr His Gln Gly Leu Ser Ser Pro Val Thr
                        660                 665                 670
        Lys Ser Phe Asn Arg Gly Glu Cys
                        675                 680

<210> SEQ ID NO 177
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 177

Asp Ile Val Met Thr Gln Ser Pro Ala Thr Leu Ser Val Thr Pro Gly
1               5                   10                  15
Asp Arg Val Ser Leu Ser Cys Arg Ala Ser Gln Ser Ile Ser Asp Tyr
                20                  25                  30
Leu His Trp Tyr Gln Gln Lys Ser His Glu Ser Pro Arg Leu Leu Ile
            35                  40                  45
Lys Tyr Ala Ser Gln Ser Ile Ser Gly Ile Pro Ser Arg Phe Ser Gly
        50                  55                  60
Ser Gly Ser Gly Ser Asp Phe Thr Leu Ser Ile Asn Ser Val Glu Pro
65                  70                  75                  80
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys Ala Ser Thr Lys Gly
                100                 105                 110
Pro Ser Val Phe Pro Leu Ala Pro Ser Ser Lys Ser Thr Ser Gly Gly
                115                 120                 125
Thr Ala Ala Leu Gly Cys Leu Val Lys Asp Tyr Phe Pro Glu Pro Val
            130                 135                 140
Thr Val Ser Trp Asn Ser Gly Ala Leu Thr Ser Gly Val His Thr Phe
```

```
                145                 150                 155                 160
Pro Ala Val Leu Gln Ser Ser Gly Leu Tyr Ser Leu Ser Ser Val Val
                    165                 170                 175
Thr Val Pro Ser Ser Leu Gly Thr Gln Thr Tyr Ile Cys Asn Val
                180                 185                 190
Asn His Lys Pro Ser Asn Thr Lys Val Asp Lys Arg Val Glu Pro Lys
            195                 200                 205
Ser Cys Asp Lys Thr His
            210

<210> SEQ ID NO 178
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 178

Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asp Ser Tyr Leu Asn Trp Tyr Gln Gln Ile Pro Gly Gln Pro Pro
            35                  40                  45
Lys Leu Leu Ile Tyr Asp Ala Ser Asn Leu Val Ser Gly Ile Pro Pro
50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
```

```
                290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 179
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 179

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
                35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
```

-continued

```
                210                 215                 220
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
            515                 520                 525

Val Asp Lys Ser Ser Ser Thr Ala Tyr Met Glu Leu Arg Ser Leu Thr
            530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Val Glu Gly
                565                 570                 575

Gly Ser Gly Gly Ser Gly Gly Ser Gly Gly Ser Gly Gly Val Asp Asp
                580                 585                 590

Ile Val Met Thr Gln Ser Pro Ala Thr Leu Ser Val Thr Pro Gly Asp
            595                 600                 605

Arg Val Ser Leu Ser Cys Arg Ala Ser Gln Ser Ile Ser Asp Tyr Leu
            610                 615                 620

His Trp Tyr Gln Gln Lys Ser His Glu Ser Pro Arg Leu Leu Ile Lys
625                 630                 635                 640
```

```
Tyr Ala Ser Gln Ser Ile Ser Gly Ile Pro Ser Arg Phe Ser Gly Ser
                645                 650                 655

Gly Ser Gly Ser Asp Phe Thr Leu Ser Ile Asn Ser Val Glu Pro Glu
            660                 665                 670

Asp Val Gly Val Tyr Tyr Cys Gln Asn Gly His Ser Phe Pro Leu Thr
        675                 680                 685

Phe Gly Ala Gly Thr Lys Leu Glu Leu Lys
    690                 695

<210> SEQ ID NO 180
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 180

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
                435                 440                 445

<210> SEQ ID NO 181
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 181

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220
```

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Ser
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
            485                 490                 495

Ser His Gly Lys Ser Leu Glu Trp Ile Gly Gly Ile Ser Pro Asn Ile
        500                 505                 510

Gly Gly Thr Ser Tyr Asn Gln Lys Phe Lys Gly Lys Ala Thr Leu Thr
    515                 520                 525

Val Asp Lys Ser Ser Ser Thr Ala Tyr Met Glu Leu Arg Ser Leu Thr
530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Val Glu Gly
            565                 570                 575

Gly Ser Gly Gly Ser Gly Gly Ser Gly Gly Ser Gly Gly Val Asp Asp
        580                 585                 590

Ile Val Met Thr Gln Ser Pro Ala Thr Leu Ser Val Thr Pro Gly Asp
    595                 600                 605

Arg Val Ser Leu Ser Cys Arg Ala Ser Gln Ser Ile Ser Asp Tyr Leu
610                 615                 620

His Trp Tyr Gln Gln Lys Ser His Glu Ser Pro Arg Leu Leu Ile Lys
625                 630                 635                 640
```

```
Tyr Ala Ser Gln Ser Ile Ser Gly Ile Pro Ser Arg Phe Ser Gly Ser
                645                 650                 655

Gly Ser Gly Ser Asp Phe Thr Leu Ser Ile Asn Ser Val Glu Pro Glu
            660                 665                 670

Asp Val Gly Val Tyr Tyr Cys Gln Asn Gly His Ser Phe Pro Leu Thr
        675                 680                 685

Phe Gly Ala Gly Thr Lys Leu Glu Leu Lys
    690                 695

<210> SEQ ID NO 182
<211> LENGTH: 454
<212> TYPE: PRT
<213> ORGANISM: Artificial
<220> FEATURE:
<223> OTHER INFORMATION: Chimeric homo sapiens mus musculus

<400> SEQUENCE: 182

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300
```

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 183
<211> LENGTH: 670
<212> TYPE: PRT
<213> ORGANISM: Artificial
<220> FEATURE:
<223> OTHER INFORMATION: Chimeric homo sapiens mus musculus

<400> SEQUENCE: 183

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

```
Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225             230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Ser Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Ser Thr Gly Ser Glu
            435                 440                 445

Val Gln Leu Gln Gln Ser Gly Pro Glu Leu Val Lys Pro Gly Ala Ser
    450                 455                 460

Val Lys Ile Ser Cys Lys Thr Ser Gly Tyr Thr Phe Thr Glu Tyr Thr
465                 470                 475                 480

Met His Trp Val Lys Gln Ser His Gly Lys Ser Leu Glu Trp Ile Gly
                485                 490                 495

Gly Ile Ser Pro Asn Ile Gly Gly Thr Ser Tyr Asn Gln Lys Phe Lys
                500                 505                 510

Gly Lys Ala Thr Leu Thr Val Asp Lys Ser Ser Ser Thr Ala Tyr Met
            515                 520                 525

Glu Leu Arg Ser Leu Thr Ser Glu Asp Ser Ala Val Tyr Tyr Cys Ala
530                 535                 540

Arg Arg Gly Gly Ser Phe Asp Tyr Trp Gly Gln Gly Thr Thr Leu Thr
545                 550                 555                 560

Val Ser Ser Arg Thr Val Ala Ala Pro Ser Val Phe Ile Phe Pro Pro
                565                 570                 575

Ser Asp Glu Gln Leu Lys Ser Gly Thr Ala Ser Val Val Cys Leu Leu
            580                 585                 590

Asn Asn Phe Tyr Pro Arg Glu Ala Lys Val Gln Trp Lys Val Asp Asn
            595                 600                 605

Ala Leu Gln Ser Gly Asn Ser Gln Glu Ser Val Thr Glu Gln Asp Ser
610                 615                 620

Lys Asp Ser Thr Tyr Ser Leu Ser Ser Thr Leu Thr Leu Ser Lys Ala
```

```
                625                 630                 635                 640
Asp Tyr Glu Lys His Lys Val Tyr Ala Cys Glu Val Thr His Gln Gly
                    645                 650                 655
Leu Ser Ser Pro Val Thr Lys Ser Phe Asn Arg Gly Glu Cys
                660                 665                 670
```

<210> SEQ ID NO 184
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 184

```
Asp Ile Val Met Thr Gln Ser Pro Ala Thr Leu Ser Val Thr Pro Gly
1               5                   10                  15
Asp Arg Val Ser Leu Ser Cys Arg Ala Ser Gln Ser Ile Ser Asp Tyr
                20                  25                  30
Leu His Trp Tyr Gln Gln Lys Ser His Glu Ser Pro Arg Leu Leu Ile
            35                  40                  45
Lys Tyr Ala Ser Gln Ser Ile Ser Gly Ile Pro Ser Arg Phe Ser Gly
        50                  55                  60
Ser Gly Ser Gly Ser Asp Phe Thr Leu Ser Ile Asn Ser Val Glu Pro
65                  70                  75                  80
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys Ala Ser Thr Lys Gly
            100                 105                 110
Pro Ser Val Phe Pro Leu Ala Pro Ser Ser Lys Ser Thr Ser Gly Gly
        115                 120                 125
Thr Ala Ala Leu Gly Cys Leu Val Lys Asp Tyr Phe Pro Glu Pro Val
    130                 135                 140
Thr Val Ser Trp Asn Ser Gly Ala Leu Thr Ser Gly Val His Thr Phe
145                 150                 155                 160
Pro Ala Val Leu Gln Ser Ser Gly Leu Tyr Ser Leu Ser Ser Val Val
                165                 170                 175
Thr Val Pro Ser Ser Ser Leu Gly Thr Gln Thr Tyr Ile Cys Asn Val
            180                 185                 190
Asn His Lys Pro Ser Asn Thr Lys Val Asp Lys Arg Val Glu Pro Lys
        195                 200                 205
Ser Cys Asp Lys Thr His
    210
```

<210> SEQ ID NO 185
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 185

```
Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asp Ser Tyr Leu Asn Trp Tyr Gln Gln Ile Pro Gly Gln Pro Pro
            35                  40                  45
```

```
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 186
<211> LENGTH: 671
<212> TYPE: PRT
```

<213> ORGANISM: Artificial
<220> FEATURE:
<223> OTHER INFORMATION: Chimeric homo sapiens mus musculus

<400> SEQUENCE: 186

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr

```
385                 390                 395                 400
Thr Pro Pro Val Leu Asp Ser Asp Gly Ser Phe Phe Leu Tyr Ser Lys
            405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Ser Thr Gly Ser Asp Ile Val Met Thr Gln Ser
    450                 455                 460
Pro Ala Thr Leu Ser Val Thr Pro Gly Asp Arg Val Ser Leu Ser Cys
465                 470                 475                 480
Arg Ala Ser Gln Ser Ile Ser Asp Tyr Leu His Trp Tyr Gln Gln Lys
                485                 490                 495
Ser His Glu Ser Pro Arg Leu Leu Ile Lys Tyr Ala Ser Gln Ser Ile
            500                 505                 510
Ser Gly Ile Pro Ser Arg Phe Ser Gly Ser Gly Ser Gly Ser Asp Phe
            515                 520                 525
Thr Leu Ser Ile Asn Ser Val Glu Pro Glu Asp Val Gly Val Tyr Tyr
    530                 535                 540
Cys Gln Asn Gly His Ser Phe Pro Leu Thr Phe Gly Ala Gly Thr Lys
545                 550                 555                 560
Leu Glu Leu Lys Ala Ser Thr Lys Gly Pro Ser Val Phe Pro Leu Ala
                565                 570                 575
Pro Ser Ser Lys Ser Thr Ser Gly Gly Thr Ala Ala Leu Gly Cys Leu
            580                 585                 590
Val Lys Asp Tyr Phe Pro Glu Pro Val Thr Val Ser Trp Asn Ser Gly
    595                 600                 605
Ala Leu Thr Ser Gly Val His Thr Phe Pro Ala Val Leu Gln Ser Ser
    610                 615                 620
Gly Leu Tyr Ser Leu Ser Ser Val Val Thr Val Pro Ser Ser Ser Leu
625                 630                 635                 640
Gly Thr Gln Thr Tyr Ile Cys Asn Val Asn His Lys Pro Ser Asn Thr
                645                 650                 655
Lys Val Asp Lys Arg Val Glu Pro Lys Ser Cys Asp Lys Thr His
            660                 665                 670

<210> SEQ ID NO 187
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 187

Glu Val Gln Leu Gln Gln Ser Gly Pro Glu Leu Val Lys Pro Gly Ala
1               5                   10                  15
Ser Val Lys Ile Ser Cys Lys Thr Ser Gly Tyr Thr Phe Thr Glu Tyr
            20                  25                  30
Thr Met His Trp Val Lys Gln Ser His Gly Lys Ser Leu Glu Trp Ile
        35                  40                  45
Gly Gly Ile Ser Pro Asn Ile Gly Gly Thr Ser Tyr Asn Gln Lys Phe
    50                  55                  60
Lys Gly Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
```

-continued

```
                    85                  90                  95
Ala Arg Arg Gly Gly Ser Phe Asp Tyr Trp Gly Gln Gly Thr Thr Leu
                100                 105                 110

Thr Val Ser Ser Arg Thr Val Ala Ala Pro Ser Val Phe Ile Phe Pro
            115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220
```

<210> SEQ ID NO 188
<211> LENGTH: 680
<212> TYPE: PRT
<213> ORGANISM: Artificial
<220> FEATURE:
<223> OTHER INFORMATION: Human-mouse chimeric

<400> SEQUENCE: 188

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

```
                225               230                235                240
    Ser Val Phe Leu Phe Pro Pro Lys Pro Lys Asp Thr Leu Met Ile Ser
                    245                250                255

Arg Thr Pro Glu Val Thr Cys Val Val Val Asp Val Ser His Glu Asp
                    260                265                270

Pro Glu Val Lys Phe Asn Trp Tyr Val Asp Gly Val Glu Val His Asn
                    275                280                285

Ala Lys Thr Lys Pro Arg Glu Glu Gln Tyr Asn Ser Thr Tyr Arg Val
    290                295                300

Val Ser Val Leu Thr Val Leu His Gln Asp Trp Leu Asn Gly Lys Glu
    305                310                315                320

Tyr Lys Cys Lys Val Ser Asn Lys Ala Leu Pro Ala Pro Ile Glu Lys
                    325                330                335

Thr Ile Ser Lys Ala Lys Gly Gln Pro Arg Glu Pro Gln Val Tyr Thr
                    340                345                350

Leu Pro Pro Ser Arg Glu Glu Met Thr Lys Asn Gln Val Ser Leu Thr
                    355                360                365

Cys Leu Val Lys Gly Phe Tyr Pro Ser Asp Ile Ala Val Glu Trp Glu
    370                375                380

Ser Asn Gly Gln Pro Glu Asn Asn Tyr Lys Thr Thr Pro Pro Val Leu
    385                390                395                400

Asp Ser Asp Gly Ser Phe Phe Leu Tyr Ser Lys Leu Thr Val Asp Lys
                    405                410                415

Ser Arg Trp Gln Gln Gly Asn Val Phe Ser Cys Ser Val Met His Glu
                    420                425                430

Ala Leu His Asn His Tyr Thr Gln Lys Ser Leu Ser Leu Ser Pro Gly
                    435                440                445

Ser Thr Gly Ser Gln Val Gln Leu Gln Gln Pro Gly Ala Glu Leu Val
    450                455                460

Lys Pro Gly Ala Ser Val Lys Met Ser Cys Lys Ala Ser Gly Tyr Thr
    465                470                475                480

Phe Thr Ser Tyr Asn Met His Trp Val Lys Gln Thr Pro Gly Arg Gly
                    485                490                495

Leu Glu Trp Ile Gly Ala Ile Tyr Pro Gly Asn Gly Asp Thr Ser Tyr
                    500                505                510

Asn Gln Lys Phe Lys Gly Lys Ala Thr Leu Thr Ala Asp Lys Ser Ser
                    515                520                525

Ser Thr Ala Tyr Met Gln Leu Ser Ser Leu Thr Ser Glu Asp Ser Ala
    530                535                540

Val Tyr Tyr Cys Ala Arg Ser Thr Tyr Tyr Gly Gly Asp Trp Tyr Phe
    545                550                555                560

Asn Val Trp Gly Ala Gly Thr Thr Val Thr Val Ser Ala Arg Thr Val
                    565                570                575

Ala Ala Pro Ser Val Phe Ile Phe Pro Pro Ser Asp Glu Gln Leu Lys
                    580                585                590

Ser Gly Thr Ala Ser Val Val Cys Leu Leu Asn Asn Phe Tyr Pro Arg
                    595                600                605

Glu Ala Lys Val Gln Trp Lys Val Asp Asn Ala Leu Gln Ser Gly Asn
                    610                615                620

Ser Gln Glu Ser Val Thr Glu Gln Asp Ser Lys Asp Ser Thr Tyr Ser
    625                630                635                640

Leu Ser Ser Thr Leu Thr Leu Ser Lys Ala Asp Tyr Glu Lys His Lys
                    645                650                655
```

```
Val Tyr Ala Cys Glu Val Thr His Gln Gly Leu Ser Ser Pro Val Thr
                660                 665                 670

Lys Ser Phe Asn Arg Gly Glu Cys
            675                 680

<210> SEQ ID NO 189
<211> LENGTH: 446
<212> TYPE: PRT
<213> ORGANISM: Artificial
<220> FEATURE:
<223> OTHER INFORMATION: Human-mouse chimeric

<400> SEQUENCE: 189

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 190
<211> LENGTH: 459
<212> TYPE: PRT
<213> ORGANISM: Artificial
<220> FEATURE:
<223> OTHER INFORMATION: Human-mouse chimeric

<400> SEQUENCE: 190

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
        195                 200                 205

Cys Asp Lys Thr His Gly Gly Ser Ser Glu Val Gln Leu Gln Gln
    210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255
```

```
Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Ser Thr Ala Tyr Met Glu Leu Arg Ser Leu
    290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
                325                 330                 335

Gly Gly Ser Gly Gly Ser Gly Gly Ser Gly Gly Ser Gly Gly Val Asp
            340                 345                 350

Asp Ile Val Met Thr Gln Ser Pro Ala Thr Leu Ser Val Thr Pro Gly
            355                 360                 365

Asp Arg Val Ser Leu Ser Cys Arg Ala Ser Gln Ser Ile Ser Asp Tyr
    370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
    435                 440                 445

Thr Phe Gly Ala Gly Thr Lys Leu Glu Leu Lys
    450                 455

<210> SEQ ID NO 191
<211> LENGTH: 446
<212> TYPE: PRT
<213> ORGANISM: Artificial
<220> FEATURE:
<223> OTHER INFORMATION: Human-mouse chimeric

<400> SEQUENCE: 191

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ser Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 192
<211> LENGTH: 680
<212> TYPE: PRT
<213> ORGANISM: Artificial
<220> FEATURE:
<223> OTHER INFORMATION: Human mouse chimeric

<400> SEQUENCE: 192

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Thr Gly Ser Gln Val Gln Leu Gln Gln Pro Gly Ala Glu Leu Val
    450                 455                 460

Lys Pro Gly Ala Ser Val Lys Met Ser Cys Lys Ala Ser Gly Tyr Thr
465                 470                 475                 480

Phe Thr Ser Tyr Asn Met His Trp Val Lys Gln Thr Pro Gly Arg Gly
                485                 490                 495
```

```
Leu Glu Trp Ile Gly Ala Ile Tyr Pro Gly Asn Gly Asp Thr Ser Tyr
                500                 505                 510

Asn Gln Lys Phe Lys Gly Lys Ala Thr Leu Thr Ala Asp Lys Ser Ser
            515                 520                 525

Ser Thr Ala Tyr Met Gln Leu Ser Ser Leu Thr Ser Glu Asp Ser Ala
        530                 535                 540

Val Tyr Tyr Cys Ala Arg Ser Thr Tyr Gly Gly Asp Trp Tyr Phe
545                 550                 555                 560

Asn Val Trp Gly Ala Gly Thr Thr Val Thr Val Ser Ala Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 193
<211> LENGTH: 459
<212> TYPE: PRT
<213> ORGANISM: Artificial
<220> FEATURE:
<223> OTHER INFORMATION: Human mouse chimeric

<400> SEQUENCE: 193

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175
```

```
Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
            195                 200                 205

Cys Asp Lys Thr His Gly Gly Ser Ser Glu Val Gln Leu Gln Gln
210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
            245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
            275                 280                 285

Thr Val Asp Lys Ser Ser Thr Ala Tyr Met Glu Leu Arg Ser Leu
            290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
            325                 330                 335

Gly Gly Ser Gly Gly Ser Gly Gly Ser Gly Gly Val Asp
            340                 345                 350

Asp Ile Val Met Thr Gln Ser Pro Ala Thr Leu Ser Val Thr Pro Gly
            355                 360                 365

Asp Arg Val Ser Leu Ser Cys Arg Ala Ser Gln Ser Ile Ser Asp Tyr
            370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
            405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
            435                 440                 445

Thr Phe Gly Ala Gly Thr Lys Leu Glu Leu Lys
            450                 455

<210> SEQ ID NO 194
<211> LENGTH: 801
<212> TYPE: PRT
<213> ORGANISM: Artificial
<220> FEATURE:
<223> OTHER INFORMATION: Human-mouse chimeric

<400> SEQUENCE: 194

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
65                  70                  75                  80
```

-continued

```
Met Glu Leu Ser Ser Leu Arg Ser Glu Asp Thr Ala Val Tyr Tyr Cys
             85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Ser Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Gly
    450                 455                 460

Gln Pro Arg Glu Pro Gln Val Tyr Thr Leu Pro Pro Ser Arg Glu Glu
465                 470                 475                 480

Met Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
```

500                 505                 510
Asn Tyr Lys Thr Thr Pro Val Leu Asp Ser Asp Gly Ser Phe Phe
            515                 520                 525

Leu Tyr Ser Lys Leu Thr Val Asp Lys Ser Arg Trp Gln Gln Gly Asn
        530                 535                 540

Val Phe Ser Cys Ser Val Met His Glu Ala Leu His Asn His Tyr Thr
545                 550                 555                 560

Gln Lys Ser Leu Ser Leu Ser Pro Gly Ser Thr Gly Ser Gln Val Gln
            565                 570                 575

Leu Gln Gln Pro Gly Ala Glu Leu Val Lys Pro Gly Ala Ser Val Lys
        580                 585                 590

Met Ser Cys Lys Ala Ser Gly Tyr Thr Phe Thr Ser Tyr Asn Met His
        595                 600                 605

Trp Val Lys Gln Thr Pro Gly Arg Gly Leu Glu Trp Ile Gly Ala Ile
        610                 615                 620

Tyr Pro Gly Asn Gly Asp Thr Ser Tyr Asn Gln Lys Phe Lys Gly Lys
625                 630                 635                 640

Ala Thr Leu Thr Ala Asp Lys Ser Ser Ser Thr Ala Tyr Met Gln Leu
            645                 650                 655

Ser Ser Leu Thr Ser Glu Asp Ser Ala Val Tyr Tyr Cys Ala Arg Ser
        660                 665                 670

Thr Tyr Tyr Gly Gly Asp Trp Tyr Phe Asn Val Trp Gly Ala Gly Thr
        675                 680                 685

Thr Val Thr Val Ser Ala Arg Thr Val Ala Ala Pro Ser Val Phe Ile
        690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
            725                 730                 735

Val Asp Asn Ala Leu Gln Ser Gly Asn Ser Gln Glu Ser Val Thr Glu
        740                 745                 750

Gln Asp Ser Lys Asp Ser Thr Tyr Ser Leu Ser Ser Thr Leu Thr Leu
        755                 760                 765

Ser Lys Ala Asp Tyr Glu Lys His Lys Val Tyr Ala Cys Glu Val Thr
        770                 775                 780

His Gln Gly Leu Ser Ser Pro Val Thr Lys Ser Phe Asn Arg Gly Glu
785                 790                 795                 800

Cys

<210> SEQ ID NO 195
<211> LENGTH: 219
<212> TYPE: PRT
<213> ORGANISM: Artificial
<220> FEATURE:
<223> OTHER INFORMATION: Human-mouse chimeric

<400> SEQUENCE: 195

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 196
<211> LENGTH: 459
<212> TYPE: PRT
<213> ORGANISM: Artificial
<220> FEATURE:
<223> OTHER INFORMATION: Human - mouse chimeric

<400> SEQUENCE: 196

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Ile
                 20                  25                  30

His Trp Phe Gln Gln Lys Pro Gly Ser Ser Pro Lys Pro Trp Ile Tyr
             35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
            115                 120                 125

Ala Ala Leu Gly Cys Leu Val Lys Asp Tyr Phe Pro Glu Pro Val Thr
130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
            195                 200                 205
```

-continued

Cys Asp Lys Thr His Gly Gly Ser Ser Ser Glu Val Gln Leu Gln Gln
        210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Thr Ala Tyr Met Glu Leu Arg Ser Leu
        290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
                325                 330                 335

Gly Gly Ser Gly Gly Ser Gly Gly Ser Gly Gly Ser Gly Gly Val Asp
            340                 345                 350

Asp Ile Val Met Thr Gln Ser Pro Ala Thr Leu Ser Val Thr Pro Gly
        355                 360                 365

Asp Arg Val Ser Leu Ser Cys Arg Ala Ser Gln Ser Ile Ser Asp Tyr
        370                 375                 380

Leu His Trp Tyr Gln Gln Lys Ser His Glu Ser Pro Arg Leu Leu Ile
385                 390                 395                 400

Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
        435                 440                 445

Thr Phe Gly Ala Gly Thr Lys Leu Glu Leu Lys
        450                 455

<210> SEQ ID NO 197
<211> LENGTH: 928
<212> TYPE: PRT
<213> ORGANISM: Artificial
<220> FEATURE:
<223> OTHER INFORMATION: Human-mouse chimeric

<400> SEQUENCE: 197

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

```
Gly Gly Gly Gly Ser Gly Gly Gly Ser Gly Gly Gly Ser Gln
            115                 120                 125
Val Gln Leu Val Gln Ser Gly Ala Glu Val Lys Lys Pro Gly Ser Ser
    130                 135                 140
Val Lys Val Ser Cys Lys Ala Ser Gly Tyr Ala Phe Ser Tyr Ser Trp
145                 150                 155                 160
Ile Asn Trp Val Arg Gln Ala Pro Gly Gln Gly Leu Glu Trp Met Gly
                165                 170                 175
Arg Ile Phe Pro Gly Asp Gly Asp Thr Asp Tyr Asn Gly Lys Phe Lys
                180                 185                 190
Gly Arg Val Thr Ile Thr Ala Asp Lys Ser Thr Ser Thr Ala Tyr Met
            195                 200                 205
Glu Leu Ser Ser Leu Arg Ser Glu Asp Thr Ala Val Tyr Tyr Cys Ala
    210                 215                 220
Arg Asn Val Phe Asp Gly Tyr Trp Leu Val Tyr Trp Gly Gln Gly Thr
225                 230                 235                 240
Leu Val Thr Val Ser Ser Ala Ser Thr Lys Gly Pro Ser Val Phe Pro
                245                 250                 255
Leu Ala Pro Ser Ser Lys Ser Thr Ser Gly Gly Thr Ala Ala Leu Gly
            260                 265                 270
Cys Leu Val Lys Asp Tyr Phe Pro Glu Pro Val Thr Val Ser Trp Asn
    275                 280                 285
Ser Gly Ala Leu Thr Ser Gly Val His Thr Phe Pro Ala Val Leu Gln
        290                 295                 300
Ser Ser Gly Leu Tyr Ser Leu Ser Ser Val Val Thr Val Pro Ser Ser
305                 310                 315                 320
Ser Leu Gly Thr Gln Thr Tyr Ile Cys Asn Val Asn His Lys Pro Ser
                325                 330                 335
Asn Thr Lys Val Asp Lys Arg Val Glu Pro Lys Ser Cys Asp Lys Thr
            340                 345                 350
His Thr Ser Pro Pro Ser Pro Ala Pro Glu Leu Leu Gly Gly Pro Ser
    355                 360                 365
Val Phe Leu Phe Pro Pro Lys Pro Lys Asp Thr Leu Met Ile Ser Arg
    370                 375                 380
Thr Pro Glu Val Thr Cys Val Val Val Asp Val Ser His Glu Asp Pro
385                 390                 395                 400
Glu Val Lys Phe Asn Trp Tyr Val Asp Gly Val Glu Val His Asn Ala
                405                 410                 415
Lys Thr Lys Pro Arg Glu Glu Gln Tyr Ser Ser Thr Tyr Arg Val Val
            420                 425                 430
Ser Val Leu Thr Val Leu His Gln Asp Trp Leu Asn Gly Lys Glu Tyr
    435                 440                 445
Lys Cys Lys Val Ser Asn Lys Ala Leu Pro Ala Pro Ile Glu Lys Thr
    450                 455                 460
Ile Ser Lys Ala Lys Gly Gln Pro Arg Glu Pro Gln Val Tyr Thr Leu
465                 470                 475                 480
Pro Pro Ser Arg Glu Glu Met Thr Lys Asn Gln Val Ser Leu Thr Cys
                485                 490                 495
Leu Val Lys Gly Phe Tyr Pro Ser Asp Ile Ala Val Glu Trp Glu Ser
            500                 505                 510
Asn Gly Gln Pro Glu Asn Asn Tyr Lys Thr Thr Pro Pro Val Leu Asp
    515                 520                 525
```

Ser Asp Gly Ser Phe Phe Leu Tyr Ser Lys Leu Thr Val Asp Lys Ser
    530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Gly
                565                 570                 575

Gly Gly Gly Ser Gly Gly Gly Ser Gly Gly Gly Ser Gly Gln
            580                 585                 590

Pro Arg Glu Pro Gln Val Tyr Thr Leu Pro Pro Ser Arg Glu Glu Met
        595                 600                 605

Thr Lys Asn Gln Val Ser Leu Thr Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Lys Leu Thr Val Asp Lys Ser Arg Trp Gln Gln Gly Asn Val
            660                 665                 670

Phe Ser Cys Ser Val Met His Glu Ala Leu His Asn His Tyr Thr Gln
        675                 680                 685

Lys Ser Leu Ser Leu Ser Pro Gly Ser Thr Gly Ser Gln Val Gln Leu
    690                 695                 700

Gln Gln Pro Gly Ala Glu Leu Val Lys Pro Gly Ala Ser Val Lys Met
705                 710                 715                 720

Ser Cys Lys Ala Ser Gly Tyr Thr Phe Thr Ser Tyr Asn Met His Trp
                725                 730                 735

Val Lys Gln Thr Pro Gly Arg Gly Leu Glu Trp Ile Gly Ala Ile Tyr
            740                 745                 750

Pro Gly Asn Gly Asp Thr Ser Tyr Asn Gln Lys Phe Lys Gly Lys Ala
        755                 760                 765

Thr Leu Thr Ala Asp Lys Ser Ser Thr Ala Tyr Met Gln Leu Ser
    770                 775                 780

Ser Leu Thr Ser Glu Asp Ser Ala Val Tyr Tyr Cys Ala Arg Ser Thr
785                 790                 795                 800

Tyr Tyr Gly Gly Asp Trp Tyr Phe Asn Val Trp Gly Ala Gly Thr Thr
                805                 810                 815

Val Thr Val Ser Ala Arg Thr Val Ala Ala Pro Ser Val Phe Ile Phe
            820                 825                 830

Pro Pro Ser Asp Glu Gln Leu Lys Ser Gly Thr Ala Ser Val Val Cys
        835                 840                 845

Leu Leu Asn Asn Phe Tyr Pro Arg Glu Ala Lys Val Gln Trp Lys Val
    850                 855                 860

Asp Asn Ala Leu Gln Ser Gly Asn Ser Gln Glu Ser Val Thr Glu Gln
865                 870                 875                 880

Asp Ser Lys Asp Ser Thr Tyr Ser Leu Ser Ser Thr Leu Thr Leu Ser
                885                 890                 895

Lys Ala Asp Tyr Glu Lys His Lys Val Tyr Ala Cys Glu Val Thr His
            900                 905                 910

Gln Gly Leu Ser Ser Pro Val Thr Lys Ser Phe Asn Arg Gly Glu Cys
        915                 920                 925

<210> SEQ ID NO 198
<211> LENGTH: 459
<212> TYPE: PRT

<213> ORGANISM: Artificial
<220> FEATURE:
<223> OTHER INFORMATION: Human - mouse chimeric

<400> SEQUENCE: 198

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Ser Leu Ser Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Arg Val Glu Pro Lys Ser
        195                 200                 205

Cys Asp Lys Thr His Gly Gly Ser Ser Glu Val Gln Leu Gln Gln
    210                 215                 220

Ser Gly Pro Glu Leu Val Lys Pro Gly Ala Ser Val Lys Ile Ser Cys
225                 230                 235                 240

Lys Thr Ser Gly Tyr Thr Phe Thr Glu Tyr Thr Met His Trp Val Lys
                245                 250                 255

Gln Ser His Gly Lys Ser Leu Glu Trp Ile Gly Gly Ile Ser Pro Asn
            260                 265                 270

Ile Gly Gly Thr Ser Tyr Asn Gln Lys Phe Lys Gly Lys Ala Thr Leu
        275                 280                 285

Thr Val Asp Lys Ser Ser Thr Ala Tyr Met Glu Leu Arg Ser Leu
    290                 295                 300

Thr Ser Glu Asp Ser Ala Val Tyr Tyr Cys Ala Arg Arg Gly Gly Ser
305                 310                 315                 320

Phe Asp Tyr Trp Gly Gln Gly Thr Thr Leu Thr Val Ser Ser Val Glu
                325                 330                 335

Gly Gly Ser Gly Gly Ser Gly Gly Ser Gly Gly Ser Gly Gly Val Asp
            340                 345                 350

Asp Ile Val Met Thr Gln Ser Pro Ala Thr Leu Ser Val Thr Pro Gly
        355                 360                 365

Asp Arg Val Ser Leu Ser Cys Arg Ala Ser Gln Ser Ile Ser Asp Tyr
    370                 375                 380

Leu His Trp Tyr Gln Gln Lys Ser His Glu Ser Pro Arg Leu Leu Ile
```

```
                385                 390                 395                 400
Lys Tyr Ala Ser Gln Ser Ile Ser Gly Ile Pro Ser Arg Phe Ser Gly
                405                 410                 415

Ser Gly Ser Gly Ser Asp Phe Thr Leu Ser Ile Asn Ser Val Glu Pro
            420                 425                 430

Glu Asp Val Gly Val Tyr Tyr Cys Gln Asn Gly His Ser Phe Pro Leu
        435                 440                 445

Thr Phe Gly Ala Gly Thr Lys Leu Glu Leu Lys
    450                 455

<210> SEQ ID NO 199
<211> LENGTH: 18
<212> TYPE: PRT
<213> ORGANISM: Artificial Sequence
<220> FEATURE:
<223> OTHER INFORMATION: Flexible Linker

<400> SEQUENCE: 199

Gly Glu Gly Thr Ser Thr Gly Ser Gly Gly Ser Gly Gly Ser Gly Gly
1               5                   10                  15

Ala Asp

<210> SEQ ID NO 200
<211> LENGTH: 15
<212> TYPE: PRT
<213> ORGANISM: Artificial Sequence
<220> FEATURE:
<223> OTHER INFORMATION: Flexible Linker

<400> SEQUENCE: 200

Gly Gly Gly Gly Ser Gly Gly Gly Gly Ser Gly Gly Gly Gly Ser
1               5                   10                  15

<210> SEQ ID NO 201
<211> LENGTH: 13
<212> TYPE: PRT
<213> ORGANISM: Homo sapiens

<400> SEQUENCE: 201

Thr His Thr Cys Ser Ser Cys Pro Ala Pro Glu Leu Leu
1               5                   10

<210> SEQ ID NO 202
<211> LENGTH: 15
<212> TYPE: PRT
<213> ORGANISM: Homo sapiens

<400> SEQUENCE: 202

Asn Ala Ser Ser Met Cys Val Pro Ser Pro Ala Pro Glu Leu Leu
1               5                   10                  15

<210> SEQ ID NO 203
<211> LENGTH: 13
<212> TYPE: PRT
<213> ORGANISM: Homo sapiens

<400> SEQUENCE: 203

Thr His Thr Ser Pro Pro Ser Pro Ala Pro Glu Leu Leu
1               5                   10

<210> SEQ ID NO 204
<211> LENGTH: 5
<212> TYPE: PRT
```

```
<213> ORGANISM: Artificial Sequence
<220> FEATURE:
<223> OTHER INFORMATION: Linker Sequence

<400> SEQUENCE: 204

Gly Gly Gly Ser Ser
1               5

<210> SEQ ID NO 205
<211> LENGTH: 10
<212> TYPE: PRT
<213> ORGANISM: Artificial Sequence
<220> FEATURE:
<223> OTHER INFORMATION: Hinge Sequence

<400> SEQUENCE: 205

Asp Lys Thr His Thr Cys Pro Pro Cys Pro
1               5                   10

<210> SEQ ID NO 206
<211> LENGTH: 4
<212> TYPE: PRT
<213> ORGANISM: Artificial Sequence
<220> FEATURE:
<223> OTHER INFORMATION: Linker Sequence

<400> SEQUENCE: 206

Arg Thr Val Ala
1
```

MULTISPECIFIC NK ENGAGER PROTEINS

CROSS-REFERENCE TO RELATED APPLICATIONS

This application claims the benefit of U.S. Provisional Application No. 62/271,459 filed Dec. 28, 2015, and is a continuation-in-part of PCT patent application No. PCT/EP2015/064063 filed 23 Jun. 2015; both of which are incorporated herein by reference in their entirety; including any drawings and sequence listings.

REFERENCE TO THE SEQUENCE LISTING

The present application is being filed along with a Sequence Listing in electronic format. The Sequence Listing is provided as a file entitled "56215o1001", created Feb. 17, 2017, which is 364,225 bytes in size. The information in the electronic format of the Sequence Listing is incorporated herein by reference in its entirety.

FIELD OF THE INVENTION

Multispecific proteins that bind and specifically redirect effector cells to lyse a target cell of interest via multiple activating receptors are provided. The proteins have utility in the treatment of disease, notably cancer or infectious disease.

BACKGROUND

Bispecific antibodies binding two different epitopes offer opportunities for increasing specificity, broadening potency, and utilizing novel mechanisms of action that cannot be achieved with a traditional monoclonal antibody. A variety of formats for bispecific antibodies that bind to two targets simultaneously have been reported. Cross-linking two different receptors using a bispecific antibody to inhibit a signaling pathway has shown utility in a number of applications (see, e.g., Jackman, et al., (2010) *J. Biol. Chem.* 285:20850-20859). Bispecific antibodies have also been used to neutralize two different receptors. In other approaches, bispecific antibodies have been used to recruit immune effector cells, where T-cell activation is achieved in proximity to tumor cells by the bispecific antibody which binds receptors simultaneously on the two different cell types (see Baeuerle, P. A., et al, (2009) *Cancer Res* 69(12): 4941-4). These antibodies have been referred to as "Bispecific T-cell engager antibodies" (or "BiTE" antibodies). However, in order to fully activate the T-cell, this T-cell and a cluster of BiTEs must interact on the surface of a target cell. Due to the difficulties of finding antibody variable regions which are functional in the BiTE format, to date only a single immune cell receptor (CD3) has been targeted, in the CD19×CD3 specific antibody blinatumamab. Bispecific antibodies developed to date also include those which link the CD3 complex on T cells to a tumor-associated antigen. Also, bispecific antibodies having one arm which binds CD16 (FcγRIIIa) and another which bound to an antigen of interest such as CD19 have been developed (see Kellner et al. (2011) *Cancer Lett.* 303(2): 128-139).

Natural killer (NK) cells are a subpopulation of lymphocytes that are involved in non-conventional immunity. NK cells provide an efficient immunosurveillance mechanism by which undesired cells such as tumor or virally-infected cells can be eliminated. Characteristics and biological properties of NK cells include the expression of surface antigens including CD16, CD56 and/or CD57, the absence of the α/β or γ/δ TCR complex on the cell surface; the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

NK cell activity is regulated by a complex mechanism that involves both activating and inhibitory signals. Several distinct NK cell receptors have been identified that play an important role in the NK cell mediated recognition and killing of HLA Class I deficient target cells. One receptor, although not specific to NK cells, is FcγR3a (CD16) which is responsible for NK cell mediated ADCC. NK cells also express a range of other activating and co-activating receptors, including CD137 (4-1BB). Agonist antibodies against anti-4-1BB are in clinical trials in patients with solid tumors, including melanoma, renal carcinoma, and ovarian cancer, and have shown strong activity in different cancer models, including breast cancer, sarcoma, glioma, colon carcinoma, myeloma, and mastocytoma.

Another NK cell receptor is NKp46, a member of the Ig superfamily. NKp46, is specific to NK cells and the cross-linking thereof, induced by specific mAbs, leads to a strong NK cell activation resulting in increased intracellular $Ca^{++}$ levels, the triggering of cytotoxicity, and lymphokine release. International patent publication number WO2005/105858 (Innate Pharma) discloses the use of monospecific full-length IgG anti-NKp46 antibodies that bind Fcγ receptors for treating hematological malignancies that are Fcγ-positive. Fc γ receptors expressed on tumor cells (e.g. B cell malignancies) were proposed to interact with the Fc domain of the anti-NKp46 antibodies which bound NK cells, such that the activated NK cells are brought into close proximity with target cells via the two reactive portions of the antibody (i.e., the antigen-recognizing domain and the Fc domain), thereby enhancing the efficiency of the treatment.

To date, no NK cell-specific bispecific antibodies have been reported. Rather depleting agents that recruit NK cytotoxicity such as anti-tumor antibodies are typically full-length IgG1 antibodies that mediate ADCC via CD16. Despite the existence of a variety of formats for bispecific antibodies, there remains a need in the art for multispecific proteins with new and well-defined mechanisms of action, particularly those that can provide therapeutic advantages over full-length antibodies.

SUMMARY OF THE INVENTION

The present invention arises from the discovery of functional multi-specific proteins (e.g. a polypeptide, a single chain protein, a multi-chain protein, including but not limited to antibody-based protein formats) that binds NKp46 on NK cells and to an antigen of interest on a target cell, and is capable of redirecting NK cells to lyse a target cell that expresses the antigen of interest, e.g. a cell that contributes to disease. Provided, inter alia, is a multispecific protein comprising a first antigen binding domain and a second antigen binding domain, wherein one of the first or second antigen binding domains binds to a human NKp46 polypeptide and the other binds an antigen of interest, wherein the multispecific protein binds the NKp46 polypeptide monovalently, and wherein the multispecific protein is capable of directing an NKp46-expressing NK cell to lyse a target cell expressing the antigen of interest. Advantageously, in on embodiment, the presence of NK cells and target cells, the multi-specific protein can bind (i) to antigen of interest on target cells and (ii) to NKp46 on NK cells, and, when bound to both antigen of interest on target cells and NKp46, can induce signaling in and/or activation of the NK cells through NKp46 (the protein acts as an NKp46 agonist), thereby promoting activation of NK cells and/or lysis of target cells, notably via the activating signal transmitted by NKp46.

In some embodiment, the multispecific protein comprises at least a portion of a human Fc domain, e.g. an Fc domain that is bound by FcRn.

In certain embodiments, the multispecific antibody is designed to have decreased or substantially lack FcγR binding compared to a conventional full-length human IgG1 antibody. Optionally the multispecific protein has decreased or abolished binding to a human CD16, CD32A, CD32B and/or CD64 polypeptide, compared to a full length wild type human IgG1 antibody. In other embodiments, the multispecific protein is designed to retain substantial FcγR binding, e.g., compared to a conventional full-length human IgG1 antibody. Optionally the multispecific protein binds (e.g. via its Fc domain) to a human CD16, CD32A, CD32B and/or CD64 polypeptide.

The present invention arises in part from the observation that multispecific proteins which bind to an antigen of interest and which are further engineered to bind to NKp46 on NK cells monovalently, and to CD16 or CD16A, exhibit an enhanced capability to promote NK cell-mediated target cell lysis (relative to conventional antibodies). Through comparison of molecules having different functionalities, it was observed that such multispecific proteins elicited the individual and combined effects of these receptors thereby better promoting the lysis of target cells by NK cells. As described in detail herein, various functional multispecific proteins were constructed that bind (a) NKp46 and CD16 on NK cells and (b) to an antigen of interest on a target cell, which are capable of redirecting NK cells to lyse a target cell that expresses the antigen of interest, e.g. a cell that contributes to a disease such as cancer or infection. Moreover, despite binding to NKp46 on NK cells, advantageously these multispecific proteins do not induce lysis of NK cells themselves.

Also provided are novel formats for multispecific Fc proteins that are capable of activating CD16 and NKp46 and which can be used to promote NK-mediated killing of desired target cells. The potency in target cell killing demonstrated by the subject multispecific proteins which bind CD16 and which in addition bind to NKp46 and to an antigen of interest is believed to arise at least in part from an induction and upregulation of the co-activating receptor CD137 which is expressed on the surface NK cells. Particularly, CD137 upregulation occurs on resting NK cells, in the absence of target cells (as well as in the presence of target cells), and without the induction of CD16-mediated lysis of NK cells. NK cells with increased CD137 expression are known to be highly active against target cells (e.g. tumor cells) expressing CD137L (CD137 ligand). Consequently, the instant multispecific proteins which bind CD16 in addition to monovalently binding NKp46 can provide a means to upregulate CD137. Further advantageously, the multispecific protein when binding additionally to an antigen of interest expressed by a target cell, can elicit a multi-pronged recognition of target cells that involves multiple activating receptors expressed on effector cells. Also, despite an ability to cause upregulation of CD137 on NK cells that is comparable to human IgG1 antibodies (in the absence of target cells), surprisingly the multispecific proteins are far more potent in inducing NK cell-mediated lysis of tumor cells than human IgG1 antibodies. This would suggest that the subject multispecific proteins trigger the combined effects of NKp46-, CD16- and/or CD137-mediated activation thereby providing for a synergistic or additive enhancement in the induction of NK cell cytotoxicity by $CD16^+$ $NKp46^+$ NK cells. Additionally, independently of any contribution of CD137, these multispecific proteins advantageously are able to potently mobilize both $CD16^+$ and $CD16^-$ NK cells (all NK cells are $NKp46^+$).

Furthermore, despite that the subject multispecific proteins are bound by CD16, unexpectedly they do not induce or increase down-modulation or internalization of the antigen of interest, even when targeting antigens of interest known to be susceptible to down-modulation or internalization when bound by conventional antibodies (such as full length human IgG1's). Based thereon, the subject multispecific proteins should be well suited for targeting antigens of interest expressed by target cells, e.g., tumor or infected cells, including antigens which are known to be capable of undergoing down-modulation or internalization when bound by conventional antibodies (e.g. antibodies with human IgG1 Fc domains that retain CD16 binding). This is a huge therapeutic benefit since it is known in the art that antigen internalization can substantially impede the ability of conventional human IgG1 antibodies to mediate ADCC against a target cell.

Therefore, in one embodiment, multispecific proteins are provided which bind to an antigen of interest expressed on the surface of a cell monovalently, wherein the protein does not increase or induce down-modulation or intracellular internalization of the antigen of interest.

In another embodiment the invention provides a multispecific protein that comprises an antigen binding domain that binds to a human a NKp46 polypeptide monovalently (e.g., via a single antigen binding domain), and which is capable of binding to human CD16, and which when incubated in soluble form with effector cells expressing a NKp46 polypeptide and CD16 (e.g. human $NKp46^+CD16^+$ NK cells), optionally in the absence and/or presence of target cells, further optionally in the absence of other cells, can cause an increase or induction of CD137 polypeptide expression on the surface of the effector cells (e.g. without inducing detectable lysis of the NK cells). Optionally, the multispecific protein further binds to an antigen of interest.

In another embodiment the invention provides a multispecific protein that comprises (i) a first antigen binding domain ("ABD") that binds to a human NKp46 polypeptide, (ii) an Fc domain that binds to human CD16A, and (iii) a second antigen binding domain that binds to an antigen of interest expressed by a target cell. In one embodiment, the multispecific protein is capable of directing an NKp46-expressing NK cell to lyse a target cell expressing the antigen of interest, wherein said lysis of the target cell is mediated by NKp46-signaling, wherein optionally said lysis of the target cell is mediated by a combination of Nkp46-mediated signaling and CD16-mediated antibody-dependent cell-mediated cytotoxicity ("ADCC").

In another embodiment the invention provides a multispecific antigen binding protein which comprises (i) a monovalent antigen binding polypeptide ("ABD") which binds to a human NKp46 polypeptide (i) an ABD which binds to an antigen of interest, wherein said antigen of interest optionally comprises an antigen expressed by a tumor cell or an infectious agent and (iii) a CD16A binding polypeptide, optionally an Fc polypeptide which Fc polypeptide is optionally modified to enhance CD16A binding relative to the corresponding wild-type Fc polypeptide, wherein the multispecific protein is capable of directing an NKp46-expressing NK cell to lyse a target cell expressing the antigen of interest by NKp46-signaling.

In another embodiment the invention provides an isolated multispecific Fc-protein comprising a first antigen binding domain, a second antigen binding domain, and an Fc domain or portion thereof, which optionally may be modified, that is capable of binding human CD16 or CD16A, wherein one of the first or second antigen binding domains binds to a human NKp46 polypeptide and the other binds an antigen of interest, and wherein the multispecific protein is capable of directing an NKp46-expressing NK cell to lyse a target cell expressing the antigen of interest. In one embodiment, the protein causes lysis of the target cell by enhancing or inducing NKp46-signaling, wherein optionally lysis of the target cell is mediated by a combination of Nkp46 signaling and CD16-mediated antibody-dependent cell-mediated cytotoxicity ("ADCC"). Optionally, the multispecific protein further comprises a third or fourth or more antigen binding domains that each bind to an antigen of interest, e.g., one other than a NKp46 polypeptide, i.e., an antigen of interest expressed by a target cell such as a tumor cell or infectious agent, wherein the antigen of interest is the same or different from the antigen of interest bound by the second antigen binding domain. In one embodiment, the third antigen binding domain binds to the same antigen of interest as the second antigen binding domain, optionally further wherein the third antigen binding domain binds to the same epitope or a different epitope on the antigen of interest as the second antigen binding domain. In one embodiment, the antigen of interest is a cancer antigen. In one embodiment, the antigen of interest is a protein expressed (optionally over-expressed) on the surface of malignant immune cells, e.g. cells involved in a hematological malignancy, leukemia cells, lymphoma cells, a CD19 protein, a CD20 protein, etc. In one embodiment, the protein is used to treat a hematological malignancy, e.g., a leukemia or lymphoma cells. In another embodiment, the antigen of interest is a protein expressed (optionally over-expressed) on the surface of infected cells or by an infectious agent such as virally, bacterially or parasite infected cells.

Optionally, the subject multispecific polypeptides when incubated in soluble form with effector cells expressing NKp46 and CD16 (e.g. human NKp46$^+$CD16$^+$ NK cells), optionally in the presence or absence of other cells (e.g. target cells), can elicit an increase or induction of CD137 polypeptide expression on the surface of the NK cells (e.g. without inducing detectable lysis of the NK cells). Optionally, in the presence of target cells expressing the antigen of interest and NKp46$^+$CD16$^+$ NK cells, the multispecific protein can induce the activation of NK cells and/or lysis of target cells, in particular via the activating signal(s) transmitted by any combination of NKp46, CD16 and/or CD137.

In some embodiments, the multispecific protein binds to NKp46 in monovalent fashion. In one aspect of any embodiment, the multispecific protein comprises an Nkp46-binding ABD which binds to an NKp46 polypeptide monovalently.

In some embodiments in the presence of target cells and NK cells, the multispecific protein is capable of inducing an increase in cell surface CD137, e.g., on NK cells that express NK46 and CD16 (NKp46$^+$CD16$^+$ NK cells).

In some embodiments in the presence of target cells and NK cells, the multispecific protein is capable of inducing signaling by NK cells through NKp46.

In some embodiments in the presence of target cells and NK cells, the multispecific protein lacks the ability to induce NKp46-mediated signaling or cellular activation of an NK cell (independently of CD16), when incubated with NK cells in the absence of target cells (cells expressing the antigen of interest); for example the multispecific protein lacks the ability to induce NKp46-mediated signaling or NK cell activation when incubated with NK cells in the absence of target cells, when the protein is modified to comprise an Fc domain that does not bind CD16 (e.g. an Fc region containing a N297S substitution); or the multispecific protein lacks the ability to induce NKp46-mediated signaling or NK cell activation when incubated with NKp46$^+$CD16$^-$ NK cells, in the absence of target cells. In any of the multispecific proteins described herein, such multispecific protein potentially possesses the following characteristics:

(a) capable of inducing human NK cells that express CD16 and NKp46 (NKp46$^+$CD16$^+$ NK cells) to lyse target cells expressing the antigen of interest, when incubated in the presence of the NK cells and target cells; and (b) capable of inducing an increase in cell surface CD137 when incubated (e.g. in soluble form) with NK cells that express CD16 and NKp46, optionally in the presence of target cells, or in the absence of target cells.

In another embodiment the invention provides multispecific protein formats adapted for use in an NKp46-based NK cell engager, including antibody-based formats comprising antigen binding domain(s) and/or constant region domain(s) from immunoglobulins capable of forming a dimeric Fc domain that binds to human CD16 (and optionally further binding to FcRn and/or other human Fcγ receptors). By combining the NK-selective expression of NKp46 with multispecific (e.g. bispecific) antibody formats in which the multispecific proteins retain and/or have increased binding to human Fcγ receptor via an Fc domain, the invention provides multispecific antibody formats with favorable pharmacology due to FcRn binding which can direct NK cell cytotoxicity to a target of interest, and which further possess increased ability to lyse target cells via the combined action of activating receptors CD16, NKp46, and in addition optionally CD137.

In another aspect of any embodiment described herein, the multispecific protein can be characterized by a lack of agonist activity for NKp46 when incubated with Fcγ receptor-negative NK cells (e.g. as purified NKp46$^+$CD16$^-$ NK cells) and in the absence of target cells (e.g. cells expressing the antigen of interest).

In another embodiment the invention provides a method for identifying, testing and/or producing a multispecific protein that binds NKp46 and CD16 on an NK cell and an antigen of interest expressed by a target cell, the method comprising:

(a) assessing whether the multispecific protein is capable of inducing an increase in cell surface CD137 on NK cells when incubated with CD16-expressing NK cells (e.g. NKp46$^+$CD16$^+$ NK cells); and (b) assessing whether the multispecific protein has the ability to induce NK cells that express CD16 and NKp46 to lyse target cells, when incubated in the presence of the NK cells and target cells.

Optionally, in any of the foregoing the NK cells are purified NK cells.

In another embodiment the invention provides a method for identifying, testing and/or producing a multispecific protein, the method comprising providing a plurality of multispecific proteins that bind NKp46 and CD16 on an NK cell and an antigen of interest expressed by a target cell:

(a) assessing whether each multispecific protein has the ability to induce NK cells that express CD16 and NKp46 to lyse target cells, when incubated in the presence of the NK cells and target cells;
(b) optionally, further assessing each multispecific protein for the ability to induce an increase in cell surface CD137 when incubated with CD16-expressing NK cells (e.g. NKp46⁺CD16⁺ NK cells); and
(c) selecting a multispecific protein (e.g. for use as a medicament, for further evaluation, for further production, etc.) if the multispecific protein:
   a. has the ability to induce NK cells that express CD16 and NKp46 to lyse target cells, when incubated in the presence of the NK cells and target cells, and
   b. optionally, has the ability to induce an increase in cell surface CD137 when incubated with CD16-expressing NK cells.

In another embodiment the invention provides a method for identifying, testing and/or producing a multispecific protein, the method comprising providing a plurality of multispecific proteins that bind NKp46 and CD16 on an NK cell and an antigen of interest expressed by a target cell:
(a) assessing each multispecific protein to determine whether it is capable of inducing NKp46-mediated signaling or NK cell activation of an NK cell independently of CD16, when incubated with NK cells in the absence of target cells;
(b) assessing each multispecific protein to determine whether the multispecific protein has the ability to induce NK cells to lyse target cells, when incubated in the presence of the NK cells and target cells;
(c) optionally, further assessing each multispecific protein to determine whether it is capable of inducing an increase in cell surface CD137 when incubated with CD16-expressing NK cells (e.g. NKp46⁺CD16⁺ NK cells); and
(d) selecting a multispecific protein (e.g. for use as a medicament, for further evaluation, for further production, etc.) if the multispecific protein:
   a. lacks the ability to induce NKp46-mediated signaling or NK cell activation in an NK cell independently of CD16, when incubated with NK cells in absence of target cells;
   b. has the ability to induce NK cells to lyse target cells, when incubated with NK cells and target cells, and
   c. optionally, has the ability to induce an increase in cell surface CD137 when incubated with CD16-expressing NK cells.

In another embodiment the invention provides a multispecific protein that binds human CD16 (e.g. polypeptide, non-antibody polypeptide, or antibody), comprising: (a) a first antigen binding domain; and (b) a second antigen binding domain, wherein one of the first antigen binding domains binds NKp46 and the other binds to an antigen of interest on a target cell (other than NKp46), wherein the multispecific protein is capable of directing NKp46-expressing NK cells to lyse said target cell. In one embodiment, the protein comprises at least a portion of a human Fc domain, optionally wherein the Fc domain is dimeric, and is bound by human CD16 (and further optionally wherein the Fc domain is also bound by FcRn), and still further optionally wherein the multispecific antibody comprises an Fc domain comprising a modification (compared to a wild-type Fc domain) that results in increased binding to CD16; in one embodiment, the Fc domain is interposed between the two ABDs (one ABD is placed N-terminal and the other is C-terminal to the Fc domain).

In one aspect, the multispecific protein comprises two or more polypeptide chains, i.e. it comprises a multi-chain protein. For example, the multispecific protein or multichain protein can be a dimer, trimer or tetramer or may comprise more than 4 polypeptide chains.

An antigen binding domain positioned on a polypeptide chain can itself bind to its target (i.e., NKp46 or an antigen of interest) (e.g. an scFv or single antigen binding domain) or can optionally bind its target when it is in association or together with one or more complementary protein domains (antigen binding domain or domains) positioned on a different polypeptide chain, wherein these polypeptide chains associate to form a multimer (e.g. dimer, trimer, etc.).

In one aspect, the multispecific protein binds an NKp46 polypeptide (e.g. expressed on the surface of a NK cell) in monovalent fashion. In one aspect, the multispecific protein binds the antigen of interest in monovalent fashion.

In another embodiment the invention provides multispecific proteins having a structure in which the freedom of motion (intrachain domain motion) or flexibility of one or more antigen binding domains (ABDs) is increased, e.g. compared to the ABDs of a conventional human IgG antibody. In one embodiment, provided is a multispecific protein comprising a structure that permits the antigen binding site of the first antigen binding domain and the antigen binding site of the second antigen binding domain to be separated by a distance that results in enhanced function, e.g., the ability of the multispecific protein to induce NKp46 signaling and lysis of target cells, e.g., optionally a distance of less than 80 ångström (Å). Multispecific proteins wherein the ABDs possess greater flexibility and/or are separated by an optimized distance may enhance the formation of a lytic NKp46-target synapse, thereby potentiating NKp46-mediated signaling.

In one embodiment, the invention provides multispecific proteins having increased freedom of motion of the antigen binding domains (e.g. compared to the ABDs of a conventional human IgG antibody, e.g., a human IgG1 antibody). One example of such a protein is a monomeric or multimeric Fc domain-containing protein (e.g. a heterodimer or heterotrimer) in which an antigen binding domain (e.g., the ABD that binds NKp46 or the ABD that bind the antigen of interest) is linked or fused to an Fc domain via a flexible linker. The linker can provide flexibility or freedom of motion of one or more ABDs by conferring the ability to bend thereby potentially decreasing the angle between the ABD and the Fc domain (or between the two ABDs) at the linker. Optionally, both antigen binding domains (and optionally more if additional ABDs are present in the multispecific protein) are linked or fused to the Fc domain via a linker, typically a flexible peptide linker. Optionally, other sequences or domains such as constant domains which optionally may be modified to alter (enhance or inhibit) one or more effector functions are placed between the Fc domain and an ABD, e.g. such that the ABD is fused to the Fc domain via a flexible linker and a constant region. The antigen binding domain can for example be comprised of variable region(s), a dAb, a VhH or a non-Ig scaffold. The antigen binding domain may be present in its entirety on a single polypeptide chain or may be formed from the association with a domain present on a separate polypeptide chain. Optionally, the protein with increased freedom of motion permits the protein to adopt a conformation in which the distance between the NKp46 binding site and the antigen of interest binding site is less that than observed in proteins in which both binding domains were Fabs, or less than in full length antibodies.

An ABD can be connected to the Fc domain (or CH2 or CH3 domain thereof) via a flexible linker (optionally via intervening sequences such as constant region domains or portions thereof, e.g. CH1 or Cκ). The linker can be a polypeptide linker, for example peptide linkers comprising a length of at least 5 residues, at least 10 residues, at least 15 residues, at least 20 residues, at least 25 residues, at least 30 residues or more. In other embodiments, the linkers comprises a length of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-30 residues, between 10-24 residues, between 10-26 residues, between 10-30 residues, or between 10-50 residues. Optionally a linker comprises an amino acid sequence derived from an antibody constant region, e.g., an N-terminal CH1 or hinge sequence. Optionally a linker comprises the amino acid sequence RTVA.

Optionally a linker is a flexible linker predominantly or exclusively comprised of glycine and/or serine residues, e.g., comprising the amino acid sequence GEGTSTGS($G_2S$)$_2$GGAD (SEQ ID NO: 199) or the amino acid sequence ($G_4S$)$_3$ (SEQ ID NO: 200).

In one embodiment, the Fc domain is interposed between the two ABDs (one ABD is placed N-terminal and the other is C-terminal to the Fc domain). The subject multispecific proteins (e.g. dimers, trimers, tetramers) may in some embodiments comprise a domain arrangement as follows, in which domains can be placed on any of the 2, 3 or 4 polypeptide chains, wherein an Fc domain is interposed between the antigen binding domains, and wherein a flexible linker is present between at least one of the ABDs and the Fc domain:

($ABD_1$) (Fc domain) ($ABD_2$).

In another embodiment, the multispecific proteins (e.g. dimers, trimers, tetramers) may comprise a domain arrangement of any of the following in which domains can be placed on any of the 2, 3 or 4 polypeptide chains, wherein the Fc domain is not interposed between ABDs (e.g. the protein has a terminal or distal Fc domain), and wherein a flexible linker is present between at least one of the ABDs and the Fc domain:

(Fc domain) ($ABD_1$ and $ABD_2$),
or
($ABD_1$ and $ABD_2$) (Fc domain).

In the above-described domain arrangements, one of $ABD_1$ and $ABD_2$ is an antigen binding domain that binds NKp46 and the other is an antigen binding domain that binds an antigen of interest, and wherein the linker is a flexible polypeptide linker. The Fc domain can be a dimeric Fc domain (e.g. that binds human FcRn and/or Fcγ receptors). In one embodiment, each of $ABD_1$ and $ABD_2$ are formed from two variable regions present within tandem variable regions, wherein the variable regions that associate to form a particular ABD can be on the same polypeptide chain or on different polypeptide chains. In another embodiment, one of $ABD_1$ and $ABD_2$ comprises a tandem variable region and the other comprises a Fab structure.

The invention also identifies specific epitopes on NKp46 which are well suited for targeting with NKp46 binding moieties, including the multispecific polypeptides disclosed herein. For example, bispecific or multispecific proteins which bind to one or more of these Nkp46 epitopes possess advantageous properties, notably high efficacy in causing or directing NK cells to lyse target cells (e.g. via NKp46-mediated signaling). Provided also are CDRs of different anti-NKp46 antibodies suitable for use in the construction of efficient multispecific proteins, e.g., bispecific and trispecific proteins particularly those which potently lyse a target cell of interest, and amino acid and nucleic acid sequences of exemplary multispecific proteins and nucleic acids which encode these proteins.

In one aspect, the protein (and/or the antigen binding domain thereof that binds NKp46) competes for binding to a NKp46 polypeptide with any one or any combination of monoclonal antibodies NKp46-1, -2, -3, -4, -6 or -9 or an Anti-CD19-F5-Anti-NKp46 antibody that comprises such NKp46-1, -2, -3, -4, -6 or -9 bispecific antibodies. In one embodiment, the antigen binding domain that binds NKp46 binds an epitope within (partly or fully within) the D2 (proximal) domain of the NKp46 polypeptide. In one embodiment, the antigen binding domain that binds NKp46 binds an epitope within (partly or fully within) the D1 (distal) domain of the NKp46 polypeptide. In one embodiment, the antigen binding domain that binds NKp46 binds an epitope on an NKp46 polypeptide of SEQ ID NO:1 comprising one, two, three or more residues selected from the residues bound by any one or combination of antibodies NKp46-1, -2, -3, -4, -6 or -9 or an Anti-CD19-F5-Anti-NKp46 antibody that comprises such NKp46-1, -2, -3, -4, -6 or -9 bispecific antibodies. In one embodiment the multispecific protein is capable of binding to human neonatal Fc receptor (FcRn). In one embodiment the multispecific protein has decreased or abolished binding to a human and/or non-human primate (e.g. cynomolgus monkey) Fcγ receptor, e.g., compared to a full length wild type human IgG1 antibody. In one embodiment the multispecific protein is capable of inducing NK-mediated lysis (e.g. as well as or better than a full length human wild-type IgG1 antibody).

In one embodiment of any of the multispecific proteins described herein, the antigen binding domain that binds to an antigen of interest binds to an antigen (e.g. polypeptide) expressed by a target cell which is sought to be lysed by an NK cell. Optionally this antigen is expressed by a cancer cell, or a virally, bacterially or parasite infected cell, an immune cell that contributes to tumor growth or escape (e.g. a tumor-associated monocyte or macrophage), or a cell that contributes to an autoimmunity, an allergic response or inflammatory disease.

In one embodiment, the multispecific protein binds NKp46 in monovalent fashion. In one embodiment, the multispecific protein binds to the antigen of interest in monovalent fashion. In one embodiment, the multispecific protein binds both NKp46 and the antigen of interest in monovalent fashion. In one embodiment, the multispecific protein binds CD16 via a dimeric Fc domain.

In one embodiment, the first antigen binding domain comprises an antibody heavy chain variable domain and a light chain variable domain. Optionally, both said heavy and light chain variable domains are involved in binding interactions with NKp46.

In one embodiment, the second ABD (and optionally third or more ABDs, when present) comprises an antibody heavy chain variable domain and a light chain variable domain. Optionally, both said heavy and light chain variable domains are involved in binding interactions with the antigen bound by the second antigen binding domain. In one embodiment, the second ABD (and optionally third or more ABD, when present) comprises a non-immunoglobulin scaffold.

Optionally, the Fc domain comprises at least a portion of a CH2 domain and at least a portion of a CH3 domain, and when present in a multispecific polypeptide, is part of a dimeric Fc domain.

In one embodiment, the CH2 domain comprises an amino acid modification, compared to a wild-type CH2 domain. In one embodiment, the CH2 modification increases binding (e.g. increases binding affinity) of the bispecific polypeptide to a human CD16 polypeptide relative to a wild-type human Fc region.

In one embodiment, the CH2 domain and/or CH3 domains are naturally occurring (non-engineered) human CH2 and/or CH3 domains. In one embodiment, the multispecific protein comprises an Fc domain that comprises N-linked glycosylation. In one embodiment, the N-linked glycosylation (at residue N297, Kabat EU numbering) comprises glycan structures typical of those found on IgG-class (e.g. IgG1) immunoglobulins produced in mammalian cells (e.g., CHO cells or other rodent cells, non-human primate or human cells). In one embodiment, the Fc domain comprises modified N-linked glycosylation, e.g. hypofucosylated glycans at N297) which increase binding affinity for a human CD16 polypeptide.

In one embodiment, the Fc-derived polypeptide is a dimer, optionally a homodimer or a heterodimer. In one embodiment, the Fc-derived polypeptide is a heterotrimer. In one embodiment, the Fc-derived polypeptide is a heterotetramer.

In one embodiment, heterotrimer proteins are provided comprising two antigen binding domains that are composed of three different polypeptide chains that each comprise at least one V-(CH1/Cκ) unit, wherein a first (central) chain comprises two V-(CH1/Cκ) units separated by an Fc domain (or portion thereof which optionally binds CD16), and each of the second and third chains comprise one V-(CH1/Cκ) unit, wherein one of the V-(CH1/Cκ) units of the central chain preferentially undergoes CH1-Cκ dimerization with the V-(CH1/Cκ) unit of the second chain thereby forming a first antigen binding domain, wherein the other of the V-(CH1/Cκ) units of the central chain preferentially undergoes CH1-Cκ dimerization with the V-(CH1/Cκ) unit of the third chain thereby forming a second antigen binding domain, and wherein the second or third chain further comprise an Fc domain (or portion thereof) placed on the polypeptide chain such that the Fc domain is capable of forming a dimeric Fc domain that binds CD16 together with the Fc domain of the central polypeptide.

In one embodiment, heterotrimer proteins having three antigen binding domains are provided that are composed of three different polypeptide chains that each comprise at least one V-(CH1/Cκ) unit, wherein a first (central) chain comprises two V-(CH1/Cκ) units and each of the second and third chains comprise one V-(CH1/Cκ) unit, wherein one of the V-(CH1/Cκ) units of the central chain preferentially undergoes CH1-Cκ dimerization with the V-(CH1/Cκ) unit of the second chain thereby forming a first antigen binding domain, wherein the other of the V-(CH1/Cκ) units of the central chain preferentially undergoes CH1-Cκ dimerization with the V-(CH1/Cκ) unit of the third chain thereby forming a second antigen binding domain, wherein one of the polypeptide chains further comprises an antigen binding domain (e.g. a tandem variable domain, an scFv) that forms third antigen binding domain, and wherein the first or second chain further comprise an Fc domain (or portion thereof) placed on the polypeptide chain such that the Fc domain is capable of forming a dimeric Fc domain that bind CD16 together with the Fc domain of the central polypeptide.

In one embodiment, the invention provides a heteromultimeric, e.g. heterodimeric, bispecific protein comprising: (a) a first polypeptide chain comprising a first variable region (V), fused to a CH1 or Cκ domain, wherein the V-(CH1/Cκ) unit is in turn fused to a first terminus (N- or C-terminus) of a human Fc domain (a full Fc domain or a portion thereof); (b) a second polypeptide chain comprising a first variable region (V) fused to a CH1 or Cκ domain that is complementary with the CH1 or Cκ of the first chain to form a CH1-Cκ dimer, wherein the V-(CH1/Cκ) unit is fused to at least a human Fc domain (a full Fc domain or a portion thereof), wherein the two first variable regions form an antigen binding domain that binds a first antigen of interest in monovalent fashion, and (c) an antigen binding domain that binds a second antigen (optionally together with a complementary antigen binding domain), and optionally a second CH1 or Cκ domain, fused to a second terminus (N- or C-terminus) of the Fc domain of the first polypeptide such that the Fc domain is interposed between the V-(CH1/Cκ) unit and the antigen binding domain that binds a second antigen, and wherein the Fc domains (or portions thereof) of the first and second chains of the heteromultimeric protein form a dimeric Fc domain capable of being bound by human CD16 polypeptide, e.g. a dimeric Fc domain comprising N-linked glycosylation at residue N297 (Kabat EU numbering). Optionally the first and second polypeptide chains are bound by non-covalent bonds and optionally further interchain disulfide bonds, e.g. formed between respective CH1 and Cκ domains and/or between respective hinge domains. Optionally a V-(CH1/Cκ) unit is fused to a human Fc domain directly, or via intervening sequences, e.g. linkers, other protein domain(s), etc. Optionally, one of the antigens is NKp46 and another of the antigens is one expressed on the surface of a cell that is to be lysed by the immune cell, e.g. a cancer or viral or bacterial antigen; optionally further, wherein such antigen present on the surface of a cell that is to be lysed by the immune cell, e.g., NK cell, is a protein that is known to undergo intracellular internalization, notably when bound by an antibody (e.g. a full length antibody of an isotype such as human IgG1 or IgG3 that is bound by CD16).

In one embodiment, the multispecific polypeptide or protein is monoclonal. In one embodiment, the multispecific polypeptide or protein is purified. In one embodiment, the multispecific polypeptide or protein is isolated. In another embodiment the multispecific polypeptide or protein is expressed by a cell, e.g., a human immune cell such as a human NK cell.

In one embodiment of the above heteromultimeric polypeptide or protein, the polypeptide or protein is a heterodimer, wherein the antigen binding domain for a second antigen is an scFv, optionally an scFv that binds NKp46.

In one embodiment of the afore-described heteromultimeric polypeptides or proteins, the heteromultimeric polypeptide or protein is a heterotrimer, comprising an antigen binding domain for a second antigen which comprises or consists of an heavy or light chain variable region, and the heteromultimeric polypeptide or protein further comprises a third polypeptide chain comprising or consisting of a variable region (V) fused to a CH1 or Cκ domain that is complementary with the CH1 or Cκ of the first chain to form a CH1-Cκ dimer wherein the variable region that is the antigen binding domain for a second antigen of the first polypeptide and the variable region of the third chain form an antigen binding domain. The double dimerization yields a trimer. The CH1 or Cκ constant region of the third polypeptide is selected to be complementary to the second CH1 or Cκ constant region of the first polypeptide chain (but not complementary to the first CH1/Cκ of the first polypeptide chain).

In one aspect a heterodimeric polypeptide according to the invention comprises:

(a) a first polypeptide chain comprising, from N- to C-terminus, a first variable domain (V), a CH1 of Cκ constant region, a Fc domain or portion thereof which optionally binds CD16, a second variable domain and third variable domain; and (b) a second polypeptide chain comprising, from N- to C-terminus, a first variable domain (V), a CH1 or Cκ constant region, an Fc domain or portion thereof, wherein the CH1 or Cκ constant region is selected to be complementary to the CH1 or Cκ constant region of the first polypeptide chain such that the first and second polypeptides form a CH1-Cκ heterodimer in which the first variable domain of the first polypeptide chain and the first variable domain of the second polypeptide form an antigen binding domain that binds the first antigen of interest; and wherein a second variable domain and third variable domain forms an antigen binding domain that binds the second antigen of interest, and wherein the Fc domains (or portions thereof) of the first and second chains of the heteromultimeric protein form a dimeric Fc domain capable of being bound by human CD16 polypeptide, e.g. a dimeric Fc domain comprising N-linked glycosylation at residue N297 (Kabat EU numbering).

In another aspect the invention provides a heterodimeric polypeptide which comprises:

(a) a first polypeptide chain comprising, from N- to C-terminus, a second variable domain and third variable domain, a Fc domain or portion thereof, a first variable domain (V), and a CH1 of Cκ constant region; and (b) a second polypeptide chain comprising, from N- to C-terminus, a first variable domain (V), a CH1 or Cκ constant region, and a Fc domain or portion thereof, wherein the CH1 or Cκ constant region is selected to be complementary to the CH1 or Cκ constant region of the first polypeptide chain such that the first and second polypeptides form a CH1-Cκ heterodimer in which the first variable domain of the first polypeptide chain and the first variable domain of the second polypeptide form an antigen binding domain that binds to the first antigen of interest; and wherein a second variable domain and third variable domain forms an antigen binding domain that binds to a second antigen of interest, wherein the Fc domains (or portions thereof) of the first and second chains of the heteromultimeric protein form a dimeric Fc domain capable of being bound by human CD16 polypeptide, e.g. a dimeric Fc domain comprising IgG-type N-linked glycosylation at residue N297 (Kabat EU numbering).

In another aspect the invention provides a heterodimeric polypeptide which comprises:

(a) a first polypeptide chain comprising, from N- to C-terminus, a first variable domain (V) fused to a first CH1 or CKκ constant region, an Fc domain or portion thereof, and a second variable domain (V) fused to a second CH1 or Cκ constant region;

(b) a second polypeptide chain comprising, from N- to C-terminus, a variable domain fused to a CH1 or Cκ constant region selected to be complementary to the first (but not the second) CH1 or Cκ constant region of the first polypeptide chain such that the first and second polypeptides form a CH1-Cκ heterodimer, and an Fc domain or portion thereof; and (c) a third polypeptide chain comprising, from N- to C-terminus, a variable domain fused to a CH1 or Cκ constant region, wherein the CH1 or Cκ constant region is selected to be complementary to the second (but not the first) variable domain and second CH1 or Cκ constant region of the first polypeptide chain, wherein the Fc domains (or portions thereof) of the first and second chains of the heteromultimeric protein form a dimeric Fc domain capable of being bound by a human CD16 polypeptide, e.g. a dimeric Fc domain comprising IgG-type N-linked glycosylation at residue N297 (Kabat EU numbering). The first and third polypeptides will therefore form a CH1-Cκ heterodimer formed between the CH1 or Cκ constant region of the third polypeptide and the second CH1 or Cκ constant region of the first polypeptide, but not between the CH1 or Cκ constant region of the third polypeptide and the first CH1 or Cκ constant region of the first polypeptide. The first, second and third polypeptides form a CH1-Cκ heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

In another embodiment, the above-described heteromultimeric polypeptides or proteins may comprise one or more additional polypeptide chains.

Any the heteromultimeric polypeptides or proteins described herein may comprise a dimeric Fc domain capable of being bound by human CD16 polypeptide, e.g. a dimeric Fc domain comprising N-linked glycosylation at residue N297 (Kabat EU numbering).

Optionally, the CH1 and/or Cκ domain are fused via a hinge region to the Fc domain. Optionally the hinge, CH2 and/or CH3 comprises one or more amino acid modifications which increase binding affinity for human CD16. Optionally the hinge, CH2 and/or CH3 comprises an amino acid modification which increases binding affinity for human FcRn. Optionally the amino acid modifications that increase binding affinity for CD16 may also increase affinity for one or more other human Fcγ receptors. Optionally the hinge, CH2 and/or CH3 comprise an amino acid modification which reduces or substantially abolishes binding to an inhibitory human Fcγ receptor (e.g. CD32B) and/or to an Fcγ receptor other than CD16 (e.g. CD32A and/or CD64). In any embodiment described herein, the CH1 and Cκ domains optionally can be of human origin.

In one aspect of any of the embodiments described herein, the bispecific protein binds more strongly or avidly (has a greater binding affinity) for the antigen of interest (e.g. a cancer or viral or other infectious agent antigen) than it binds NKp46. Such antibodies may possess advantageous pharmacological properties. In one aspect of any of the embodiments herein, the polypeptide has a Kd (monovalent binding affinity) to NKp46 of less than $10^{-7}$ M, preferably less than $10^{-8}$ M, or preferably less than $10^{-9}$ M; optionally the polypeptide has a Kd for binding (monovalent binding affinity) to a cancer, viral, bacterial or other antigen that is less than (i.e. has better binding affinity than) the Kd (monovalent binding affinity) to a NKp46 polypeptide. In one aspect of any of the embodiments described herein, the polypeptide has a Kd (monovalent binding affinity) to NKp46 of between $10^{-7}$ M (100 nanomolar) and $10^{-10}$ M (0.1 nanomolar) for binding to a NKp46 polypeptide. In one aspect of any of the embodiments disclosed herein, the polypeptide has a Kd (monovalent binding affinity) to NKp46 of between $10^{-8}$ M (10 nanomolar) and $10^{-10}$ M (0.1 nanomolar). In one aspect of any of the embodiments herein the multimeric polypeptide has a Kd (monovalent binding affinity) to NKp46 of between $10^{-8}$ M (10 nanomolar) and $10^{-9}$ M (1 nanomolar). Binding can be assessed as in the Examples herein, e.g. by surface plasmon resonance.

In one aspect of any of the embodiments of the invention, the antigen binding domain that binds NKp46 binds to at least one residue on NKp46 corresponding to any of the amino acid residues bound by any one of monoclonal antibodies NKp46-1, -2, -3, -4, -6 or -9 or the Anti-CD19-Anti-NKp46-1, -2, -3, -4, -6 or -9 bispecific antibodies. In one aspect, the antigen binding domain that binds NKp46 binds at least 1, 2, 3, 4 or more amino acids of NKp46 within the epitope bound by any one or combination of monoclonal antibodies NKp46-1, -2, -3, -4, -6 or -9 or the Anti-CD19-Anti-NKp46-1, -2, -3, -4, -6 or -9 bispecific antibodies. In one aspect of any of the embodiments of the invention, the antigen binding domain that binds NKp46 binds to the same epitope on a NKp46 polypeptide as any of monoclonal antibodies NKp46-1, -2, -3, -4, -6 or -9 or to any of the Anti-CD19-Anti-NKp46-1, -2, -3, -4, -6 or -9 bispecific antibodies. In one embodiment, the antigen binding domain that binds NKp46 binds to an epitope on the NKp46 polypeptide of SEQ ID NO:1 wherein the epitope comprises one, two, three or more residues selected from the group of residues bound by any of antibodies NKp46-1, -2, -3, -4, -6 or -9.

In some embodiments, the protein that binds NKp46 exhibits significantly lower binding for a mutant NKp46 polypeptide in which a residue bound by any of antibodies NKp46-1, -2, -3, -4, -6 or -9 is substituted with a different amino acid, compared to a wild-type NKp46 polypeptide of SEQ ID NO: 1.

In one aspect of any of the embodiments of the invention, the protein that binds NKp46 competes for binding to a NKp46 polypeptide with any one or any combination of monoclonal antibodies NKp46-1, NKp46-2, NKp46-3, NKp46-4, NKp46-6 or NKp46-9, or any of the Anti-CD19-anti-NKp46-1, -2, -3, -4, -6 or -9 bispecific antibodies. In one embodiment, the protein that binds NKp46 competes for binding to an NKp46 polypeptide with an antibody selected from the group consisting of:
(a) an antibody having respectively a $V_H$ and $V_L$ region of SEQ ID NOS: 3 and 4 (NKp46-1);
(b) an antibody having respectively a $V_H$ and $V_L$ region of SEQ ID NOS: 5 and 6 (NKp46-2);
(c) an antibody having respectively a $V_H$ and $V_L$ region of SEQ ID NOS: 7 and 8 (NKp46-3);
(d) an antibody having respectively a $V_H$ and $V_L$ region of SEQ ID NOS: 9 and 10 (NKp46-4);
(e) an antibody having respectively a $V_H$ and $V_L$ region of SEQ ID NOS:11 and 12 (NKp46-6); and
(f) an antibody having respectively a $V_H$ and $V_L$ region of SEQ ID NOS: 13 and 14 (NKp46-9).

In one embodiment, the invention provides a protein (or nucleic acid encoding such) that specifically binds NKp46 (e.g. a monospecific monoclonal antibody or fragment, a multispecific protein or fragment, a bispecific antibody, etc.) that competes for binding to an NKp46 polypeptide with an antibody selected from the group consisting of:
(a) an antibody having respectively a $V_H$ and $V_L$ region of SEQ ID NOS: 3 and 4 (NKp46-1);
(b) an antibody having respectively a $V_H$ and $V_L$ region of SEQ ID NOS: 5 and 6 (NKp46-2);
(c) (a) an antibody having respectively a $V_H$ and $V_L$ region of SEQ ID NOS: 7 and 8 (NKp46-3);
(d) (a) an antibody having respectively a $V_H$ and $V_L$ region of SEQ ID NOS: 9 and 10 (NKp46-4);
(e) an antibody having respectively a $V_H$ and $V_L$ region of SEQ ID NOS:11 and 12 (NKp46-6); and
(f) an antibody having respectively a $V_H$ and $V_L$ region of SEQ ID NOS: 13 and 14 (NKp46-9).

In one aspect of any of the embodiments of the invention, the antigen binding domain that binds NKp46 comprises the hypervariable regions of any one of monoclonal antibodies NKp46-1, NKp46-2, NKp46-3, NKp46-4, NKp46-6 or NKp46-9 or a combination of any of the foregoing.

In one aspect of any of the embodiments of the invention, the antigen binding domain that binds NKp46 has a heavy and/or light chain variable region having one, two or three CDRs of the respective heavy and/or light chain of an antibody selected from the group consisting of antibody NKp46-1, NKp46-2, NKp46-3, NKp46-4, NKp46-6 and NKp46-9.

In one embodiment, an isolated multispecific protein that binds NKp46 according to the invention comprises or an antigen binding domain thereof comprises heavy chain CDR1, 2 and 3 and light chain CDR 1, 2 and 3 of any of the antibodies selected from the group consisting of:
(a) an antibody having respectively a $V_H$ and $V_L$ region of SEQ ID NOS: 3 and 4 (NKp46-1);
(b) an antibody having respectively a $V_H$ and $V_L$ region of SEQ ID NOS: 5 and 6 (NKp46-2);
(c) (a) an antibody having respectively a $V_H$ and $V_L$ region of SEQ ID NOS: 7 and 8 (NKp46-3);
(d) (a) an antibody having respectively a $V_H$ and $V_L$ region of SEQ ID NOS: 9 and 10 (NKp46-4);
(e) an antibody having respectively a $V_H$ and $V_L$ region of SEQ ID NOS:11 and 12 (NKp46-6); and
(f) an antibody having respectively a $V_H$ and $V_L$ region of SEQ ID NOS: 13 and 14 (NKp46-9).

In one embodiment, the invention provides an antibody (e.g. a full length monospecific antibody or a bispecific antibody) or antigen binding domain (which optionally may be humanized, chimerized or affinity matured) that binds NKp46 and comprises:
(a) (i) a polypeptide chain comprising a CDR 1, 2 and 3 of the heavy chain variable region of NKp46-1 of Table A, and (ii) a polypeptide chain comprising a CDR 1, 2 and 3 of the light chain variable region of NKp46-1 of Table A;
(b) (i) a polypeptide chain comprising a CDR 1, 2 and 3 of the heavy chain variable region of NKp46-2 of Table A and (ii) a polypeptide chain comprising a CDR 1, 2 and 3 of the light chain variable region of NKp46-2 of Table A;
(c) (i) a polypeptide chain comprising a CDR 1, 2 and 3 of the heavy chain variable region of NKp46-3 of Table A and (ii) a polypeptide chain comprising a CDR 1, 2 and 3 of the light chain variable region of NKp46-3 of Table A;
(d) (i) a polypeptide chain comprising a CDR 1, 2 and 3 of the heavy chain variable region of NKp46-4 of Table A and (ii) a polypeptide chain comprising a CDR 1, 2 and 3 of the light chain variable region of NKp46-4 of Table A;
(e) (i) a polypeptide chain comprising a CDR 1, 2 and 3 of the heavy chain variable region of NKp46-6 of Table A and (ii) a polypeptide chain comprising CDR 1, 2 and 3 of the light chain variable region of NKp46-6 of Table A; or
(f) (i) a polypeptide chain comprising a CDR 1, 2 and 3 of the heavy chain variable region of NKp46-9 of Table A and (ii) a polypeptide chain comprising a CDR 1, 2 and 3 of the light chain variable region of NKp46-9 of Table A.

In one aspect, the invention provides a protein (a monomeric or multimeric protein) that specifically binds NKp46 (e.g. a monospecific monoclonal antibody, a multispecific protein, a bispecific antibody) that binds the same or overlapping epitope on NKp46 as an antibody selected from the group consisting of antibody NKp46-1, NKp46-2, NKp46-3, NKp46-4, NKp46-6 and NKp46-9. The isolated polypeptide may be, for example, a monospecific monoclonal antibody, a multispecific polypeptide or a bispecific antibody.

In one aspect the invention provides an isolated multispecific heterotrimeric protein comprising a first polypeptide chain comprising an amino acid sequence which is at least 50%, 60%, 70%, 80%, 85%, 90%, 95%, 98 or 99% identical to the sequence of a first polypeptide chain of a F5, F13 or T5 protein disclosed herein; a second polypeptide chain comprising an amino acid sequence which is at least 50%, 60%, 70%, 80%, 85%, 90%, 95%, 98 or 99% identical to the sequence of a second polypeptide chain of the respective F5, F13 or T5 protein disclosed herein; and a third polypeptide chain comprising an amino acid sequence which is at least 50%, 60%, 70%, 80%, 85%, 90%, 95%, 98 or 99% identical to the sequence of a third polypeptide chain of a F5, F13 or T5 protein disclosed herein. In one aspect, the protein comprises a dimeric Fc domain capable of being bound by a human CD16 polypeptide, e.g. a dimeric Fc domain comprising N-linked glycosylation at residue N297 (Kabat EU numbering). Optionally any or all of the variable regions or CDRs of the first, second and/or third chains are substituted with different variable regions; optionally any or all of the V-CH1/Cκ units of the first, second and/or third chains are substituted with different V-CH1/Cκ units. Optionally variable regions, CDRs or V-CH1/Cκ units are excluded from the sequences that are considered for computing identity; optionally wherein the anti-NKp46 variable regions, CDRs or V-CH1/Cκ units are included for computing identity and the variable regions, CDRs or V-CH1/Cκ units for the antigen binding domain that binds the other antigen are excluded from the sequences that are considered for computing identity.

In one embodiment of any of the polypeptides described herein, the multispecific polypeptide is capable of directing NKp46-expressing NK cells to lyse a target cell of interest (e.g. a target cell expressing an antigen other than NKp46).

In one aspect of any of the embodiments described herein, the invention provides a recombinant nucleic acid encoding a first polypeptide chain, and/or a second polypeptide chain, and/or a third polypeptide chain and/or a fourth polypeptide. In one aspect of any of the embodiments described herein, the invention provides a recombinant host cell comprising a nucleic acid encoding a first polypeptide chain, and/or a second polypeptide chain and/or a third polypeptide chain, optionally wherein the host cell produces a multimeric or other protein according to the invention with a yield (final productivity or concentration before or after purification) of at least 1, 2, 3 or 4 mg/L. Also provided is a kit or set of nucleic acids comprising a recombinant nucleic acid encoding a first polypeptide chain of the according to the invention, a recombinant nucleic acid encoding a second polypeptide chain according to the invention, and, optionally, a recombinant nucleic acid encoding a third polypeptide chain according to the invention. Also provided are methods of making dimeric, trimeric and tetrameric proteins according to the invention.

Any of the methods can further be characterized as comprising any step described in the application, including notably in the "Detailed Description of the Invention"). The invention further relates to methods of identifying, testing and/or making proteins described herein. The invention further relates to a multispecific protein obtainable by any of present methods. The disclosure further relates to pharmaceutical or diagnostic formulations containing at least one of the multispecific proteins disclosed herein. The disclosure further relates to methods of using the subject multispecific proteins in methods of treatment or diagnosis.

These and additional advantageous aspects and features of the invention may be further described elsewhere herein.

BRIEF DESCRIPTION OF THE FIGURES

FIG. 1 shows that Anti-CD19-F1-Anti-CD3 does not cause T/B cell aggregation in the presence of B221 (CD19) or JURKAT (CD3) cell lines when separate, but it does cause aggregation of cells when both B221 and JURKAT cells are co-incubated.

FIGS. 2A to 2F show different domain arrangements of bispecific anti-NKp46 proteins produced.

FIG. 4A shows that bispecific antibodies having NKp46 and CD19 binding regions in an F2 format protein do not activate resting NK cells in the absence of target cells; by contrast full length anti-NKp46 antibodies as well as positive control alemtuzumab did activate NK cells. FIG. 4B shows that bispecific anti-NKp46×anti-CD19 antibodies (including each of the NKp46-1, NKp46-2, NKp46-3 or NKp46-4 binding domains) activated resting NK cells in presence of Daudi target cells, while full-length anti-CD19 showed at best only very low activation of NK cells and neither full-length anti-NKp46 antibodies nor alemtuzumab elicited a substantial increase in activation beyond what was observed in the presence of NK cells alone.

DETAILED DESCRIPTION OF THE INVENTION

Definitions

Figure 2A:
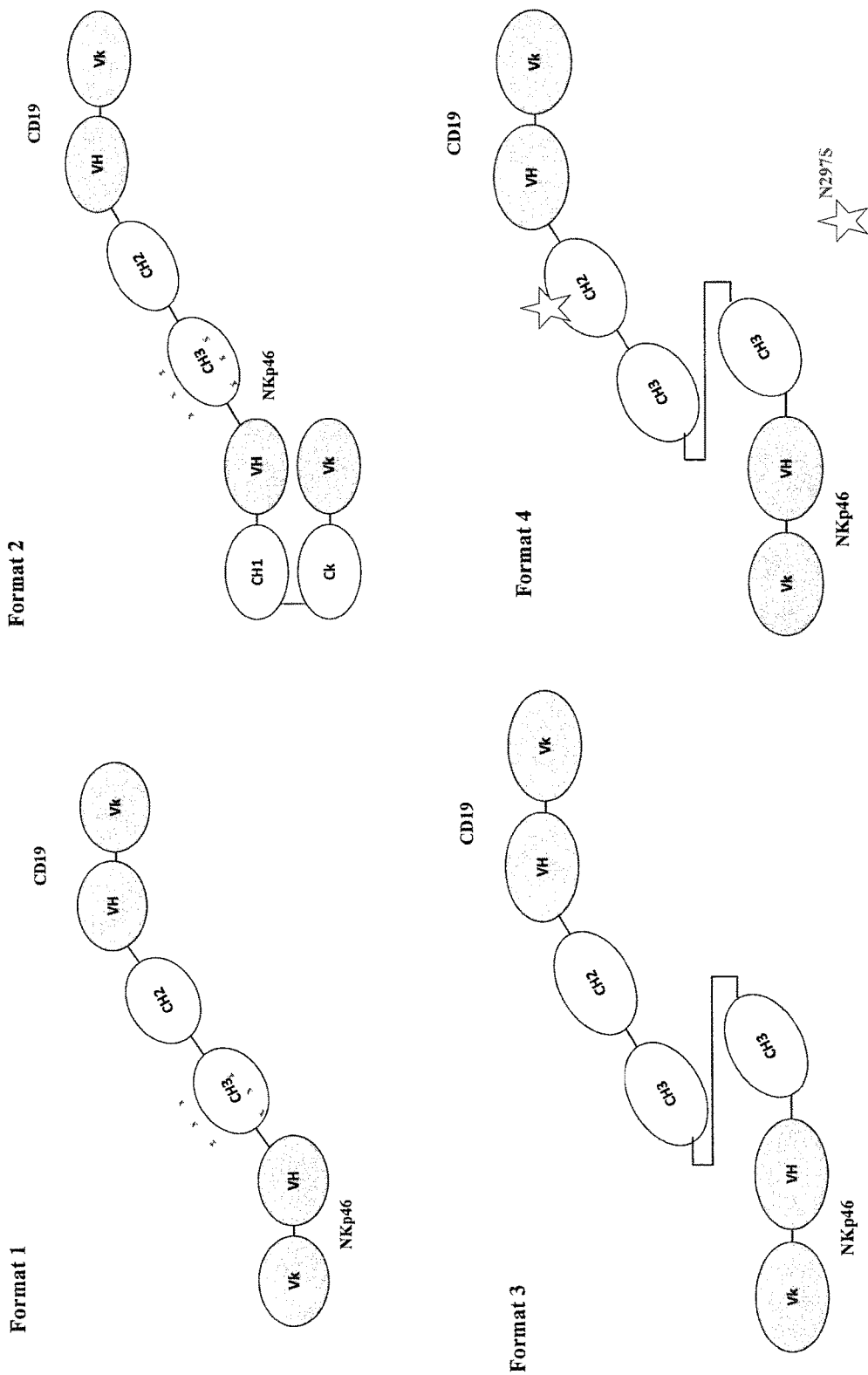

As used in the specification, "a" or an may mean one or more. As used in the claim(s), when used in conjunction with the word "comprising", the words "a" or an may mean one or more than one.

Where "comprising" is used, this can optionally be replaced by "consisting essentially of", or optionally by "consisting of".

As used herein, the term "antigen binding domain" or "ABD" refers to a domain comprising a three-dimensional structure capable of immunospecifically binding to an epitope. Thus, in one embodiment, said domain can comprise a hypervariable region, optionally a $V_H$ and/or $V_L$ domain of an antibody chain, optionally at least a $V_H$ domain. In another embodiment, the binding domain may comprise at least one complementarity determining region (CDR) of an antibody chain. In another embodiment, the binding domain may comprise a polypeptide domain from a non-immunoglobulin scaffold.

The term "antibody" herein is used in the broadest sense and specifically includes full-length monoclonal antibodies, polyclonal antibodies, multispecific antibodies (e.g., bispecific antibodies), and antibody fragments and derivatives, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988). An "antibody fragment" comprises a portion of a full-length antibody, e.g. antigen-binding or variable regions thereof. Examples of antibody fragments include Fab, Fab', F(ab)$_2$, F(ab')$_2$, F(ab)$_3$, Fv (typically the $V_L$ and $V_H$ domains of a single arm of an antibody), single-chain Fv (scFv), dsFv, Fd fragments (typically the $V_H$ and CH1 domain), and dAb (typically a $V_H$ domain) fragments; $V_H$, $V_L$, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, e.g. comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" as defined herein is meant an antibody-derived constant region that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ, or Cλ, wherein numbering is according to the EU index (Kabat et al., 1991, Sequences of Proteins of Immunological Inter-

*est,* 5th Ed., United States Public Health Service, National Institutes of Health, Bethesda).

By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the $V_H$, CH1, $V_L$, and $C_L$ immunoglobulin domains. Fab may refer to this region in isolation, or this region in the context of a polypeptide, multi-specific polypeptide or ABD, or any other embodiments as outlined herein.

By "single-chain Fv" or "scFv" as used herein are meant antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994).

By "Fv" or "Fv fragment" or "Fv region" as used herein is meant a polypeptide that comprises the $V_L$ and $V_H$ domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 (CH2) and Cγ3 (CH3) and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" or "Fc-derived polypeptide" as used herein is meant a polypeptide that comprises all or part of an Fc region. Fc polypeptides herein include but are not limited to antibodies, Fc fusions and Fc fragments. Also, Fc regions according to the invention include variants containing at least one modification that alters (enhances or diminishes) an Fc associated effector function. Also, Fc regions according to the invention include chimeric Fc regions comprising different portions or domains of different Fc regions, e.g., derived from antibodies of different isotype or species.

By "variable region" as used herein is meant the region of an antibody that comprises one or more Ig domains substantially encoded by any of the $V_L$ (including Vκ (Vκ) and Vλ) and/or $V_H$ genes that make up the light chain (including κ and λ) and heavy chain immunoglobulin genetic loci respectively. A light or heavy chain variable region ($V_L$ or $V_H$) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

The term "specifically binds to" means that an antibody or polypeptide can bind preferably in a competitive binding assay to the binding partner, e.g. NKp46, as assessed using either recombinant forms of the proteins, epitopes therein, or native proteins present on the surface of isolated target cells. Competitive binding assays and other methods for determining specific binding are further described below and are well known in the art.

When an antibody or polypeptide is said to "compete with" a particular monoclonal antibody (e.g. NKp46-1, -2, -4, -6 or -9 in the context of an anti-NKp46 mono- or bi-specific antibody), it means that the antibody or polypeptide competes with the monoclonal antibody in a binding assay using either recombinant target (e.g. NKp46) molecules or surface expressed target (e.g. NKp46) molecules. For example, if a test antibody reduces the binding of NKp46-1, -2, -4, -6 or -9 to a NKp46 polypeptide or NKp46-expressing cell in a binding assay, the antibody is said to "compete" respectively with NKp46-1, -2, -4, -6 or -9.

The term "affinity", as used herein, means the strength of the binding of an antibody or polypeptide to an epitope. The affinity of an antibody is given by the dissociation constant $K_D$, defined as $[Ab] \times [Ag]/[Ab-Ag]$, where [Ab-Ag] is the molar concentration of the antibody-antigen complex, [Ab] is the molar concentration of the unbound antibody and [Ag] is the molar concentration of the unbound antigen. The affinity constant $K_A$ is defined by $1/K_D$. Preferred methods for determining the affinity of mAbs can be found in Harlow, et al., *Antibodies: A Laboratory Manual*, Cold Spring Harbor Laboratory Press, Cold Spring Harbor, N.Y., 1988), Coligan et al., eds., *Current Protocols in Immunology*, Greene Publishing Assoc. and Wiley Interscience, N.Y., (1992, 1993), and Muller, *Meth. Enzymol.* 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

Within the context of this invention a "determinant" designates a site of interaction or binding on a polypeptide.

The term "epitope" refers to an antigenic determinant, and is the area or region on an antigen to which an antibody or polypeptide binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'. Epitopes may be identified by different methods known in the art including but not limited to alanine scanning, phage display, X-ray crystallography, array-based oligo-peptide scanning or pepscan analysis, site-directed mutagenesis, high throughput mutagenesis mapping, H/D-Ex Mass Spectroscopy, homology modeling, docking, hydrogen-deuterium exchange, among others. (See e.g., Tong et al., Methods and Protocols for prediction of immunogenic epitopes", *Briefings in Bioinformatics* 8(2):96-108; Gershoni, Jonathan M; Roitburd-Berman, Anna; Siman-Tov, Dror D; Tarnovitski Freund, Natalia; Weiss, Yael (2007). "Epitope Mapping". *BioDrugs* 21 (3): 145-56; and Flanagan, Nina (May 15, 2011); "Mapping Epitopes with H/D-Ex Mass Spec: ExSAR Expands Repertoire of Technology Platform Beyond Protein Characterization", *Genetic Engineering & Biotechnology News* 31 (10).

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; *Sequence Analysis Primer*, Gribskov, M. and Devereux, J., eds., M. Stockton Press, New York, 1991; and Carillo et al., SIAM *J. Applied Math.* 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., *Nucl. Acid. Res.* 12, 387 (1984); Genetics Computer Group, University of Wisconsin, Madison, Wis.), BLASTP, BLASTN, and FASTA (Altschul et al., *J. Mol. Biol.* 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a polypeptide will exhibit 98%, 98%, or 99% homogeneity for polypeptides in the context of all present peptide species in the composition or at least with respect to substantially active peptide species in the context of proposed use.

In the context herein, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

As used herein, the phrase "NK cells" refers to a subpopulation of lymphocytes that is involved in non-conventional immunity. NK cells can be identified by virtue of certain characteristics and biological properties, such as the expression of specific surface antigens including CD56 and/or NKp46 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in *Natural Killer Cells Protocols* (edited by Campbell K S and Colonna M). Humana Press. pp. 219-238 (2000).

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" refer to events wherein intracellular internalization is initiated and/or the rate and/or extent of intracellular internalization is increased.

As used herein, an agent that has "agonist" activity at NKp46 is an agent that can cause or increase "NKp46 signaling". "NKp46 signaling" refers to an ability of an NKp46 polypeptide to activate or transduce an intracellular signaling pathway. Changes in NKp46 signaling activity can be measured, for example, by assays designed to measure changes in NKp46 signaling pathways, e.g. by monitoring phosphorylation of signal transduction components, assays to measure the association of certain signal transduction components with other proteins or intracellular structures, or in the biochemical activity of components such as kinases, or assays designed to measure expression of reporter genes under control of NKp46-sensitive promoters and enhancers, or indirectly by a downstream effect mediated by the NKp46 polypeptide (e.g. activation of specific cytolytic machinery in NK cells). Reporter genes can be naturally occurring genes (e.g. monitoring cytokine production) or they can be genes artificially introduced into a cell. Other genes can be placed under the control of such regulatory elements and thus serve to report the level of NKp46 signaling.

"NKp46" refers to a protein or polypeptide encoded by the Ncr1 gene or by a cDNA prepared from such a gene. Any naturally occurring isoform, allele, ortholog or variant is encompassed by the term NKp46 polypeptide (e.g., an NKp46 polypeptide 90%, 95%, 98% or 99% identical to SEQ ID NO 1, or a contiguous sequence of at least 20, 30, 50, 100 or 200 amino acid residues thereof). The 304 amino acid residue sequence of human NKp46 (isoform a) is shown below:

```
                                           (SEQ ID NO: 1)
MSSTLPALLC VGLCLSQRIS AQQQTLPKPF IWAEPHFMVP

KEKQVTICCQ GNYGAVEYQL HFEGSLFAVD RPKPPERINK

VKFYIPDMNS RMAGQYSCIY RVGELWSEPS NLLDLVVTEM

YDTPTLSVHP GPEVISGEKV TFYCRLDTAT SMFLLLKEGR

SSHVQRGYGK VQAEFPLGPV TTAHRGTYRC FGSYNNHAWS

FPSEPVKLLV TGDIENTSLA PEDPTFPADT WGTYLLTTET

GLQKDHALWD HTAQNLLRMG LAFLVLVALV WFLVEDWLSR

KRTRERASRA STWEGRRRLN TQTL.
```

SEQ ID NO: 1 corresponds to NCBI accession number NP_004820, the disclosure of which is incorporated herein by reference. The human NKp46 mRNA sequence is described in NCBI accession number NM_004829, the disclosure of which is incorporated herein by reference.

Producing Polypeptides

The antigen binding domains used in the proteins described herein can be readily derived from any of a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin III, anticalins derived from lipocalins, DARPins (designed ankyrin repeat domains, multimerized LDLR-A module, avimers or cysteine-rich knottin peptides. See, e.g., Gebauer and Skerra (2009) *Current Opinion in Chemical Biology* 13:245-255, the disclosure of which is incorporated herein by reference.

Variable domains are commonly derived from antibodies (immunoglobulin chains), for example in the form of associated $V_L$ and $V_H$ domains found on two polypeptide chains, or a single chain antigen binding domain such as a scFv, a $V_H$ domain, a $V_L$ domain, a dAb, a V-NAR domain or a $V_H H$ domain. In certain advantageous proteins formats disclosed herein that directly enable the use of a wide range of variable regions from Fab or scFv without substantial further requirements for pairing and/or folding, the an antigen binding domain (e.g., $ABD_1$ and $ABD_2$) can also be readily derived from antibodies as a Fab or scFv.

Typically, antibodies are initially obtained by immunization of a non-human animal, e.g., a mouse, rat, guinea pig or rabbit, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, *Antibodies: A Laboratory Manual.*, Cold Spring Harbor Laboratory Press, Cold Spring Harbor, N.Y. (1988), the entire disclosure of which is herein incorporated by reference). Human antibodies may also be produced by using, for immunization, transgenic animals that have been engineered to express a human antibody repertoire (Jakobovitz et Nature 362 (1993) 255), or by selection of antibody repertoires using phage display methods. For example, a Xeno-Mouse (Abgenix, Fremont, Calif.) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. Antibodies may also be produced by selection of combinatorial libraries of immunoglobulins, as disclosed for instance in (Ward et al. *Nature,* 341 (1989) p. 544, the entire disclosure of which is herein incorporated by reference). Phage display technology (McCafferty et al (1990) *Nature* 348:552-553) can be used to produce antibodies from immunoglobulin variable (V) domain gene repertoires from unimmunized donors. See, e.g., Griffith et al (1993) *EMBO J.* 12:725-734; U.S. Pat. No. 5,565,332; U.S. Pat. No. 5,573,905; U.S. Pat. No. 5,567,610; and U.S. Pat. No. 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Antibodies will typically be directed to a pre-determined antigen. Examples of antibodies include antibodies that recognize an antigen expressed by a target cell that is to be eliminated, for example a proliferating cell or a cell contributing to a disease pathology. Examples include antibodies that recognize tumor antigens, microbial (e.g. bacterial or parasite) antigens or viral antigens.

Antigen binding domains that bind NKp46 can be derived from the anti-NKp46 antibodies provided herein (see section "CDR Sequences"). Variable regions can be used directly, or can be modified by selecting hypervariable or CDR regions from the NKp46 antibodies and placing them into an appropriate $V_L$ or $V_H$ framework, for example human frameworks. Antigen binding domains that bind NKp46 can also be derived de novo using methods for generating antibodies. Antibodies can be tested for binding to NKp46 polypeptides. In one aspect of any embodiment herein, a polypeptide (e.g. multispecific polypeptide, bispecific or monospecific antibody) that binds to NKp46 will be capable of binding NKp46 expressed on the surface of a cell, e.g. native NKp46 expressed by a NK cell.

Antigen binding domains (ABDs) that bind antigens of interest can be selected based on the desired antigen of interest (e.g. an antigen other than NKp46), and may include for example cancer antigens such as antigens present on tumor cells and/or on immune cells capable of mediating a pro-tumoral effect, e.g. a monocyte or a macrophage, optionally a suppressor T cell, regulatory T cell, or myeloid-derived suppressor cell (for the treatment of cancer); bacterial or viral antigens (for the treatment of infectious disease); or antigens present on pro-inflammatory immune cells, e.g. T cells, neutrophils, macrophages, etc. (for the treatment of inflammatory and/or autoimmune disorder). As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In some embodiments the bacterial antigen is derived from a bacterium selected from the group consisting of *Helicobacter* species, in particular *Helicobacter pyloris; Borrelia* species, in particular *Borrelia burgdorferi; Legionella* species, in particular *Legionella pneumophilia; Mycobacteria* s species, in particular *M. tuberculosis, M. avium, M. intracellulare, M. kansasii, M. gordonae; Staphylococcus* species, in particular *Staphylococcus aureus; Neisseria* species, in particular *N. gonorrhoeae, N. meningitidis; Listeria* species, in particular *Listeria monocytogenes; Streptococcus* species, in particular *S. pyogenes, S. agalactiae; S. faecalis; S. bovis, S. pneumoniae*; anaerobic *Streptococcus* species; pathogenic *Campylobacter* species; *Enterococcus* species; *Haemophilus* species, in particular *Haemophilus influenzae; Bacillus* species, in particular *Bacillus anthracis; Corynebacterium* species, in particular *Corynebacterium diphtheriae; Erysipelothrix* species, in particular *Erysipelothrix rhusiopathiae; Clostridium* species, in particular *C. perfringens, C. tetani; Enterobacter* species, in particular *Enterobacter aerogenes, Klebsiella* species, in particular *Klebsiella* 1S *pneumoniae, Pasteurella* species, in particular *Pasteurella multocida, Bacteroides* species; *Fusobacterium* species, in particular *Fusobacterium nucleatum; Streptobacillus* species, in particular *Streptobacillus moniliformis; Treponema* species, in particular *Treponema pertenue; Leptospira*; pathogenic *Escherichia* species; and *Actinomyces* species, in particular *Actinomyces israeli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens (other than NKp46 or CD16) that are differentially expressed by cancer cells or are expressed by non-tumoral cells (e.g. immune cells) having a pro-tumoral effect (e.g. an immunosuppressive effect), and can thereby be exploited in order to target cancer cells. Cancer antigens are antigens which can potentially stimulate apparently tumor-specific immune responses. Some of these antigens are encoded, although not necessarily expressed, or expressed at lower levels or less frequently, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Still other cancer antigens can be expressed on immune cells capable of contributing to or mediating a pro-tumoral effect, e.g. cell that contributes to immune evasion, a monocyte or a macrophage, optionally a suppressor T cell, regulatory T cell, or myeloid-derived suppressor cell.

The cancer antigens are usually normal cell surface antigens which are either over-expressed or expressed at abnormal times, or are expressed by a targeted population of cells. Ideally the target antigen is expressed only on proliferative cells (e.g., tumor cells) or pro-tumoral cells (e.g. immune cells having an immunosuppressive effect), however this is rarely observed in practice. As a result, target antigens are in many cases selected on the basis of differential expression between proliferative/disease tissue and healthy tissue.

Example of cancer antigens include: Receptor Tyrosine Kinase-like Orphan Receptor 1 (ROR1), Crypto, CD4, CD20, CD30, CD19, CD38, CD47, Glycoprotein NMB, CanAg, Her2 (ErbB2/Neu), a Siglec family member, for example CD22 (Siglec2) or CD33 (Siglec3), CD79, CD138, CD171, PSCA, L1-CAM, PSMA (prostate specific membrane antigen), BCMA, CD52, CD56, CD80, CD70, E-selectin, EphB2, Melanotransferrin, Mud 6 and TMEFF2. Examples of cancer antigens also include Immunoglobulin superfamily (IgSF) such as cytokine receptors, Killer-Ig Like Receptor, CD28 family proteins, for example, Killer-Ig Like Receptor 3DL2 (KIR3DL2), B7-H3, B7-H4, B7-H6, PD-L1, IL-6 receptor. Examples also include MAGE, MART-1/Melan-A, gp100, major histocompatibility complex class I-related chain A and B polypeptides (MICA and MICB), adenosine deaminase-binding protein (ADAbp), cyclophilin b, colorectal associated antigen (CRC)-C017-1A/GA733, protein tyrosine kinase 7(PTK7), receptor protein tyrosine kinase 3 (TYRO-3), nectins (e.g. nectin-4), major histocompatibility complex class I-related chain A and B polypeptides (MICA and MICB), proteins of the UL16-binding protein (ULBP) family, proteins of the retinoic acid early transcript-1 (RAET1) family, carcinoembryonic antigen (CEA) and its immunogenic epitopes CAP-1 and CAP-2, etv6, aml1 prostate specific antigen (PSA), T-cell receptor/CD3-zeta chain, MAGE-family of tumor antigens, GAGE-family of tumor antigens, anti-Müllerian hormone Type II receptor, delta-like ligand 4 (DLL4), DR5, ROR1 (also known as Receptor Tyrosine Kinase-Like Orphan Receptor 1 or NTRKR1 (EC 2.7.10.1), BAGE, RAGE, LACE-1, NAG, GnT-V, MUM-1, CDK4, MUC family, VEGF, VEGF receptors, Angiopoietin-2, PDGF, TGF-alpha, EGF, EGF receptor, members of the human EGF-like receptor family, e.g., HER-2/neu, HER-3, HER-4 or a heterodimeric receptor comprised of at least one HER subunit, gastrin releasing peptide receptor antigen, Muc-1, CA125, integrin receptors, $\alpha v\beta 3$ integrins, $\alpha 5\beta 1$ integrins, $\alpha IIb\beta 3$-integrins, PDGF beta receptor, SVE-cadherin, IL-8 receptor, hCG, IL-6 receptor, CSF1R (tumor-associated monocytes and macrophages), $\alpha$-fetoprotein, E-cadherin, $\alpha$-catenin, $\beta$-catenin and $\gamma$-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive. In one aspect, the antigen of interest is an antigen (e.g. any one of the antigens listed above) capable of undergoing intracellular internalization, for example when bound by a conventional human IgG1 antibody, either in the presence of absence of Fcγ receptor cells. In one aspect, the antigen of interest is a CD19 or CD20 polypeptide; in one aspect, the multispecific protein comprises a $V_H$ and/or $V_L$, or a scFv or another ABD that binds CD19 or CD20 comprising an amino acid sequence which is at least 60%, 70%, 80%, 85%, 90% or 95% identical to the sequence of the anti-CD19 or anti-CD20 respective $V_H$, $V_L$ or scFv described in the Examples herein, or comprises the heavy and light chain CDR1, -2 and -3 of the anti-CD19 or anti-CD20 heavy and light chain variable regions disclosed herein. In one aspect, the multispecific protein competes for binding to a human CD19 or CD20 polypeptide with an antibody, or a F5 or T6 protein, comprising the respective anti-CD19 or anti-CD20 $V_H$, $V_L$ or scFv disclosed in the Examples.

In one embodiment, the ABD that binds an antigen of interest is derived from (e.g. comprises the hypervariable region of, or comprises one, two, three, four, five or six of the CDRs of) a parental antibody that binds an antigen of interest (e.g. a murine antibody, a human antibody) which, when bound to its antigenic target (the antigen of interest on cells), increases or induces down-modulation or intracellular internalization of the antigen of interest. In one embodiment, the antigen of interest is a cancer antigen, e.g. one of the cancer antigens listed above known to internalize (e.g. Immunoglobulin superfamily (IgSF) members, for example cytokine receptor α or β chains, Killer-Ig Like Receptors, CD28 family proteins, B7-H3, B7-H4, B7-H6, KIR3DL2, PTK7, ROR1, L1-CAM, Siglec family members, EGF receptor and EGF-like receptor family members, EGFR, HER-2, integrins, anti-Müllerian hormone Type II receptor, CSF-1R, and others) In one embodiment, the antigen target is a polypeptide present on an immune cell capable of mediating a pro-tumoral effect, e.g. a monocyte or a macrophage, optionally a suppressor T cell, regulatory T cell, or myeloid-derived suppressor cell.

In one embodiment, the ABD binds to a cancer antigen, a viral antigen, a microbial antigen, or an antigen present on an infected cell (e.g. virally infected) or on a pro-inflammatory immune cell. In one embodiment, said antigen is a polypeptide selectively expressed or overexpressed on a tumor cell, and infected cell or a pro-inflammatory cell. In one embodiment, said antigen is a polypeptide that when inhibited, decreases the proliferation and/or survival of a tumor cell, an infected cell or a pro-inflammatory cell.

The ABDs which are incorporated into the polypeptides can be tested for any desired activity prior to inclusion in a multispecific NKp46-binding protein, for example the ABD can be tested for binding to an antigen of interest.

An ABD derived from an antibody will generally comprise at minimum a hypervariable region sufficient to confer binding activity. It will be appreciated that an ABD may comprise other amino acids or functional domains as may be desired, including but not limited to linker elements (e.g. linker peptides, CH1, Cκ or Cλ domains, hinges, or fragments thereof). In one example an ABD comprises a scFv, a $V_H$ domain and a $V_L$ domain, or a single domain antibody (nanobody or dAb) such as a V-NAR domain or a $V_H$H domain. Exemplary antibody formats are further described herein and an ABD can be selected based on the desired format.

In any embodiment, an antigen binding domain can be obtained from a humanized antibody in which residues from a complementary-determining region (CDR) of a human antibody are replaced by residues from a CDR of the original antibody (the parent or donor antibody, e.g. a murine or rat antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, *Nature* 321:522-525, Verhoeyen et al., 1988, *Science* 239:1534-1536. An antigen binding domain can thus have non-human hypervariable regions or CDRs and human frameworks region sequences (optionally with back mutations).

Once appropriate antigen binding domains having desired specificity and/or activity are identified, DNA encoding each of the or ABD can be separately placed, in suitable arrangements, in an appropriate expression vector, together with DNA encoding any elements such as CH1, CK, CH2 and CH3 domains or portions thereof and any other optional elements (e.g. DNA encoding a hinge-derived or linker elements) for transfection into an appropriate host. ABDs will be arranged in an expression vector, or in separate vectors as a function of which type of polypeptide is to be produced, so as to produce the Fc-polypeptides having the desired domains operably linked to one another. The host is then used for the recombinant production of the multispecific polypeptide.

For example, a polypeptide fusion product can be produced from a vector in which the first of the two ABD is operably linked (e.g. directly, or via a CH1, Cκ or Cλ constant region and/or hinge region) to the N-terminus of a CH2 domain, and the CH2 domain is operably linked at its C-terminus to the N-terminus a CH3 domain. The second of the two ABD can be on a second polypeptide chain that forms a dimer, e.g. heterodimer, with the polypeptide comprising the first ABD. The polypeptide may comprise a full length and/or dimeric Fc domain.

The multispecific polypeptide can then be produced in an appropriate host cell or by any suitable synthetic process. A host cell chosen for expression of the multispecific polypeptide is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein such that the multispecific polypeptide retains FcRn and CD16 binding. The host cell may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. The host cell may be any suitable species or organism capable of producing N-linked glycosylated polypeptides, e.g. a mammalian host cell capable of producing human or rodent IgG type N-linked glycosylation.

Multimeric bispecific proteins such as heterodimers, heterotrimers and tetramers (the latter including for example bispecific antibodies with two heavy chains and two light chains) can be produced according to a variety of formats. The multimeric polypeptide will generally comprise a dimeric Fc domain that is capable of binding to human CD16 or CD16A and optionally other Fcγ receptors, e.g., CD16B, CD32A, CD32B and/or CD64). Fc moieties with substantial FcRn and CD16 (CD16A) binding can be obtained through the use of suitable CH2 and/or CH3 domains, as further described herein. In one embodiment, an Fc moiety is derived from a human IgG1 isotype constant region. In one embodiment, an Fc moiety may be obtained by production of the polypeptide in a host cell or by a process that yields N297-linked glycosylation, e.g. a mammalian cell. In one embodiment, an Fc moiety comprises one or more amino acid modifications, e.g. in the CH2 domain, that increases binding to CD16 or CD16A.

In one example, the protein comprises a first and a second polypeptide chain each comprising a variable domain fused to a human Fc domain (comprising a CH3 domain capable of undergoing preferential CH3-CH3 hetero-dimerization), wherein the first and second chain associate via CH3-CH3 dimerization and the protein comprises a dimeric Fc domain. The variable domains of each chain can be part of the same or different antigen binding domains.

One advantageous way of making multimeric polypeptides is through the assembly of different polypeptide chains that each comprise at least one heavy or light chain variable domain fused to a human CH1 or Cκ constant domain (a V-(CH1/Cκ) unit), wherein the protein chains undergo CH1-Cκ dimerization and are bound to one another by non-covalent bonds and optionally further disulfide bonds formed between respective CH1 and Cκ domains. In one embodiment, the invention provides an isolated or purified heterodimeric or heterotrimeric protein that binds to a first and second antigen, wherein the protein comprises at least two or three polypeptide chains, each comprising a V-(CH1/Cκ) unit, whereby the chains are bound to one another by non-covalent bonds and optionally further bound via disulfide bonds between CH1 and Cκ domains, and still further optionally, whereby the chains are bound by non-covalent bonds between the respective variable regions, CH1 and Cκ domains, and CH3 domains of the Fc portion.

In one example, the protein comprises a first and a second polypeptide chain each comprising a variable domain fused to a CH1 or Cκ domain (a V-(CH1/Cκ) unit), in turn fused at its C-terminus to a human Fc domain (comprising a CH3 domain capable of undergoing CH3-CH3 dimerization), wherein the first and second chain associate via CH1-Cκ and CH3-CH3 dimerization and the protein comprises a dimeric Fc domain. The variable domains of each chain can be part of the same or different antigen binding domains.

The variable and constant regions can be selected and configured such that each chain will preferentially associate with its desired complementary partner chain. The resulting multimeric protein will therefore be simple to produce using conventional production methods using recombinant host cells. The choice of which $V_H$ or $V_L$ to associate with a CH1 and Cκ in a unit is based on affinity between the units to be paired so as to drive the formation of the desired multimer. The resulting multimer will be bound by non-covalent bonds between complementary $V_H$ and $V_L$ domains, by non-covalent bonds between complementary CH1 and Cκ domains, and optionally by further disulfide bonding between complementary CH1 and Cκ domains (and optionally further disulfide bonds between complementary hinge domains). $V_H$-$V_L$ associations are stronger than $V_H$-$V_H$ or $V_L$-$V_L$, consequently, as shown herein, one can place a $V_H$ or a $V_L$ next to either a CH1 or a Cκ, and the resulting V-C unit will partner preferably with its V-C counterpart. For example $V_H$-Cκ will pair with $V_L$-CH1 preferentially over $V_H$-CH1. Additionally, by including an Fc domain, preferred chain pairing is further improved, as the two Fc-containing chains are bound by non-covalent bonds between CH3 domains of the Fc domains. The different V-C combinations, optionally further combined with Fc pairing thereby provides tools to make heteromultimeric proteins.

In one example, the multispecific protein comprises a first and a second polypeptide chain each comprising a variable domain fused to a CH1 or Cκ domain (a V-(CH1/Cκ) unit), in turn fused at its C-terminus to a human Fc domain, wherein the V-(CH1/Cκ) unit of the first chain has undergone CH1-Cκ dimerization with the V-(CH1/Cκ) unit of the second chain thereby forming a first antigen binding domain (ABD$_1$) and a dimeric Fc domain, wherein one of the polypeptide chains further comprises an antigen binding domain that forms a second antigen binding domain (ABD$_2$), and wherein the Fc domain binds to a human CD16 polypeptide. In one embodiment, the Fc domain comprises N-linked glycosylation at residue N297 (Kabat EU numbering). In one example, the protein has a domain arrangement:

$V_{a1}$—(CH1 or CK)$_a$—Fc domain—$V_{a-2}$—$V_{b-2}$ (first/central polypeptide chain)
|
$V_{b1}$—(CH1 or CK)$_b$—Fc domain (second polypeptide chain).

In one example, the protein comprises three polypeptide chains, each comprising a variable domain fused to a CH1 or Cκ domain (a V-(CH1/Cκ) unit), wherein a first (central) chain comprises two V-(CH1/Cκ) units and a human Fc domain interposed between the units, the second chain comprises one V-(CH1/Cκ) unit and a human Fc domain, and the third chain comprises one V-(CH1/Cκ) unit, wherein one of the V-(CH1/Cκ) units of the central chain has undergone CH1-Cκ dimerization with the V-(CH1/Cκ) unit of the second chain thereby forming a first antigen binding domain (ABD$_1$) and a dimeric Fc domain, and wherein the other of the V-(CH1/Cκ) units of the central chain has undergone CH1-Cκ dimerization with the V-(CH1/Cκ) unit of the third chain thereby forming a second antigen binding domain (ABD$_2$), and wherein the Fc domain binds to a human CD16 polypeptide. In one embodiment, the Fc domain comprises N-linked glycosylation at residue N297 (Kabat EU numbering). In one example, the protein has a domain arrangement:

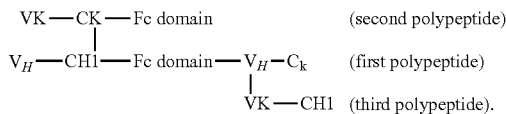

In certain formats, heterodimers are formed in which variable domains adjacent to the CH1 or Cκ domain do not require association with the second chain to form an antigen binding domain. For example, through use of single variable domains, or scFv, each chain will contain a functional ABD. Examples based CH1-Cκ dimerization with single variable exemplary heterodimer molecules can have a domain arrangement:

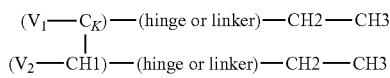

wherein $V_1$ and $V_2$ are single variable domains (e.g. $V_H$ domain, a $V_L$ domain, a dAb, a V-NAR domain or a $V_HH$ domain), and one of $V_1$ and $V_2$ binds NKp46 and the other binds an antigen of interest.

In one embodiment, exemplary heterodimer molecules can have a domain arrangement:

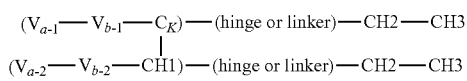

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a $V_H$ and the other is a $V_L$ such that $V_{a-1}$ and $V_{b-1}$ form a first antigen binding domain (ABD), wherein one of $V_{a-2}$ and $V_{b-2}$ is a $V_H$ and the other is a $V_L$ such that $V_{a-2}$ and $V_{b-2}$ form a second antigen binding domain, wherein one of the ABD binds NKp46 and the other binds an antigen of interest. In one variant of the foregoing, any of, or each of the $V_{a-1}$, $V_{b-1}$, $V_{a-2}$ and $V_{b-2}$ are a scFv (made up of two variable domains). Each pair of V domains can be separated by a linker peptide (e.g. to form a scFv).

In similar approaches, trimers can be constructed. Exemplary heterotrimer molecules can have the following domain arrangement:

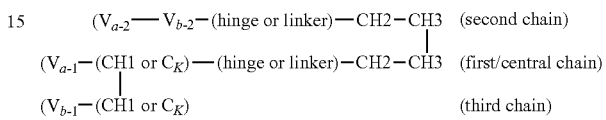

wherein the first/central chain and the second chain associate by CH3-CH3 dimerization and the first/central chain and the third chain associate by the CH1 or Cκ dimerization, wherein the domains of the first/central chain and the third chain are selected to be complementary to permit the first and third chains to associate by CH1-Cκ dimerization, and wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a $V_H$ and the other is a $V_L$ such that $V_{a-1}$ and $V_{b-1}$ form a first antigen binding domain (ABD), wherein one of $V_{a-2}$ and $V_{b-2}$ is a VH and the other is a $V_L$ such that $V_{a-2}$ and $V_{b-2}$ form a second antigen binding domain (e.g. an scFv wherein $V_{a-2}$ and $V_{b-2}$ are separated by a linker), wherein one of the ABD binds NKp46 and the other binds an antigen of interest.

In one embodiment, multimeric proteins are constructed based upon two Fc-containing chains (e.g. chains 1 and 2) to create a dimer via CH3-CH3 dimerization and/or hinge dimerization, and a further chain (e.g. chain 3) comprising a V-C$_H$/Cκ unit that dimerizes with one of chains 1 or 2. Exemplary molecules can have the following domain arrangement:

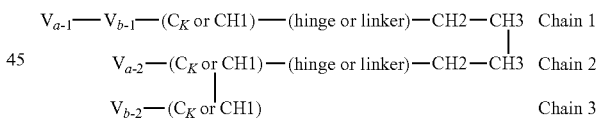

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a VH and the other is a $V_L$ such that $V_{a-1}$ and $V_{b-1}$ form a first antigen binding domain (ABD), wherein one of $V_{a-2}$ and $V_{b-2}$ is a VH and the other is a $V_L$ such that $V_{a-2}$ and $V_{b-2}$ form a second antigen binding domain.

Exemplary molecules may possess the following domain arrangement:

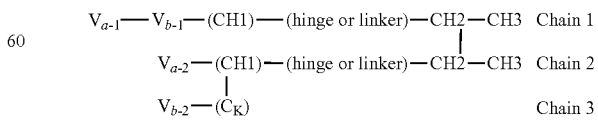

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a $V_H$ and the other is a $V_L$ such that $V_{a-1}$ and $V_{b-1}$ form a first antigen binding domain (ABD), wherein one of $V_{a-2}$ and $V_{b-2}$ is a $V_H$ and the other is a $V_L$ such that $V_{a-2}$ and $V_{b-2}$ form a second antigen binding domain. The CH1 and Cκ are selected such that chain 1 is capable of associating with chain 2 and chain 2 with chain 3. The protein can be configured such that chains 1 and 2 associate via CH3-CH3 dimerization and chains 2 and 3 associate via CH1-Cκ dimerization.

Optionally, any of the multispecific proteins of the invention may include, CH3 domains which comprise amino acid substitutions, wherein the CH3 domain interface of the antibody Fc region is mutated to create altered charge polarity across the Fc dimer interface such that co-expression of electrostatically matched Fc chains supports favorable attractive interactions thereby promoting desired Fc heterodimer formation, whereas unfavorable repulsive charge interactions suppress unwanted Fc homodimer formation.

Heterodimeric or heterotrimeric polypeptides with two ABDs and a dimeric Fc domain can optionally be produced as one or more chains that each associate with a central chain, e.g. by CH1-Cκ heterodimerization. Such multimers may be composed of a central (first) polypeptide chain comprising two immunoglobulin variable domains that are part of separate antigen binding domains (of different antigen specificities), the one or more other chains that provide the additional and/or complementary variable domains, and an Fc domain placed on the central and/or one or more other chains. In one embodiment, the Fc domain is interposed between the two ABDs in the multimeric protein.

In one example, the first (central) polypeptide chain will provide one variable domain that will, together with a complementary variable domain on a second polypeptide chain, form an antigen binding domain specific for one (e.g. a first) antigen of interest. The first (central) polypeptide chain will also provide a second variable domain (e.g., placed on the opposite end of the interposed Fc domain) that will be paired with a complementary variable domain to form an antigen binding domain specific for another (e.g. a second) antigen of interest; the variable domain that is complementary to the second variable domain can be placed on the central polypeptide (e.g. adjacent to the second variable domain in a tandem variable domain construct such as an scFv), or can be placed on a separate polypeptide chain, notably a third polypeptide chain. The second (and third, if present) polypeptide chains will associate with the central polypeptide chain by CH1-Cκ heterodimerization, forming non-covalent bonds and optionally further interchain disulfide bonds between complementary CH1 and Cκ domains (and optionally interchain disulfide bonds between hinge regions), with a primary multimeric polypeptide being formed so long as CH/CK and $V_H/V\kappa$ domains are chosen to give rise to a preferred dimerization configuration that results preferentially in the desired $V_H$-$V_L$ pairings. Remaining unwanted pairings can remain minimal during production and/or are removed during purification steps. In a trimer, or when polypeptides are constructed for preparation of a trimer, there will generally be one polypeptide chain that comprises a non-naturally occurring VH-CK or VK-CH1 domain arrangement.

Examples of the domain arrangements (N- to C-termini) of central polypeptide chains for use in such heterodimeric proteins include any of the following:

V-(CH1 or Cκ)-Fc domain-V-V;

and

V-V-(CH1 or Cκ)-Fc domain;

and

Fc domain-V-V;

and

V-V-Fc domain;

and

V-V-Fc domain-V-(CH1 or Cκ).

For example, the domain arrangements (N- to C-termini) of central polypeptide chains for use in such heterodimeric proteins can include:

$V_{a-1}$-(CH1 or Cκ)$_a$-Fc domain-$V_{a-2}$-$V_{b-2}$;

and $V_{a-2}$-$V_{b-2}$-Fc domain-$V_{a-1}$-(CH1 or CK)$_a$ wherein $V_{a-1}$ is a light chain or heavy chain variable domain, and wherein one of $V_{a-2}$ and $V_{b-2}$ is a light chain variable domain and the other is a heavy chain variable domain.

Further examples include:

$V_{a-1}$-(CH1 or CK)$_a$-Fc domain-$V_b$;

and $V_b$-Fc domain-$V_{a-1}$-(CH1 or CK)$_a$ wherein $V_b$ is a single variable domain (e.g. dAb, VhH).

The Fc domain of the central chain may be a full Fc domain (CH2-CH3) or a portion thereof sufficient to confer the desired functionality (e.g. CD16 and optionally FcRn or another Fc receptor binding) when it forms a dimeric Fc with a second chain. A second polypeptide chain will then be configured which will comprise an immunoglobulin variable domain and a CH1 or Cκ constant region, e.g., a (CH1 or Cκ)$_b$ unit, selected so as to permit CH1-Cκ heterodimerization with the central polypeptide chain; the immunoglobulin variable domain will be selected so as to complement the variable domain of the central chain that is adjacent to the CH1 or Cκ domain, whereby the complementary variable domains form an antigen binding domain for a first antigen of interest.

For example, a second polypeptide chain can comprise a domain arrangement:

$V_{b-1}$-(CH1 or Cκ)$_b$-Fc domain such that the (CH1 or Cκ)$_2$ dimerizes with the (CH1 or Cκ)$_1$ on the central chain, and the $V_{b-1}$ forms an antigen binding domain together with $V_{a-1}$ of the central chain. If the $V_{a-1}$ of the central chain is a light chain variable domain, then $V_{b-1}$ will be a heavy chain variable domain; and if $V_{a-1}$ of the central chain is a heavy chain variable domain, then $V_{b-1}$ will be a light chain variable domain.

The antigen binding domain for the second antigen of interest can then be formed from $V_{a-2}$ and $V_{b-2}$ which are configured as tandem variable domains on the central chain forming the antigen binding domain for the second antigen of interest (e.g. a heavy chain variable domain ($V_H$) and a light chain (κ) variable domain (Vκ), for example forming an scFv unit). The antigen binding domain for the second antigen of interest can also alternatively be formed from a single variable domain $V_b$ present on the central chain.

Figure 2E:
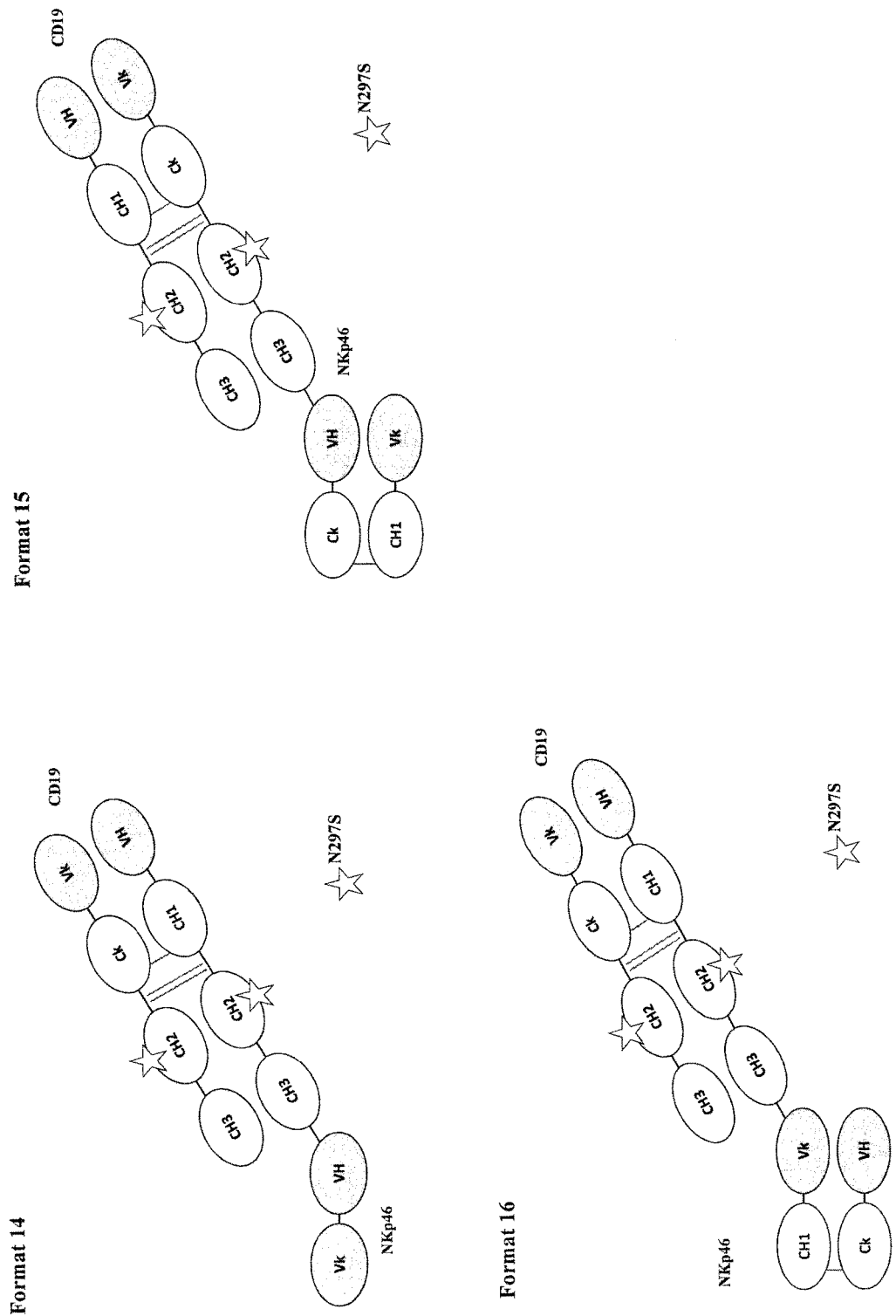

The resulting heterodimer can, for example, have the following configuration (see further Examples of such proteins shown as formats 13 and 14 shown in FIGS. 2D and 2E):

$V_{a-1}$—(CH1 or CK)$_a$—Fc domain—$V_{a-2}$—$V_{b-2}$ (first/central polypeptide chain)
|
$V_{b-1}$—(CH1 or CK)$_b$—Fc domain      (second polypeptide chain)

wherein one of $V_{a-1}$ of the first polypeptide chain and $V_{b-1}$ of the second polypeptide chain is a light chain variable domain and the other is a heavy chain variable domain, and wherein one of $V_{a-2}$ and $V_{b-2}$ is a light chain variable domain and the other is a heavy chain variable domain.

In one embodiment, the heterodimeric bispecific Fc-derived polypeptide comprises a domain arrangement selected from one of the following, optionally wherein one or both of the hinge domains are replaced by a peptide linker, optionally wherein the Fc domain is fused to anti-NKp46 scFv via a peptide linker):
or (Vk—Ck—hinge)—Fc domain—(anti-NKp46) or
|
($V_H$—CH1—hinge)—Fc domain ($V_H$—CH1—hinge)—Fc domain—(anti-NKp46) or
|
(Vk—Ck—hinge)—Fc domain ($V_H$—CH1—hinge)—Fc domain
|
(Vk—CK—hinge)—Fc domain—(anti-NKp46)

Other examples of potential domain arrangements for the heterodimeric polypeptides according to the invention include but are not limited to those shown in the table below:

$V_K$-$V_H$-Fc domain-$V_H$-(CH1)
|
Fc domain-$V_K$-($C_K$)

$V_H$-$V_K$-Fc domain-$V_H$-(CH1)
|
Fc domain-VK-($C_K$)

$V_K$-$V_H$-Fc domain-$V_K$-(CH1)
|
Fc domain-$V_H$-($C_K$)

$V_H$-$V_K$-Fc domain-$V_K$-(CH1)
|
Fc domain-$V_H$-($C_K$)

$V_H$-(CH1)-Fc domain-$V_H$-$V_K$
|
$V_K$-($C_K$)-Fc domain $V_H$-(CH1)-Fc domain-$V_K$-$V_H$
|
$V_K$-($C_K$)-Fc domain $V_K$-(CH1)-Fc domain-$V_H$-$V_K$
|
$V_H$-($C_K$)-Fc domain $V_K$-(CH1)-Fc domain-$V_K$-$V_H$
|
$V_H$-($C_K$)-Fc domain Heterotrimeric proteins can for example be formed by using a central (first) polypeptide chain comprising a first variable domain (V) fused to a first CH1 or Cκ constant region, a second variable domain (V) fused to a second CH1 or Cκ constant region, and an Fc domain or portion thereof interposed between the first and second variable domains (i.e. the Fc domain is interposed between the first and second (V-(CH1/Cκ) units. For example, a central polypeptide chain for use in a heterotrimeric protein according to the invention can have the domain arrangements (N- to C-termini) as follows:

$V_{a-1}$-(CH1 or Cκ)$_a$-Fc domain-$V_{a-2}$-(CH1 or Cκ)$_b$.

A second polypeptide chain can then comprise a domain arrangement (N- to C-termini):

$V_{b-1}$-(CH1 or Cκ)$_c$-Fc domain such that the (CH1 or Cκ)$_c$ dimerizes with the (CH1 or Cκ)$_a$ on the central chain, and the $V_{a-1}$ and $V_{b-1}$ form an antigen binding domain.

A third polypeptide chain can then comprise the following domain arrangement (N- to C-termini):

$V_{b-2}$-(CH1 or Cκ)$_d$, such that the (CH1 or Cκ)$_d$ dimerizes with the (CH1 or Cκ)$_b$ unit on the central chain, and the $V_{a-2}$ and $V_{b-2}$ form an antigen binding domain.

An example of a domain configuration of a resulting heterotrimer with a dimeric Fc domain (also shown as formats 5, 6, 7 and 16 in FIGS. 2D and 2E) is shown below:

$V_{b-1}$—(CH1 or Ck)$_c$—Fc domain      (second polypeptide)
|
$V_{a-1}$—(CH1 or Ck)$_a$—Fc domain—$V_{a-2}$—(CH1 or Ck)$_b$ (first polypeptide)
|
$V_{b-2}$—(CH1 or K$_d$)    (third polypeptide)

Thus, in a trimeric polypeptide according to the invention, the first polypeptide can have two variable domains that each form an antigen binding domain with a variable domain on a separate polypeptide chain (i.e. the variable domain of the second and third chains), the second polypeptide chain has one variable domain, and the third polypeptide has one variable domain.

A trimeric polypeptide according to the invention may further comprise the following:
(a) a first polypeptide chain comprising a first variable domain (V) fused to a first CH1 of Cκ constant region, a second variable domain (V) fused to a second CH1 of Cκ constant region, and an Fc domain or portion thereof interposed between the first and second variable domains;
(b) a second polypeptide chain comprising a variable domain fused at its C-terminus to a CH1 or Cκ constant region selected to be complementary to the first CH1 or Cκ constant region of the first polypeptide chain such that the first and second polypeptides form a CH1-Cκ heterodimer, and an Fc domain; and
(c) a third polypeptide chain comprising a variable domain fused (e.g. at its C-terminus) to a CH1 or Cκ constant region, wherein the variable domain and the constant region are selected to be complementary to the second variable domain and second CH1 or Cκ constant region of the first polypeptide chain such that the first and third polypeptides form a CH1-Cκ heterodimer bound by non-covalent and optionally further disulfide bond(s) formed between the CH1 or Cκ constant region of the third polypeptide and the second CH1 or Cκ constant region of the first polypeptide, but not between the CH1 or Cκ constant region of the third polypeptide and the first CH1 or Cκ constant region of the first polypeptide wherein the first, second and third polypeptides form a CH1-Cκ heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

such that the (CH1 or Cκ)$_c$ dimerizes with the (CH1 or Cκ)$_a$ on the central chain, and the V$_{a1}$ and V$_{b1}$ form an antigen binding domain.

A third polypeptide chain can then comprise a domain arrangement (N- to C-termini):

V$_2$-(CH1 or Cκ)$_d$-scFv, such that the (CH1 or Cκ)$_d$ dimerizes with the (CH1 or Cκ)$_b$ unit on the central chain, and the V$_{a2}$ and V$_{b2}$ form an antigen binding domain.

An example of a configuration of a resulting heterotrimer with a dimeric Fc domain (also shown as formats T5 and T6 in FIG. 2F) has a domain arrangement:

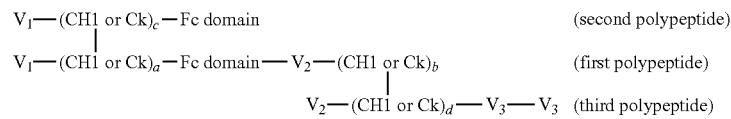

Examples of potential domain arrangements for such trimeric bispecific polypeptides include but are not limited to those shown below:

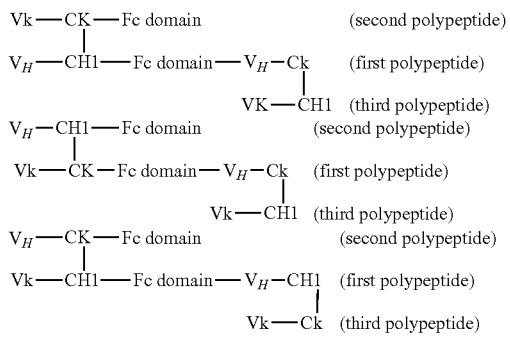

In further examples, heterotrimers can be constructed with three ABDs and a dimeric Fc. One of the ABDs will bind to NKp46, and the other two ABDs can bind to an antigen of interest, wherein the antigen of interest bound by the two ABDs can be the same antigen or a different antigen. Thus, in one aspect of such an embodiment, the multimeric polypeptide can bind the antigen of interest in a bivalent manner (with two ABDs).

Heterotrimeric proteins can for example be formed by using a central (first) polypeptide chain comprising a first variable domain (V) fused to a first CH1 or Cκ constant region, a second variable domain (V) fused to a second CH1 or Cκ constant region, and an Fc domain or portion thereof interposed between the first and second variable domains (i.e. the Fc domain is interposed between the first and second (V-(CH1/Cκ)) units. For example, a central polypeptide chain for use in a heterotrimeric protein can have the domain arrangements (N- to C-termini) as follows:

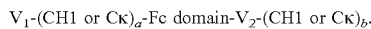

A second polypeptide chain can then comprise a domain arrangement (N- to C-termini):

or

In any of the polypeptide chains herein, a hinge region will typically be present on a polypeptide chain between a CH1 domain and a CH2 domain of an Fc domain, and/or can be present between a Cκ domain and a CH2 domain. A hinge region can optionally be replaced, e.g., by a suitable linker peptide.

In any of the domain arrangements, the Fc domain may comprise a CH2-CH3 unit (a full length CH2 and CH3 domain or a fragment thereof). In heterodimers or heterotrimers comprising two chains with Fc domains (a dimeric Fc domain), the CH3 domain will be capable of CH3-CH3 dimerization (e.g. it will comprise a wild-type CH3 domain).

In some exemplary configurations, the multispecific protein can be a heterodimer, a heterotrimer or a heterotetramers, wherein the polypeptide chains are engineered for heterodimerization among each other so as to produce the desired protein. In embodiments where the desired chain pairings are not driven by CH1-Cκ dimerization, the chains may comprise constant or Fc domains with amino acid modifications (e.g., substitutions) that favor the preferential hetero-dimerization of the two different chains over the homo-dimerization of two identical chains. In some embodiments, a "knob-into-holes" approach is used in which the CH3 domain interface of the antibody Fc region is mutated so that the antibodies preferentially form heterodimers (further including the attached light chains). These mutations create altered charge polarity across the Fc dimer interface such that co-expression of electrostatically matched Fc chains support favorable attractive interactions thereby promoting desired Fc heterodimer formation, whereas unfavorable repulsive charge interactions suppress unwanted Fc homodimer formation. For example one heavy chain comprises a T366W substitution and the second heavy chain comprises a T366S, L368A and Y407V substitution, see, e.g. Ridgway et al (1996) *Protein Eng.,* 9, pp. 617-621; Atwell (1997) *J. Mol. Biol.,* 270, pp. 26-35; and WO2009/089004, the disclosures of which are incorporated herein by reference. In another approach, one heavy chain comprises a F405L substitution and the second heavy chain comprises a K409R substitution, see, e.g., Labrijn et al. (2013) *Proc. Natl. Acad. Sci. U.S.A.,* 110, pp. 5145-5150. In another approach, one heavy chain comprises T350V, L351Y, F405A, and Y407V substitutions and the second heavy chain comprises T350V, T366S, K392L, and T394W substitutions, see, e.g. Von Kreudenstein et al., (2013) *mAbs*

5:646-654. In another approach, one heavy chain comprises both K409D and K392D substitutions and the second heavy chain comprises both D399K and E356K substitutions, see, e.g. Gunasekaran et al., (2010) *J. Biol. Chem.* 285:19637-19646. In another approach, one heavy chain comprises D221E, P228E and L368E substitutions and the second heavy chain comprises D221R, P228R, and K409R substitutions, see, e.g. Strop et al., (2012) *J. Mol. Biol.* 420: 204-219. In another approach, one heavy chain comprises S364H and F405A substitutions and the second heavy chain comprises Y349T and, T394F substitutions, see, e.g. Moore et al., (2011) *mAbs* 3: 546-557. In another approach, one heavy chain comprises a H435R substitution and the second heavy chain optionally may or may not comprise a substitution, see, e.g. U.S. Pat. No. 8,586,713. When such hetero-multimeric antibodies have Fc regions derived from a human IgG2 or IgG4, the Fc regions of these antibodies can be engineered to contain amino acid modifications that permit CD16 binding. In some embodiments, the antibody may comprise mammalian antibody-type N-linked glycosylation at residue N297 (Kabat EU numbering).

In some embodiments the invention also comprises a heterodimeric or heterotrimeric protein that comprises an NKp46-binding ABD and an antigen of interest-binding ABD, in which one or both of the ABDs (e.g., a variable region or other antigen binding domain such as a non-immunoglobulin scaffold) is linked to a constant region, e.g., an Fc domain or portion thereof via a linker, e.g., a flexible polypeptide linker. Optionally, the ABD is placed on a single polypeptide chain (e.g. a tandem variable domain, a $V_H$H or single V domain, a non-immunoglobulin scaffold).

In some embodiments, one or both of the ABDs is comprised in a $V_H$ and $V_L$ domain that associate with one another to form the ABD. In one embodiment, the $V_H$ and $V_L$ that form an ABD are each within a tandem variable region (a $V_H$ and $V_L$ domain separated by a flexible polypeptide linker).

In some embodiments, one of the ABDs is comprised in a Fab or Fab-like structure, in which a variable domain is linked to a CH1 domain and a complementary variable domain is linked to a complementary Cκ (or Cλ) constant domain, wherein the CH1 and Cκ (or Cλ) constant domains associate (dimerize). In some embodiments, one of the ABDs is comprised in such a Fab or Fab-like structure and the other ABD is placed on a single polypeptide chain (e.g. a tandem variable domain) and is linked to a constant region, e.g., an Fc domain or portion thereof via a linker, e.g., a flexible polypeptide linker.

In some embodiments, one of the ABDs comprises a Fab or Fab-like structure, in which a variable domain is linked to a CH1 domain and a complementary variable domain is linked to a complementary Cκ (or Cλ) constant domain, wherein the CH1 and Cκ (or Cλ) constant domains associate to form a heterodimeric protein. For example, a first and second ABD can advantageously comprise or consist of single variable domains (e.g. VhH domains) having different antigen binding specificities (e.g., VhH$_1$ and VhH$_2$). Also the VhH$_1$ can be fused to a CH1 domain and VhH$_2$ can be fused to a Cκ or Cλ domain. The $V_1$-Cκ (or Cλ) chain associates with a $V_2$-CH1 chain such that a Fab is formed. See, e.g., WO2006/064136 and WO2012/089814 which disclose examples of such antibodies lacking Fc domains, the disclosures of which PCT applications are incorporated herein by reference. The CH1 and/or Cκ domains can then be linked to a CH2 domain, optionally via a hinge region (or a linker peptide, e.g., one that has similar functional properties, e.g., dimerization). The CH2 domain(s) is/are then linked to a CH3 domain. The CH2-CH3 domains can thus optionally be embodied as a full-length Fc domain.

In any multispecific protein according to the invention, a hinge region can and generally will be present on a polypeptide chain between a CH1 domain and a CH2 domain, and/or can be present between a Cκ domain and a CH2 domain. A hinge region can optionally be replaced for example by a suitable linker peptide, e.g. a flexible polypeptide.

The proteins domains described in the present disclosure can optionally be specified as being from N- to C-termini. Protein arrangements of the disclosure for purposes of illustration are shown from N-terminus (on the left) to C-terminus. Domains can be referred to as fused to one another (e.g. a domain can be said to be fused to the C-terminus of the domain on its left, and/or a domain can be said to be fused to the N-terminus of the domain on its right).

The proteins domains described in the present disclosure can be fused to one another directly or via intervening amino acid sequences. For example, a CH1 or Cκ domain can be fused to an Fc domain (or CH2 or CH3 domain thereof) via a linker peptide, optionally a hinge region or a fragment thereof. In another example, a $V_H$ or Vκ domain can be fused to a CH3 domain via a linker peptide. $V_H$ and $V_L$ domains linked to another in tandem can and generally will be fused via a linker peptide (e.g. a scFv). $V_H$ and $V_L$ domains linked to an Fc domain will be fused via a linker peptide. Two polypeptide chains will be bound to one another (indicated by "|"), by non-covalent bonds, and optionally can further be attached via interchain disulfide bonds, formed between cysteine residues within complementary CH1 and Cκ domains.

Linkers

When ABD(s) or a polypeptide chain(s) comprise(s) a tandem variable region (e.g. scFv), two V domains (e.g. a $V_H$ domain and $V_L$ domains are generally linked together by a linker of sufficient length to enable the ABD to fold in such a way as to permit binding to the antigen for which the ABD is intended to bind. Similarly, when an ABD is linked to a constant domain or Fc domain, the linkage may be via a flexible linker (e.g. polypeptide linker) that permits the ABD to be positioned such that it binds to its target antigen and exhibits the desired functionality, e.g. it possesses a sufficient range of motion relative to the rest of the multispecific protein (the Fc domain and/or other ABD) and thereby mediates NKp46 signalling.

Examples of linkers include, for example, linkers derived from antibody hinge regions, an amino acid sequence RTVA (SEQ ID NO: 206), or linkers comprising glycine and serine residues, e.g., the amino acid sequence GEGTSTGS($G_2$S)$_2$GGAD (SEQ ID NO: 199).

In another specific embodiment, the $V_H$ domain and $V_L$ domains of a scFv are linked together by the amino acid sequence ($G_4$S)$_3$ (SEQ ID NO: 200).

Any of the peptide linkers contained in the subject multispecific proteins may comprise a length of at least 4 residues, at least 5 residues, at least 10 residues, at least 15 residues, at least 20 residues, at least 25 residues, at least 30 residues or more. In other embodiments, the linkers comprise a length of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, between 2-30 residues, between 2 and 50 residues, or between 10 and 50 residues.

An ABD (e.g. an immunoglobulin variable region) can optionally be linked to a constant domain or Fc domain via a flexible linker (e.g. polypeptide linker) that leads to less structural rigidity or stiffness (e.g. between or amongst the ABD and Fc domain) compared to a conventional (e.g. wild-type full length human IgG) antibody. For example, the multispecific protein may have a structure or a flexible linker between the ABD and constant domain or Fc domain that permits an increased range of domain motion compared to the ABD in a conventional (e.g. wild-type full length human IgG) antibody. In particular, the structure or a flexible linker can be configured to confer on the antigen binding sites greater intrachain domain movement compared to antigen binding sites in a conventional human IgG1 antibody. Rigidity or domain motion/interchain domain movement can be determined, e.g., by computer modeling, electron microscopy, spectroscopy such as Nuclear Magnetic Resonance (NMR), X-ray crystallography, or Sedimentation Velocity Analytical ultracentrifugation (AUC) to measure or compare the radius of gyration of proteins comprising the linker or hinge. A test protein or linker may have lower rigidity relative to a comparator protein if the test protein has a value obtained from one of the tests described in the previous sentence differs from the value of the comparator, e.g., an IgG1 antibody or a hinge, by at least 5%, 10%, 25%, 50%, 75%, or 100%. A person of skill in the art would be able to determine from the tests whether a test protein has at lower rigidity to that of another protein, respectively, by interpreting the results of these tests.

In one embodiment, the multispecific protein may have a structure or a flexible linker between the ABD and constant domain or Fc domain that permits the NKp46 ABD and the ABD which binds an antigen of interest to have a spacing between said ABDs comprising less than about 80 angstroms, less than about 60 angstroms or ranges from about 40-60 angstroms.

In one embodiment, the hinge region will be a fragment of a hinge region (e.g. a truncated hinge region without cysteine residues) or may comprise one or more amino acid modifications which remove (e.g. substitute by another amino acid, or delete) a cysteine residue, optionally both cysteine residues in a hinge region. Removing cysteines can be useful to prevent undesired disulfide bond formation, e.g., the formation of disulfide bridges in a monomeric polypeptide.

In one embodiment, a (poly)peptide linker used to link a CH1 or CK domain to a CH2 or CH3 domain of an Fc domain comprises a fragment of a CH1 domain and/or hinge region. For example, an N-terminal amino acid sequence of CH1 can be fused to a variable domain in order to mimic as closely as possible the natural structure of a wild-type antibody. In one embodiment, the linker comprises an amino acid sequence from a hinge domain or an N-terminal CH1 amino acid. The sequence can be, for example, between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues.

In one embodiment the linker comprises or consists of the amino acid sequence RTVA (SEQ ID NO: 206).

In one embodiment, the hinge region (or fragment thereof) is derived form a hinge domain of a human IgG1 antibody.

For example a hinge domain may comprise the amino acid sequence: T-H-T-C-S-S-C-P-A-P-E-L-L (one letter code) (SEQ ID NO: 201), or an amino acid sequence at least 60%, 70%, 80% or 90% identical thereto, optionally wherein one or both cysteines are deleted or substituted by a different amino acid residue.

In one embodiment, the hinge region (or fragment thereof) is derived from a Cµ2-C Cµ3 hinge domain of a human IgM antibody.

For example a hinge domain may comprise the amino acid sequence: N-A-S-S-M-C-V-P-S-P-A-P-E-L-L (one letter code) (SEQ ID NO: 202), or an amino acid sequence at least 60%, 70%, 80% or 90% identical thereto, optionally wherein one or both cysteines are deleted or substituted by a different amino acid residue.

Polypeptide chains that dimerize and associate with one another via non-covalent bonds may or may not additionally be bound by an interchain disulfide bond formed between respective CH1 and Cκ domains, and/or between respective hinge domains on the chains. CH1, Cκ and/or hinge domains (or other suitable linking amino acid sequences) can optionally be configured such that interchain disulfide bonds are formed between chains such that the desired pairing of chains is favored and undesired or incorrect disulfide bond formation is avoided. For example, when two polypeptide chains to be paired each possess a CH1 or Cκ adjacent to a hinge domain, the polypeptide chains can be configured such that the number of available cysteines for interchain disulfide bond formation between respective CH1/Cκ-hinge segments is reduced (or is entirely eliminated). For example, the amino acid sequences of respective CH1, Cκ and/or hinge domains can be modified to remove cysteine residues in both the CH1/Cκ and the hinge domain of a polypeptide; thereby the CH1 and Cκ domains of the two chains that dimerize will associate via non-covalent interaction(s).

In another example, the CH1 or Cκ domain adjacent (e.g., N-terminal to) a hinge domain comprises a cysteine capable of interchain disulfide bond formation, and the hinge domain which is placed at the C-terminus of the CH1 or Cκ comprises a deletion or substitution of one or both cysteines of the hinge (e.g. Cys 239 and Cys 242, as numbered for human IgG1 hinge according to Kabat).

In one embodiment, the hinge region (or fragment thereof) comprise the amino acid sequence: T-H-T-S-P-P-S-P-A-P-E-L-L (one letter code) (SEQ ID NO: 203), or an amino acid sequence at least 60%, 70%, 80% or 90% identical thereto.

In another example, the CH1 or Cκ domain adjacent (e.g., N-terminal to) a hinge domain comprises a deletion or substitution at a cysteine residue capable of interchain disulfide bond formation, and the hinge domain placed at the C-terminus of the CH1 or CK comprises one or both cysteines of the hinge (e.g. Cys 239 and Cys 242, as numbered for human IgG1 hinge according to Kabat).

In one embodiment, the hinge region (or fragment thereof) comprises the amino acid sequence: T-H-T-C-S-S-C-P-A-P-E-L-L (one letter code) (SEQ ID NO: 201), or an amino acid sequence at least 60%, 70%, 80% or 90% identical thereto.

In another example, a hinge region is derived from an IgM antibody. In such embodiments, the CH1/CK pairing mimics the Cµ2 domain homodimerization in IgM antibodies. For example, the CH1 or Cκ domain adjacent (e.g., N-terminal to) a hinge domain comprises a deletion or substitution at a cysteine capable of interchain disulfide bond formation, and an IgM hinge domain which is placed at the C-terminus of the CH1 or Cκ comprises one or both cysteines of the hinge.

In one embodiment, the hinge region (or fragment thereof) comprises the amino acid sequence: T-H-T-C-S-S-

C-P-A-P-E-L-L (one letter code) (SEQ ID NO: 201), or an amino acid sequence at least 60%, 70%, 80% or 90% identical thereto.

Constant Regions

Constant region domains can be derived from any suitable human antibody, including, the constant heavy (CH1) and light (Cκ) domains, hinge domains, CH2 and CH3 domains. With respect to heavy chain constant domains, "CH1" generally refers to positions 118-220 according to the EU index as in Kabat.

"CH2" generally refers to positions 237-340 according to the EU index as in Kabat, and "CH3" generally refers to positions 341-447 according to the EU index as in Kabat.

A "hinge" or "hinge region" or "antibody hinge region" herein refers to the flexible polypeptide or linker between the first and second constant domains of an antibody. Structurally, the IgG CH1 domain ends at EU position 220, and the IgG CH2 domain begins at residue EU position 237. Thus for an IgG the hinge generally includes positions 221 (D221 in IgG1) to 236 (G236 in IgG1), wherein the numbering is according to the EU index as in Kabat. References to specific amino acid residues within constant region domains found within the polypeptides shall be, unless otherwise indicated or as otherwise dictated by context, be defined according to Kabat, in the context of an IgG antibody.

CH2 and CH3 domains which may be present in the subject antibodies or multispecific proteins can be derived from any suitable antibody. Such CH2 and CH3 domains can be used as wild-type domains or may serve as the basis for a modified CH2 or CH3 domain. Optionally the CH2 and/or CH3 domain is of human origin or may comprise that of another species (e.g., rodent, rabbit, non-human primate) or may comprise a modified or chimeric CH2 and/or CH3 domain, e.g., one comprising portions or residues from different CH2 or CH3 domains, e.g., from different antibody isotypes or species antibodies.

In embodiments where a multispecific is intended not to bind to human CD16 polypeptide, a CH2 and/or CH3 domain (or Fc domain comprising same) may comprise a modification to decrease or abolish binding to FcγRIIIA (CD16). For example, CH2 mutations in a dimeric Fc domain proteins at reside N297 (Kabat numbering) can eliminate CD16 binding. However the person of skill in the art will appreciate that other configurations can be implemented. For example, substitutions into human IgG1 or IgG2 residues at positions 233-236 and IgG4 residues at positions 327, 330 and 331 were shown to greatly reduce binding to Fcγ receptors and thus ADCC and CDC. Furthermore, Idusogie et al. (2000) J. Immunol. 164(8):4178-84 demonstrated that alanine substitution at different positions, including K322, significantly reduced complement activation.

In certain embodiments herein where binding to CD16A is desired, a CH2 and/or CH3 domain (or Fc domain comprising same) may be a wild-type domain or may comprise one or more amino acid modifications (e.g. amino acid substitutions) which increase binding to human CD16 and optionally another receptor such as FcRn. Optionally, the modifications will not substantially decrease or abolish the ability of the Fc-derived polypeptide to bind to neonatal Fc receptor (FcRn), e.g. human FcRn. Typical modifications include modified human IgG1-derived constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells and/or decrease binding to FcγRIIB. Examples of modifications are provided in PCT publication no. WO2014/044686, the disclosure of which is incorporated herein by reference. Specific mutations (in IgG1 Fc domains) which affect (enhance) FcγRIIIa or FcRn binding are also set forth below.

| Isotype | Species | Modification | Effector Function | Effect of Modification |
|---|---|---|---|---|
| IgG1 | Human | T250Q/M428L | Increased binding to FcRn | Increased half-life |
| IgG1 | Human | 1M252Y/S254T/ T256E + H433K/ N434F | Increased binding to FcRn | Increased half-life |
| IgG1 | Human | E333A | Increased binding to FcγRIIIa | Increased ADCC and CDC |
| IgG1 | Human | S239D/I332E or S239D/A330L/ I332E | Increased binding to FcγRIIIa | Increased ADCC |
| IgG1 | Human | P257I/Q311 | Increased binding to FcRn | Unchanged half-life |
| IgG1 | Human | S239D/I332E/ G236A | Increased FcγRIIa/FcγRIIb ratio | Increased macrophage phagocytosis |

In some embodiments, the multispecific protein comprises a variant Fc region comprise at least one amino acid modification (for example, possessing 1, 2, 3, 4, 5, 6, 7, 8, 9, or more amino acid modifications) in the CH2 and/or CH3 domain of the Fc region, wherein the modification enhances binding to a human CD16 polypeptide. In other embodiments, the multispecific protein comprises at least one amino acid modification (for example, 1, 2, 3, 4, 5, 6, 7, 8, 9, or more amino acid modifications) in the CH2 domain of the Fc region from amino acids 237-341, or within the lower hinge-CH2 region that comprises residues 231-341. In some embodiments, the multispecific protein comprises at least two amino acid modifications (for example, 2, 3, 4, 5, 6, 7, 8, 9, or more amino acid modifications), wherein at least one of such modifications is within the CH3 region and at least one such modifications is within the CH2 region. Encompassed also are amino acid modifications in the hinge region. In one embodiment, encompassed are amino acid modifications in the CH1 domain, optionally in the upper hinge region that comprises residues 216-230 (Kabat EU numbering). Any suitable functional combination of Fc modifications can be made, for example any combination of the different Fc modifications which are disclosed in any of U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; and/or in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and/or in Lazar et al. (2006) Proc. Nat. Acad. Sci. U.S.A. 103(11): 405-410; Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

In some embodiments, the multispecific protein comprises an Fc domain comprising at least one amino acid modification (for example, 1, 2, 3, 4, 5, 6, 7, 8, 9, or more amino acid modifications) relative to a wild-type Fc region, such that the molecule has an enhanced binding affinity for human CD16 relative to the same molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439 (Kabat EU numbering).

In one embodiment, the multispecific protein comprises an Fc domain comprising at least one amino acid modification (for example, 1, 2, 3, 4, 5, 6, 7, 8, 9, or more amino acid modifications) relative to a wild-type Fc region, such that the molecule has enhanced binding affinity for human CD16 relative to a molecule comprising a wild-type Fc region, optionally wherein the variant Fc region comprises a substitution at any one or more of positions 239, 298, 330, 332, 333 and/or 334 (e.g. S239D, S298A, A330L, I332E, E333A and/or K334A substitutions), optionally wherein the variant Fc region comprises a substitution at residues S239 and I332, e.g. a S239D and I332E substitution (Kabat EU numbering).

In some embodiments, the multispecific protein comprises an Fc domain comprising altered glycosylation patterns that increase binding affinity for human CD16. Such carbohydrate modifications can be accomplished by, for example, by expressing a nucleic acid encoding the multispecific protein in a host cell with altered glycosylation machinery. Cells with altered glycosylation machinery are known in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 06/133148; WO 03/035835; WO 99/54342, each of which is incorporated herein by reference in its entirety. In one aspect, the multispecific protein contains one or more hypofucosylated constant regions. Such multispecific protein may comprise an amino acid alteration or may not comprise an amino acid alteration and/or may be expressed or synthesized or treated under conditions that result in hypofucosylation. In one aspect, a multispecific protein composition comprises a multispecific protein described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is a multispecific protein composition which is free of N-linked glycans comprising a core carbohydrate structure having fucose. The core carbohydrate will preferably be a sugar chain at Asn297.

Optionally, a multispecific protein comprising a dimeric Fc domain can be characterized by having a binding affinity to a human CD16 polypeptide that is within 1-log of that of a conventional human IgG1 antibody, e.g., as assessed by surface plasmon resonance.

In one embodiment, the multispecific protein comprising a dimeric Fc domain engineered to enhance Fc receptor binding can be characterized by having a binding affinity to a human CD16 polypeptide that is at least 1-log greater than that of a conventional or wild-type human IgG1 antibody, e.g., as assessed by surface plasmon resonance.

Optionally a multispecific protein comprising a dimeric Fc domain can be characterized by a Kd for binding (monovalent) to a human CD16 polypeptide of less than $10^{-5}$ M (10 μmolar), optionally less than $10^{-6}$ M (1 μmolar), as assessed by surface plasmon resonance (e.g. as in Example 16, SPR measurements performed on a Biacore™ T100 apparatus (Biacore™ GE Healthcare), with bispecific antibodies immobilized on a Sensor Chip CM5 and serial dilutions of soluble CD16 polypeptide injected over the immobilized bispecific antibodies.

CDR Sequences and Epitopes

In some embodiments, the proteins and antibodies herein bind the D1 domain of NKp46, the D2 domain of NKp46, or bind a region spanning the D1 and D2 domains (at the border of the D1 and D2 domains, the D1/D2 junction), of the NKp46 polypeptide of SEQ ID NO: 1. In some embodiments, the multispecific proteins or antibodies according to the invention have an affinity for human NKp46 characterized by a $K_D$ of less than $10^{-8}$ M, less than $10^{-9}$ M, or less than $10^{-10}$ M.

In another embodiment, the inventive antibodies or multispecific proteins bind NKp46 at substantially the same epitope on NKp46 as antibody NKp46-1, NKp46-2, NKp46-3, NKp46-4, NKp46-6 or NKp46-9. In another embodiment, the antibodies at least partially overlaps, or includes at least one residue in the segment or epitope bound by NKp46-1, NKp46-2, NKp46-3, NKp46-4, NKp46-6 or NKp46-9. In one embodiment, all key residues of the epitope are in a segment corresponding to domain D1 or D2. In one embodiment, the antibody or multispecific protein binds a residue present in the D1 domain as well as a residue present in the D2 domain. In one embodiment, the antibodies bind an epitope comprising 1, 2, 3, 4, 5, 6, 7 or more residues in the segment corresponding to domain D1 or D2 of the NKp46 polypeptide of SEQ ID NO: 1. In one embodiment, the antibodies bind domain D1 and further bind an epitope comprising 1, 2, 3, or 4 of the residues R101, V102, E104 and/or L105.

In another embodiment, the antibodies or multispecific proteins bind Nkp46 at the D1/D2 domain junction and bind an epitope comprising or consisting of 1, 2, 3, 4 or 5 of the residues K41, E42, E119, Y121 and/or Y194.

In another embodiment, the antibodies or multispecific proteins bind domain D2 and bind an epitope comprising 1, 2, 3, or 4 of the residues P132, E133, I135, and/or S136.

The Examples section provided infra further describes the construction of a series of mutant human NKp46 polypeptides. In the examples, the binding of anti-NKp46 antibody or multispecific protein to cells transfected with the NKp46 mutants was measured and compared to the ability of anti-NKp46 antibody to bind wild-type NKp46 polypeptide (SEQ ID NO:1). A reduction in binding between an anti-NKp46 antibody or NKp46 binding multispecific protein and a mutant NKp46 polypeptide as described herein means that there is a reduction in binding affinity (e.g., as measured by known methods such FACS testing of cells expressing a particular mutant, or by Biacore™ (SPR) testing of binding to mutant polypeptides) and/or a reduction in the total binding capacity of the anti-NKp46 antibody (e.g., as evidenced by a decrease in Bmax in a plot of anti-NKp46 antibody concentration versus polypeptide concentration). A significant reduction in binding indicates that the mutated residue is directly involved in the binding to the anti-NKp46 antibody to NKp46 or is in close proximity to the binding protein when the anti-NKp46 antibody or NKp46 binding multispecific protein is bound to NKp46. An antibody epitope will thus preferably include such residue and may include additional residues adjacent to such residue.

In some embodiments, a significant reduction in binding means that the binding affinity and/or capacity between an anti-NKp46 antibody or NKp46 binding multispecific protein and a mutant NKp46 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type NKp46 polypeptide (e.g., the polypeptide shown in SEQ ID NO:1). In certain embodiments, binding is reduced below detectable limits. In some embodiments, a significant reduction in binding is evidenced when binding of an anti-NKp46 antibody to a mutant NKp46 polypeptide is less than 50% (e.g., less than 45%, 40%, 35%, 30%, 25%, 20%, 15% or 10%) of the binding observed between the anti-NKp46 antibody and a wild-type NKp46 polypeptide (e.g., the polypeptide shown in SEQ ID NO: 1 (or the extracellular domain thereof)). Such binding measurements can be made using a variety of binding assays known in the art. A specific example of one such assay is described in the Example section.

In some embodiments, anti-NKp46 antibodies or NKp46 binding multispecific proteins are provided that exhibit significantly lower binding for a mutant NKp46 polypeptide in which a residue in a wild-type NKp46 polypeptide (e.g., SEQ ID NO:1) is substituted. In the shorthand notation used here, the format is: Wild type residue: Position in polypeptide: Mutant residue, with the numbering of the residues as indicated in SEQ ID NO: 1.

In some embodiments, an anti-NKp46 antibody binds a wild-type NKp46 polypeptide but has decreased binding to a mutant NKp46 polypeptide having a mutation (e.g., an alanine substitution) any one or more of the residues R101, V102, E104 and/or L105 (with reference to SEQ ID NO:1) compared to binding to the wild-type NKp46).

In some embodiments, an anti-NKp46 antibody or NKp46-binding multispecific protein binds a wild-type NKp46 polypeptide but has decreased binding to a mutant NKp46 polypeptide having a mutation (e.g., an alanine substitution) at one or more of residues K41, E42, E119, Y121 and/or Y194 (with reference to SEQ ID NO:1) compared to binding to the wild-type NKp46).

In some embodiments, an anti-NKp46 antibody or NKp46-binding multispecific protein binds a wild-type NKp46 polypeptide but has decreased binding to a mutant NKp46 polypeptide having a mutation (e.g., an alanine substitution) at one or more of residues P132, E133, I135, and/or S136 (with reference to SEQ ID NO:1) compared to binding to the wild-type NKp46).

The amino acid sequence of the heavy chain variable region of antibodies NKp46-1, NKp46-2, NKp46-3, NKp46-4, NKp46-6 and NKp46-9 are listed herein in Table B (SEQ ID NOS: 3, 5, 7, 9, 11 and 13 respectively), the amino acid sequence of the light chain variable region of antibodies NKp46-1, NKp46-2, NKp46-3, NKp46-4, NKp46-6 and NKp46-9 are also listed herein in Table B (SEQ ID NOS: 4, 6, 8, 10, 12 and 14 respectively).

In a specific embodiment, the invention provides is an antibody, e.g. a full length monospecific antibody, a multispecific or bispecific antibody, including a bispecific monomeric polypeptide, or a NKp46-binding multispecific protein that binds essentially the same epitope or determinant as monoclonal antibody NKp46-1, NKp46-2, NKp46-3, NKp46-4, NKp46-6 or NKp46-9; optionally the antibody comprises a hypervariable region of antibody NKp46-1, NKp46-2, NKp46-3, NKp46-4, NKp46-6 or NKp46-9. In any of the embodiments herein, antibody NKp46-1, NKp46-2, NKp46-3, NKp46-4, NKp46-6 or NKp46-9 can be characterized by its amino acid sequence and/or nucleic acid sequence encoding it. In one embodiment, the antibody comprises the Fab or F(ab')$_2$ portion of NKp46-1, NKp46-2, NKp46-3, NKp46-4, NKp46-6 or NKp46-9. Also provided is an antibody that comprises the heavy chain variable region of NKp46-1, NKp46-2, NKp46-3, NKp46-4, NKp46-6 or NKp46-9. According to one embodiment, an antibody comprises the three CDRs of the heavy chain variable region of NKp46-1, NKp46-2, NKp46-3, NKp46-4, NKp46-6 or NKp46-9. Also provided is a polypeptide that further comprises one, two or three of the CDRs of the light chain variable region of NKp46-1, NKp46-2, NKp46-3, NKp46-4, NKp46-6 or NKp46-9. Optionally any one or more of said light or heavy chain CDRs may contain one, two, three, four or five or more amino acid modifications (e.g. substitutions, insertions or deletions). Optionally, provided is a multispecific protein or antibody polypeptide where any of the light and/or heavy chain variable regions comprising part or all of an antigen binding region of antibody NKp46-1, NKp46-2, NKp46-3, NKp46-4, NKp46-6 or NKp46-9 are fused to an immunoglobulin constant region of the human IgG type.

In another aspect, the invention provides a protein, e.g., an antibody, a full length monospecific antibody, a multispecific or a bispecific protein, or a polypeptide chain or fragment thereof, or an NKp46-binding multispecific protein as well as a nucleic acid encoding any of the foregoing, wherein the protein comprises the heavy chain CDRs of NKp46-1, NKp46-2, NKp46-3, NKp46-4, NKp46-6 or NKp46-9, comprising, for the respective antibody: a HCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a HCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a HCDR3 region comprising an amino acid sequence as set forth in as set forth in Table A, or a sequence of at least 4, 5, 6, 7, 8, 9 or 10 contiguous amino acids thereof, wherein one or more of these amino acids may be substituted by a different amino acid.

In another aspect, the invention provides a protein, e.g., an antibody, a full length monospecific antibody, a multispecific or a bispecific protein, or a polypeptide chain or fragment thereof, or an NKp46-binding multispecific protein as well as a nucleic acid encoding any of the foregoing, wherein the protein comprises light chain CDRs of NKp46-1, NKp46-2, NKp46-3, NKp46-4, NKp46-6 or NKp46-9, comprising, for the respective antibody: a LCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a LCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a LCDR3 region comprising an amino acid sequence as set forth in Table A, or a sequence of at least 4, 5, 6, 7, 8, 9 or 10 contiguous amino acids thereof, wherein one or more of these amino acids may be deleted or substituted by a different amino acid.

In another aspect, the invention provides a multispecific protein or antibody that binds to human NKp46, comprising:
(a) the heavy chain variable region of NKp46-1, NKp46-2, NKp46-3, NKp46-4, NKp46-6 or NKp46-9 as set forth in Table B, optionally wherein one, two, three or more amino acids may be substituted by a different amino acid;
(b) the light chain variable region NKp46-1, NKp46-2, NKp46-3, NKp46-4, NKp46-6 or NKp46-9 as set forth in Table B, optionally wherein one, two, three or more amino acids may be substituted by a different amino acid;
(c) the heavy chain variable region of NKp46-1, NKp46-2, NKp46-3, NKp46-4, NKp46-6 or NKp46-9 as set forth in Table B, optionally wherein one or more of these amino acids may be substituted by a different amino acid; and the respective light chain variable region of NKp46-1, NKp46-2, NKp46-3, NKp46-4, NKp46-6 or NKp46-9 as set forth in Table B, optionally wherein one, two, three or more amino acids may be substituted by a different amino acid;
(d) the heavy chain CDR 1, 2 and 3 (HCDR1, HCDR2) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid;
(e) the light chain CDR 1, 2 and 3 (LCDR1, LCDR2, LCDR3) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid; or
(f) the heavy chain CDR 1, 2 and 3 (HCDR1, HCDR2, HCDR3) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid; and the light chain CDRs 1, 2 and 3 (LCDR1, LCDR2, LCDR3) amino acid sequence of the respective NKp46-1, NKp46-2, NKp46-3, NKp46-4, NKp46-6 or NKp46-9 antibody as shown in Table A, optionally wherein one, two, three or more amino acids in a CDR may be substituted by a different amino acid.

In one embodiment, the aforementioned CDRs are according to Kabat, e.g. as shown in Table A. In one embodiment, the aforementioned CDRs are according to Chothia numbering, e.g. as shown in Table A. In one embodiment, the aforementioned CDRs are according to IMGT numbering, e.g. as shown in Table A.

In another aspect of any of the embodiments herein, any of the CDR1, CDR2 and CDR3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO or Table A.

In another aspect, the invention provides an antibody that competes for NKp46 binding with a monoclonal antibody according to (a) to (f), above.

In another aspect, the invention provides a bispecific antibody comprising an antibody that binds human NKp46 according to (a) to (f), above, or an antibody that competes for binding to NKp46 with any of such antibodies, fused (optionally via intervening amino acid sequences) to a monomeric Fc domain, optionally further fused (optionally via intervening amino acid sequences) to a second antigen binding domain (e.g. a scFv, a $V_H$ domain, a $V_L$ domain, a dAb, a V-NAR domain or a $V_HH$ domain). Optionally the second antigen binding domain will bind a cancer antigen, a viral antigen, a parasitic antigen or a bacterial antigen. The sequences of the CDRs, according to IMGT, Kabat and Chothia definitions systems, are summarized in Table A below. The sequences of the variable chains of the antibodies according to the invention are listed in Table B below. In any embodiment herein, a $V_L$ or $V_H$ sequence can be specified or numbered so as to contain or lack a signal peptide or any part thereof.

TABLE A

| mAb | CDR definition | HCDR1 SEQ ID | Sequence | HCDR2 SEQ ID | Sequence | HCDR3 SEQ ID | Sequence |
|---|---|---|---|---|---|---|---|
| NKp46-1 | Kabat | 15 | DYVIN | 18 | EIYPGSGTNYYNEKFKA | 21 | RGRYGLYAMDY |
|  | Chothia | 16 | GYTFTDY | 19 | PGSG | 22 | GRYGLYAMD |
|  | IMGT | 17 | GYTFTDYV | 20 | GYTFTDYVIYPGSGTN | 23 | ARRGRYGLYAMDY |
| NKp46-2 | Kabat | 31 | SDYAWN | 34 | YITYSGSTSYNPSLES | 36 | GGYYGSSWGVFAY |
|  | Chothia | 32 | GYSITSDY |  | YSG | 37 | GYYGSSWGVFA |
|  | IMGT | 33 | GYSITSDYA | 35 | ITYSGST | 38 | ARGGYYGSSWGVFAY |
| NKp46-3 | Kabat | 46 | EYTMH | 49 | GISPNIGGTSYNQKFKG | 51 | RGGSFDY |
|  | Chothia | 47 | GYTFTEY |  | PNIG | 52 | GGSFD |
|  | IMGT | 48 | GYTFTEYT | 50 | ISPNIGGT | 53 | ARRGGSFDY |
| NKp46-4 | Kabat | 60 | SFTMH | 63 | YINPSSGYTEYNQKFKD | 65 | GSSRGFDY |
|  | Chothia | 61 | GYTFTSF |  | PSSG | 66 | SSRGFD |
|  | IMGT | 62 | GYTFTSFT | 64 | INPSSGYT | 67 | VRGSSRGFDY |
| NKp46-6 | Kabat | 73 | SSWMH | 76 | HIHPNSGISNYNEKFKG | 78 | GGRFDD |
|  | Chothia | 74 | GYTFTSS |  | PNSG |  | GRFD |
|  | IMGT | 75 | GYTFTSSW | 77 | IHPNSGIS | 79 | ARGGRFDD |
| NKp46-9 | Kabat | 85 | SDYAWN | 88 | YITYSGSTNYNPSLKS | 89 | CWDYALYAMDC |
|  | Chothia | 86 | GYSITSDY |  | YSG | 90 | WDYALYAMD |
|  | IMGT | 87 | GYSITSDYA | 35 | ITYSGST | 91 | ARCWDYALYAMDC |

TABLE A-continued

| Bab281 | Kabat | 97 | NYGMN | 100 | WINTNTGEPTYAEEFKG | 102 | DYLYYFDY |
|---|---|---|---|---|---|---|---|
| | Chothia | 98 | GYTFTNY | | TNTG | 103 | YLYYFD |
| | IMGT | 99 | GYTFTNYG | 101 | INTNTGEP | 104 | ARDYLYYFDY |

| | | LCDR1 | | LCDR2 | | LCDR3 | |
|---|---|---|---|---|---|---|---|
| mAb | CDR definition | SEQ ID | Sequence | SEQ ID | Sequence | SEQ ID | Sequence |
| NKp46-1 | Kabat | 24 | RASQDISNYLN | 27 | YTSRLHS | 28 | QQGNTRPWT |
| | Chothia | 25 | SQDISNY | | YTS | 29 | YTSGNTRPW |
| | IMGT | 26 | QDISNY | | YTS | 30 | YTSQQGNTRPWT |
| NKp46-2 | Kabat | 39 | RVSENIYSYLA | 42 | NAKTLAE | 43 | QHHYGTPVVT |
| | Chothia | 40 | SENIYSY | | NAK | 44 | HYGTPW |
| | IMGT | 41 | ENIYSY | | NAK | 45 | QHHYGTPVVT |
| NKp46-3 | Kabat | 54 | RASQSISDYLH | 57 | YASQSIS | 58 | QNGHSFPLT |
| | Chothia | 55 | SQSISDY | | YAS | 59 | GHSFPL |
| | IMGT | 56 | QSISDY | | YAS | | QNGHSFPLT |
| NKp46-4 | Kabat | 68 | RASENIYSNLA | 70 | AATNLAD | 71 | QHFWGTPRT |
| | Chothia | | SENIYSN | | AAT | 72 | FWGTPR |
| | IMGT | 69 | ENIYSN | | AAT | | QHFWGTPRT |
| NKp46-6 | Kabat | 80 | RASQDIGSSLN | 81 | ATSSLDS | 82 | LQYASSPWT |
| | Chothia | | SQDIGSS | | ATS | 83 | YASS PWT |
| | IMGT | | QDIGSS | | ATS | 84 | LQYASSPWT |
| NKp46-9 | Kabat | 92 | RTSENIYSYLA | 93 | NAKTLAE | 94 | QHHYDTPLT |
| | Chothia | | SENIYSY | | NAK | 95 | NAKHYDTPL |
| | IMGT | | ENIYSY | | NAK | 96 | QHHYDTPLT |
| Bab281 | Kabat | 105 | KASENVVTYVS | 108 | GASNRYT | 109 | GQGYSYPYT |
| | Chothia | 106 | SENVVTY | | GAS | 110 | GYSYPY |
| | IMGT | 107 | ENVVTY | | GAS | 111 | GQGYSYPYT |

TABLE B

| Antibody | SEQ ID NO | Amino acid sequence |
|---|---|---|
| NKp46-1 VH | 3 | QVQLQQSGPELVKPGASVKMSCKASGYTFTDYVINWGKQRSGQGLEWIGEIYPGSGTNYYNEKFKAKATLTADKSSNIAYMQLSSLTSEDSAVYFCARRGRYGLYAMDYWGQGTSVTVSS |
| NKp46-1 VL | 4 | DIQMTQTTSSLSASLGDRVTISCRASQDISNYLNWYQQKPDGTVKLLIYYTSRLHSGVPSRFSGSGSGTDYSLTINNLEQEDIATYFCQQGNTRPWTFGGGTKLEIK |
| NKp46-2 VH | 5 | EVQLQESGPGLVKPSQSLSLTCTVTGYSITSDYAWNWIRQFPGNKLEWMGYITYSGSTSYNPSLESRISITRDTSTNQFFLQLNSVTTEDTATYYCARGGYYGSSWGVFAYWGQGTLVTVSA |
| NKp46-2 VL | 6 | DIQMTQSPASLSASVGETVTITCRVSENIYSYLAWYQQKQGKSPQLLVYNAKTLAEGVPSRFSGSGSGTQFSLKINSLQPEDFGSYYCQHHYGTPWTFGGGTKLEIK |
| NKp46-3 VH | 7 | EVQLQQSGPELVKPGASVKISCKTSGYTFTEYTMHWVKQSHGKSLEWIGGISPNIGGTSYNQKFKGKATLTVDKSSSTAYMELRSLTSEDSAVYYCARRGGSFDYWGQGTTLTVSS |
| NKp46-3 VL | 8 | DIVMTQSPATLSVTPGDRVSLSCRASQSISDYLHWYQQKSHESPRLLIKYASQSISGIPSRFSGSGSGSDFTLSINSVEPEDVGVYYCQNGHSFPLTFGAGTKLELK |
| NKp46-4 VH | 9 | QVQLQQSAVELARPGASVKMSCKASGYTFTSFTMHWVKQRPGQGLEWIGYINPSSGYTEYNQKFKDKTTLTADKSSSTAYMQLDSLTSDDSAVYYCVRGSSRGFDYWGQGTLVTVSA |
| NKp46-4 VL | 10 | DIQMIQSPASLSVSVGETVTITCRASENIYSNLAWFQQKQGKSPQLLVYAATNLADGVPSRFSGSGSGTQYSLKINSLQSEDFGIYYCQHFWGTPRTFGGGTKLEIK |
| NKp46-6 VH | 11 | QVQLQQPGSVLVRPGASVKLSCKASGYTFTSSWMHWAKQRPGQGLEWIGHIHPNSGISNYNEKFKGKATLTVDTSSSTAYVDLSSLTSEDSAVYYCARGGRFDDWGAGTTVTVSS |

TABLE B-continued

| Antibody | SEQ ID NO | Amino acid sequence |
|---|---|---|
| NKp46-6 VL | 12 | DIQMTQSPSSLSASLGERVSLTCRASQDIGSSLNWLQQEPDGTIKR LIYATSSLDSGVPKRFSGSRSGSDYSLTISSLESEDFVDYYCLQYAS SPWTFGGGTKLEIK |
| NKp46-9 VH | 13 | DVQLQESGPGLVKPSQSLSLTCTVTGYSITSDYAWNWIRQFPGNKL EWMGYITYSGSTNYNPSLKSRISITRDTSKNQFFLQLNSVTTEDTAT YYCARCWDYALYAMDCWGQGTSVTVSS |
| NKp46-9 VL | 14 | DIQMTQSPASLSASVGETVTITCRTSENIYSYLAWCQQKQGKSPQL LVYNAKTLAEGVPSRFSGSGSGTHFSLKINSLQPEDFGIYYCQHHY DTPLTFGAGTKLELK |

Also provided, as described in the Examples herein, is a multispecific protein or antibody comprising the amino acid sequences of monomeric bispecific polypeptides which respectively comprise an scFv comprising the heavy and light chain CDR1, 2 and 3 of the respective heavy and light chain variable region listed as SEQ ID NOS: 3-14 of antibodies NKp46-1, NKp46-2, NKp46-3, NKp46-4, NKp46-6 and NKp46-9, a monomeric Fc domain, and an scFv comprising the heavy and light chain CDR1, 2 and 3 of the heavy and light chain variable region of an anti-CD19 antibody, e.g. any of the anti-CD19 antibodies described in the Examples herein.

Once the multispecific protein is produced it can be assessed for biological activity, e.g., antigen binding, ability to elicit target cell lysis and/or specific signaling activities elicited thereby.

In one aspect of any embodiment described herein, the inventive multispecific protein is capable of inducing activation of an NKp46-expressing cell (e.g. an NK cell, a reporter cell) when the protein is incubated in the presence of the NKp46-expressing cell (e.g. purified NK cells) and a target cell that expresses the antigen of interest).

In one aspect of any embodiment described herein, the inventive multispecific protein is capable of inducing an increase of CD137 present on the cell surface of an NKp46- and/or a CD16-expressing cell (e.g. an NK cell, a reporter cell) when the protein is incubated in the presence of the NKp46- and/or a CD16-expressing cell (e.g. purified NK cells), optionally in the absence of target cells.

In one aspect of any embodiment described herein, the inventive multispecific protein is capable of inducing NKp46 signaling in an NKp46-expressing cell (e.g. an NK cell, a reporter cell) when the protein is incubated in the presence of an NKp46-expressing cell (e.g. purified NK cells) and a target cell that expresses the antigen of interest).

Optionally, NK cell activation or signaling in characterized by the increased expression of a cell surface marker of activation, e.g. CD107, CD69, Sca-1 or Ly-6A/E, KLRG 1, etc.

Activity can be measured for example by bringing target cells and NKp46-expressing cells into contact with one another, in presence of the multispecific polypeptide. In one example, the aggregation of target cells and NK cells is measured. In another example, the multispecific protein may, for example, be assessed for the ability to cause a measurable increase in any property or activity known in the art as associated with NK cell activity, respectively, such as marker of cytotoxicity (CD107) or cytokine production (for example IFN-γ or TNF-α), increases in intracellular free calcium levels, the ability to lyse target cells in a redirected killing assay, etc.

In the presence of target cells (target cells expressing the antigen of interest) and NK cells that express NKp46, the multispecific protein will be capable of causing an increase in a property or activity associated with NK cell activity (e.g. activation of NK cell cytotoxicity, CD107 expression, IFNγ production) in vitro. For example, a multispecific protein according to the invention can be selected based on its ability to increase an NK cell activity by more than about 20%, preferably by least about 30%, at least about 40%, at least about 50%, or more compared to that achieved with the same effector: target cell ratio with the same NK cells and target cells that are not brought into contact with the multispecific protein, as measured by an assay that detects NK cell activity, e.g., an assay which detects the expression of an NK activation marker or which detects NK cell cytotoxicity, e.g., an assay that detects CD107 or CD69 expression, IFNγ production, or a classical in vitro chromium release test of cytotoxicity. Examples of protocols for detecting NK cell activation and cytotoxicity assays are described in the Examples herein, as well as for example, in Pessino et al, *J. Exp. Med*, 1998, 188 (5): 953-960; Sivori et al, *Eur J Immunol*, 1999. 29:1656-1666; Brando et al, (2005) *J. Leukoc. Biol.* 78:359-371; El-Sherbiny et al, (2007) *Cancer Research* 67(18):8444-9; and Nolte-'t Hoen et al, (2007) *Blood* 109:670-673). Optionally, a multispecific protein according to the invention can be selected for or characterized by its ability to have greater ability to induce NK cell activity towards target cells, i.e., lysis of target cells compared to a conventional human IgG1 antibody that binds to the same antigen of interest, as measured by an assay of NK cell activity (e.g. an assay that detects NK cell-mediated lysis of target cells that express the antigen of interest).

As shown herein, a multispecific protein according to the invention which possesses an Fc domain that does not bind CD16, does not, substantially induce NKp46 signaling (and/or NK activation that results therefrom) of NK cells when the protein is not bound to the antigen of interest on target cells (e.g. in the absence of the antigen of interest and/or target cells). Thus, the monovalent NKp46 binding component of the multispecific protein does not itself cause NKp46 signalling. Accordingly, in the case of multispecific proteins possessing an Fc domain that binds CD16, such multispecific protein can be assessed for its ability to elicit NKp46 signaling or NKp46-mediated NK cell activation by testing the effect of this multispecific protein on NKp46 expression, by CD16-negative NK cells. The multispecific protein can optionally be characterized as not substantially causing (or increasing) NKp46 signaling by an NKp46-expressing, CD16-negative cell (e.g. a NKp46$^+$CD16$^-$ NK cell, a reporter cell) when the multispecific protein is incubated with such NKp46-expressing, CD16-negative cells (e.g., purified NK cells or purified reporter cells) in the absence of target cells.

In one aspect of any embodiment herein, a multispecific protein described herein that binds CD16 can for example be characterized by:

(a) being capable of inducing NK cells that express CD16 and NKp46 to lyse target cells, when incubated in the presence of the NK cells and target cells; and (b) lack of agonist activity at NKp46 when incubated with CD16-negative NK cells, e.g. NKp46-expressing NK cells that do not express CD16, in the absence of target cells. Optionally, the NK cells are purified NK cells.

In one aspect of any embodiment herein, a multispecific protein described herein can for example be characterized by:

(a) agonist activity at NKp46, when incubated in the presence of NKp46-expressing NK cells and target cells; and (b) lack of agonist activity at NKp46 (e.g. when incubated with CD16-negative NK cells, for example CD16-NKp46+ NK cells, or when incubated with NK cells and where in the protein comprises (e.g. by modification) an Fc domain that lacks binding to CD16) in the absence of target cells. Optionally, the NK cells are purified NK cells.

Uses of Compounds

In one aspect, provided is the use of any of the compounds defined herein, particularly the inventive multispecific proteins or antibodies and/or cells which express same for the manufacture of a pharmaceutical preparation for the treatment, prevention or diagnosis of a disease in a mammal in need thereof. Provided also are the use any of the compounds defined above as a medicament or an active component or active substance in a medicament. In a further aspect the invention provides methods for preparing a pharmaceutical composition containing a compound as defined herein, to provide a solid or a liquid formulation for administration orally, topically, or by injection. Such a method or process at least comprises the step of mixing the compound with a pharmaceutically acceptable carrier.

In one aspect, provided is a method to treat, prevent or more generally affect a predefined condition in an individual or to detect a certain condition by using or administering a multispecific protein or antibody described herein, or a (pharmaceutical) composition comprising same.

For example, in one aspect, the invention provides a method of restoring or potentiating the activity of NKp46+ NK cells (e.g. NKp46+CD16+ NK cells) in a patient in need thereof (e.g. a patient having a cancer, or a viral or bacterial infection), comprising the step of administering a multispecific protein described herein to said patient. In one embodiment, the method is directed at increasing the activity of NKp46+ lymphocytes (e.g. NKp46+CD16+ NK cells) in patients having a disease in which increased lymphocyte (e.g. NK cell) activity is beneficial or which is caused or characterized by insufficient NK cell activity, such as a cancer, or a viral or microbial/bacterial infection.

In another aspect, the invention provides a method of restoring or potentiating the activity of NKp46+ NK cells (e.g. NKp46+CD16+ NK cells) in a patient in need thereof (e.g. a patient having a cancer, or a viral, parasite or bacterial infection), comprising the step of contacting cells derived from the patient, e.g., immune cells and optionally target cells expressing an antigen of interest with a multispecific protein according to the invention and reinfusing the multispecific protein treated cells into the patient. In one embodiment, this method is directed at increasing the activity of NKp46+ lymphocytes (e.g. NKp46+CD16+ NK cells) in patients having a disease in which increased lymphocyte (e.g. NK cell) activity is beneficial or which is caused or characterized by insufficient NK cell activity, such as a cancer, or a viral or microbial, e.g., bacterial or parasite infection.

In another embodiment the subject multispecific proteins may be used or administered in combination with immune cells, particularly NK cells, derived from a patient who is to be treated or from a different donor, and these NK cells administered to a patient in need thereof such as a patient having a disease in which increased lymphocyte (e.g. NK cell) activity is beneficial or which is caused or characterized by insufficient NK cell activity, such as a cancer, or a viral or microbial, e.g., bacterial or parasite infection. As NK cells (unlike CAR-T cells) do not express TCRs, these NK cells, even those derived from different donors will not induce a GVHD reaction (see e.g., Glienke et al., "Advantages and applications of CAR-expressing natural killer cells", *Front. Pharmacol.* 6, Art. 21:1-6 (2015); Hermanson and Kaufman, Front. Immunol. 6, Art. 195:1-6 (2015))

In one embodiment, the multispecific protein disclosed herein that mediates NK cell activation and/or target cell lysis via multiple activating receptors of effector cells, including NKp46, CD16 and CD137, can be used advantageously for treatment of individuals whose effector cells (e.g. NKp46+CD16+ NK cells) cells are hypoactive, exhausted or suppressed, for example a patient who has a significant population of effector cells characterized by the expression and/or upregulation of one or multiple inhibitory receptors (e.g. TIM-3, PD1, CD96, TIGIT, etc.).

The multispecific polypeptides described herein can be used to prevent or treat disorders that can be treated with antibodies, such as cancers, solid and non-solid tumors, hematological malignancies, infections such as viral infections, and inflammatory or autoimmune disorders.

In one embodiment, the antigen of interest (the non-NKp46 antigen) is an antigen expressed on the surface of a malignant cell of a type of cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sézary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal)

T-cell lymphoma; anaplastic (Ki 1+) large cell lymphoma; intestinal T-cell lymphoma; T-lymphoblastic; and lymphoma/leukemia (T-Lbly/T-ALL).

In one embodiment, the inventive multispecific polypeptides described herein can be used to prevent or treat a cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sézary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one example, the tumor antigen is an antigen expressed on the surface of a lymphoma cell or a leukemia cell, and the multispecific protein is administered to, and/or used for the treatment of, an individual having a lymphoma or a leukemia. Optionally, the tumor antigen is selected from CD19, CD20, CD22, CD30 or CD33.

In one aspect, the methods of treatment comprise administering to an individual a multispecific protein described herein in a therapeutically effective amount, e.g., for the treatment of a disease as disclosed herein, for example any of the cancers identified above. A therapeutically effective amount may be any amount that has a therapeutic effect in a patient having a disease or disorder (or promotes, enhances, and/or induces such an effect in at least a substantial proportion of patients with the disease or disorder and substantially similar characteristics as the patient).

In one embodiment, a multispecific protein according to the invention is used to treat a cancer that is responsive to CD137 activation, e.g. a solid tumor or a hematological cancer, including but not limited to breast cancer, sarcoma, glioma, colon carcinoma, myeloma, mastocytoma, melanoma, renal carcinoma, and ovarian cancer. In one embodiment, the multispecific protein according to the invention is used to treat a CD137L-expressing cancer. As shown herein, the strong efficacy in inducing tumor cell lysis of the multispecific protein is hypothesized to in part mediated by the upregulation of CD137 (4-1BB) on the surface of NK cells. The co-activating CD137 protein can bind and recognize CD137 ligand (CD137L, 4-1BBL) on tumor cells, resulting in enhanced NK cell activation and cytotoxicity of CD137L-expressing cells. CD137L has been found to be expressed on a variety of tumors, and is more commonly expressed by malignant tumors, especially in moderate or low-differentiated tumors (see, e.g., Vinay et al., (2012) *Mol. Cancer Ther.* 11(5):1062-1070). CD137L-expressing cancers include, for example, lung squamous cell carcinoma, nasal cavity squamous cell carcinoma, esophageal squamous cell carcinoma, cervical squamous cell carcinoma, colonic adenocarcinoma, rectal adenocarcinoma, gallbladder adenocarcinoma, pancreatic adenocarcinoma and breast adenocarcinoma.

The multispecific protein according to the invention may be used with our without a prior step of detecting the expression of the antigen of interest on target cells in a biological sample obtained from an individual (e.g. a biological sample comprising cancer cells, cancer tissue or cancer-adjacent tissue). In another embodiment, the disclosure provides a method for the treatment or prevention of a cancer in an individual in need thereof, the method comprising:

a) detecting cells (e.g. tumor cells) in a sample from the individual that express an antigen of interest, and b) upon a determination that cells which express an antigen of interest are comprised in the sample, optionally at a level that is increased compared to a reference level (e.g. corresponding to a healthy individual or an individual not deriving substantial benefit from a protein described herein), administering to the individual a multispecific protein (e.g. a multispecific protein according to the invention) that binds to an antigen of interest, to NKp46 (e.g., monovalently), and to CD16 (e.g., via its Fc domain). Optionally, the antigen of interest is a cancer antigen (e.g. a cancer antigen disclosed herein), optionally a cancer antigen known to be capable of undergoing intracellular internalization when contacted with a full length human IgG1 antibody that binds specifically thereto.

In one embodiment, the invention provides a method for the treatment or prevention of a cancer in an individual in need thereof, the method comprising:

a) detecting cells (e.g. tumor cells) in a sample from an individual (or within the tumor and/or within adjacent tissue) that express CD137L (CD137 ligand), and b) upon a determination that cells that express CD137L are comprised in the sample (or within the tumor and/or within adjacent tissue), optionally at a level that is increased compared to a reference level (e.g. corresponding to a healthy individual or an individual not deriving substantial benefit from a protein described herein), administering to the individual a multispecific protein (e.g. a protein of the disclosure) that binds to a cancer antigen, to NKp46 (e.g., monovalently), and to CD16. Optionally, the cancer antigen is a cancer antigen disclosed herein), optionally a cancer antigen known to be capable of undergoing intracellular internalization when contacted with a full length human IgG1 antibody that binds specifically thereto.

In one embodiment, the disclosure provides a method for the treatment or prevention of a disease (e.g. a cancer) in an individual in need thereof, the method comprising:

a) detecting cell surface expression of one or a plurality inhibitory receptors on immune effector cells (e.g. NK cells, T cells) in a sample from the individual (e.g. in circulation or in the tumor environment), and b) upon a determination of cell surface expression of one or a plurality inhibitory receptors on immune effector cells, optionally at a level that is increased compared to a reference level (e.g. corresponding to a healthy individual, an individual not suffering from immune exhaustion or suppression, or an individual not deriving substantial benefit from a protein described herein), administering to the individual a multispecific protein (e.g. a multispecific protein according to the invention) that binds to an antigen of interest (e.g. a cancer antigen), to NKp46 (e.g., monovalently), and to CD16. Optionally, the cancer antigen is a cancer antigen disclosed herein), optionally a cancer antigen known to be capable of undergoing intracellular internalization when contacted with a full length human IgG1 antibody that binds specifically thereto.

In one embodiment, a multispecific protein according to the invention may be used as a monotherapy (without other therapeutic agents), or in combined treatments with one or more other therapeutic agents, including agents normally utilized for the particular therapeutic purpose for which the antibody is being administered. The additional therapeutic agent or agents will normally be administered in amounts and treatment regimens typically used for that agent in a monotherapy for the particular disease or condition being treated. Such therapeutic agents when used in the treatment of cancer, include, but are not limited to anti-cancer agents and chemotherapeutic agents; in the treatment of infectious disease, include, but are not limited to anti-viral agents and antibiotics. Such other therapeutic agents may further include other immunomodulatory polypeptides such as Ig-fusion proteins, antibodies, cytokines and the like. In some embodiments the administration of the multispecific protein according to the invention and the other therapeutic agent may elicit an additive or synergistic effect on immunity and/or on therapeutic efficacy.

The multispecific proteins can also be included in kits. The kits may optionally further contain any number of polypeptides and/or other compounds, e.g., 1, 2, 3, 4, or any other number of multispecific proteins according to the invention and/or other compounds. It will be appreciated that this description of the contents of the kits is not limiting in any way. For example, the kit may contain other types of therapeutic compounds. Optionally, the kits also include instructions for using the polypeptides, e.g., detailing the herein-described methods such as in the detection or treatment of specific disease conditions.

The invention also provides pharmaceutical compositions comprising the subject multispecific proteins and optionally other compounds as defined above. A multispecific protein and optionally another compound may be administered in purified form together with a pharmaceutical carrier as a pharmaceutical composition. The form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids A pharmaceutically acceptable carrier may further contain physiologically acceptable compounds that act for example to stabilize or to increase the absorption of the compounds Such physiologically acceptable compounds include, for example, carbohydrates, such as glucose, sucrose or dextrans, antioxidants, such as ascorbic acid or glutathione, chelating agents, low molecular weight proteins or other stabilizers or excipients One skilled in the art would know that the choice of a pharmaceutically acceptable carrier, including a physiologically acceptable compound, depends, for example, on the route of administration of the composition Pharmaceutically acceptable adjuvants, buffering agents, dispersing agents, and the like, may also be incorporated into the pharmaceutical compositions. Non-limiting examples of such adjuvants include by way of example inorganic and organic adjuvants such as alum, aluminum phosphate and aluminum hydroxide, squalene, liposomes, lipopolysaccharides, double stranded (ds) RNAs, single stranded(s-s) DNAs, and TLR agonists such as unmethylated CpG's.

Multispecific proteins according to the invention can be administered parenterally. Preparations of the compounds for parenteral administration must be sterile. Sterilization is readily accomplished by filtration through sterile filtration membranes, optionally prior to or following lyophilization and reconstitution. The parenteral route for administration of compounds is in accord with known methods, e.g. injection or infusion by intravenous, intraperitoneal, intramuscular, intraarterial, or intralesional routes. The compounds may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound, depending on the particular type of compound and its required dosing regimen. Methods for preparing parenterally administrable compositions are well known in the art.

EXAMPLES

Example 1

Generation of Anti-huNKp46 Antibodies

Balb/c mice were immunized with a recombinant human NKp46 extracellular domain recombinant-Fc protein comprising the extracellular domain of the protein of SEQ ID NO: 1. Mice received one primo-immunization with an emulsion of 50 μg NKp46 protein and Complete Freund Adjuvant, intraperitoneally, a 2nd immunization with an emulsion of 50 μg NKp46 protein and Incomplete Freund Adjuvant, intraperitoneally, and finally a boost with 10 μg NKp46 protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using a cell line expressing the human NKp46 construct at the cell surface. Briefly, for FACS screening, the presence of reactive antibodies in supernatants was revealed by Goat anti-mouse polyclonal antibody (pAb) labeled with PE.

A panel of antibodies that bound NKp46 was selected, produced and their variable regions sequenced and these antibodies and derivatives thereof further evaluated for their activity in the context of a bispecific molecule.

Example 2

Identification of a Bispecific Antibody Format That Binds FcRn but not FcγR for Targeting Effector Cell Receptors Experiments were conducted with the objective being the development of a new bispecific protein format that places an Fc domain on a polypeptide together with an anti-NKp46 binding domain and an anti-target antigen binding domain. Such bispecific proteins should bind to NKp46 monovalently via its anti-NKp46 binding domain. The monomeric Fc domain should retain at least partial binding to the human neonatal Fc receptor (FcRn), yet not substantially bind human CD16 and/or other human Fcγ receptors. Consequently, such bispecific proteins should not induce Fcγ-mediated (e.g. CD16-mediated) target cell lysis.

Example 2-1

Construction and Binding Analysis of Anti-CD19-IgG1-Fcmono-Anti-CD3

Since no anti-NKp46 bispecific antibody has been produced that could indicate whether such a protein could be functional, CD3 was used as a model antigen in place of NKp46 in order to investigate the possible functionality of a new monovalent bispecific protein format prior to targeting NK cells via NKp46.

A bispecific Fc-based on a scFv specific for tumor antigen CD19 (anti-CD19 scFv) and a scFv specific for activating receptor CD3 on a T cell (anti-CD3 scFv) was used to assess FcRn binding and CD19-binding functions of a new monomeric bispecific polypeptide format. The domain arrangement of the final polypeptide is referred to as the "F1" format (the star in the CH2 domain indicates an optional N297S mutation, not included in the polypeptide tested here). (See FIG. 2)

A bispecific monomeric Fc-containing polypeptide was constructed based on a scFv specific for the tumor antigen CD19 (anti-CD19 scFv) and a scFv specific for an activating receptor CD3 on a T cell (anti-CD3 scFv). The CH3 domain incorporated the mutations (EU numbering) L351K, T366S, P395V, F405R, T407A and K409Y. The polypeptide has domains arranged as follows: anti-CD19-CH2-CH3-anti-CD3. A DNA sequence coding for a CH3/VH linker peptide having the amino acid sequence STGS was also designed in order to insert a specific SalI restriction site at the CH3-VH junction.

This CH3 domain incorporated the mutations (EU numbering) L351K, T366S, P395V, F405R, T407A and K409Y. The selected CH2 domain was a wild-type CH2. DNA and amino acid sequences for the monomeric CH2-CH3 Fc portion and the anti-CD19 are shown below.

The light chain and heavy chain DNA and amino acid sequences corresponding to the anti-CD19 scFv were as follows:

| Sequence | SEQ ID NO |
|---|---|
| Anti-CD19-Vκ DNA | 113 |
| Anti-CD19-Vκ amino acid | 114 |
| Anti-CD19-V$_H$ DNA | 115 |
| Anti-CD19-V$_H$ amino acid | 116 |

The DNA sequences for the monomeric CH2-CH3 Fc portion and final bispecific IgG1-Fcmono polypeptide (the last K was removed in that construct) is shown in SEQ ID NO: 117. The amino acid sequence encoded thereby is shown in SEQ ID NO: 2. The Anti-CD19-F1-Anti-CD3 complete sequence (mature protein) is shown in SEQ ID NO: 118.

Cloning and the Production of the Recombinant Proteins

Coding sequences were generated by direct synthesis and/or by PCR. PCR was performed using the PrimeSTAR MAX™ DNA polymerase (Takara, #R045A) and PCR products were purified from 1% agarose gel using the Nucleo-Spin™ gel and PCR clean-up kit (Macherey-Nagel, #740609.250). Once purified the PCR products were quantified prior to the In-Fusion ligation reaction which was performed as described in the manufacturer's protocol (ClonTech™, #ST0345). The plasmids were obtained after a miniprep preparation run on an EVO200 (Tecan) using the NucleoSpin™ 96 plasmid kit (Macherey-Nagel, #740625.4). Plasmids were then sequenced for sequence confirmation before to transfecting the CHO cell line.

CHO cells were grown in the CD-CHO medium (Invitrogen) complemented with phenol red and 6 mM Gluta-Max™. The day before the transfection, cells were counted and seeded at 175,000 cells/ml. For the transfection, cells (200.000 cells/transfection) were prepared as described in the AMAXA™ SF cell line kit (AMAXA, #V4XC-2032) and nucleofected using the DS137 protocol with the Nucleofector 4D device. All the transfections were performed using 300 ng of verified plasmids. After transfection, cells were seeded into 24 well plates in pre-warmed culture medium. After 24 hours, hygromycin B was added in the culture medium (200 μg/ml). Protein expression was monitored after one week in culture. Cells expressing the proteins were then sub-cloned to obtain the best producers. Sub-cloning was performed using 96 flat-bottom well plates in which the cells are seeded at one cell per well into 200 μl of culture medium complemented with 200 μg/ml of hygromycin B. Cells were left for three weeks before testing the clone's productivity.

Recombinant proteins which contain an IgG1-Fc fragment were purified using Protein-A beads (rProteinA Sepharose fast flow, GE Healthcare). Briefly, cell culture supernatants were concentrated, clarified by centrifugation and injected onto Protein-A columns to capture the recombinant Fc containing proteins. Proteins were eluted at acidic pH (citric acid 0.1M pH 3), and the eluate immediately neutralized using TRIS-HCL pH 8.5 and dialyzed against 1×PBS. Recombinant scFvs which contain a "six his" tag were purified by affinity chromatography using Cobalt resin. Other recombinant scFvs were purified by size exclusion chromatography (SEC).

Example 2-2

Binding Analysis of Anti-CD19-IgG1-Fcmono-Anti-CD3 to B221, JURKAT, HUT78 and CHO Cell Lines Cells were harvested and stained with the cell supernatant of the anti-CD19-F1-anti-CD3 producing cells during 1H at 4° C. After two washes in staining buffer (PBS1X/BSA 0.2%/EDTA 2 mM), cells were stained for 30 min at 4° C. with goat anti-human (Fc)-PE antibody (IM0550 Beckman Coulter—1/200). After two washes, stainings were conducted on a BD FACS Canto II and analyzed using the FlowJo™ software.

CD3 and CD19 expression were also controlled by flow cytometry: Cells were harvested and stained in PBS1X/BSA 0.2%/EDTA 2 mM buffer during 30 min at 4° C. using 5 μl of the anti-CD3-APC and 5 μl of the anti-CD19-FITC antibodies. After two washes, stainings were conducted on a BD FACS Canto II and analyzed using the FlowJo™ software.

The results of these experiments revealed that the Anti-CD19-F1-Anti-CD3 protein binds to CD3 cell lines (HUT78 and JURKAT cell lines) and to the CD19 cell line (B221 cell line) but not to the CHO cell line which was used as a negative control.

Example 2-3

T- and B-Cell Aggregation by Purified Anti-CD19-F1-Anti-CD3

Purified Anti-CD19-F1-Anti-CD3 was tested in a T/B cell aggregation assay to evaluate whether the antibody promotes the aggregation of CD19 and CD3 expressing cells.

The results of this assay are shown in FIG. 1. The top panel shows that Anti-CD19-F1-Anti-CD3 does not cause aggregation in the presence of B221 (CD19) or JURKAT (CD3) cell lines, but it does cause aggregation of cells when both B221 and JURKAT cells are co-incubated, indicating that the bispecific antibody is functional. The lower panel shows the results of the control experiment conducted without antibody.

Example 2-4

Binding of Bispecific Monomeric Fc Polypeptide to FcRn

Affinity Study by Surface Plasmon Resonance (SPR) Biacore™ T100 General Procedure and Reagents SPR measurements were performed on a Biacore™ T100 apparatus (Biacore GE Healthcare) at 25° C. In all Biacore™ (SPR) experiments Acetate Buffer (50 mM Acetate pH5.6, 150 mM NaCl, 0.1% surfactant p20) and HBS-EP+ (Biacore™ GE Healthcare) were used as the running buffer and regeneration buffer respectively. Sensorgrams were analyzed with Biacore™ T100 Evaluation software. Recombinant mouse FcRn was purchased from R&D Systems.
Immobilization of FcRn Recombinant FcRn proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). FcRn proteins were diluted to 10 µg/ml in coupling buffer (10 mM acetate, pH 5.6) and injected until the appropriate immobilization level was reached (i.e. 2500 RU). Deactivation of the remaining activated groups was performed using 100 mM ethanolamine pH 8 (Biacore™ GE Healthcare).
Affinity Study Monovalent affinity study was conducted following the Single Cycle Kinetic (SCK) protocol. Five serial dilutions of soluble analytes (antibodies and bi-specific molecules) ranging from 41.5 to 660 nM were injected over the FcRn (without regeneration) and allowed to dissociate for 10 min before regeneration. For each analyte, the entire sensorgram was fitted using the 1:1 SCK binding model.
Results Anti-CD19-F1-Anti-CD3 having its CH2-CH3 domains placed between two antigen binding domains, particularly two scFvs, was evaluated to assess whether such bispecific monomeric Fc protein could retain binding to FcRn and possess an improved in vivo half-life compared to conventional bispecific antibodies. The results of these experiments showed that FcRn binding was retained, the model suggesting a 1:1 ratio (1 FcRn for each monomeric Fc) instead of a 2:1 ratio (2 FcRn for each antibody) for a regular or wild-type IgG.

The binding affinity of this multispecific protein was evaluated using SPR, and was compared to a chimeric full length antibody containing intact human IgG1 constant regions. The monomeric Fc retained significant monomeric binding to FcRn (monomeric Fc: affinity of KD=194 nM; full length antibody with bivalent binding: avidity of KD=15.4 nM).

Example 3

Construction of Anti-CD19×Anti-NKp46 Bispecific Monomeric Fc Domain Polypeptides It was unknown what activating receptors on NK cells would contribute to the lysis of target cells, and moreover since anti-NKp46 antibodies may block NKp46, it was further unknown whether cytotoxicity could be mediated by NKp46. We therefore investigated whether the bispecific protein format could induce NKp46 triggering, and whether it would induce NKp46 agonism in the absence of target cells, which could lead to inappropriate NK activation distant from the target and/or decreased overall activity toward target cells.

A new bispecific protein format was developed as a single chain protein which binds to FcRn but not FcγR. Additionally, multimeric proteins that comprise two or three polypeptide chains, wherein the Fc domain remains monomeric, were developed that are compatible for use with antibody variable regions that do not maintain binding to their target when converted to scFv format. The latter formats can be used conveniently for antibody screening; by incorporating at least one binding region as a F(ab) structure, any anti-target (e.g. anti-tumor) antibody variable region can be directly expressed in a bispecific construct as the F(ab) format within the bispecific protein and tested, irrespective of whether the antibody would retain binding as an scFv, thereby simplifying screening and enhancing the number of antibodies available. These formats in which the Fc domain remains monomeric have the advantage of maintaining maximum conformational flexibility and as shown infra may permit optimal binding to NKp46 or target antigens.

Different constructs were made for use in the preparation of bispecific antibodies using the variable domains from the scFv specific for tumor antigen CD19 described in Example 2-1, and different variable regions from antibodies specific for the NKp46 receptor identified in Example 1. A construct was also made using as the anti-NKp46 the variable regions from a commercially available antibody Bab281 (mIgG1, available commercially from Beckman Coulter, Inc. (Brea, Calif., U.S.A.) (see also Pessino et al, *J. Exp. Med*, 1998, 188 (5): 953-960 and Sivori et al, *Eur J Immunol*, 1999. 29:1656-1666) specific for the NKp46 receptor.

In order for the Fc domain to remain monomeric in single chain polypeptides or in multimers in which only one chain had an Fc domain, CH3-CH3 dimerization was prevented through two different strategies: (1) through the use of CH3 domain incorporating specific mutations (EU numbering), i.e., L351K, T366S, P395V, F405R, T407A and K409Y; or (2) through the use of a tandem CH3 domain in which the tandem CH3 domains are separated by a flexible linker associated with one another, which prevents interchain CH3-CH3 dimerization. The DNA and amino acid sequences for the monomeric CH2-CH3 Fc portion containing the above-identified point mutations were the same as in Example 2-1. The DNA and amino acid sequences for the monomeric CH2-CH3-linker-CH3 Fc portion with tandem CH3 domains are shown in FIGS. 2A-2D.

The light chain and heavy chain DNA and amino acid sequences for the anti-CD19 scFv were also the same as in Example 2-1. Proteins were cloned, produced and purified as in Example 2-1. Shown below are the light chain and heavy chain DNA and amino acid sequences for different anti-NKp46 scFvs.

TABLE 1

Amino acid sequences of different anti-NKp46 scFvs

| scFv anti-NKp46 | scFV sequence (VHVK) / - stop |
|---|---|
| NKp46-1 | STGSQVQLQQSGPELVKPGASVKMSCKASGYTFTDYVINWKQRSGQ GLEWIGEIYPGSGTNYYNEKFKAKATLTADKSSNIAYMQLSSLTSEDSAV YFCARRGRYGLYAMDYWGQGTSVTVSSVEGGSGGSGGSGGSGGVDD IQMTQTTSSLSASLGDRVTISCRASQDISNYLNWYQQKPDGTVKLLIYYT SRLHSGVPSRFSGSGSGTDYSLTINNLEQEDIATYFCQQGNTRPWTFG GGTKLEIK- (SEQ ID NO: 119) |
| NKp46-2 | STGSEVQLQESGPGLVKPSQSLSLTCTVTGYSITSDYAWNWIRQFPGNK LEWMGYITYSGSTSYNPSLESRISITRDTSTNQFFLQLNSVTTEDTATYY CARGGYYGSSWGVFAYWGQGTLVTVSAVEGGSGGSGGSGGSGGVD DIQMTQSPASLSASVGETVTITCRVSENIYSYLAWYQQKQGKSPQLLVY NAKTLAEGVPSRFSGSGSGTQFSLKINSLQPEDFGSYYCQHHYGTPWT FGGGTKLEIK- (SEQ ID NO: 120) |
| NKp46-3 | STGSEVQLQQSGPELVKPGASVKISCKTSGYTFTEYTMHWVKQSHGKS LEWIGGISPNIGGTSYNQKFKGKATLTVDKSSSTAYMELRSLTSEDSAVY YCARRGGSFDYWGQGTTLTVSSVEGGSGGSGGSGGSGGVDDIVMTQ SPATLSVTPGDRVSLSCRASQSISDYLHWYQQKSHESPRLLIKYASQSIS GIPSRFSGSGSGSDFTLSINSVEPEDVGVYYCQNGHSFPLTFGAGTKLE LK- (SEQ ID NO: 121) |
| NKp46-4 | STGSQVQLQQSAVELARPGASVKMSCKASGYTFTSFTMHWVKQRPGQ GLEWIGYINPSSGYTEYNQKFKDKTTLTADKSSSTAYMQLDSLTSDDSA VYYCVRGSSRGFDYWGQGTLVTVSAVEGGSGGSGGSGGSGGVDDIQ MIQSPASLSVSVGETVTIITCRASENIYSNLAWFQQKQGKSPQLLVYAATN LADGVPSRFSGSGSGTQYSLKINSLQSEDFGIYYCQHFWGTPRTFGGG TKLEIK- (SEQ ID NO: 122) |
| NKp46-6 | STGSQVQLQQPGSVLVRPGASVKLSCKASGYTFTSSWMHWAKQRPGQ GLEWIGHIHPNSGISNYNEKFKGKATLTVDTSSSTAYVDLSSLTSEDSAV YYCARGGRFDDWGAGTTVTVSSVEGGSGGSGGSGGSGGVDDIVMTQ SPATLSVTPGDRVSLSCRASQSISDYLHWYQQKSHESPRLLIKYASQSIS GIPSRFSGSGSGSDFTLSINSVEPEDVGVYYCQNGHSFLMYTFGGGTKL EIK- (SEQ ID NO: 123) |
| NKp46-9 | STGSDVQLQESGPGLVKPSQSLSLTCTVTGYSITSDYAWNWIRQFPGNK LEWMGYITYSGSTNYNPSLKSRISITRDTSKNQFFLQLNSVTTEDTATYY CARCWDYALYAMDCWGQGTSVTVSSVEGGSGGSGGSGGSGGVDDIQ MTQSPASLSASVGETVTITCRTSENIYSYLAWCQQKQGKSPQLLVYNAK TLAEGVPSRFSGSGSGTHFSLKINSLQPEDFGIYYCQHHYDTPLTFGAG TKLELK- (SEQ ID NO: 124) |
| Bab281 | STGSQIQLVQSGPELQKPGETVKISCKASGYTFTNYGMNWVKQAPGKG LKWMGWINTNTGEPTYAEEFKGRFAFSLETSASTAYLQINNLKNEDTAT YFCARDYLYYFDYWGQGTTLTVSSVEGGSGGSGGSGGSGGVDNIVMT QSPKSMSMSVGERVTLTCKASENVVTYVSWYQQKPEQSPKLLIYGASN RYTGVPDRFTGSGSATDFTLTISSVQAEDLADYHCGQGYSYPYTFGGG TKLEIK- (SEQ ID NO: 125) |

TABLE 2A

DNA sequences corresponding to different anti-NKp46 scFvs

| scFv anti-NKp46 | scFV sequences |
|---|---|
| NKp46-1 | SEQ ID NO: 126 |
| NKp46-2 | SEQ ID NO: 127 |
| NKp46-3 | SEQ ID NO: 128 |
| NKp46-4 | SEQ ID NO: 129 |
| NKp46-6 | SEQ ID NO: 130 |
| NKp46-9 | SEQ ID NO: 131 |
| Bab281 | SEQ ID NO: 132 |

Format 1 (F1) (Anti-CD19-IgG1-Fcmono-Anti-NKp46 (scFv))

The domain structure of Format 1 (F1) is shown in FIG. 2A. A bispecific Fc-containing polypeptide was constructed based on a scFv specific for the tumor antigen CD19 (anti-CD19 scFv) and an scFV specific for the NKp46 receptor. The polypeptide is a single chain polypeptide having domains arranged (N- to C-termini) as follows:

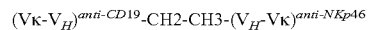

$(V\kappa\text{-}V_H)^{anti\text{-}CD19}\text{-}CH2\text{-}CH3\text{-}(V_H\text{-}V\kappa)^{anti\text{-}NKp46}$ A DNA sequence coding for a CH3/VH linker peptide having the amino acid sequence STGS was designed in order to insert a specific SalI restriction site at the CH3-$V_H$ junction. The domain arrangement of the final polypeptide in shown in FIG. 2 (the star in the CH2 domain indicates an optional N297S mutation), where the anti-CD3 scFv is replaced by an anti-NKp46 scFv. The (V$\kappa$-V$_H$) units include a linker between the $V_H$ and V$\kappa$ domains. Proteins were cloned, produced and purified as in Example 2-1. The amino acid sequences of the bispecific polypeptides (complete sequence (mature protein)) are shown in the corresponding SEQ ID NOS listed in the Table 2B below.

TABLE 2B

| Sequence | SEQ ID NO |
|---|---|
| CD19-F1-NKp46-1 | 133 |
| CD19-F1-NKp46-2 | 134 |
| CD19-F1-NKp46-3 | 135 |
| CD19-F1-NKp46-4 | 136 |
| CD19-F1-NKp46-6 | 137 |
| CD19-F1-NKp46-9 | 138 |
| CD19-F1-Bab281 | 139 |

Format 2 (F2): CD19-F2-NKp46-3

The domain structure of F2 polypeptides is shown in FIG. 2A. The DNA and amino acid sequences for the monomeric CH2-CH3 Fc portion were as in Example 2-1 and it similarly contains CH3 domain mutations (the mutations (EU numbering) L351K, T366S, P395V, F405R, T407A and K409Y. The heterodimer is made up of:

(1) a first (central) polypeptide chain having domains arranged as follows (N- to C-termini):

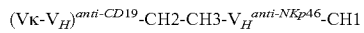
$(V\kappa\text{-}V_H)^{anti\text{-}CD19}\text{-}CH2\text{-}CH3\text{-}V_H{}^{anti\text{-}NKp46}\text{-}CH1$ and (2) a second polypeptide chain having domains arranged as follows (N- to C-termini): $V\kappa^{anti\text{-}NKp46}$-Cκ.

The (Vκ-$V_H$) unit was made up of a $V_H$ domain, a linker and a Vκ unit (i.e. an scFv). As with other formats of the inventive bispecific polypeptides, the DNA sequence coded for a CH3/VH linker peptide having the amino acid sequence STGS designed in order to insert a specific SalI restriction site at the CH3-VH junction. Proteins were cloned, produced and purified as in Example 2-1. The amino acid sequences for the first and second chains of the F2 protein are shown in SEQ ID NO: 140 and 141.

Format 3 (F3): CD19-F3-NKp46-3

The domain structure of F3 polypeptides is shown in FIG. 2A. The DNA and amino acid sequences for the CH2-CH3 Fc portion comprised a tandem CH3 domain in which the two CH3 domains on the same polypeptide chain associated with one another, thereby preventing dimerization between different bispecific proteins.

The single chain polypeptide has domains arranged (N- to C-termini) as follows:

$(V\kappa\text{-}V_H)^{anti\text{-}CD19}\text{-}CH2\text{-}CH3\text{-}CH3\text{-}(V_H\text{-}V\kappa)^{anti\text{-}NKp46}$ The (Vκ-$V_H$) units were made up of a $V_H$ domain, a linker and a Vκ unit (scFv). Proteins were cloned, produced and purified as in Example 2-1. Bispecific protein was purified from cell culture supernatant by affinity chromatography using prot-A beads and analyzed and purified by SEC. The protein showed a high production yield of 3.4 mg/L and the purified proteins exhibited a simple SEC profile. The amino acid sequence for the F3 protein is shown in SEQ ID NO: 142.

Format 4 (F4): CD19-F4-NKp46-3

The domain structure of F4 polypeptides is shown in FIG. 2A. The DNA and amino acid sequences for the CH2-CH3 Fc portion comprised a tandem CH3 domain as in Format F3, and additionally comprise a N297S mutation which prevents N-linked glycosylation and abolishes FcγR binding. Proteins were cloned, produced and purified as in Example 2-1. Bispecific proteins was purified from cell culture supernatant by affinity chromatography using prot-A beads and analyzed and purified by SEC. The protein showed a good production yield of 1 mg/L and the purified proteins exhibited a simple SEC profile. The amino acid sequence for the F4 protein with NKp46-3 variable domains is shown in SEQ ID NO: 143.

Format 8 (F8)

The domain structure of F8 polypeptides is shown in FIG. 2B. The DNA and amino acid sequences for the monomeric CH2-CH3 Fc portion were as in Format F2 and it similarly contains CH3 domain mutations (the mutations (EU numbering) L351K, T366S, P395V, F405R, T407A and K409Y, as well as a N297S mutation which prevents N-linked glycosylation and moreover abolishes FcγR binding. Three variants of F8 proteins were produced: (a) one wherein the cysteine residues in the hinge region were left intact (wild-type, referred to as F8A), (b) a second wherein the cysteine residues in the hinge region were replaced by serine residues (F8B), and (c) a third including a linker sequence GGGSS replacing residues DKTHTCPPCP in the hinge (F8C). Variants F8B and F8C provided production advantages as these versions avoided the formation of homodimers of the central chain. This heterotrimer is made up of;

(1) a first (central) polypeptide chain having domains arranged as follows (N- to C-termini):

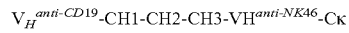
$V_H{}^{anti\text{-}CD19}\text{-}CH1\text{-}CH2\text{-}CH3\text{-}VH^{anti\text{-}NK46}\text{-}C\kappa$ and (2) a second polypeptide chain having domains arranged as follows (N- to C-termini): $V\kappa^{anti\text{-}NKp46}$-CH1 and (3) a third polypeptide chain having domains arranged as follows (N- to C-termini):

$V\kappa^{anti\text{-}CD19}$-Cκ

Proteins were cloned, produced and purified as in Example 2-1. Bispecific proteins was purified from cell culture supernatant by affinity chromatography using prot-A beads and analyzed and purified by SEC. The protein showed a high production yield of 3.7 mg/L (F8C) and the purified proteins again exhibited a simple SEC profile. The amino acid sequences of the three chains of the F8 protein (C variant) with NKp46-3 variable regions are shown in SEQ ID NOS: 144, 145 and 146.

Format 9 (F9): CD19-F9-NKp46-3

The F9 polypeptide is a trimeric polypeptide having a central polypeptide chain and two polypeptide chains each of which associate with the central chain via CH1-Cκ dimerization. The domain structure of the trimeric F9 protein is shown in FIG. 2B, wherein the bonds between the CH1 and Cκ domains are interchain disulfide bonds. The two antigen binding domains have a F(ab) structure permitting the use of these antibodies irrespective of whether they remain functional in a scFv format. The DNA and amino acid sequences for the CH2-CH3 Fc portion comprise a tandem CH3 domain as in Format F4 and comprise a CH2 domain comprising a N297S substitution. Three variants of F9 proteins were produced: (a) a first wherein the cysteine residues in the hinge region left intact (wild-type, referred to as F9A), (b) a second wherein the cysteine residues in the hinge region were replaced by serine residues (F9B), and (c) a third containing a linker sequence GGGSS which replaces residues DKTHTCPPCP in the hinge (F9C). Variants F9B and F9C provided advantages in production by avoiding the formation of homodimers of the central chain. The heterotrimer is made up of:

(1) a first (central) polypeptide chain having domains arranged as follows (N- to C-termini):

$V_H{}^{anti\text{-}CD19}\text{-}CH1\text{-}CH2\text{-}CH3\text{-}CH3\text{-}V_H{}^{anti\text{-}NKp46}\text{-}C\kappa$ and (2) a second polypeptide chain having domains arranged as follows (N- to C-termini): Vκ$^{anti-NKp46}$-CH1 and (3) a third polypeptide chain having domains arranged as follows (N- to C-termini):

Vκ$^{anti-CD19}$-Cκ.

Proteins were cloned, produced and purified as in Example 2-1. Bispecific proteins was purified from cell culture supernatant by affinity chromatography using prot-A beads and analyzed and purified by SEC. The protein showed a high production yield of 8.7 mg/L (F9A) and 3.0 mg/L (F9B), and the purified proteins again exhibited a simple SEC profile.

The amino acid sequences of the three chains of the F9 protein variant F9A are shown in the SEQ ID NOS: 147, 148 and 149. The amino acid sequences of the three chains of the F9 protein variant F9B are shown in the SEQ ID NOS: 150, 151 and 152. The amino acid sequences of the three chains of the F9 protein variant F9C are shown in the SEQ ID NOS: 153, 154 and 155.

Format 10 (F10): CD19-F10-NKp46-3

The F10 polypeptide is a dimeric protein having a central polypeptide chain and a second polypeptide chain which associates with the central chain via CH1-Cκ dimerization. The domain structure of the dimeric F10 protein is shown in FIG. 2B wherein the bonds between the CH1 and Cκ domains are interchain disulfide bonds. One of the two antigen binding domains has a Fab structure, and the other is a scFv. The DNA and amino acid sequences for the CH2-CH3 Fc portion comprise a tandem CH3 domain as shown in Format F4 and comprise a CH2 domain containing a N297S substitution.

Three variants of F10 proteins were also produced: (a) a first wherein the cysteine residues in the hinge region were left intact (wild-type, referred to as F10A), (b) a second wherein the cysteine residues in the hinge region were replaced by serine residues (F10B), and (c) a third containing a linker sequence GGGSS (SEQ ID NO: 204) replacing residues DKTHTCPPCP (SEQ ID NO: 205) in the hinge (F10C). Variants F10B and F10C provided advantages in production as they avoid the formation of homodimers of the central chain. The (Vκ-V$_H$) unit was made up of a V$_H$ domain, a linker and a Vκ unit (scFv). The heterodimer is made up of:

(1) a first (central) polypeptide chain having domains arranged as follows (N- to C-termini):

V$_H$$^{anti-CD19}$-CH1-CH2-CH3-CH3-(V$_H$-Vκ)$^{anti-NK46}$ and (2) a second polypeptide chain having domains arranged as follows (N- to C-termini): Vκ$^{anti-CD19}$-Cκ.

These proteins were cloned, produced and purified as in Example 2-1. Bispecific proteins was purified from cell culture supernatant by affinity chromatography using prot-A beads and analyzed and purified by SEC. The protein showed a good production yield of 2 mg/L (F10A) and the purified proteins again exhibited a simple SEC profile. The amino acid sequences of the two chains of the F10A protein variant are shown in SEQ ID NOS: 156 (second chain) and 157 (first chain). The amino acid sequences of the two chains of the F10B protein variant are shown in SEQ ID NOS: 158 (second chain) and 159 (first chain). The amino acid sequences of the two chains of the F10C protein variant are shown in the SEQ ID NOS: 160 (second chain) and 161 (first chain).

Format 11 (F11): CD19-F11-NKp46-3

The domain structure of F11 polypeptides is shown in FIG. 2C. The heterodimeric protein is similar to F10 except that the structures of the antigen binding domains are reversed. One of the two antigen binding domains has a Fab-like structure, and the other is a scFv. The heterodimer is made up of:

(1) a first (central) polypeptide chain having domains arranged as follows (N- to C-termini):

(Vκ-V$_H$)$^{anti-CD19}$-CH2-CH3-CH3-VH$^{anti-NK46}$-Cκ and (2) a second polypeptide chain having domains arranged as follows (N- to C-termini): Vκ$^{anti-NKp46}$-CH1.

Proteins were cloned, produced and purified as in Example 2-1. Bispecific proteins was purified from cell culture supernatant by affinity chromatography using prot-A beads and analyzed and purified by SEC. The protein showed a good production yield of 2 mg/L and the purified proteins similarly exhibited a simple SEC profile. The amino acid sequences of the two chains of the F11 protein are shown in SEQ ID NO: 162 (chain 1) and SEQ ID NO: 163 (chain 2).

Format 12 (F12): CD19-F12-NKp46-3

The domain structure of the dimeric F12 polypeptides is shown in FIG. 2C, wherein the bonds between the CH1 and Cκ domains are disulfide bonds. The heterodimeric protein is similar to F11 but the CH1 and Cκ domains within the F(ab) structure are inversed. The heterodimer is made up of:

(1) a first (central) polypeptide chain having domains arranged as follows (N- to C-termini):

(Vκ-V$_H$)$^{anti-CD19}$-CH2-CH3-CH3-V$_H$$^{anti-NKp46}$-CH1 and (2) a second polypeptide chain having domains arranged as follows (N- to C-termini): Vκ$^{anti-NKp46}$-Cκ.

Proteins were cloned, produced and purified as in Example 2-1. Bispecific proteins were purified from the cell culture supernatant by affinity chromatography using prot-A beads and analyzed and purified by SEC. The protein showed a good production yield of 2.8 mg/L and the purified proteins similarly exhibited a simple SEC profile. The amino acid sequences of the two chains of the F12 protein are shown in SEQ ID NO: 164 (chain 1) and SEQ ID NO: 165 (chain 2).

Format 17 (F17): CD19-F17-NKp46-3

The domain structure of the trimeric F17 polypeptides is shown in FIG. 2C, wherein the bonds between the CH1 and Cκ domains are disulfide bonds. The heterodimeric protein is similar to F9 but the V$_H$ and Vκ domains, and the CH1 and Cκ, domains within the C-terminal F(ab) structure are each respectively inversed with their partner. The heterotrimer is made up of:

(1) a first (central) polypeptide chain having domains arranged as follows (N- to C-termini):

V$_H$$^{anti-CD19}$-CH1-CH2-CH3-CH3-Vκ$^{anti-NKp46}$-CH1 and (2) a second polypeptide chain having domains arranged as follows (N- to C-termini): V$_H$$^{anti-NKp46}$-Cκ and (3) a third polypeptide chain having domains arranged as follows (N- to C-termini):

Vκ$^{anti-CD19}$-Cκ

Additionally, three variants of F17 proteins were produced: (a) a first where the cysteine residues in the hinge region were left intact (wild-type, referred to as F17A), (b) a second wherein the cysteine residues in the hinge region were replaced by serine residues (F10B, and (c) a third containing a linker sequence GGGSS (SEQ ID NO: 204) which replaces residues DKTHTCPPCP (SEQ ID NO: 205) in the hinge (F17C). Proteins were cloned, produced and purified as in Example 2-1. The amino acid sequences of the three chains of the F17B protein are shown in SEQ ID NOS: 166, 167 and 168.

Example 4

Bispecific NKp46 Antibody Formats with Dimeric Fc Domains

New protein constructions with dimeric Fc domains were developed that share many of the advantages of the monomeric Fc domain proteins of Example 3 but bind to FcRn with greater affinity. Different protein formats were produced that either had low or substantially lack of binding to FcγR (including CD16) or which had binding to FcγRs (including CD16), e.g. the binding affinity to human CD16 was within 1-log of that of wild-type human IgG1 antibodies, as assessed by SPR (e.g. see methods of Example 16. The different polypeptide formats were tested and compared to investigate the functionality of heterodimeric proteins comprising a central chain with a ($V_H$-(CH1/Cκ)-CH2-CH3-) unit or a (Vκ-(CH1 or Cκ)-CH2-CH3-) unit. One of both of the CH3 domains are fused, optionally via intervening amino acid sequences or domains, to a variable domain(s) (a single variable domain that associates with a variable domain on a separated polypeptide chain, a tandem variable domain (e.g., an scFv), or a single variable domain that is capable of binding antigen as a single variable domain). The two chains associate by CH1-Cκ dimerization to form disulfide linked dimers, or if associated with a third chain, to form trimers.

Different constructs were made for use in the preparation of a bispecific antibody using the variable domains DNA and amino acid sequences derived from the scFv specific for tumor antigen CD19 described in Example 2-1 and different variable regions from antibodies specific for NKp46 identified in Example 1. Proteins were cloned, produced and purified as in Example 2-1. Domains structures are shown in FIGS. 2A-6D.

Format 5 (F5): CD19-F5-NKp46-3

The domain structure of the trimeric F5 polypeptide is shown in FIG. 2D, wherein the interchain bonds between hinge domains (indicated in the figures between CH1/Cκ and CH2 domains on a chain) and interchain bonds between the CH1 and Cκ domains are interchain disulfide bonds. The heterotrimer is made up of:

(1) a first (central) polypeptide chain having domains arranged as follows (N- to C-termini):

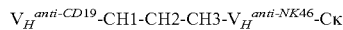
$V_H^{anti-CD19}$-CH1-CH2-CH3-$V_H^{anti-NK46}$-Cκ and (2) a second polypeptide chain having domains arranged as follows (N- to C-termini): Vκ$^{anti-CD19}$-CK-CH2-CH3 and (3) a third polypeptide chain having domains arranged as follows (N- to C-termini):

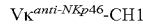
Vκ$^{anti-NKp46}$-CH1

Proteins were cloned, produced and purified as in Example 2-1. Bispecific proteins was purified from cell culture supernatant by affinity chromatography using prot-A beads and analyzed and purified by SEC. The protein showed a high production yield of 37 mg/L and the purified proteins again exhibited a simple SEC profile. The amino acid sequences of the three polypeptide chains are shown in SEQ ID NOS 169 (second chain), 170 (first chain) and 171 (third chain).

Format 6 (F6): CD19-F6-NKp46-3

The domain structure of heterotrimeric F6 polypeptides is shown in FIG. 2D. The F6 protein is the same as F5, but contains a N297S substitution to avoid N-linked glycosylation. Proteins were cloned, produced and purified as in Example 2-1. Bispecific proteins were purified from cell culture supernatant by affinity chromatography using prot-A beads and analyzed and purified by SEC. The protein showed a high production yield of 12 mg/L and the purified proteins exhibited a simple SEC profile. The amino acid sequences of the three polypeptide chains are shown in SEQ ID NOS: 172 (second chain), 173 (first chain) and 174 (third chain).

Format 7 (F7): CD19-F7-NKp46-3

The domain structure of heterotrimeric F7 polypeptides is shown in FIG. 2D. The F7 protein is the same as F6, except for cysteine to serine substitutions in the CH1 and Cκ domains that are linked at their C-termini to Fc domains, in order to prevent formation of a minor population of dimeric species of the central chain with the Vκ$^{anti-NKp46}$ CH1 chain. Proteins were cloned, produced and purified as in Example 2-1. Bispecific proteins were purified from the cell culture supernatant by affinity chromatography using prot-A beads and analyzed and purified by SEC. The protein showed a high production yield of 11 mg/L and the purified proteins exhibited a simple SEC profile. The amino acid sequences of the three polypeptide chains are shown in SEQ ID NOS: 175 (second chain), 176 (first chain) and 177 (third chain).

Format 13 (F13): CD19-F13-NKp46-3

The domain structure of the dimeric F13 polypeptide is shown in FIG. 2D, wherein the interchain bonds between hinge domains (indicated between CH1/Cκ and CH2 domains on a chain) and interchain bonds between the CH1 and Cκ domains are interchain disulfide bonds. The heterodimer is made up of:

(1) a first (central) polypeptide chain having domains arranged as follows (N- to C-termini):

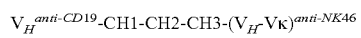
$V_H^{anti-CD19}$-CH1-CH2-CH3-($V_H$-Vκ)$^{anti-NK46}$ and (2) a second polypeptide chain having domains arranged as follows (N- to C-termini): Vκ$^{anti-CD19}$-Cκ-CH2-CH3.

The ($V_H$-Vκ) unit was made up of a $V_H$ domain, a linker and a Vκ unit (scFv). Proteins were cloned, produced and purified as in Example 2-1. Bispecific proteins were purified from the cell culture supernatant by affinity chromatography using prot-A beads and analyzed and purified by SEC. The protein showed a high production yield of 6.4 mg/L and the purified proteins exhibited a simple SEC profile. The amino acid sequences of the two polypeptide chains are shown in SEQ ID NOS: 178 (second chain) and 179 (first chain).

Format 14 (F14): CD19-F14-NKp46-3

The domain structure of the dimeric F14 polypeptide is shown in FIG. 2E. The F14 polypeptide is a dimeric polypeptide which shares the structure of the F13 format, but instead of a wild-type Fc domain (CH2-CH3), the F14 bispecific format has CH2 domain mutations N297S to abolish N-linked glycosylation. Proteins were cloned, produced and purified as in Example 2-1. Bispecific proteins were purified from cell culture supernatant by affinity chromatography using prot-A beads and analyzed and purified by SEC. The protein showed a high production yield of 2.4 mg/L and the purified proteins exhibited a simple SEC profile. The amino acid sequences of the two polypeptide chains are shown in SEQ ID NOS: 180 (second chain) and 181 (first chain).

Format 15 (F15): CD19-F15-NKp46-3

The domain structure of the trimeric F15 polypeptides is shown in FIG. 2E. The F15 polypeptide is a dimeric polypeptide which shares the structure of the F6 format, but differs by inversion of the N-terminal $V_H$-CH1 and Vκ-Cκ units between the central and second chains. Proteins were cloned, produced and purified as in Example 2-1. Bispecific proteins were purified from the cell culture supernatant by affinity chromatography using prot-A beads and analyzed and purified by SEC. The protein showed a good production yield of 0.9 mg/L and the purified proteins possessed a simple SEC profile. The amino acid sequences of the three polypeptide chains are shown in SEQ ID NOS: 182 (second chain), 183 (first chain) and 184 (third chain).

Format 16 (F16): CD19-F16-NKp46-3

The domain structure of the trimeric F16 polypeptide is shown in FIG. 2E. The F16 polypeptide is a dimeric polypeptide which shares the structure of the F6 format, but differs by inversion of the C-terminal $V_H$-CK and Vκ-CH1 units between the central and second chains. Proteins were cloned, produced and purified as in Example 2-1. The amino acid sequences of the three polypeptide chains are shown in SEQ ID NOS: 185 (second chain), 186 (first chain) and 187 (third chain).

Format T5 (T5)

Figure 2F:
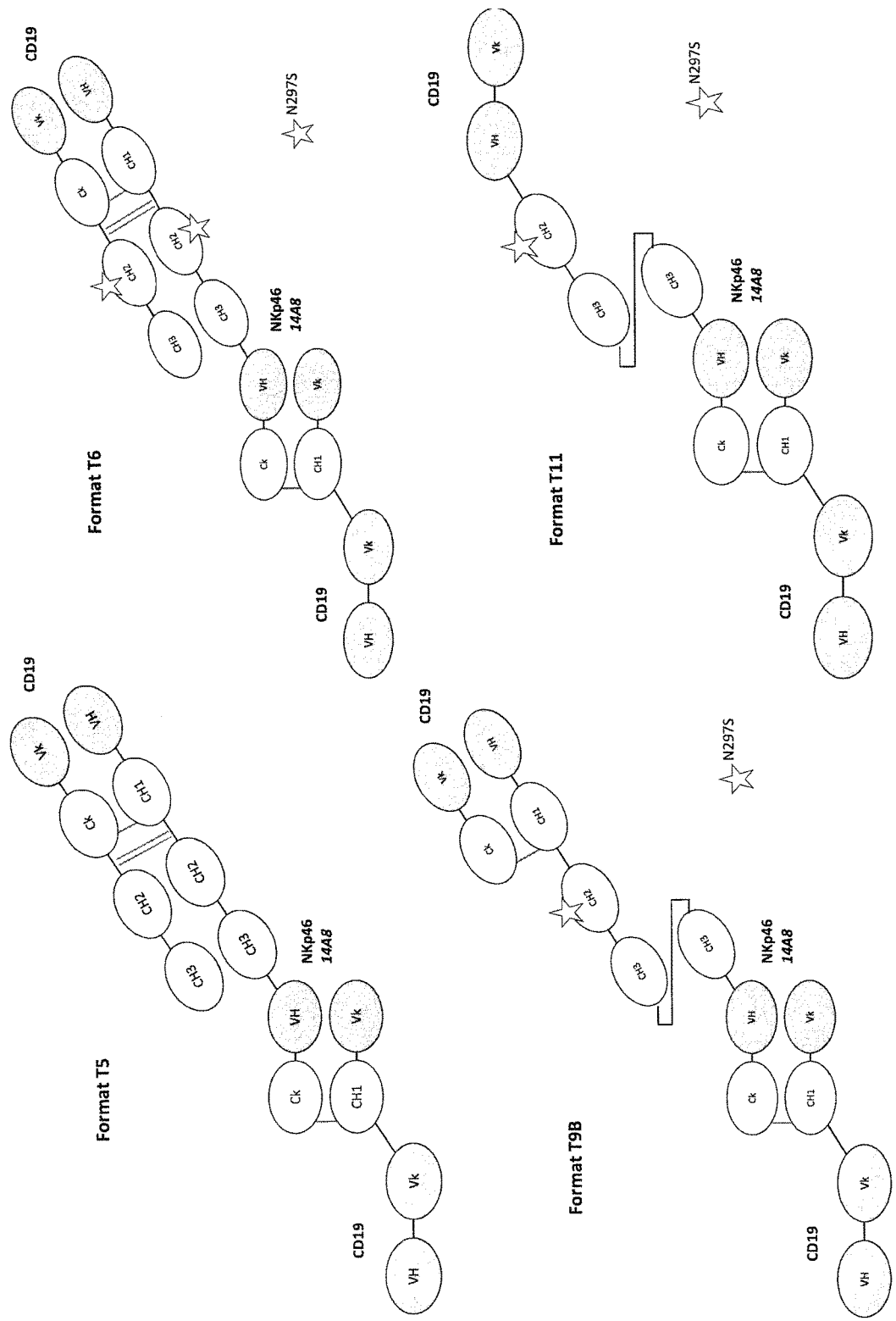

The domain structure of a trimeric T5 polypeptide is shown in FIG. 2F. The T5 polypeptide is a trimeric polypeptide which shares the structure of the F5 format, but differs by fusion of an scFv unit at the C-terminus of the third chain (the chain lacking the Fc domain). This protein will therefore have two antigen binding domains for antigens of interest, and one for NKp46, and will bind CD16 via its Fc domain. Proteins were cloned, produced and purified as in Example 2-1. The T5 protein had two antigen binding domains that bind human CD20, originating from different antibodies (and binding to different epitopes on CD20). The first anti-CD20 ABD contained the $V_H$ and $V_L$ of the parent antibody GA101 (GAZYVA®, Gazyvaro®, obinutuzumab, Roche Pharmaceuticals). The second anti-CD20 ABD contained the $V_H$ and $V_L$ of the parent antibody rituximab (Rituxan®, Mabthera®, Roche Pharmaceuticals). The third antigen binding domain binds human NKp46. The amino acid sequences of the three chains of the T5 protein are shown below (Rituximab sequences are in bold and underlined, anti-GA101 sequences are underlined, anti-NKp46 sequences are in italics).

GA101-T5-Ritux-NKp46
Polypeptide 1
(SEQ ID NO: 188)
<u>QVQLVQSGAEVKKPGSSVKVSCKASGYAFSYSWINWVRQAPGQGLEWMGR</u>

<u>IFPGDGDTDYNGKFKGRVTITADKSTSTAYMELSSLRSEDTAVYYCARNV</u>

<u>FDGYWLVYWGQGTLVTVSS</u>ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGST

GS<u>QVQLQQPGAELVKPGASVKMSCKASGYTFTSYNMHWVKQTPGRGLEWI</u>

<u>GAIYPGNGDTSYNQKFKGKATLTADKSSSTAYMQLSSLTSEDSAVYYCAR</u>

<u>STYYGGDWYENVWGAGTTVTVSA</u>RTVAAPSVFIFPPSDEQLKSGTASVVC

LLNNFYPREAKVQWKVDNALQSGNSQESVTEQDSKDSTYSLSSTLTLSKA

DYEKHKVYACEVTHQGLSSPVTKSFNRGEC-

Polypeptide 2
(SEQ ID NO: 189)
<u>DIVMTQTPLSLPVTPGEPASISCRSSKSLLHSNGITYLYWYLQKPGQSPQ</u>

<u>LLIYQMSNLVSGVPDRFSGSGSGTDFTLKISRVEAEDVGVYYCAQNLELP</u>

<u>YTFGGGTKVEIK</u>RTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGECDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK-

Polypeptide 3:
(SEQ ID NO: 190)
<u>QIVLSQSPAILSASPGEKVTMTCRASSSVSYIHWFQQKPGSSPKPWIYAT</u>

<u>SNLASGVPVRFSGSGSGTSYSLTISRVEAEDAATYYCQQWTSNPPTEGGG</u>

<u>TKLEIK</u>ASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSSS

*EVQLQQSGPELVKPGASVKISCKTSGYTFTEYTMHWVKQSHGKSLEWIGG*

*ISPNIGGTSYNQKFKGKATLTVDKSSSTAYMELRSLTSEDSAVYYCARRG*

*GSFDYWGQGTTLTVSSVEGGSGGSGGSGGSGGVDDIVMTQSPATLSVTPG*

*DRVSLSCRASQSISDYLHWYQQKSHESPRLLIKYASQSISGIPSRFSGSG*

*SGSDFTLSINSVEPEDVGVYYCQNGHSFPLTFGAGTKLELK*-

Format T6 (T6)

The domain structure of the trimeric T6 polypeptide is shown in FIG. 2F. The T6 polypeptide is a trimeric polypeptide which shares the structure of the F6 format, but differs by the fusion of an scFv unit at the C-terminus of the third chain (the chain lacking the Fc domain). This trimeric protein contains two antigen binding domains for antigens of interest, and one for NKp46, and does not bind CD16 via its Fc domain due to the N297 substitution. Proteins were cloned, produced and purified as in Example 2-1. The T6 protein contains two antigen binding domains that bind human CD20. The first anti-CD20 ABD comprises the $V_H$ and $V_L$ of the parent antibody GA101 and the second anti-CD20 ABD comprises the $V_H$ and $V_L$ of rituximab. The amino acid sequences of the three chains of the T6 proteins are shown in SEQ ID NOS: 191, 192 and 193.

Format T98 (T98)

The domain structure of the trimeric T9B polypeptide is shown in FIG. 2F. The T9B polypeptide is a trimeric polypeptide which shares the structure of the F9 format (F9B variant), but differs by the fusion of an scFv unit at the C-terminus of the free CH1 domain (on the third chain). This protein contains two antigen binding domains for antigen of interest, and one for NKp46, but will not bind CD16 via its Fc domain due to the monomeric Fc domain and/or the N297 substitution. Trimeric proteins as above described were cloned, produced and purified as in Example 2-1. The T9B protein had two antigen binding domains that bind human CD20. The first anti-CD20 ABD contained the $V_H$ and $V_L$ of the parent antibody GA101 and the second anti-CD20 ABD contained the $V_H$ and $V_L$ of the parent antibody rituximab. The amino acid sequences of the three chains of the T9B proteins are shown below.

```
GA101-T9B-Ritux-NKp46
Polypeptide 2: (SEQ ID NO: 195)
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC-

Polypeptide 1: (SEQ ID NO: 194)
QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTSPPSPAPELLGGPSVFLFPPKPK

DTLMISRTPEVTCVVVDVSHEDPEVKFNWYVDGVEVHNAKTKPREEQYSS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGGG

GGSGGGGSGGGGSGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGSTGSQVQLQQPGAELVKPGASVKMSCKASGY

TFTSYNMHWVKQTPGRGLEWIGAIYPGNGDTSYNQKFKGKATLTADKSSS

TAYMQLSSLTSEDSAVYYCARSTYYGGDWYFNVWGAGTTVTVSARTVAAP

SVFIFPPSDEQLKSGTASVVCLLNNFYPREAKVQWKVDNALQSGNSQESV

TEQDSKDSTYSLSSTLTLSKADYEKHKVYACEVTHQGLSSPVTKSFNRGE

C-

Polypeptide 3 (SEQ ID NO: 196):
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSSSEVQLQQSGPELVKPGASVKISCKTSGYTFTEY

TMHWVKQSHGKSLEWIGGISPNIGGTSYNQKFKGKATLTVDKSSSTAYME

LRSLTSEDSAVYYCARRGGSFDYWGQGTTLTVSSVEGGSGGSGGSGGSGG

VDDIVMTQSPATLSVTPGDRVSLSCRASQSISDYLHWYQQKSHESPRLLI

KYASQSISGIPSRFSGSGSGSDFTLSINSVEPEDVGVYYCQNGHSFPLTF

GAGTKLELK-
```

Format T11 (T1): CD19-T11-NKp46-3

The domain structure of the dimeric T11 polypeptide is shown in FIG. 2F. The T11 polypeptide is a trimeric polypeptide which shares the structure of the F11 format, but differs by the fusion of an scFv unit at the C-terminus of the free CH1 domain. This dimeric protein contains two antigen binding domains for antigen of interest, and one for NKp46, and does not bind CD16 via its Fc domain due to the monomeric Fc domain and/or the N297 substitution. Proteins were cloned, produced and purified as in Example 2-1. The T11 protein contains two antigen binding domains that bind human CD20. The first anti-CD20 ABD contained the $V_H$ and $V_L$ of the parent antibody GA101 and the second anti-CD20 ABD contained the $V_H$ and $V_L$ of rituximab. The amino acid sequences of the two chains of the T11 protein are shown below.

```
GA101-T11-Ritux-NKp46
Polypeptide 1 (SEQ ID NO: 197):
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKGGGSGGGGSGGGGSQVQLVQSGAEVKKPGSSVKVSCK

ASGYAFSYSWINWVRQAPGQGLEWMGRIFPGDGDTDYNGKFKGRVTITAD

KSTSTAYMELSSLRSEDTAVYYCARNVFDGYWLVYWGQGTLVTVSSASTK

GPSVFPLAPSSKSTSGGTAALGCLVKDYFPEPVTVSWNSGALTSGVHTFP

AVLQSSGLYSLSSVVTVPSSSLGTQTYICNVNHKPSNTKVDKRVEPKSCD

KTHTSPPSPAPELLGGPSVFLFPPKPKDTLMISRTPEVTCVVVDVSHEDP

EVKFNWYVDGVEVHNAKTKPREEQYSSTYRVVSVLTVLHQDWLNGKEYKC

KVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGN

VFSCSVMHEALHNHYTQKSLSLSPGGGGSGGGGSGGGGSGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGSTGS

QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSARTVAAPSVFIFPPSDEQLKSGTASVVCLL

NNFYPREAKVQWKVDNALQSGNSQESVTEQDSKDSTYSLSSTLTLSKADY

EKHKVYACEVTHQGLSSPVTKSFNRGEC-

Polypeptide 2 (SEQ ID NO: 198):
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKRVEPKSCDKTHGGSSSEVQLQQSGPELVKPGASVKISCKTSGYTFTEY

TMHWVKQSHGKSLEWIGGISPNIGGTSYNQKFKGKATLTVDKSSSTAYME
```

-continued
LRSLTSEDSAVYYCARRGGSFDYWGQGTTLTVSSVEGGSGGSGGSGGSGG

VDDIVMTQSPATLSVTPGDRVSLSCRASQSISDYLHWYQQKSHESPRLLI

KYASQSISGIPSRFSGSGSGSDFTLSINSVEPEDVGVYYCQNGHSFPLTF

GAGTKLELK-

Example 5

NKp46 Binding Affinity by Bispecific Proteins Detected by Surface Plasmon Resonance (SPR)

Biacore™ T100 General Procedure and Reagents

SPR measurements were performed on a Biacore™ T100 apparatus (Biacore GE Healthcare) at 25° C. In all Biacore™ (SPR) experiments HBS-EP+ (Biacore™ GE Healthcare) and NaOH 10 mM served as running buffer and regeneration buffer respectively, Sensorgrams were analyzed with Biacore™ T100 Evaluation software. Protein-A was purchased from (GE Healthcare). Human NKp46 recombinant proteins were cloned, produced and purified at Innate Pharma.

Immobilization of Protein-A

Protein-A proteins were immobilized covalently to carboxyl groups in the dextranlayer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A was diluted to 10 μg/ml in coupling buffer (10 mM acetate, pH 5.6) and injected until the appropriate immobilization level was reached (i.e. 2000 RU). Deactivation of the remaining activated groups was performed using 100 mM ethanolamine pH 8 (Biacore GE Healthcare).

Binding Study

The bispecific proteins were first tested in Format F1 as described in Example 2 having different anti-NKp46 variable regions from NKp46-1, NKp46-2, NKp46-3 or NKp46-4 antibodies. Antibodies were next tested as different formats (F3, F4, F5, F6, F9, F10, F11, F13, F14) having the anti-NKp46 variable regions from the NKp46-3 antibody, and were compared to the NKp46-3 antibody as a full-length human IgG1.

Bispecific proteins at 1 μg/mL were captured onto Protein-A chip and recombinant human NKp46 proteins were injected at 5 μg/mL over captured bispecific antibodies. For blank subtraction, cycles were performed again replacing NKp46 proteins with running buffer.

The Bab281 antibody was separately tested for binding to NKp46 by SPR, and additionally by flow cytometry using a cell line expressing the human NKp46 construct on the cell surface. For FACS screening, the presence of reactive antibodies in the supernatants was detected using Goat anti-mouse polyclonal antibody (pAb) labeled with PE. SPC and FACS results showed that the Bab281 based antibody did not bind the NKp46 cell line or to NKp46-Fc proteins. Bab281 lost the ability to bind to its target when presented in the bispecific format.

Affinity Study

Monovalent affinity study was conducted following a regular Capture-Kinetic protocol as recommended by the manufacturer (Biacore GE Healthcare kinetic wizard). Seven serial dilutions of human NKp46 recombinant proteins, ranging from 6.25 to 400 nM were sequentially injected over the captured Bi-Specific antibodies and allowed to dissociate for 10 min before regeneration. The entire sensorgram sets were fitted using the 1:1 kinetic binding model.

Results

SPR showed that the bispecific polypeptides of format F1 having the NKp46-1, 2, 3 and 4 scFv binding domains bound to NKp46, while the other bispecific polypeptides having the scFv of different anti-NK46 antibodies did not retain NKp46 binding. The binding domains that did not retain binding in monomeric bispecific format initially bound to NKp46 but lost the ability to bindNKp46 upon conversion to the bispecific format. All of the bispecific polypeptides of formats F1, F2 F3, F4, F5, F6, F9, F10, F11, F13, and F14 retained binding to NKp46 when using the NKp46-3 variable regions. Monovalent affinities and kinetic association and dissociation rate constants are shown below in Table 3 below.

TABLE 3

| Bispecific mAb | ka (1/Ms) | kd (1/s) | KD (M) |
| --- | --- | --- | --- |
| CD19-F1-Bab281 | n/a | n/a | n/a (loss of binding) |
| CD19-F1-NKp46-1 | 1.23E+05 | 0.001337 | 1.09E−08 |
| CD19-F1-NKp46-2 | 1.62E+05 | 0.001445 | 8.93E−09 |
| CD19-F1-NKp46-3 | 7.05E+04 | 6.44E−04 | 9.14E−09 |
| CD19-F1-NKp46-4 | 1.35E+05 | 6.53E−04 | 4.85E−09 |
| CD19-F3-NKp46-3 | 3.905E+5 | 0.01117 | 28E−09 |
| CD19-F4-NKp46-3 | 3.678E+5 | 0.01100 | 30E−09 |
| CD19-F5-NKp46-3 | 7.555E+4 | 0.00510 | 67E−09 |
| CD19-F6-NKp46-3 | 7.934E+4 | 0.00503 | 63E−09 |
| CD19-F9A-NKp46-3 | 2.070E+5 | 0.00669 | 32E−09 |
| CD19-F10A-NKp46-3 | 2.607E+5 | 0.00754 | 29E−09 |
| CD19-F11A-NKp46-3 | 3.388E+5 | 0.01044 | 30E−09 |
| CD19-F13-NKp46-3 | 8.300E+4 | 0.00565 | 68E−09 |
| CD19-F14-NKp46-3 | 8.826E+4 | 0.00546 | 62E−09 |
| NKp46-3 IgG1 | 2.224E+5 | 0.00433 | 20E−09 |

Example 6

Engagement of NK Cells Against Daudi Tumor Target with Fc-Containing NKp46×CD19 Bispecific Protein Bispecific antibodies having a monomeric Fc domain and a domain arrangement according to the single chain F1 or dimeric F2 formats described in Example 3, and a NKp46 binding region based on NKp46-1, NKp46-2, NKp46-3 or NKp46-4 were tested for functional ability to direct NK cells to lyse CD19-positive tumor target cells (Daudi, a well characterized B lymphoblast cell line). The F2 proteins additionally included NKp46-9 variable regions which lost the ability to bindNKp46 in the scFv format but which retained the ability to bindNKp46 in the F(ab)-like format of F2.

Briefly, the cytolytic activity of each of (a) resting human NK cells, and (b) human NK cell line KHYG-1 transfected with human NKp46, was assessed in a classical 4-h $^{51}$Cr-release assay in U-bottom 96 well plates. Daudi cells were labelled with $^{51}$Cr (50 μCi (1.85 MBq)/1×10$^6$ cells), then mixed with KHYG-1 transfected with hNKp46 at an effector/target ratio equal to 50 for KHYG-1, and 10 (for F1 proteins) or 8.8 (for F2 proteins) for resting NK cells, in the presence of monomeric bi-specific antibodies at different concentrations. After brief centrifugation and 4 hours of incubation at 37° C., samples of supernatant were removed and transferred into a LumaPlate™ (Perkin Elmer Life Sciences, Boston, Mass.), and $^{51}$Cr release was measured with a TopCount™ NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

In the KHYG-1 hNKp46 NK experimental model, each bi-specific antibody NKp46-1, NKp46-2, NKp46-3, NKp46-4 or NKp46-9 induced specific lysis of Daudi cells by human KHYG-1 hNKp46 NK cell line compared to negative controls (Human IgG1 isotype control (IC) and CD19/CD3 bi-specific antibodies), thereby showing that these antibodies induce Daudi target cell lysis by KHYG-1 hNKp46 through CD19/NKp46 cross-linking.

Figure 3A:
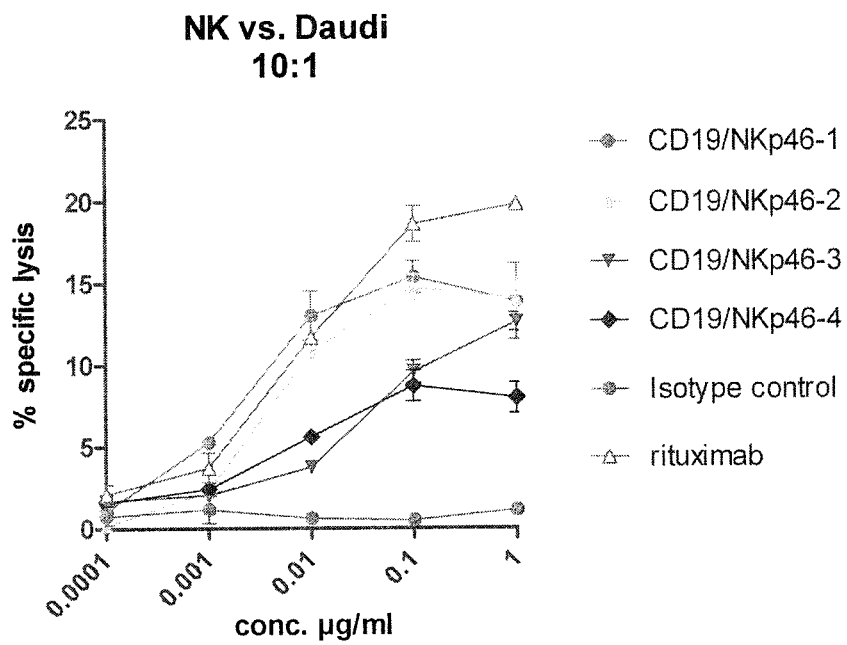
FIGS. 3A and 3B respectively demonstrate that bispecific F1 and F2 format proteins having NKp46 binding region based on NKp46-1, NKp46-2, NKp46-3 or NKp46-4 are able to direct resting NK cells to their CD19-positive Daudi tumor target cells, while isotype control antibody did not lead to the elimination of the Daudi cells. Rituximab (RTX) served as the positive control of ADCC, where the maximal response obtained with RTX (at 10 µg/ml in this assay) was 21.6% specific lysis.
Figure 3B:
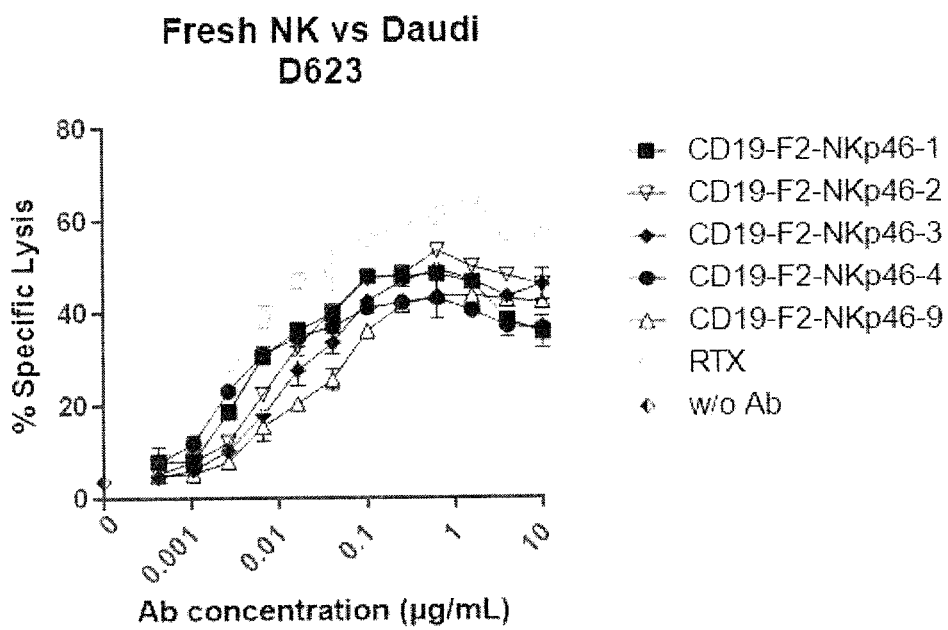

When resting NK cells were used as effectors, each bi-specific antibody NKp46-1, NKp46-2, NKp46-3, NKp46-4 or NKp46-9 again induced specific lysis of Daudi cells by human NK cells compared to the negative control (Human IgG1 isotype control (IC) antibody), thereby showing that these antibodies induce Daudi target cell lysis by human NK cells through CD19/NKp46 cross-linking. Rituximab (RTX, chimeric IgG1) was used as a positive control of ADCC (Antibody-Dependent Cell Cytotoxicity) by resting human NK cells. The maximal response obtained with RTX (at 10 µg/ml in this assay) was 21.6% specific lysis illustrating that the inventive bispecific antibodies have high target cell lysis activity. Results for experiments with resting NK cells are shown in FIG. 3A for the single chain F1 proteins and 3B for the dimeric F2 proteins.

Example 7

Comparison with Full Length Anti-NKp46 mAbs and Depleting Anti-Tumor mAbs: Only NKp46×CD19 Bispecific Proteins Prevent Non-Specific NK Activation In these experiments bispecific antibodies possessing a specific bispecific format were produced in order to assess whether such bispecific antibodies can mediate NKp46-mediated NK activation toward cancer target cells without triggering non-specific NK cell activation.

Particularly, NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:

(a) full-length monospecific anti-NKp46 antibodies (NKp46-3 as human IgG1), and (b) the anti-CD19 antibody as a full-length human IgG1 as ADCC inducing antibody control comparator.

The experiments further included as controls: rituximab, an anti-CD20 ADCC inducing antibody control for a target antigen with high expression levels; an anti-CD52 antibody alemtuzumab, a human IgG1 which binds CD52 target present on both targets and NK cells; and a negative control isotype control therapeutic antibody (a human IgG1 that does not bind a target present on the target cells (HUG1-IC).

The different proteins were tested in order to assess their relative functional effects on NK cell activation in the presence of CD19-positive tumor target cells (Daudi cells), in the presence of CD19-negative, CD16-positive target cells (HUT78 T-lymphoma cells), and in the absence of target cells.

Briefly, NK activation was tested by assessing CD69 and CD107 expression on NK cells by flow cytometry. The assay was carried out in 96 U well plates in completed RPMI, 150 µL final/well. Effector cells were fresh NK cells purified from donors. Target cells were Daudi (CD19-positive), HUT78 (CD19-negative) or K562 (NK activation control cell line). In addition to K562 positive control, three conditions were tested, as follows:

NK cell alone
NK cells vs Daudi (CD19$^+$)
NK cells vs HUT78 (CD19$^-$)

Effector:Target (E:T) ratio was 2.5:1 (50 000 E:20 000 T), with an antibody dilution range starting to 10 µg/mL with 1/4 dilution (n=8 concentrations). Antibodies, target cells and effector cells were mixed; spun 1 min at 300 g; incubated 4 h at 37° C.; spun 3 min at 500 g; washed twice with Staining Buffer (SB); added 50 µL of staining Ab mix; incubated 30 min at 300 g; washed twice with SB resuspended pellet with CellFix; stored overnight at 4° C.; and fluorescence was detected with Canto II (HTS).

Results

1. NK Cells Alone

Results of these experiments are shown in FIG. 4A. In the absence of target-antigen expressing cells, none of the bispecific anti-NKp46×anti-CD19 antibodies (including each of the NKp46-1, NKp46-2, NKp46-3, NKp46-4 and NKp46-9 variable regions) activated NK cells as assessed by CD69 or CD107 expression. The full-length anti-CD19 also did not activate NK cells. However, the full-length anti-NKp46 antibodies did cause detectable activation of NK cells. Alemtuzumab also induced activation of NK cells, at a very high level. The isotype control antibody did not induce activation.

2. NK Cells vs Daudi (CD19$^+$)

Results of these experiments are shown in FIG. 4B. In the presence of target-antigen expressing cells, each of the bispecific anti-NKp46×anti-CD19 antibodies (including each of the NKp46-1, NKp46-2, NKp46-3, NKp46-4 and NKp46-9 binding domains) activated NK cells. The full-length anti-CD19 antibody showed at best only very low activation of NK cells. Neither full-length anti-NKp46 antibodies nor alemtuzumab showed a substantial increase in activation beyond what was observed in presence of NK cells alone. The data in FIG. 4 shows that full-length anti-NKp46 antibodies elicited a similar level of baseline activation as was observed in the presence of NK cells alone. Alemtuzumab also induced the activation of NK cells at a similar level of activation to what was observed in the presence of NK cells alone, and at higher antibody concentrations in this setting (ET 2.5:1) the activation was greater than with the bispecific anti-NKp46×anti-CD19 antibody. The isotype control antibody did not induce activation.

3. NK Cells vs HUT78 (CD19$^-$)

Figure 4C:
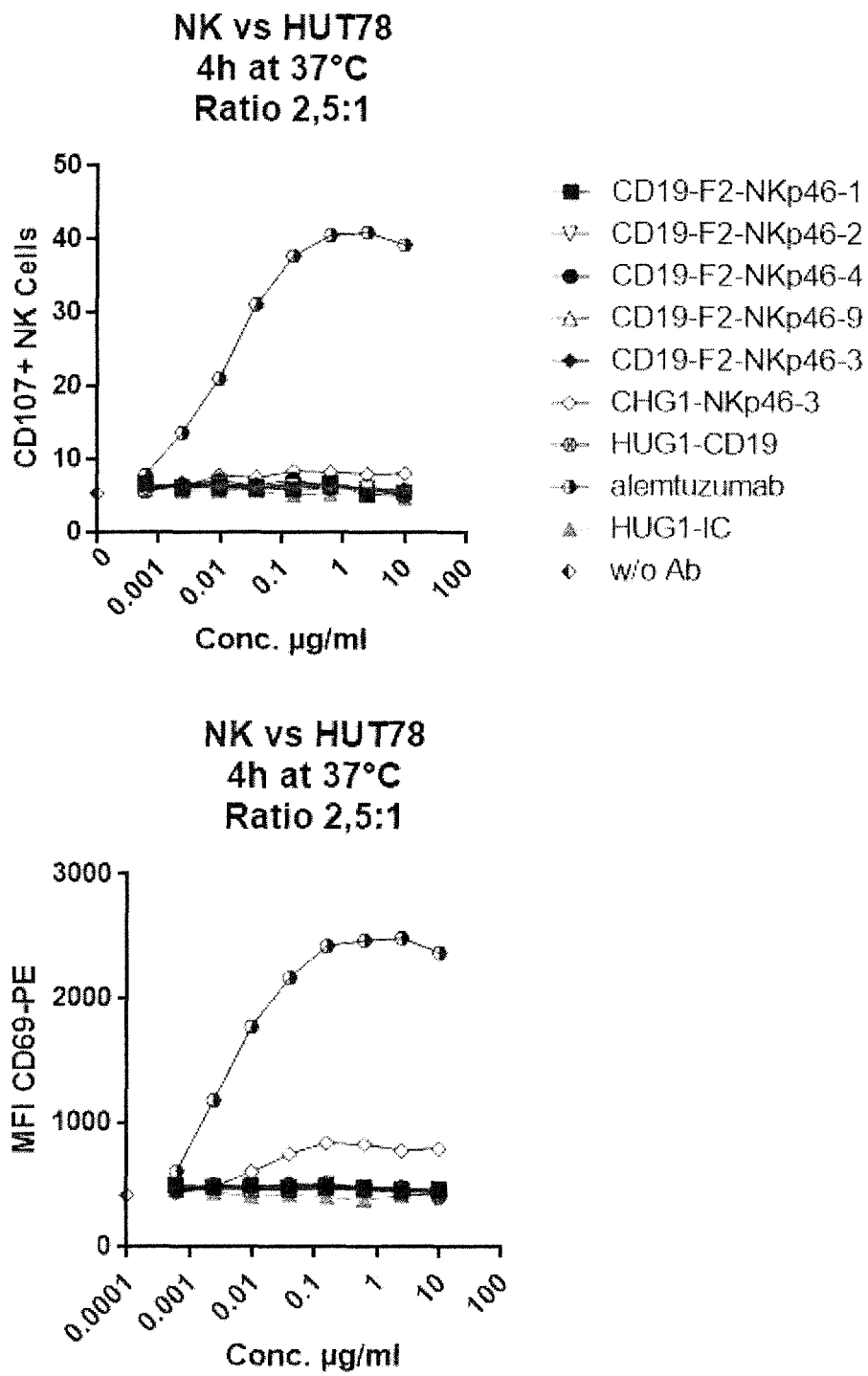
FIG. 4C shows that in the presence of CD19-negative HUT78 cells, none of the bispecific anti-NKp46×anti-CD19 antibodies (including each of the NKp46-1, NKp46-2, NKp46-3 or NKp46-4 variable regions) activated NK cells. However, the full-length anti-NKp46 antibodies and alemtuzumab resulted in detectable activation of NK cells, i.e., at a similar level observed in presence of NK cells alone. Isotype control antibody did not induce activation.

Results of these experiments are shown in FIG. 4C. In the presence of target-antigen-negative HUT78 cells, none of the bispecific anti-NKp46×anti-CD19 antibody (including each of the NKp46-1, NKp46-2, NKp46-3, NKp46-4 and NKp46-9 variable regions) activated NK cells. However, the full-length anti-NKp46 antibodies and alemtuzumab caused detectable activation of NK cells at a similar level observed in presence of NK cells alone. Isotype control antibody did not induce activation.

The foregoing results indicate that the inventive bispecific anti-NKp46 proteins are able to activate NK cells in a target-cell specific manner, unlike full-length monospecific anti-NKp46 antibodies and further unlike full-length antibodies of depleting IgG isotypes which also activate NK cells in the absence of target cells. The NK cell activation achieved with anti-NKp46 bispecific proteins remarkably was higher than that observed with full length anti-CD19 IgG1 antibodies. Therefore these bispecific antibodies should elicit less non-specific cytotoxicity and may be more potent when used in therapy.

Example 8

Comparative Efficacy with Depleting Anti-Tumor mAbs: NKp46×CD19 Bispecific Proteins at Low ET Ratio These studies aimed to investigate whether bispecific antibodies can mediate NKp46-mediated NK cell activation toward cancer target cells at lower effector: target ratios. The ET ratio used in this Example was 1:1 which is believed to be closer to the setting that would be encountered in vivo than the 2.5:1 ET ratio used in Example 7 or the 10:1 ET ratio of Example 6.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:

(a) full-length monospecific anti-NKp46 antibodies (NKp46-3 as human IgG1), and (b) the anti-CD19 antibody as a full-length human IgG1 as ADCC inducing antibody control comparator.

The experiments further included as controls: rituximab (an anti-CD20 ADCC inducing antibody control for a target antigen with high expression levels); anti-CD52 antibody alemtuzumab (a human IgG1, binds CD52 target present on both targets and NK cells), and negative control isotype control therapeutic antibody (a human IgG1 that does not bind a target present on the target cells (HUG1-IC). The different proteins were tested for their functional effect on NK cell activation as assessed by CD69 or CD107 expression in the presence of CD19-positive tumor target cells (Daudi cells), in the presence of CD19-negative, CD16-positive target cells (HUT78 T-lymphoma cells), and in the absence of target cells. The experiments were carried out as in Example 7 except that the ET ratio was 1:1.

Results

Figure 5A:
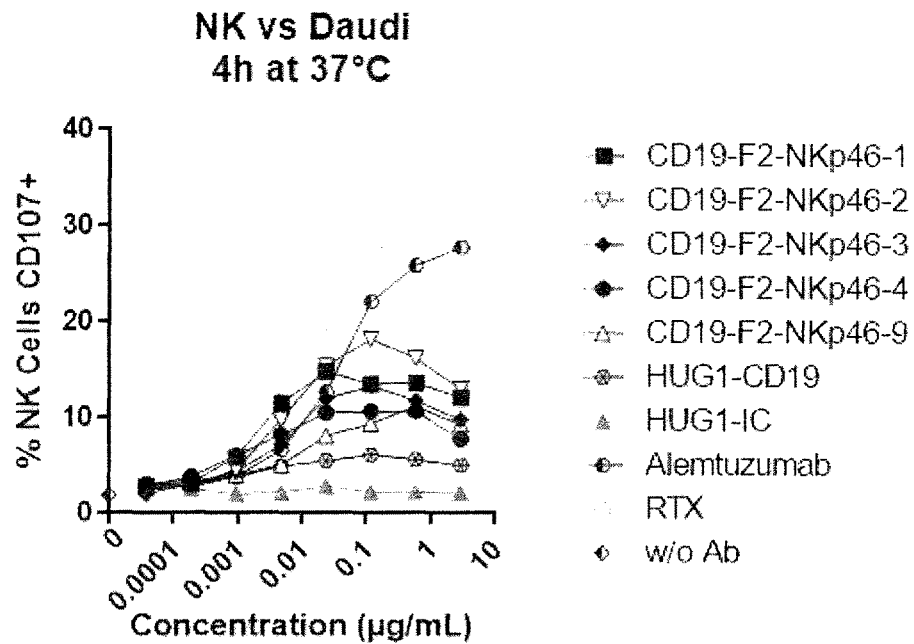
FIGS. 5A and 5B shows that at low effector:target ratios of 1:1 each of the tested bispecific anti-NKp46×anti-CD19 antibodies activated NK cells in the presence of Daudi cells, and that bispecific anti-NKp46×anti-CD19 antibodies were far more potent (better elicited lysis of target cells) than a control anti-CD19 antibody as well as a full-length human IgG1 ADCC inducing antibody.
Figure 5B:
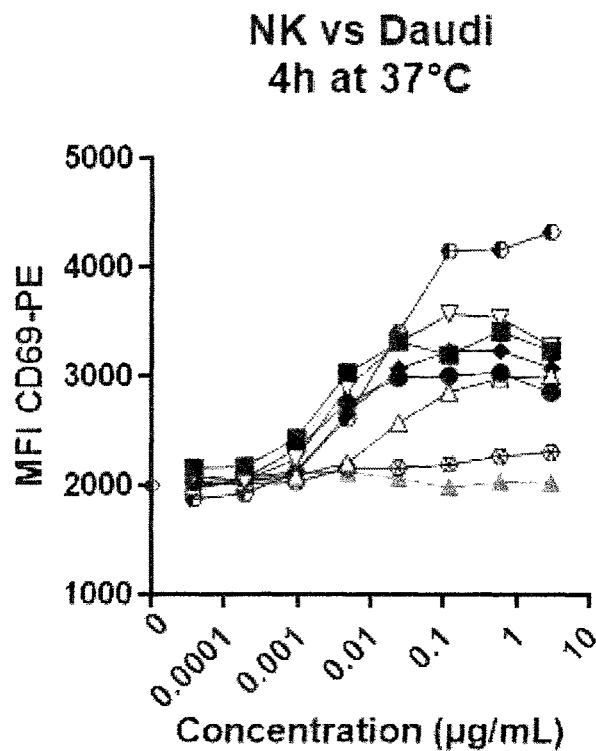

The results of the above experiments are shown in FIG. 5 (5A: CD107 and 5B: CD69). In the presence of target-antigen expressing cells, each of the bispecific anti-NKp46× anti-CD19 antibodies (respectively including NKp46-1, NKp46-2, NKp46-3, NKp46-4 or NKp46-9 variable regions) activated NK cells in the presence of Daudi cells.

The activation induced by bispecific anti-NKp46×anti-CD19 antibody in the presence of Daudi cells was far more potent than that elicited by the full-length human IgG1 anti-CD19 antibody. This ADCC inducing antibody had low activity in this setting. Furthermore, in this low E:T ratio setting the activation induced by the bispecific anti-NKp46× anti-CD19 antibody was as potent as the anti-CD20 antibody rituximab, with a difference being observed only at the highest concentrations that were 10 fold higher than concentrations in which differences were observed at the 2.5:1 ET ratio.

In the absence of target cells or in the presence of target antigen-negative HUT78 cells, full-length anti-NKp46 antibodies and alemtuzumab showed a similar level of baseline activation as was observed in the presence of Daudi cells. Anti-NKp46×anti-CD19 antibody did not activate NK cells in presence of HUT78 cells.

The foregoing results indicate that the bispecific anti-NKp46 proteins of the invention are able to activate NK cells in a target-cell specific manner and at lower effector: target ratios and are more effective in mediating NK cell activation that traditional human IgG1 antibodies.

Example 9

NKp46 Mechanism of Action

NKp46×CD19 bispecific proteins having an arrangement according to the F2, F3, F5 or F6 formats described in Examples 3 or 4 with anti-NKp46 variable domains from NKp46-3 were compared to rituximab (anti-CD20 ADCC inducing antibody), and to a human IgG1 isotype control antibody for their functional ability to direct CD16-/NKp46+ NK cell lines to lyse CD19-positive tumor target cells.

Briefly, the cytolytic activity of the CD16-/NKp46+ human NK cell line KHYG-1 was assessed in a classical 4-h $^{51}$Cr-release assay in U-bottom 96 well plates. Daudi or B221 cells were labelled with $^{51}$Cr (50 µCi (1.85 MBq)/1× $10^6$ cells), then mixed with KHYG-1 at an effector/target ratio equal to 50:1, in the presence of test antibodies at dilution ranges starting from $10^{-7}$ mol/L with 1/5 dilution (n=8 concentrations).

After a brief centrifugation and 4 hours of incubation at 37° C., 50 µL of the supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

Figure 6A:
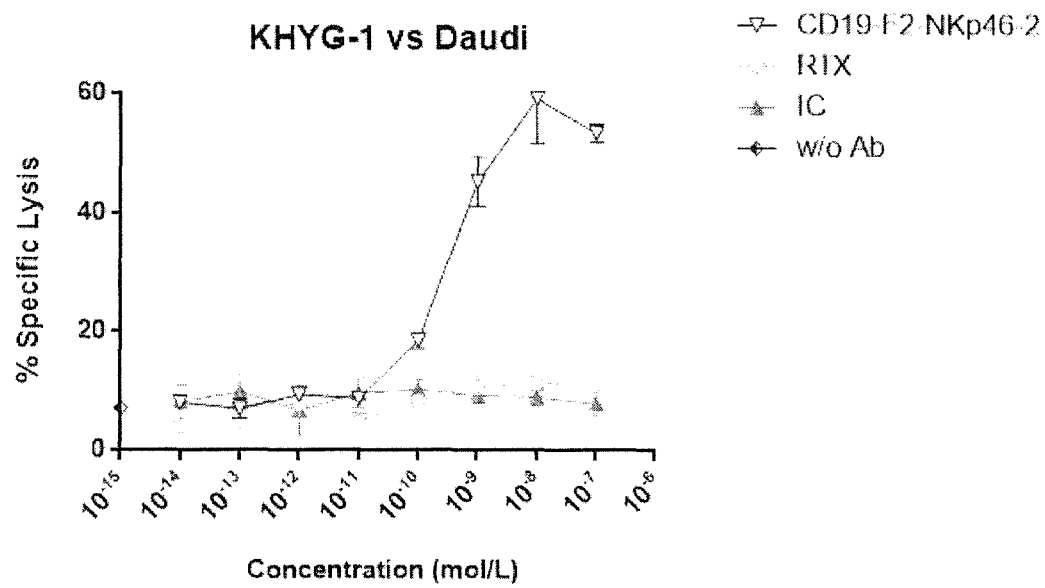
FIGS. 6A and 6B show that each NKp46×CD19 bispecific protein (Format F3, F5 and F6) induced specific lysis of Daudi (FIG. 6A) or B221 (FIG. 6B) cells by human KHYG-1 CD16-negative hNKp46-positive NK cell line, while rituximab and human IgG1 isotype control (IC) antibodies did not.
Figure 6B:
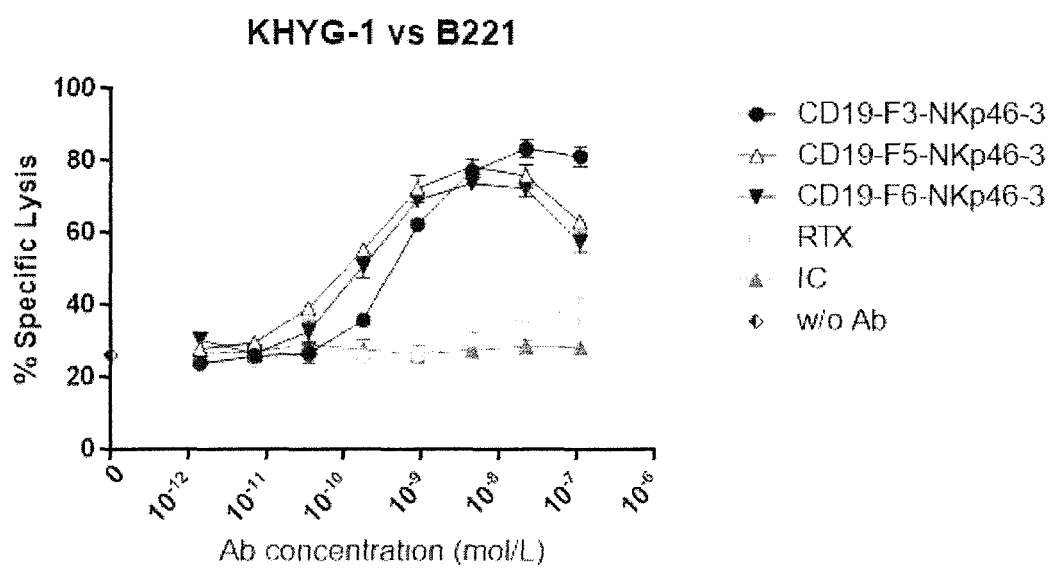

The results of the above experiments are shown in FIG. 6A (KHYG-1 vs Daudi) and 6B (KHYG-1 vs B221). In the KHYG-1 hNKp46 NK experimental model, each NKp46× CD19 bispecific protein (Format F2, F3, F5 and F6) induced specific lysis of Daudi or B221 cells by human KHYG-1 hNKp46 NK cell line, while rituximab and the human IgG1 isotype control (IC) antibodies did not.

Example 10

Bispecific proteins targeting human KIR3DL2 (KIR3DL2×NKp46 bispecific) were constructed as F6 formats and tested for activity. KIR3DL2 (CD158k; killer cell immunoglobulin like receptor, three Ig domains and long cytoplasmic tail 2) is a disulphide-linked homodimer of three-Ig domain molecules of about 140 kD, described in Pende et al. (1996) J. Exp. Med. 184: 505-518, the disclosure of which is incorporated herein by reference. Several allelic variants have been reported for KIR3DL2 polypeptides, each of these are encompassed by the term KIR3DL2. The amino acid sequence of the mature human KIR3DL2 (allele *002) is shown in Genbank accession no. AAB52520. Briefly, the cytolytic activity of NK cells from Buffy coat from donors was assessed in a classic 4-h 51Cr-release assay in U-bottom 96 well plates. HUT78 tumor cells (CTCL) that express KIR3DL2 were labelled with $^{51}$Cr, then mixed with NK cells at an effector/target ratio equal to 10:1 (25 000: 2500), in the presence of test antibodies at dilution ranges starting from 10 µg/mL (or 100 µg/mL) with 1/10 dilution (n=8). Assays were in cRPMI, 150 µL final/well, in triplicates.

Figure 6C:
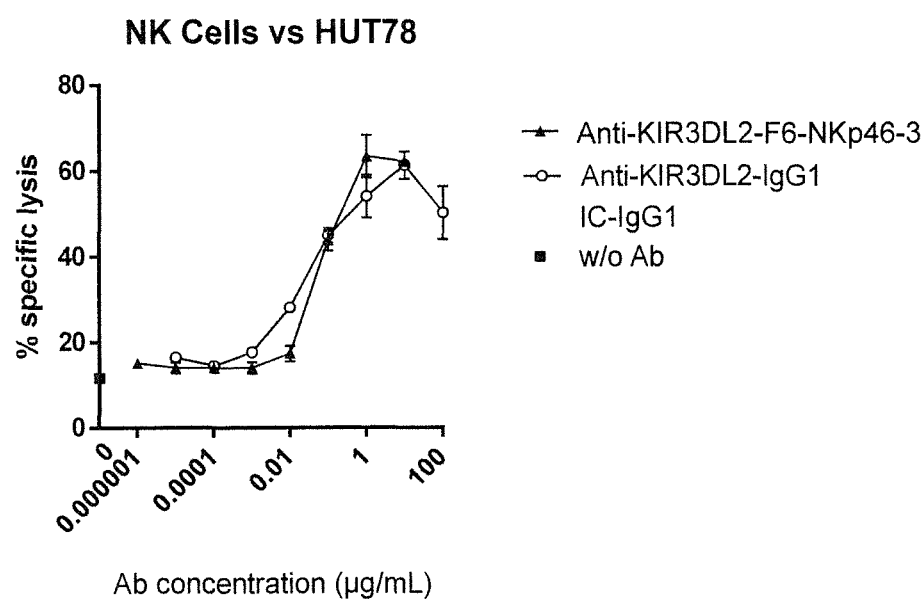
FIG. 6C shows that a NKp46×KIR3DL2 bispecific protein (Format F6) induced specific lysis of HUT78 tumor cells via NKp46 binding (without CD16 binding) comparably to a conventional IgG1 antibody with the same anti-KIR3DL2 variable regions.

Results are shown in FIG. 6C. Despite its Fc domain not binding to CD16 in this format, the F6 protein structure produced as an NKp46×KIR3DL2 bispecific protein surprisingly exhibited comparable ability to lyse target cells as a known anti-KIR3DL2 human IgG1 antibody that contained the same variable regions and which binds KIR3DL2 bivalently.

Example 11

Effect of Intrachain Domain Motion Within Multimeric Proteins

It was theorized by the inventors that the ability of NKp46 bispecific proteins to promote NKp46-mediated lysis of target cells may be affected by the distance between the two antigen binding domains in the bispecific protein which may impact the ability of one or both of the NKp46 antigen binding domain and the antigen binding domain which interacts with an antigen of interest to interact with their respective targets. Also, it was further theorized that NKp46 mediated lysis of target cells may be impacted by the structure of the two antigen binding domains and/or their respective conformation, freedom of motion or flexibility which may be impacted by the structure of the two antigen binding domains as well as the manner by which they are associated with each other, e.g., by a linker peptide and its particular length and chemical composition. Particularly, it was theorized that a lytic NKp46-target cell synapse may vary as a function of the size and structure of the bispecific protein. Therefore, the inventors posited that bispecific proteins wherein the antigen binding domains are in a format whereby the antigen binding domains more closely mimics or approximates the conformation, spacing and flexibility of the antigen binding domains of This was theorized because conformational flexibility, notably intrachain domain motion or movement, may for example affect the effective distance between NKp46 and antigen-of-interest binding sites, which in turn might have an effect on the NKp46-target cell synapse and the ability of a multimeric bispecific protein to mediate NKp46-mediated signaling and lysis. Based on these suppositions the inventors evaluated the lytic function of multimeric proteins of different bispecific protein formats and which comprise more or less freedom of motion of the antigen binding domains based on the structure of the antigen binding sites and the specific linkers separating these antigen binding sites.

Specifically, different NKp46× tumor antigen bispecific proteins of different formats such as the F3, F4, F9, F10 and F11 format that bound different tumor antigens were evaluated for their relative ability to induce NKp46-mediated lysis of tumor target cells by KHYG-1 NK cells (NKp46$^+$ CD16). F5 and F6 bispecific protein formats have distances between the NKp46 binding site and the antigen of interest binding site that are less than that of full-length antibodies. By contrast bispecific proteins targeting human CD19 (CD19×NKp46 bispecific) in F9 format have binding sites that are spaced farther apart, similar to distances in the two binding sites in conventional full-length antibodies. Bispecific proteins were therefore constructed as F9 formats and compared to F10 and F11 formats. Structurally speaking, format F9, F10 and F11 are very close to one another, however formats F10 and F11 are characterized by one antigen binding domain with a Fab structure and the other antigen binding domain with a tandem variable domain structure (two variable domains separated by a flexible linker). F10 and F11 therefore have greater intrachain domain motion and/or less local steric hindrance, as well as possibly less distance between binding sites than in the F9 proteins.

The cytolytic activity of the CD16-/NKp46+ human NK cell line KHYG-1 was assessed in a classical 4-h $^{51}$Cr-release assay in U-bottom 96 well plates. Daudi or B221 cells were labelled with $^{51}$Cr (50 µCi (1.85 MBq)/1×10$^6$ cells), then mixed with KHYG-1 at an effector/target ratio equal to 50:1, in the presence of test antibodies at dilution range starting from $10^{-7}$ mol/L with 1/5 dilution (n=8 concentrations). The results showed that formats F10 and F11 were both more potent than format F9 in inducing Daudi cell lysis by NK cells. As noted above F9 format proteins have distances between the NKp46 binding site and the antigen of interest binding site which is similar to full-length antibodies or about 80 Å, and the F10 and F11 proteins comprise a single chain domain connected to the Fc by a flexible linker and have substantially less than 80 Å between the antigen binding sites (in the case of F10, about 55 Å).

Based thereon we studied the effects of even further shortened distances between the NKp46 and antigen of interest binding domains using other CD19×NKp46 bispecific proteins. In these experiments F3, F4 protein formats were selected for comparison with protein formats F10 and F11. Each of these proteins have distances between antigen binding sites of less than 80 Å, however, F3 and F4 are shorter than F10 and F11, and F3 and F4 have distances between antigen binding sites that are equivalent to F11 but 25 Å less than that of F10. The results of these experiments indicated that the F3, F4, F10 and F11 formats did not significantly differ in their ability to induce Daudi cell lysis by NK cells. These results would suggest that there may be an optimal minimal spacing between the antigen binding domains that improves potency and/or that potency is affected by a combination of the spacing between the antigen binding domains and the flexibility and/or conformation of the antigen binding domains.

Example 12

Combining NKp46 and CD16 Triggering

NKp46×CD19 bispecific proteins that bind human CD16 having an arrangement according to the F5 format with anti-NKp46 variable domains from NKp46-3 were compared to the same bispecific antibody in a F6 format (which lacks CD16 binding), and to a human IgG1 isotype anti-CD19 antibody, as well as to a human IgG1 isotype control antibody for functional ability to direct purified NK cells to lyse CD19-positive Daudi tumor target cells.

Briefly, the cytolytic activity of fresh human purified NK cells from EFS Buffy Coat was assessed in a classical 4-h $^{51}$Cr-release assay in U-bottom 96 well plates. Daudi or HUT78 cells (negative control cells that do not express CD19) were labelled with $^{51}$Cr and then mixed with NK cells at an effector/target ratio equal to 10:1, in the presence of test antibodies at dilution range starting from 10 µg/ml with 1/10 dilution (n=8 concentrations).

After brief centrifugation and 4 hours of incubation at 37° C., 50 µL of supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Figure 7:
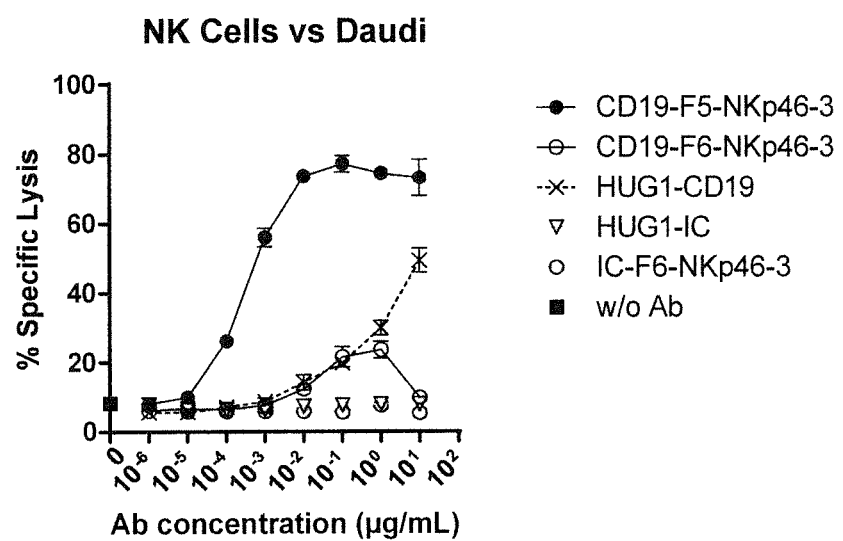
FIG. 7 shows a NKp46×CD19 bispecific protein in F5 format whose Fc domain binds CD16 is far more potent in mediating Daudi target cell lysis than a full-length IgG1 anti-CD19 antibody or a F6 format bispecific protein. The figure also shows that a bispecific anti-CD19 in F6 format whose Fc domain does not bind CD16 was as potent in mediating NK cell lysis of Daudi target cells as the full-length IgG1 anti-CD19 antibody, which is unexpected considering that the control IgG1 anti-CD19 antibody binds CD19 bivalently. At comparable levels of target cell lysis, CD19-F5-NKp46-3 was at least 1000 times more potent than the full-length anti-CD19 IgG1.

The results of these experiments are shown in FIG. 7. The CD19-F6-NKp46 (bispecific protein in F6 format) whose Fc domain does not bind CD16 due to a N297 substitution was as potent in mediating NK cell lysis of Daudi target cells as the full-length IgG1 anti-CD19 antibody. This result is remarkable especially considering that the control IgG1 anti-CD19 antibody binds CD19 bivalently and further since the anti-CD19 antibody is bound by CD16. The F6 protein was also compared to a protein CD19-F5-NKp46 that was identical to the CD19-F6-NKp46 protein with the exception of an asparagine at Kabat residue 297. Surprisingly, despite the strong NK activation mediated by CD16 triggering by the CD19-F5-NKp46 (F5 format protein) whose Fc domain binds CD16, the F5 format was far more potent in mediating Daudi target cell lysis that the full-length IgG1 anti-CD19 antibody or the F6 format bispecific protein. This would suggest that NKp46 can enhance target cell lysis even when CD16 is triggered. In fact, at comparable levels of target cell lysis, the CD19-F5-NKp46 was at least 1000 times more potent than the full-length anti-CD19 IgG1. These potency results would suggest that the inventive multispecific NKp46 antibodies should be well suited for use in human therapy, e.g., in treating cancer or infectious diseases.

Example 13

Mechanisms of Action of CD16-Binding NKp46×CD19 Bispecific

Lysis of Daudi cells by NKp46×CD19 bispecific F5 and F6 were compared to a conventional human IgG1 antibody. As a control, lysis was also tested on HUT78 cells that lack CD19; positive control for HUT78 cell lysis was an anti-KIR3DL2 of human IgG1 isotype (HUT78 are KIR3DL2-positive). Cytotoxicity assays were carried out as in Example 10. Flow cytometry staining of NK cell surface markers was carried out as in Example 7.

Figure 8:
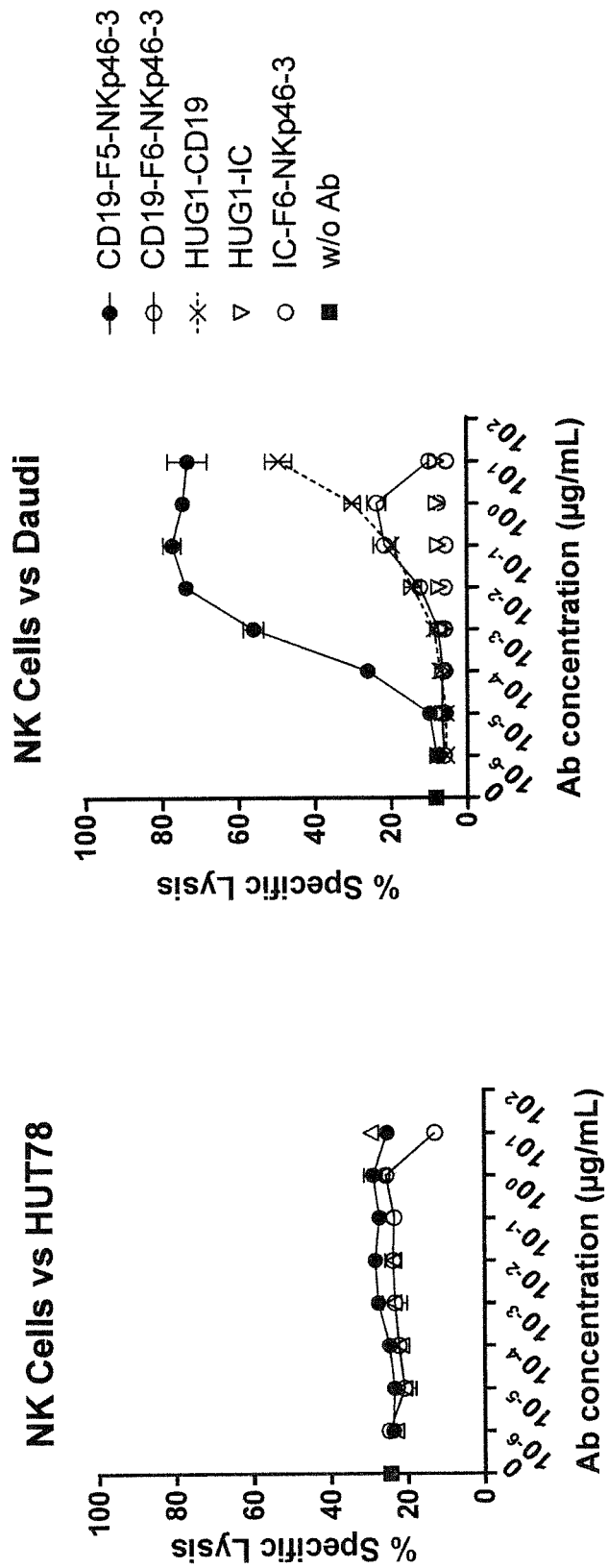
FIG. 8 shows the results of cytotoxicity assays using fresh NK cells (Daudi cell in the right hand panel and HUT78 cells in the left hand panel); the CD19-F6-NKp46-3 whose Fc domain does not bind CD16 due to a N297 substitution has as mode of action NKp46 triggering when NK cells encounter the target cell, while the CD19-F5-NKp46-3 bispecific protein demonstrated a far higher potency in mediating cytotoxicity toward Daudi cells. Neither the F5 nor F6 proteins mediated any NK cell cytotoxicity towards HUT78 cells.

Results for the cytotoxicity assays are shown in FIG. 8 (Daudi cell in the right hand panel and HUT78 cells in the left hand panel). the CD19-F6-NKp46-3 whose Fc domain does not bind CD16 due to a N297 substitution has as mode of action NKp46 triggering when NK cells encounter the target cell, while the CD19-F5-NKp46-3 bispecific protein demonstrated a far higher potency in mediating cytotoxicity toward Daudi cells. Neither the F5 nor the F6 protein mediated any NK cell cytotoxicity towards HUT78 cells.

Figure 9:
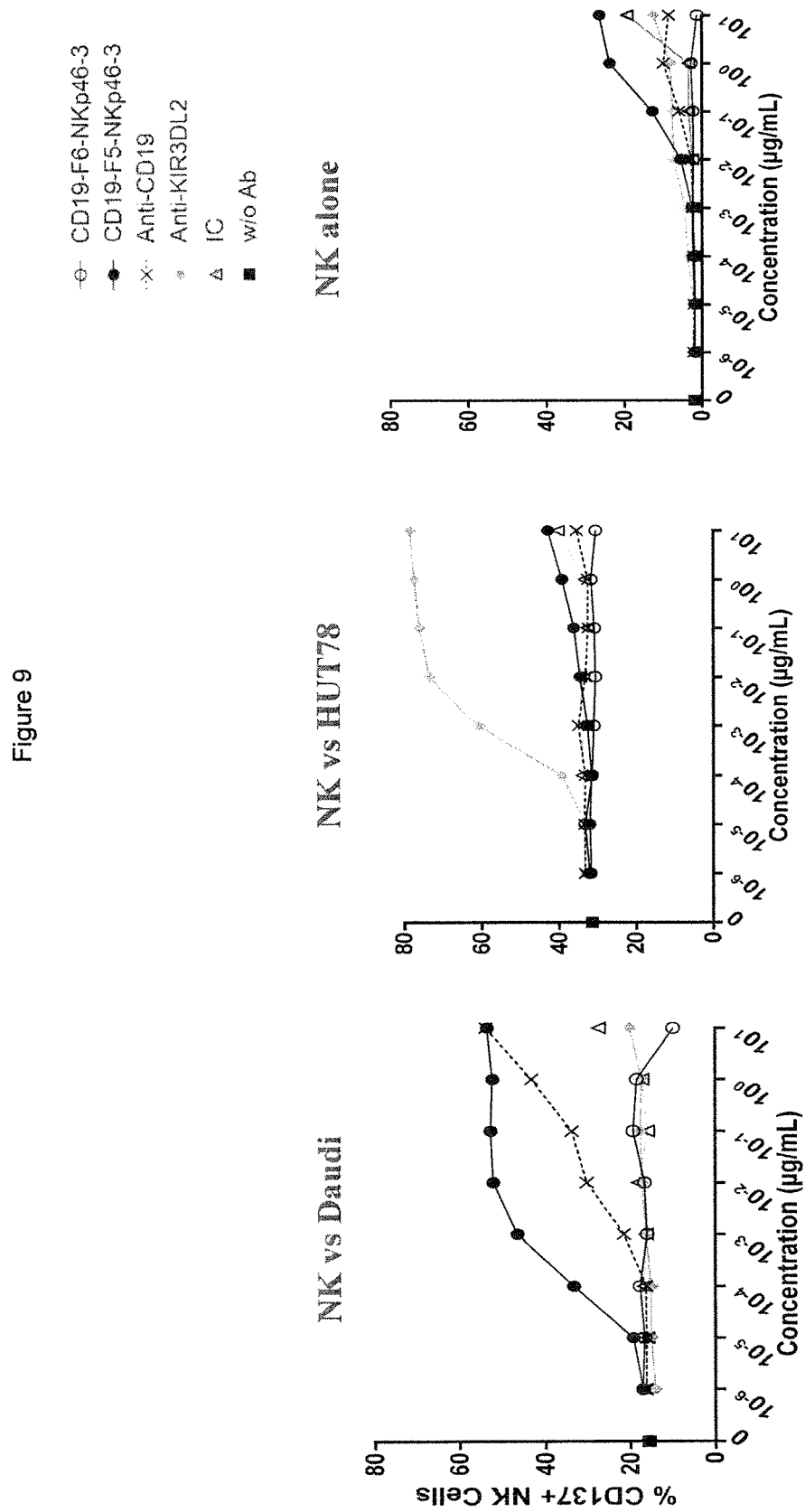
FIG. 9 shows the results of flow cytometry staining of NK cell surface markers showed a strong upregulation of CD137 on the surface of NK cells by F5 proteins (Left-most panel: NK cells vs. Daudi; middle panel: NK cells vs. HUT78; right-most panel: NK cells alone). The full-length anti-CD19 IgG1 antibody that binds CD16 also showed CD137 upregulation, but to a far lesser extent than the CD19-F5-NKp46-3 protein. The CD19-F6-NKp46-3 which functions via NKp46 but not CD16 did not show any CD137 upregulation.

The results of flow cytometry staining of NK cell surface markers showed a strong upregulation of CD137 on the surface of NK cells by F5 proteins. These results are shown in FIG. 9 (Left-most panel: NK cells vs. Daudi; middle panel: NK cells vs. HUT78; right-most panel: NK cells alone). The CD19-F5-NKp46-3 whose Fc domain binds CD16 demonstrated the highest CD137 upregulation. The full-length anti-CD19 IgG1 antibody that binds CD16 also elicited CD137 upregulation, but to a far lesser extent than CD19-F5-NKp46-3. The CD19-F6-NKp46-3 which functions via NKp46 but not via CD16 did not elicit any detectable CD137 upregulation. It is hypothesized that the remarkable potency of the F5 format may arise from a particularly strong CD137 upregulation on NK cells which may be mediated by the dual targeting of NKp46 and CD16.

Example 14

Fc-Engineered CD16-Binding NKp46×CD20 Bispecific

New bispecific proteins were further constructed in an attempt to generate an agent that could improve on the most potent new generation of Fc enhanced antibodies. In these experiments as the comparison antibody we selected the commercial antibody GA101 (GAZYVA®, Gazyvaro®, obinutuzumab, Roche Pharmaceuticals), which is an Fc-modified human IgG1 antibody having enhanced CD16A binding as a result of hypofucosylated N-linked glycosylation.

NKp46×CD20 bispecific proteins were produced as proteins without CD16 binding (F6 format), with CD16 binding (F5 format), or as Fc-engineered format based on F5 but comprising two amino acid substitutions in the CH2 domain of the heavy chain that increase binding affinity for human CD16A (referred to as "F5+"). In these constructs the anti-CD20 ABDs comprise the $V_H$ and $V_L$ of GA101.

Lysis of Daudi cells by NKp46×CD20 bispecific F5, F5+ and F6 antibodies were compared to the commercial antibody GA101 (GAZYVA®). Cytotoxicity assays were carried out as in Example 10.

Figure 10:
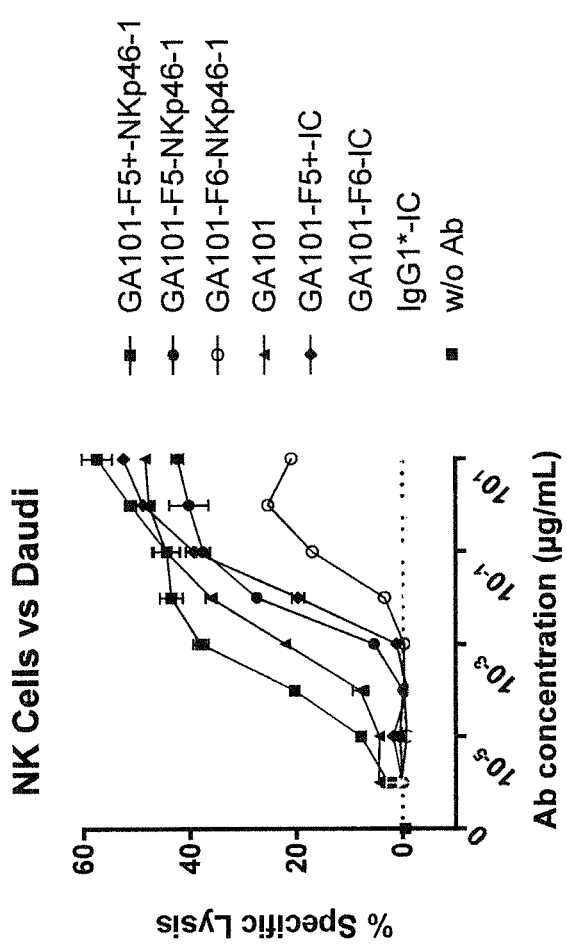
FIG. 10 shows the results of cytotoxicity assays which compared the ability of the GA101-F5+-NKp46-1 bispecific protein to a comparison antibody (GA101) containing the same variable regions to lyse Daudi cells. The results therein show that the GA101-F5$^+$-NKp46-1 bispecific protein possesses far higher potency (approximately 10-fold increase in $EC_{50}$) in mediating cytotoxicity toward Daudi cells than GA101.

Results for the cytotoxicity assays are shown in FIG. 10. As shown therein the GA101-F5+-NKp46-1 bispecific protein demonstrated a far higher potency (approximately 10-fold increase in $EC_{50}$) in mediating cytotoxicity toward Daudi cells that GA101.

Moreover, when ADCC optimized Fc are used for the bispecific format (F5$^+$) a significant difference was observed between F5+-BS lacking the Nkp46 arm (GA101-F5+-IC; black diamond) and F5+-BS co-engaging CD16+NKp46 (GA101-F5$^+$-NKp46-1; black square) confirming the contribution of NKp46 in GA101-F5$^+$-NKp46-1 activity. Surprisingly, despite the high affinity of GA101-F5$^+$-NKp46-1 for CD16 and the presumable maximum NK-cell mediated lysis, NKp46 nevertheless elicited a substantial further increase in cytotoxic activity. These results would suggest that agents capable of inducing ADCC via CD16, can be improved by further conferring on them the ability to induce NKp46-mediated lysis, and also that the potency of bispecific anti-NKp46 agents can be improved by enhancing affinity for CD16 via Fc engineering.

Example 15

Binding of Different Bispecific Formats to FcRn

The affinity of different antibody formats for human FcRn was studied by Surface Plasmon Resonance (SPR) by immobilizing recombinant FcRn proteins covalently to carboxyl groups in the dextran layer on a Sensor Chip CM5, as described in Example 2-6.

A chimeric full length anti-CD19 antibody having intact human IgG1 constant regions and NKp46×CD19 bispecific proteins having an arrangement according to the F3, F4, F5, F6, F9, F10, F11, F13 or F14 formats described in Examples 3 or 4 with anti-NKp46 variable domains from NKp46-3 (NKp46-2 for F2) were tested; for each analyte, the entire sensorgram was fitted using the steady state or 1:1 SCκ binding model.

The results of these experiments are shown in Table 4 below. The bispecific proteins having dimeric Fc domains (formats F5, F6, F13, F14) bound to FcRn with affinity similar to that of the full-length IgG1 antibody. The bispecific proteins with monomeric Fc domains (F3, F4, F9, F10, F11) also displayed binding affinity to FcRn, however with lower affinity that the bispecific proteins having dimeric Fc domains.

TABLE 4

| Antibody/Bispecific | SPR method | KD nM |
|---|---|---|
| Human IgG1/K Anti-CD19 | SCK/Two state reaction | 7.8 |
| CD19-F5-NKp46-3 | SCK/Two state reaction | 2.6 |
| CD19-F6-NKp46-3 | SCK/Two state reaction | 6.0 |
| CD19-F13-NKp46-3 | SCK/Two state reaction | 15.2 |
| CD19-F14-NKp46-3 | SCK/Two state reaction | 14.0 |
| CD19-F3-NKp46-3 | Steady State | 474.4 |
| CD19-F4-NKp46-3 | Steady State | 711.7 |
| CD19-F9A-NKp46-3 | Steady State | 858.5 |
| CD19-F10A-NKp46-3 | Steady State | 432.8 |
| CD19-F11-NKp46-3 | Steady State | 595.5 |

Example 16

Binding to FcγR

Different multimeric Fc proteins were evaluated to assess whether such bispecific monomeric Fc proteins could retain binding to Fcγ receptors.

SPR measurements were performed on a Biacore™ T100 apparatus (Biacore GE Healthcare) at 25° C. In all Biacore™ (surface plasmon resonance) experiments HBS-EP+ (Biacore GE Healthcare) and 10 mM NaOH, 500 mM NaCl served as running buffer and regeneration buffer respectively. Sensorgrams were analyzed with Biacore™ T100 Evaluation software. Recombinant human FcR's (CD64, CD32a, CD32b, CD16a and CD16b) were cloned, produced and purified.

F5 and F6 bispecific antibodies CD19-F5-NKp46-3 or CD19-F6-NKp46-3 were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore™ (GE Healthcare)). Bispecific antibodies were diluted to 10 µg/ml in coupling buffer (10 mM acetate, pH 5.6) and injected until the appropriate immobilization level was reached (i.e. 800 to 900 RU). Deactivation of the remaining activated groups was performed using 100 mM ethanolamine pH 8 (Biacore™ GE Healthcare).

Monovalent affinity study was assessed following a classical kinetic wizard (as recommended by the manufacturer). Serial dilutions of soluble analytes (FcRs) ranging from 0.7 to 60 nM for CD64 and from 60 to 5000 nM for all the other FcRs were injected over the immobilized bispecific antibodies and allowed to dissociate for 10 min before regeneration.

The entire sensorgram sets were fitted using the 1:1 kinetic binding model for CD64 and with the Steady State Affinity model for all the other FcRs.

The results showed that while full length wild type human IgG1 bound to all cynomolgus and human Fcγ receptors, the CD19-F6-NKp46-3 bi-specific antibodies did not bind to any of the receptors. The CD19-F5-NKp46-3, on the other hand, bound to each of the human receptors CD64 (KD=0.7 nM), CD32a (KD=846 nM), CD32b (KD=1850 nM), CD16a (KD=1098 nM) and CD16b (KD=2426 nM). Conventional human anti-IgG1 antibodies have comparable binding to these Fc receptors (KD shown in the table below).

| Human FCγ receptor | CD19-F5-NKp46-3 KD (nM) | Full length human IgG1 antibody KD (nM) |
|---|---|---|
| CD64 | 0.7 | 0.24 |
| CD32a | 846 | 379 |
| CD32b | 1850 | 1180 |
| CD16a | 1098 | 630 |
| CD16b | 2426 | 2410 |

Example 17

Epitope Mapping of Anti-NKp46 Antibodies

A. Competition Assays

Competition assays were conducted by Surface Plasmon Resonance (SPR according to the methods described below.

SPR measurements were performed on a Biacore™ T100 apparatus (Biacore GE Healthcare) at 25° C. In all Biacore™ (surface plasmon resonance) experiments HBS-EP+ (Biacore™ GE Healthcare) and NaOH 10 mM NaCl 500 mM served as running buffer and regeneration buffer respectively. Sensorgrams were analyzed with Biacore T100 Evaluation software. Anti-6×His tag antibody was purchased from QIAGEN. Human 6×His tagged NKp46 recombinant proteins (NKp46-His) were cloned, produced and purified at Innate Pharma.

Anti-His antibodies were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore™ GE Healthcare)). Protein-A and anti-His antibodies were diluted to 10 µg/ml in coupling buffer (10 mM acetate, pH 5.6) and injected until the appropriate immobilization level was reached (i.e. 2000 to 2500 RU). Deactivation of the remaining activated groups was performed using 100 mM ethanolamine pH 8 (Biacore™ GE Healthcare).

Parental regular human IgG1 chimeric antibodies having NKp46 binding region corresponding to NKp46-1, NKp46-2, NKp46-3 or NKp46-4 were used for the competition study which has been performed using an Anti-6×His tag antibody chip. Bispecific antibodies having NKp46 binding region based on NKp46-1, NKp46-2, NKp46-3 or NKp46-4 at 1 µg/mL were captured onto Protein-A chip and recombinant human NKp46 proteins were injected at 5 µg/mL together with a second test bispecific antibody of the NKp46-1, NKp46-2, NKp46-3 or NKp46-4 group.

The results demonstrated that none of NKp46-1, NKp46-2, NKp46-3 or NKp46-4 competed with one another for binding to NKp46. Accordingly these antibodies each bind or interact with a different NKp46epitope.

B. Binding to NKp46 Mutants

In order to define the epitopes of these anti-NKp46 antibodies, we designed NKp46 mutants defined by one, two or three substitutions of amino acids exposed at the molecular surface over the 2 domains of NKp46. This approach led to the generation of 42 mutants which were transfected in Hek-293T cells, as shown in the table below. The targeted amino acid mutations in Table 5 below are shown both according to the numbering of SEQ ID NO: 1 (also corresponding to the numbering used in Jaron-Mendelson et al. (2012) *J. Immunol.* 88(12):6165-74.

TABLE 5

| Mutant | Substitution (Numbering according to: Jaron-Mendelson and SEQ ID NO 1) | | |
|---|---|---|---|
| 1 | P40A | K43S | Q44A |
| 2 | K41S | E42A | E119A |
| 3 | P86A | D87A | |
| 4 | N89A | R91A | |
| 5 | K80A | K82A | |
| 5bis | E34A | T46A | |
| 6 | R101A | V102A | |
| 7 | N52A | Y53A | |
| 8 | V56A | P75A | E76A |
| 9 | R77A | I78A | |
| 10 | S97A | I99A | |
| 10bis | Q59A | H61A | |
| 11 | L66A | V69A | |
| 12 | E108A | | |
| 13 | N111A | L112A | |
| 14 | D114A | | |
| 15 | T125A | R145S | D147A |
| 16 | S127A | Y143A | |
| 17 | H129A | K139A | |
| 18 | K170A | V172A | |
| 19 | I135A | S136A | |
| 19bis | T182A | R185A | |
| 20 | R160A | | |
| 21 | K207A | | |
| 22 | M152A | R166A | |
| 23 | N195A | N196A | |
| Stalk1 | D213A | I214A | T217A |
| Stalk2 | F226A | T233A | |
| Stalk3 | L236A | T240A | |
| Supp1 | F30A | W32A | |
| Supp2 | F62A | F67A | |
| Supp3 | E63A | Q95A | |
| Supp4 | R71A | K73A | |
| Supp5 | Y84A | | |
| Supp6 | E104A | L105A | |
| Supp7 | Y121A | Y194A | |
| Supp8 | P132A | E133A | |
| Supp9 | S151A | Y168A | |
| Supp10 | S162A | H163A | |
| Supp11 | E174A | P176A | |
| Supp12 | P179A | H184A | |
| Supp13 | R189A | E204A | P205A |

C. Generation of Mutants

NKp46 mutants were generated by PCR. The sequences amplified were run on agarose gel and purified using the Macherey Nagel PCR Clean-Up Gel Extraction kit. Two or three purified PCR products generated for each mutant were then ligated into an expression vector, with the ClonTech InFusion system. The vectors containing the mutated sequences were prepared as Miniprep and sequenced. After sequencing, the vectors containing the mutated sequences were prepared as Midiprep using the Promega PureYield™ Plasmid Midiprep System. HEK293T cells were grown in DMEM medium (Invitrogen), transfected with vectors using Invitrogen's Lipofectamine 2000 and incubated at 37° C. in a $CO_2$ incubator for 24 hours prior to testing for transgene expression.

D. Flow Cytometry Analysis of Anti-NKp46 Binding to the HEK293T Transfected Cells All the anti-NKp46 antibodies were tested for their binding to each mutant by flow cytometry. A first experiment was performed to identify antibodies that lose their binding to one or several mutants at a particular concentration (10 µg/ml). To confirm the loss of binding, titration of antibodies was done using antibodies for which binding seemed to be affected by the NKp46 mutations (1-0.1-0.01-0.001 µg/ml).

E. Results

Antibody NKp46-1 had decreased binding to the mutant 2 (having a mutation at residues K41, E42 and E119) (numbering in NKp46 wild-type) compared to wild-type NK46. Similarly, NKp46-1 also had decreased binding to the supplementary mutant Supp7 (having a mutation at residues Y121 and Y194).

Antibody NKp46-3 had decreased binding to the mutant 19 (having a mutation at residues I135, and S136). Similarly, NKp46-1 also had decreased binding to the supplementary mutant Supp8 (having a mutation at residues P132 and E133).

Antibody NKp46-4 had decreased binding to the mutant 6 (having a mutation at residues R101, and V102). Similarly, NKp46-1 also had decreased binding to the supplementary mutant Supp6 having a mutation at residues E104 and L105.

Using these methods we identified the epitopes for anti-NKp46 antibodies NKp46-1, NKp46-3 and NKp46-4. We determined that the epitopes of NKp46-4, NKp46-3 and NKp46-1 are on NKp46 D1 domain, D2 domain and D1/D2 junction, respectively. R101, V102, E104 and L105 are essential residues for NKp46-4 binding and defined a part of NKp46-4 epitope.

The epitope of NKp46-1 epitope includes K41, E42, E119, Y121 and Y194 residues. The epitope of NKp46-3 includes P132, E133, I135, and S136 residues.

Example 18

Improved Product Profile and Yield of Different Bispecific Formats Compared to Existing Formats Blinatumomab and two bispecific antibodies having NKp46 and CD19 binding regions based on F1 to F17 formats and NKp46-3, and blinatumomab, respectively were cloned and produced under format 6 (F6), DART™ and BiTE™ formats following the same protocol and using the same expression system. F6, DART™ and BiTE™ bispecific proteins were purified from cell culture supernatant by affinity chromatography using prot-A beads for F6 or Ni-NTA beads for DART™ and BiTE™. Purified proteins were further analyzed and purified by SEC. DART™ and BiTE™ showed a very low production yield compared to F6 and the purified proteins have a very complex SEC profile. DART™ and BiTE™ are barely detectable by SDS-PAGE after Coomassie staining in the expected SEC fractions (3 and 4 for BiTE™ and 4 and 5 for DART™), whereas the F6 format showed a clear and simple SEC and SDS-PAGE profiles with a major peak (fraction 3) containing the multimeric bispecific proteins. The major peak for the F6 format corresponded to about 30% of the total proteins. These results are consistent for those seen with the F1 to F17 proteins (data not shown) indicating that the Fc domain (or Fc-derived domain) present in those formats facilitates the production and improves the quality and solubility of bispecific proteins.

Moreover, the Fc domains present in proteins F1 to F17 have the advantage of being suitable for usage in affinity chromatography without the need for the incorporation of peptide tags. This is desirable as such tags are undesirable in a therapeutic product as they may potentially elicit undesired immunogenicity. By contrast, DART™ and BiTE™ antibodies cannot be purified using protein A, whereas F1 to F17 antibodies are all bound by protein A. Table 6 below shows the productivity of different formats.

TABLE 6

| Format | SEC | SDS PAGE Reduced | SDS PAGE Non Reduced | Final « productivity » yield |
|---|---|---|---|---|
| F3 | 2 peaks | ✓ | ✓ | 3.4 mg/L |
| F4 | 2 peaks | ✓ | ✓ | 1 mg/L |
| F5 | ✓ | ✓ | ✓ | 37 mg/L |
| F6 | ✓ | ✓ | ✓ | 12 mg/L |
| F7 | ✓ | ✓ | ✓ | 11 mg/L |
| F8C | ✓ | ✓ | ✓ | 3.7 mg/L |
| F9A | ✓ | ✓ | ✓ | 8.7 mg/L |
| F9B | ✓ | ✓ | ✓ | 3.0 mg/L |
| F10A | ✓ | ✓ | ✓ | 2.0 mg/L |
| F11 | ✓ | ✓ | ✓ | 2.0 mg/L |
| F12 | ✓ | ✓ | ✓ | 2.8 mg/L |
| F13 | ✓ | ✓ | ✓ | 6.4 mg/L |
| F14 | ✓ | ✓ | ✓ | 2.4 mg/L |
| F15 | ✓ | ✓ | ✓ | 0.9 mg/L |
| BiTe ™ | — | — | — | — |
| DART ™ | — | — | — | — |

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of promoting the specific lysis of cancer cells expressing an antigen of interest which is specifically bound by a therapeutic anti-cancer antibody or therapeutic anti-cancer antigen-binding antibody fragment in a subject in need thereof comprising contacting said cancer cells with an amount of a multispecific antigen binding protein sufficient to promote the specific lysis of said cancer cells expressing said antigen of interest, wherein said multispecific antigen binding protein comprises:
   (i) a first antigen binding domain (ABD) which monovalently binds to a human NKp46 polypeptide having the amino acid sequence set forth in SEQ ID NO:1,
   (ii) a second ABD which comprises a therapeutic anti-cancer antibody or a therapeutic anti-cancer antigen-binding antibody fragment which binds to said antigen of interest-expressed by said cancer cells, and
   (iii) a CD16A binding polypeptide,
wherein:
   (1) said NKp46-binding ABD comprises a Fab or comprises a variable heavy ($V_H$) domain and a variable light ($V_L$) domain separated by a linker ("scFv");
   (2) said cancer-antigen-binding ABD, which comprises said therapeutic anti-cancer antibody or therapeutic anti-cancer antigen-binding antibody fragment, is monovalent or bivalent;
   (3) said CD16A binding polypeptide comprises a dimeric human Fc domain polypeptide which binds CD16A;
   (4) said multispecific antigen binding protein binds to the NKp46 polypeptide monovalently;
   (5) said multispecific antigen binding protein directs NKp46-expressing natural killer (NK) cells and CD16A-expressing NK cells to lyse cancer cells expressing the cancer antigen of interest by a combination of NKp46-mediated signaling and CD16A-mediated antibody-dependent cell-mediated cytotoxicity ("ADCC");
   (6) said dimeric Fc domain interposes said first ABD and said second ABD;
   (7) said first and second ABD are each connected to said dimeric Fc domain, and one or both of said first and second ABD are connected to the dimeric Fc domain via a flexible polypeptide linker.

2. The method of claim 1, wherein the cancer-antigen-binding ABD comprises a Fab or comprises a $V_H$ domain and a $V_L$ domain separated by a linker comprising a linear or cyclic peptide.

3. The method of claim 1, wherein the NKp46-binding ABD comprises a Fab.

4. The method of claim 1, wherein the NKp46-binding ABD comprises a $V_H$ domain and a $V_L$ domain separated by a linker comprising a linear or cyclic peptide.

5. The method of claim 1 wherein said dimeric Fc polypeptide of (3) comprises a modification that enhances CD16A binding relative to the corresponding wild-type Fc region.

6. The method of claim 1, wherein the administration of said multispecific antigen binding protein increases the expression of CD137 on the surface of NK cells in said subject.

7. The method of claim 1, wherein the NKp46-binding ABD is comprised of a $V_H$ domain and a $V_L$ domain, wherein each of the $V_H$ and $V_L$ domains are positioned within a tandem variable region comprising a $V_H$ domain and a $V_L$ domain separated by a polypeptide linker.

8. The method of claim 1, wherein the NKp46-binding ABD is a Fab comprised of a $V_H$ domain and a $V_L$ domain, wherein each of the $V_H$ and $V_L$ domains is fused to a human $C_{H1}$ or $C_\kappa$ constant domain.

9. The method of claim 8, wherein the NKp46-binding ABD is a Fab comprised of (a) a $V_H$ domain fused to a human $C_{H1}$ constant domain and a $V_L$ domain fused to a human $C_\kappa$ constant domain, or (b) a $V_H$ domain fused to a human $C_\kappa$ constant domain and a $V_L$ domain fused to a human $C_{H1}$ constant domain.

10. The method of claim 1, wherein the cancer-antigen-binding ABD is a Fab comprised of a $V_H$ domain and a $V_L$ domain, wherein each of the $V_H$ and $V_L$ domains is fused to a human $C_{H1}$ or $C_\kappa$ constant domain.

11. The method of claim 10, wherein the cancer-antigen-binding ABD is a Fab comprised of (a) a $V_H$ domain fused to a human $C_{H1}$ constant domain and a $V_L$ domain fused to a human $C_\kappa$ constant domain, or (b) a $V_H$ domain fused to a human $C_\kappa$ constant domain and a $V_L$ domain fused to a human $C_{H1}$ constant domain.

12. The method of claim 1, wherein either or both the NKp46-binding ABD or the cancer-antigen-binding ABD is bound to the Fc domain by a flexible polypeptide linker.

13. The method of claim 1, wherein the monovalent NKp46 ABD comprises $V_H$ and $V_L$ domain polypeptides selected from the group consisting of:
(a) the $V_H$ and $V_L$ domains of SEQ ID NOS: 3 and 4 (NKp46-1);
(b) the $V_H$ and $V_L$ domains of SEQ ID NOS: 5 and 6 (NKp46-2);
(c) the $V_H$ and $V_L$ domains of SEQ ID NOS: 7 and 8 (NKp46-3);
(d) the $V_H$ and $V_L$ domains of SEQ ID NOS: 9 and 10 (NKp46-4);
(e) the $V_H$ and $V_L$ domains of SEQ ID NOS: 11 and 12 (NKp46-6); and
(f) the $V_H$ and $V_L$ domains of SEQ ID NOS: 13 and 14 (NKp46-9).

14. The method of claim 1, wherein said combination of NKp46-mediated signaling and CD16A-mediated ADCC has an additive or synergistic effect on the lysis of cancer cells expressing the antigen of interest.

15. A method of promoting the specific lysis of hematological cancer cells expressing an antigen of interest which is specifically bound by a therapeutic anti-cancer antibody or therapeutic anti-cancer antigen-binding antibody fragment in a subject in need thereof, comprising contacting said hematological cancer cells with an amount of a multispecific antigen binding protein which is sufficient to promote the specific lysis of said hematological cancer cells expressing said therapeutic cancer antigen, wherein said multispecific antigen binding protein comprises:
(i) a first antigen binding domain (ABD) which monovalently binds to a human NKp46 polypeptide having the amino acid sequence set forth in SEQ ID NO:1,
(ii) a second ABD which comprises a therapeutic anti-cancer antibody or a therapeutic anti-cancer antigen-binding antibody fragment which binds to said antigen of interest expressed by said hematological cancer cells, and
(iii) a CD16A binding polypeptide,
wherein:
(1) said NKp46-binding ABD comprises a Fab or comprises a $V_H$ chain domain and a $V_L$ chain domain separated by a linker ("scFv");
(2) (2) said cancer-antigen-binding ABD, which comprises said therapeutic anti-cancer antibody or therapeutic anti-cancer antigen-binding antibody fragment, is monovalent or bivalent;
(3) said CD16A binding polypeptide comprises a dimeric human Fc domain polypeptide which binds CD16A;
(4) said multispecific antigen binding protein binds to the NKp46 polypeptide monovalently;
(5) said multispecific antigen binding protein directs NKp46-expressing NK cells and CD16A-expressing NK cells to lyse hematological cancer cells expressing the cancer antigen of interest by a combination of NKp46-mediated signaling and CD16A-mediated ADCC;
(6) said dimeric Fc domain interposes said first ABD and said second ABD;
(7) said first and second ABD are each attached to said dimeric Fc domain, and one or both of said first and second ABD are connected to the Fc domain via a flexible polypeptide linker.

16. The method of claim 15, wherein said combination of NKp46-mediated signaling and CD16A-mediated ADCC has an additive or synergistic effect on the lysis of hematological cancer cells expressing the antigen of interest.

17. The method of claim 15, wherein the antigen of interest expressed by said hematological cancer cells comprises CD19 or CD20.

18. A method of promoting the specific lysis of cancer cells expressing an antigen of interest which is specifically bound by a therapeutic anti-cancer antibody or therapeutic anti-cancer antigen-binding antibody fragment in a subject in need thereof, comprising contacting said cancer cells with an amount of a multispecific antigen binding protein which is sufficient to promote the specific lysis of said cancer cells expressing said antigen of interest, wherein said multispecific antigen binding protein comprises:
(i) a first antigen binding domain (ABD) which monovalently binds to a human NKp46 polypeptide having the amino acid sequence set forth in SEQ ID NO:1,
(ii) a second ABD which comprises a therapeutic anti-cancer antibody or a therapeutic anti-cancer antigen-binding antibody fragment which binds to said antigen of interest expressed by said hematological cancer cells, and
(iii) a CD16A binding polypeptide,
wherein:
(1) said NKp46-binding ABD comprises a Fab or comprises a $V_H$ chain domain and a $V_L$ chain domain separated by a linker ("scFv");
(2) said cancer-antigen-binding ABD, which comprises said therapeutic anti-cancer antibody or therapeutic anti-cancer antigen-binding antibody fragment is monovalent or bivalent;
(3) said CD16A binding polypeptide comprises a dimeric human Fc domain polypeptide which binds CD16A;
(4) said multispecific antigen binding protein binds to the NKp46 polypeptide monovalently;
(5) said multispecific antigen binding protein directs NKp46-expressing NK cells and CD16A-expressing NK cells to lyse hematological cancer cells expressing the cancer antigen of interest by a combination of NKp46-mediated signaling and CD16A-mediated ADCC;
(6) said cancer antigen of interest is selected from the list consisting of CD19, CD20, EGFR, ROR1, KIR3DL2, and B7-H3;
(6) said dimeric Fc domain interposes said first ABD and said second ABD;
(7) said first and second ABD are each attached to said dimeric Fc domain, and wherein one or both of said first and second ABD are connected to the Fc domain via a flexible polypeptide linker.

19. The method of claim 18, wherein said combination of NKp46-mediated signaling and CD16A-mediated ADCC has an additive or synergistic effect on the lysis of cancer cells expressing the antigen of interest.

20. The method of claim 18, wherein said cancer antigen of interest is CD20.

21. The method of claim 1, wherein said flexible polypeptide linker is 2-50 amino acids in length.

22. The method of claim 15, wherein said flexible polypeptide linker is 2-50 amino acids in length.

23. The method of claim 18, wherein said flexible polypeptide linker is 2-50 amino acids in length.

24. The method of claim 1, wherein one of the ABDs is connected to the Fc region via a peptide linker which comprises a hinge domain.

25. The method of claim 15, wherein one of the ABDs is connected to the Fc region via a peptide linker which comprises a hinge domain.

26. The method of claim 18, wherein one of the ABDs is connected to the Fc region via a peptide linker which comprises a hinge domain.

27. The method of claim 9, wherein the $C_\kappa$ constant domain and the human $C_{H1}$ constant domain are each connected to the Fc domain via a hinge domain.

28. The method of claim 11, wherein the $C_\kappa$ constant domain and the human $C_{H1}$ constant domain are each connected to the Fc domain via a hinge domain.

\* \* \* \* \*

UNITED STATES PATENT AND TRADEMARK OFFICE
CERTIFICATE OF CORRECTION

| | | |
|---|---|---|
| PATENT NO. | : 10,113,003 B2 | Page 1 of 1 |
| APPLICATION NO. | : 15/190337 | |
| DATED | : October 30, 2018 | |
| INVENTOR(S) | : Laurent Gauthier | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
Fourteenth Day of February, 2023

Katherine Kelly Vidal
*Director of the United States Patent and Trademark Office*